US010478448B2

(12) United States Patent
Crooke et al.

(10) Patent No.: US 10,478,448 B2

(45) **Date of Patent: *Nov. 19, 2019**

(54) METHODS AND COMPOSITIONS FOR MODULATING APOLIPOPROTEIN (A) EXPRESSION

(71) Applicant: Ionis Pharmaceuticals, Inc., Carlsbad, CA (US)

(72) Inventors: Rosanne M. Crooke, Carlsbad, CA (US); Mark J. Graham, San Clemente, CA (US); Susan M. Freier, San Diego, CA (US); Marc Lim, Oceanside, CA (US); Andrew Dibble, Vista, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/855,203

(22) Filed: Dec. 27, 2017

(65) Prior Publication Data

US 2018/0256629 A1 Sep. 13, 2018

Related U.S. Application Data

(60) Continuation of application No. 15/401,914, filed on Jan. 9, 2017, now Pat. No. 9,884,072, which is a division of application No. 14/552,436, filed on Nov. 24, 2014, now Pat. No. 9,574,193, which is a continuation-in-part of application No. 14/401,761, filed on Nov. 17, 2014, now abandoned, which is a continuation of application No. PCT/US2013/042532, filed as application No. PCT/US2013/041701 on May 17, 2013.

(60) Provisional application No. 61/651,539, filed on May 24, 2012, provisional application No. 61/648,556, filed on May 17, 2012.

(51) Int. Cl.

| | |
|---|---|
| *A61K 31/713* | (2006.01) |
| *C12N 15/113* | (2010.01) |
| *A61K 31/7125* | (2006.01) |
| *A61K 31/7115* | (2006.01) |
| *A61K 31/712* | (2006.01) |

(52) U.S. Cl.

CPC ........ *A61K 31/7115* (2013.01); *A61K 31/712* (2013.01); *A61K 31/7125* (2013.01); *C12N 15/113* (2013.01); *C12N 2310/11* (2013.01); *C12N 2310/315* (2013.01); *C12N 2310/321* (2013.01); *C12N 2310/323* (2013.01); *C12N 2310/3341* (2013.01); *C12N 2310/3525* (2013.01)

(58) Field of Classification Search

None

See application file for complete search history.

(56) References Cited

U.S. PATENT DOCUMENTS

| | | | |
|---|---|---|---|
| 2005/0026169 | A1 | 2/2005 | Cargill et al. |
| 2009/0318536 | A1 | 12/2009 | Isis et al. |
| 2010/0035983 | A1 | 2/2010 | Celera et al. |
| 2010/0197762 | A1 | 8/2010 | Swayze |

FOREIGN PATENT DOCUMENTS

| | | |
|---|---|---|
| EP | 2316968 | 5/2011 |

*Primary Examiner* — Tracy Vivlemore

(74) *Attorney, Agent, or Firm* — Grant IP, Inc.

(57) ABSTRACT

Disclosed herein are antisense compounds and methods for decreasing apo(a) to treat, prevent, or ameliorate diseases, disorders or conditions related to apo(a) or Lp(a). Certain diseases, disorders or conditions related to apo(a) or Lp(a) include inflammatory, cardiovascular and/or metabolic diseases, disorders or conditions. The antisense compounds disclosed herein can be used to treat such diseases, disorders or conditions in an individual in need thereof.

25 Claims, No Drawings

Specification includes a Sequence Listing.

METHODS AND COMPOSITIONS FOR MODULATING APOLIPOPROTEIN (A) EXPRESSION

This application is a continuation of U.S. application Ser. No. 15/401,914 filed Jan. 9, 2017 (now U.S. Pat. No. 9,884,072), which is a divisional of U.S. application Ser. No. 14/552,436 filed Nov. 24, 2014 (now U.S. Pat. No. 9,574,193), which is a continuation-in-part of U.S. application Ser. No. 14/401,761 filed Nov. 17, 2014 (now abandoned), which is a continuation of International Ser. No. PCT/US2013/042532 filed May 23, 2013, which is a U.S. National Phase filing under 35 U.S.C. 371 claiming priority to International Serial No. PCT/US2013/041701 filed May 17, 2013, which claims priority to U.S. Provisional application No. 61/651,539 filed May 24, 2012 and U.S. Provisional Application No. 61/648, 556 filed May 17, 2012, each of which is incorporated herein by reference in its entirety.

SEQUENCE LISTING

The present application is being filed along with a Sequence Listing in electronic format. The Sequence Listing is provided as a file entitled BIOL0177USC4SEQ_ST25.txt created Dec. 27, 2017, which is 424 Kb in size. The information in the electronic format of the sequence listing is incorporated herein by reference in its entirety.

FIELD

Embodiments described herein provide methods, compounds, and compositions for reducing expression of apolipoprotein (a) mRNA and protein in an animal. Such methods, compounds, and compositions are useful to treat, prevent, or ameliorate cardiovascular and/or metabolic diseases, disorders or conditions.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a) [apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Erqou et al., JAMA 2009; 302:412-23; Kamstrup et al., Circulation 2008; 117:176-84). Further, in the recent Precocious Coronary Artery Disease (PROCARDIS) study, Clarke et al. (Clarke et al., NEJM (2009)361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; U.S. Pat. No. 8,138,328; Merki et al., J Am Coll Cardiol 2011; 57:1611-1621) have been developed, but none of the compounds directly targeting apo(a) are currently used in the clinic.

Thus, there remains a clear unmet medical need for novel agents which can potently and selectively reduce apo(a) levels in patients at enhanced risk for cardiovascular events due to chronically elevated plasma Lp(a) levels.

SUMMARY

Provided herein are compositions and methods for modulating expression of apo(a) mRNA and protein. In certain embodiments, the apo(a) specific inhibitor decreases expression of apo(a) mRNA and protein.

In certain embodiments, the composition is an apo(a) specific inhibitior. In certain embodiments, the apo(a) specific inhibitor is a nucleic acid, protein, or small molecule. In certain embodiments, the apo(a) specific inhibitor is an antisense oligonucleotide targeting apo(a). In certain embodiments, the apo(a) specific inhibitor is a modified oligonucleotide consisting of 12 to 30 linked nucleosides and comprising a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1. In certain embodiments, the apo(a) specific inhibitor is a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 1-130, 133, 134. In certain embodiments, the apo(a) specific inhibitor is a modified oligonucleotide consisting of 20 linked nucleosides and having a nucleobase sequence comprising at least 8 contiguous nucleobases of any of SEQ ID NO: 58, wherein the modified oligonucleotide comprises: (a) a gap segment consisting often linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a composition comprising a compound described herein, or a salt thereof, and a pharmaceutically acceptable carrier or diluent.

In certain embodiments, the modulation of apo(a) expression occurs in a cell or tissue. In certain embodiments, the modulations occur in a cell or tissue in an animal. In certain embodiments, the animal is a human. In certain embodiments, the modulation is a reduction in apo(a) mRNA level. In certain embodiments, the modulation is a reduction in apo(a) protein level. In certain embodiments, both apo(a) mRNA and protein levels are reduced. Such reduction may occur in a time-dependent or in a dose-dependent manner.

Certain embodiments provide compositions and methods for use in therapy. Certain embodiments provide compositions and methods for preventing, treating, delaying, slowing the progression and/or ameliorating apo(a) related diseases, disorders, and conditions. Certain embodiments provide compositions and methods for preventing, treating, delaying, slowing the progression and/or ameliorating Lp(a) related diseases, disorders, and conditions. In certain embodiments, such diseases, disorders, and conditions are inflammatory, cardiovascular and/or metabolic diseases, disorders, and conditions. In certain embodiments, the compositions and methods for therapy include administering an apo(a) specific inhibitor to an individual in need thereof. In certain embodiments, the apo(a) specific inhibitor is a nucleic acid. In certain embodiments, the nucleic acid is an antisense compound. In certain embodiments, the antisense compound is a modified oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or", unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE, MOE, 2'-O$(CH_2)_2$—$OCH_3$ and 2'-O-(2-methoxyethyl)) refers to an O-methoxyethyl modification of the 2' position of a furanosyl ring. A 2'-O-methoxyethyl modified sugar is a modified sugar.

"2'-deoxyribonucleoside" means a nucleoside comprising 2'-H furanosyl sugar moiety, as found in naturally occurring deoxyribonucleosides (DNA).

"2'-MOE nucleoside" (also 2'-O-methoxyethyl nucleoside) means a nucleoside comprising a 2'-MOE modified sugar moiety. "2'-O-methoxyethyl nucleotide" means a nucleotide comprising a 2'-O-methoxyethyl modified sugar moiety.

"3'-fluoro-HNA" (also "F-HNA" or "3'-F-HNA") means the sugar moiety of a nucleoside having the following structure:

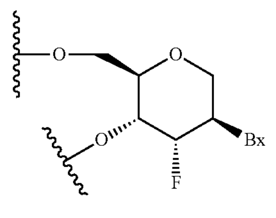

wherein Bx is a nucleobase.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within +10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to apo(a) is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

"Agent" means an active substance that can provide a therapeutic benefit when administered to an animal. "First Agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo(a) therapeutic compound.

"Amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody can refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats. As used herein, the term "antisense compound" encompasses pharmaceutically acceptable derivatives of the compounds described herein.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"Apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

"Apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

"Apo(a) mRNA" means a mRNA encoding an apo(a) protein.

"Apo(a) protein" means any protein sequence encoding Apo(a).

"Apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-estrified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Constrained ethyl" or "cEt" refers to a bicyclic nucleoside having a furanosyl sugar that comprises a methyl (methyleneoxy) (4'-$CH(CH_3)$—O-2') bridge between the 4' and the 2' carbon atoms.

"Constrained ethyl nucleoside" (also cEt nucleoside) means a nucleoside comprising a bicyclic sugar moiety comprising a 4'-$CH(CH_3)$—O-2' bridge.

"Contiguous nucleobases" means nucleobases immediately adjacent to each other.

"Cross-reactive" means an oligomeric compound targeting one nucleic acid sequence can hybridize to a different nucleic acid sequence. For example, in some instances an antisense oligonucleotide targeting human apo(a) can cross-react with an apo(a) from another species. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides can be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides (TG), and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Furanosyl" means a structure comprising a 5-membered ring comprising four carbon atoms and one oxygen atom.

"Gapmer" means a chimeric antisense compound in which an internal region having a plurality of nucleosides that support RNaseH cleavage is positioned between external regions having one or more nucleosides, wherein the nucleosides comprising the internal region are chemically distinct from the nucleoside or nucleosides comprising external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"High density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ,* 2007, 176:1113-1120).

"Identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Individual in need thereof" refers to a human or non-human animal selected for treatment or therapy that is in need of such treatment or therapy.

"Induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

"Inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

"Lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

"Lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

"Lp(a)" comprises apo(a) and a LDL like particle containing apoB. The apo(a) is linked to the apoB by a disulfide bond.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond). For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"MOE nucleoside" means a nucleoside comprising a 2'-substituted sugar moiety comprising MOE at the 2'-position.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to apo(a) is a pharmaceutical agent.

"Pharmaceutical composition" or "composition" means a mixture of substances suitable for administering to an individual. For example, a pharmaceutical composition can comprise one or more active agents and a pharmaceutical carrier e.g., a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage (P═S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Subject" means a human or non-human animal selected for treatment or therapy.

"Sugar moiety" means a naturally occurring sugar moiety or a modified sugar moiety of a nucleoside.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutically effective amount" means an amount of a pharmaceutical agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" or "treating" refers to administering a compound described herein to effect an alteration or improvement of a disease, disorder, or condition.

"Triglyceride" or "TG" means a lipid or neutral fat consisting of glycerol combined with three fatty acid molecules.

"Type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide a compounds and methods for decreasing apo(a) mRNA and protein expression. In certain embodiments, the compound is an apo(a) specific inhibitor for treating, preventing, or ameliorating an apo(a) associated disease. In certain embodiments, the compound is an antisense oligonucleotide targeting apo(a).

Certain embodiments provide a compounds and methods for decreasing Lp(a) levels. In certain embodiments, the compound is an apo(a) specific inhibitor for treating, preventing, or ameliorating an Lp(a) associated disease. In certain embodiments, the compound is an antisense oligonucleotide targeting apo(a).

Certain embodiments provide a compound comprising a modified oligonucleotide targeting apo(a) consisting of 12 to 30 linked nucleosides. In certain embodiments, the modified oligonucleotide consists of 15 to 30, 18 to 24, 19 to 22, 13 to 25, 14 to 25, 15 to 25 linked nucleosides. In certain embodiments, the modified oligonucleotide comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide consists of 20 linked nucleosides.

Certain embodiments provide a compound comprising a modified oligonucleotide targeting apo(a) comprising at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-4. Certain embodiments provide a compound comprising a modified oligonucleotide targeting an apo(a) segment comprising at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in Tables 3-13 and 28-30. In the tables, the "Start Site" refers to the 5'-most nucleotide of a target segment and "Stop Site" refers to the 3'-most nucleotide of a target segment. A target segment can range from the start site to the stop site of each sequence listed in the tables. Alternatively, the target segment can range from the start site of one sequence and end at the stop site of another sequence. For example, as shown in Table 5, a target segment can range from 3901-3920, the start site to the stop site of SEQ ID NO: 58. In another example, as shown in Table 5, a target segment can range from 3900-3923, the start site of SEQ ID NO: 57 to the stop site of SEQ ID NO: 61.

Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of SEQ ID NOs: 1-4. Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of the target segments shown in Tables 3-13 and 28-30.

Certain embodiments provide a compound comprising a modified oligonucleotide targeting apo(a) consisting of 12 to 30 linked nucleosides and comprising a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3900 to 3923 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-130, 133, 134. In certain embodiments, the modified oligonucleotide has a nucleobase sequence comprising at least 8 contiguous nucleobases of any one of the nucleobase sequences of SEQ ID NOs: 12-130, 133, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-19, 26-30, 32, 35, 38-44, 46-47, 50, 57-58, 61, 64-66, 68, 72-74, 76-77, 92-94, 103-110.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 111, 114-121, 123-129.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 17, 18, 26-28, 39, 71, 106-107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 26-29, 39-40, 82.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 16-18.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 26-27,107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28-29, 39-40, 47.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28, 93, 104, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 58.

In certain embodiments, the modified oligonucleotide has a nucleobase sequence comprising at least 8 contiguous nucleobases of the nucleobase sequence of SEQ ID NO: 58.

Certain embodiments provide a compound comprising a modified oligonucleotide targeting apo(a), wherein the modified oligonucleotide is single-stranded.

Certain embodiments provide a compound comprising a modified oligonucleotide targeting apo(a), wherein at least one internucleoside linkage is a modified internucleoside linkage. In certain embodiments, each internucleoside linkage is a phosphorothioate internucleoside linkage.

Certain embodiments provide a compound comprising a modified oligonucleotide targeting apo(a), wherein at least one nucleoside comprises a modified nucleobase. In certain embodiments, the modified nucleobase is a 5-methylcytosine.

Certain embodiments provide a compound comprising a modified oligonucleotide targeting apo(a), wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-$(CH_2)_n$—O-2' bridge, wherein n is 1 or 2.

Certain embodiments provide a compound comprising a modified oligonucleotide targeting apo(a), wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting apo(a), wherein the modified oligonucleotide consists of 20 linked nucleosides and comprises: (a) a gap segment consisting often linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of any of SEQ ID NOs: 12-130, 133, 134, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a modified oligonucleotide targeting apo(a), wherein the modified oligonucleotide consists of 20 linked nucleosides with the nucleobase sequence of SEQ ID NO: 58, wherein the modified oligonucleotide comprises: (a) a gap segment consisting often linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

In certain embodiments, the compound is in a salt form. In further embodiments, the compound further comprises of a pharmaceutically acceptable carrier or diluent. In certain embodiments, the compound comprising a modified oligonucleotide targeting apo(a), or a salt thereof, and a pharmaceutically acceptable carrier or diluent.

Certain embodiments provide a composition comprising a compound as described herein, wherein the viscosity level of the compound is less than 40 centipoise (cP). In certain embodiments, the antisense compounds as described herein are efficacious by virtue of having a viscosity of less than 40 cP, less than 35 cP, less than 30 cP, less than 25 cP, less than 20 cP or less than 15 cP when measured by the parameters as described in Example 13.

Certain embodiments provide compositions and methods for use in therapy to treat an apo(a) related disease, disorder or condition. Certain embodiments provide compositions and methods for use in therapy to treat an Lp(a) related disease, disorder or condition. In certain embodiments, the composition is a compound comprising an apo(a) specific inhibitor. In certain embodiments, the apo(a) specific inhibitor is a nucleic acid. In certain embodiments, the nucleic acid is an antisense compound. In certain embodiments, the antisense compound is a modified oligonucleotide targeting apo(a). In certain embodiments, the modified oligonucleotide targeting apo(a), is used in treating, preventing, slowing progression, ameliorating a cardiovascular and/or metabolic disease, disorder or condition. In certain embodiments, the compositions and methods for therapy include administering an apo(a) specific inhibitor to an individual in need thereof.

Certain embodiments provide compositions and methods for reducing apo(a) levels. Certain embodiments provide compositions and methods for reducing Lp(a) levels. In certain embodiments, reducing apo(a) levels in a tissue, organ or subject improves the ratio of LDL to HDL or the ratio of TG to HDL.

Certain embodiments provide compositions and methods for preventing, treating, delaying, slowing the progression and/or ameliorating apo(a) related diseases, disorders, and conditions in a subject in need thereof. Certain embodiments provide compositions and methods for preventing, treating, delaying, slowing the progression and/or ameliorating Lp(a) related diseases, disorders, and conditions in a subject in need thereof. In certain embodiments, such diseases, disorders, and conditions include cardiovascular and/or metabolic diseases, disorders, and conditions. Certain such cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease, peripheral artery occlusive disease), retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, coronary artey disease (CAD), Alzheimer's Disease and thromboembolic diseases, disorder or conditions Certain thromboembolic diseases, disorders or conditions include, but are not limited to, stroke, thrombosis (e.g., venous thromboembolism), myocardial infarction and peripheral vascular disease.

Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever.

In certain embodiments, the modulation of apo(a) or Lp(a) expression occurs in a cell, tissue or organ. In certain embodiments, the modulations occur in a cell, tissue or organ in an animal. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

In certain embodiments, the subject or animal is human.

In certain embodiments, the compound is parenterally administered. In further embodiments, the parenteral administration is subcutaneous.

In certain embodiments, the compound is co-administered with a second agent or therapy. In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). The therapy can be, but is not limited to, Lp(a) apheresis. Agents or therapies can be co-administered or administered concomitantly. Agents or therapies can be sequentially or subsequently administered.

Certain embodiments provide use of a compound targeted to apo(a) for decreasing apo(a) levels in an animal. Certain embodiments provide use of a compound targeted to apo(a) for decreasing Lp(a) levels in an animal. Certain embodiments provide use of a compounds targeted to apo(a) for the treatment, prevention, or amelioration of a disease, disorder, or condition associated with apo(a). Certain embodiments provide use of a compounds targeted to apo(a) for the treatment, prevention, or amelioration of a disease, disorder, or condition associated with Lp(a).

Certain embodiments provide use of a compound targeted to apo(a) in the preparation of a medicament for decreasing apo(a) levels in an animal. Certain embodiments provide use of a compound targeted to apo(a) in the preparation of a medicament for decreasing Lp(a) levels in an animal. Certain embodiments provide use of a compound for the preparation of a medicament for the treatment, prevention, or amelioration of a disease, disorder, or condition associated with apo(a). Certain embodiments provide use of a compound for the preparation of a medicament for the treatment, prevention, or amelioration of a disease, disorder, or condition associated with Lp(a).

Certain embodiments provide a kit for treating, preventing, or ameliorating a disease, disorder or condition as described herein wherein the kit comprises: (i) an apo(a) specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

Antisense Compounds

Oligomeric compounds include, but are not limited to, oligonucleotides, oligonucleosides, oligonucleotide analogs, oligonucleotide mimetics, antisense compounds, antisense oligonucleotides, ribozymes, microRNAs and siRNAs. An oligomeric compound may be “antisense” to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an apo(a) nucleic acid is 12 to 30 subunits in length. In other words, such antisense compounds are from 12 to 30 linked subunits. In other embodiments, the antisense compound is 8 to 80, 10 to 80, 12 to 50, 15 to 30, 18 to 24, 19 to 22, 13 to 25, 14 to 25 or 15 to 25 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain such embodiments, the antisense compounds are 8 linked subunits in length. In some embodiments the antisense compound is an antisense oligonucleotide. In some embodiments, the linked subunits are nucleosides.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the central portion, 5' or 3' end of the oligonucleotide. When two or more additional nucleosides are present, the added nucleosides can be adjacent to each other, for example, in an oligonucleotide having two nucleosides added to the central portion, to the 5' end (5' addition), or alternatively to the 3' end (3' addition), of the oligonucleotide. Alternatively, the added nucleosides can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an apo(a) nucleic acid have chemically modified subunits arranged in patterns, or motifs, to confer to the antisense compounds properties, such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of a RNA: DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH2)_n$—O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-12-2, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an apo(a) nucleic acid possess a 5-10-5 gapmer motif.

In certain embodiments, an antisense compound targeted to an apo(a) nucleic acid has a gap-widened motif.

Target Nucleic Acids, Target Regions and Nucleotide Sequences

Nucleotide sequences that encode the apo(a) target sequence include, without limitation, the following: GENBANK Accession No. NM_005577.2, incorporated herein as SEQ ID NO: 1; GENBANK Accession No. NT_007422.12 truncated from nucleotides 3230000 to 3380000, incorporated herein as SEQ ID NO: 2; GENBANK Accession No. NT_025741.15 truncated from nucleotides 65120000 to 65/258,000, designated herein as SEQ ID NO: 3; and GENBANK Accession No. NM_005577.1, incorporated herein as SEQ ID NO: 4.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage or a nucleobase. Antisense compounds described by Isis Number (Isis No.) indicate a combination of nucleobase sequence and motif.

In certain embodiments, a "target region" is a structurally defined region of the target nucleic acid. For example, a target region can encompass a 3' UTR, a 5' UTR, an exon, an intron, an exon/intron junction, a coding region, a translation initiation region, a translation termination region, or other defined nucleic acid region. The structurally defined regions for apo(a) can be obtained by accession number from sequence databases such as NCBI and such information is incorporated herein by reference. In certain embodiments, a target region can encompass the sequence from a 5' target site of one target segment within the target region to a 3' target site of another target segment within the same target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region, such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in apo(a) mRNA levels can be indicative of inhibition of apo(a) expression. Reductions in levels of an apo(a) protein can be indicative of inhibition of target mRNA expression. Further, phenotypic changes can be indicative of inhibition of apo(a) expression. For example, an increase in HDL levels, decrease in LDL levels, decrease in cholesterol levels or decrease in triglyceride levels, are among phenotypic changes that can be assessed for inhibition of apo(a) expression. Other phenotypic indications, e.g., symptoms associated with a cardiovascular disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an apo(a) nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, $3^{rd}$ Ed., 2001). In certain embodiments, the antisense compounds provided herein are specifically hybridizable with an apo(a) nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an apo(a) nucleic acid).

Noncomplementary nucleobases between an antisense compound and an apo(a) nucleic acid can be tolerated provided that the antisense compound remains able to specifically hybridize to a target nucleic acid. Moreover, an antisense compound can hybridize over one or more segments of an apo(a) nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an apo(a) nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an apo(a) nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an apo(a) nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an apo(a) nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an apo(a) nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_l)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, “bicyclic nucleosides” refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—$C(H)(CH_3)$-2' (see Chattopadhyaya et al., *J. Org. Chem.,* 2009, 74, 118-134); and 4'-$CH_2$—C—(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=O)—, —C(=$NR_a$)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'—$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

(A)

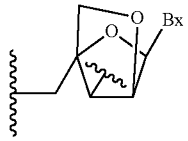

(B)

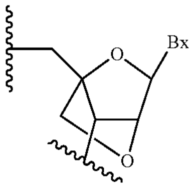

(C)

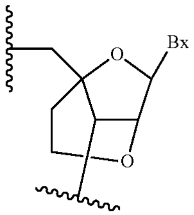

(D)

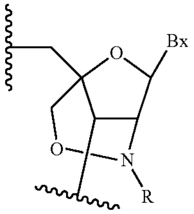

(E)

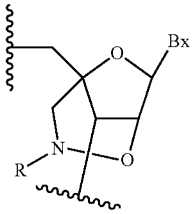

-continued (F)

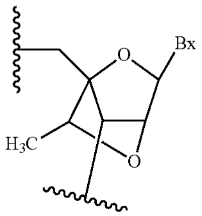

(G)

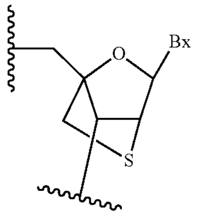

(H)

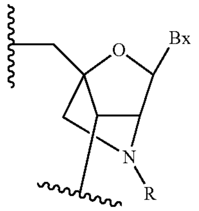

(I)

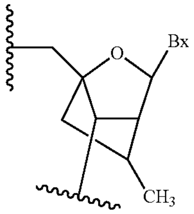

(J)

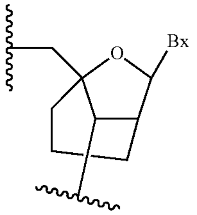

wherein Bx is the base moiety and R is independently H, a protecting group or $C_1$-$C_{12}$ alkyl.

In certain embodiments, bicyclic nucleosides are provided having Formula I:

I

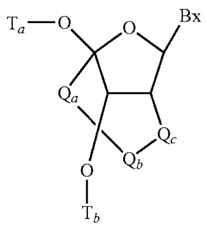

wherein:

Bx is a heterocyclic base moiety;

$-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

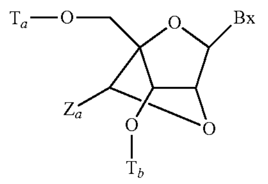

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

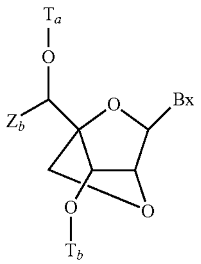

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl ($C(=O)-$).

In certain embodiments, bicyclic nucleosides are provided having Formula IV:

IV

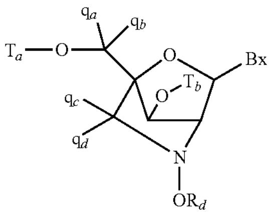

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

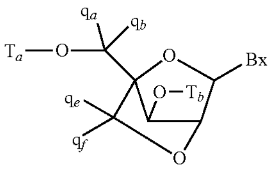

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

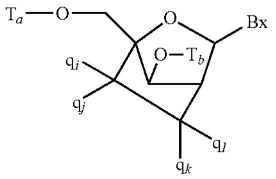

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), fluoro HNA (F-HNA) or those compounds having Formula VII:

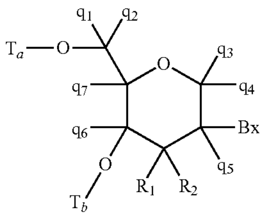

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H. In certain embodiments, $R_1$ is H and $R_2$ is fluoro; $R_1$ is H and $R_2$ is methoxy, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'—CH($CH_3$)—O-2') modified nucleosides are arranged throughout the wings of a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an apo(a) nucleic acid comprise one or more modified nucleobases. In certain embodiments, gap-widened antisense oligonucleotides targeted to an apo(a) nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an apo(a) nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an apo(a) nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602, published on Jan. 16, 2003.

Cell Culture and Antisense Compounds Treatment

The effects of antisense compounds on the level, activity or expression of apo(a) nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g., Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 μL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 μL of FuGENE 6 per 100 nM.

Another technique used to introduce antisense oligonucleotides into cultured cells includes electroporation (Sambrooke and Russell in *Molecular Cloning. A Laboratory*

*Manual*. Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrooke and Russell in *Molecular Cloning. A Laboratory Manual*. Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrooke and Russell in *Molecular Cloning. A Laboratory Manual*. Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000® (Invitrogen, Carlsbad, Calif.), Lipofectin® (Invitrogen, Carlsbad, Calif.) or Cytofectin® (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrooke and Russell in *Molecular Cloning. A Laboratory Manual*. Third Edition. Cold Spring Harbor Laboratory Press, Cold Spring Harbor, N.Y. 2001). For example, RNA can be prepared using TRIZOL® (Invitrogen, Carlsbad, Calif.) according to the manufacturer's recommended protocols.

Analysis of Inhibition of Target Levels or Expression

Inhibition of levels or expression of an apo(a) nucleic acid can be assayed in a variety of ways known in the art (Sambrooke and Russell in *Molecular Cloning. A Laboratory Manual*. Third Edition. Cold Spring Harbor Laboratory Press, Cold Spring Harbor, N.Y., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems (Foster City, Calif.) and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A or GAPDH, or by quantifying total RNA using RIBOGREEN® (Invitrogen, Inc. Carlsbad, Calif.). Cyclophilin A or GAPDH expression can be quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers can be designed to hybridize to an apo(a) nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of apo(a) nucleic acids can be assessed by measuring apo(a) protein levels. Protein levels of apo(a) can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of apo(a) are commercially available.

In Vivo Testing of Antisense Compounds

Antisense compounds, for example, antisense oligonucleotides, are tested in animals to assess their ability to inhibit expression of apo(a) and produce phenotypic changes. Testing can be performed in normal animals, or in experimental disease models. For administration to animals, antisense oligonucleotides are formulated in a pharmaceutically acceptable diluent, such as saline or phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in apo(a) nucleic acid expression are measured. Changes in apo(a) protein levels are also measured.

Certain Indications

In certain embodiments, provided herein are methods of treating an individual comprising administering one or more pharmaceutical compositions as described herein. In certain embodiments, the individual has an apo(a) related disease. In certain embodiments, the individual has an Lp(a) related disease. In certain embodiments, the individual has an inflammatory, cardiovascular and/or a metabolic disease, disorder or condition.

In certain embodiments, the cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, the compounds targeted to apo(a) described herein modulate physiological markers or phenotypes of the cardiovascular disease, disorder or condition. For example, administration of the compounds to animals can decrease LDL and cholesterol levels in those animals compared to untreated animals. In certain embodiments, the modulation of the physiological markers or phenotypes can be associated with inhibition of apo(a) by the compounds.

In certain embodiments, the physiological markers of the cardiovascular disease, disorder or condition can be quantifiable. For example, LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of a compound targeted to an apo(a) nucleic acid to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, compounds targeted to apo(a) as described herein modulate physiological markers or phenotypes of the metabolic disease, disorder or condition. For example, administration of the compounds to animals can decrease glucose and insulin resistance levels in those animals compared to untreated animals. In certain embodiments, the modulation of the physiological markers or phenotypes can be associated with inhibition of apo(a) by the compounds.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of a compound targeted to an apo(a) nucleic acid to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, coronary artey disease (CAD), Alzheimer's Disease and thromboembolic diseases, disorder or conditions. Certain thromboembolic diseases, disorders or conditions include, but are not limited to, stroke, thrombosis, myocardial infarction and peripheral vascular disease.

In certain embodiments, the compounds targeted to apo(a) described herein modulate physiological markers or phenotypes of the inflammatory disease, disorder or condition. For example, administration of the compounds to animals can decrease inflammatory cytokine or other inflammatory markers levels in those animals compared to untreated animals. In certain embodiments, the modulation of the physiological markers or phenotypes can be associated with inhibition of apo(a) by the compounds.

In certain embodiments, the physiological markers of the inflammatory disease, disorder or condition can be quantifiable. For example, cytokine levels can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of a compound targeted to an apo(a) nucleic acid to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of an antisense compound targeted to an apo(a) nucleic acid is accompanied by monitoring of apo(a) or Lp(a) levels. In certain embodiments, administration of a therapeutically effective amount of an antisense compound targeted to an apo(a) nucleic acid is accompanied by monitoring of markers of inflammatory, cardiovascular and/or metabolic disease, or other disease process associated with the expression of apo(a), to determine an individual's response to the antisense compound. An individual's response to administration of the antisense compound targeting apo(a) can be used by a physician to determine the amount and duration of therapeutic intervention with the compound.

In certain embodiments, administration of an antisense compound targeted to an apo(a) nucleic acid results in reduction of apo(a) expression by at least about 15, 20, 25, 30, 35, 40, 45, 50, 55, 60, 65, 70, 75, 80, 85, 90, 95 or 99%, or a range defined by any two of these values. In certain embodiments, apo(a) expression is reduced to ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of an antisense compound targeted to an apo(a) nucleic acid results in reduction of Lp(a) expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to apo(a) are used for the preparation of a medicament for treating a patient suffering or susceptible to an inflammatory, cardiovascular and/or a metabolic disease, disorder or condition.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of apo(a) or the prevention, reduction, amelioration or slowing the progression of a disease or condition associated with apo(a).

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 μg to 100 mg per kg of body weight, or within a range of 0.001 mg-1000 mg dosing, and may be given once or more daily, weekly, monthly or yearly, or even once every 2 to 20 years. Following successful treatment, it can be desirable to have the patient undergo maintenance therapy to prevent the recurrence of the disease state, wherein the oligonucleotide is administered in maintenance doses, ranging from 0.01 μg to 100 mg per kg of body weight or ranging from 0.001 mg to 1000 mg dosing, once or more daily, weekly, monthly, yearly to once every 2 to 20 years.

Certain Combination Therapies

In certain embodiments, a first agent comprising the compound described herein is co-administered with one or more secondary agents or therapy. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, an apo(a) lowering agent, a Lp(a) lowering agent, an agent for treating Azheimer's Disease, an agent to reduce thromboembolism formation, a cholesterol lowering agent, a non-HDL lipid lowering (e.g., LDL) agent, a HDL raising agent, fish oil, niacin, nicotinic acid, a fibrate, a statin, DCCR (salt of diazoxide), a glucose-lowering agent, an anti-inflammatory agent and/or an anti-diabetic agent. In certain embodiments, the first agent is administered in combination with the maximally tolerated dose of the second agent. In certain embodiments, the first agent is administered to a subject that fails to respond to a maximally tolerated dose of the second agent.

Examples of apo(a) lowering agents include an apo(a) antisense oligonucleotide different from the first agent, niacin, nicotinic acid, or an apoB antisense oligonucleotide (i.e. Mipomersen). An example of an apo(a) lowering therapy is Lp(a) apheresis.

Examples of glucose-lowering and/or anti-diabetic agents include, but are not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

Examples of cholesterol or lipid lowering therapy include, but are not limited to, a therapeutic lifestyle change, statins, bile acids sequestrants, niacin, nicotinic acid, CETP inhibitors and peroxisome proliferation activated receptor agonists such as fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The CETP inhibitor can be a CETP antisense oligonucleotide or Torcetrapib.

Certain Treatment Populations

Certain subjects with high Lp(a) levels are at a significant risk of various diseases (Lippi et al., Clinica Chimica Acta, 2011, 412:797-801; Solfrizz et al.). In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human animal with elevated apo(a) levels and/or Lp(a) levels. In certain embodiments, the human has elevated apo(a) levels ≥30 mg/dL, ≥40 mg/dL, ≥50 mg/dL, ≥60 mg/dL, ≥70 mg/dL, ≥80 mg/dL, ≥90 mg/dL or ≥100 mg/dL.

Certain Compounds

Selected gapmer antisense oligonucleotides from PCT application WO2005/000201 (incorporated by reference in its entirety herein) were assessed (Example 1) and the most potent compound, ISIS 144367, was used as a benchmark comparison for the newly designed antisense oligonucleotides described herein.

About 90 of the newly designed antisense oligonucleotides were found to be more potent than the benchmark, ISIS 144367, as assessed by single dose in vitro studies (Examples 2-3, 5). Of the about 90 antisense oligonucleotides, about 83 were selected for in vitro multi-dose response studies and 64 antisense oligonucleotides were found to be more potent than the benchmark (Examples 4, 6).

About 32 antisense oligonucleotides were further selected for in vivo studies in human apo(a) transgenic mice (Example 7). Multiple antisense oligonucleotides were identified that were more potent than the benchmark in vivo.

About 24 antisense oligonucleotides were further selected for viscosity testing in vitro (Example 13). Antisense oligonucleotides that were viscous were not carried forward in further studies.

About 14 antisense oligonucleotides were further selected for in vivo studies in rodent tolerability and pharmacokinetics (Examples 8-10). The studies indicated that ISIS 494372 was the best tolerated antisense oligonucleotide.

ISIS 494283, 494284, 494286, 494301, 494302 and 494372 were tested in cynomolgus monkeys (Examples 11-12). The studies indicated that ISIS 494372 was well tolerated and potent in monkeys.

EXAMPLES

Non-limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Dose-dependent Antisense Inhibition of Human Apolipoprotein (a) (Apo(a)) in Human Primary Hepatocytes Selected gapmer antisense oligonucleotides from a previous publication (WO2005/000201, the content of which is incorporated by reference in its entirety herein) were tested in a single dose assay in human primary hepatocytes. Cells were obtained from Tissue Transformation Technologies (BD Biosciences, Franklin Lakes, N.J.) and treated with 150 nM of antisense oligonucleotide. After a treatment period of approximately 16 hours, RNA was isolated from the cells and apo(a) mRNA levels were measured by quantitative real-time PCR. Human apo(a) primer probe set hAPO(a)3' (forward sequence ACAGCAATCAAACGAAGACACTG, designated herein as SEQ ID NO: 5; reverse sequence AGCTTATACACAAAAATACCAAAAATGC, designated herein as SEQ ID NO: 6; probe sequence TCCCAGCTACCAGCTATGCCAAACCTT, designated herein as SEQ ID NO: 7) was used to measure mRNA levels. Additionally, mRNA levels were also measured using human apo(a) primer probe set hAPO(a)12kB (forward sequence CCACAGTGGCCCCGGT, designated herein as SEQ ID NO: 8; reverse sequence ACAGGGCTTTTCTCAGGTGGT, designated herein as SEQ ID NO: 9; probe sequence CCAAGCACAGAGGCTCCTTCTGAACAAG, designated herein as SEQ ID NO: 10). Apo(a) mRNA levels were normalized to GAPDH mRNA expression. Results are presented in Table 1 as percent inhibition of apo(a), relative to untreated control cells.

TABLE 1

Antisense inhibition of human apo(a) in human primary hepatocytes

| ISIS No | % inhibition (hAPO(a)3' PPset) | % inhibition (hAPO(a)12kB PPset) |
|---|---|---|
| 144367 | 68 | 77 |
| 144368 | 42 | 59 |
| 144369 | 43 | 69 |
| 144370 | 80 | 75 |
| 144371 | 42 | 57 |
| 144372 | 87 | 54 |
| 144373 | 63 | 49 |
| 144374 | 45 | 80 |
| 144375 | 33 | 11 |
| 144376 | 62 | 82 |
| 144377 | 42 | 72 |
| 144378 | 0 | 72 |
| 144379 | 73 | 46 |
| 144380 | 75 | 78 |
| 144381 | 63 | 64 |
| 144382 | 0 | 58 |
| 144383 | 63 | 79 |
| 144384 | 38 | 0 |
| 144385 | 40 | 94 |
| 144386 | 47 | 61 |

TABLE 1-continued

| Antisense inhibition of human apo(a) in human primary hepatocytes | | |
|---|---|---|
| ISIS No | % inhibition (hAPO(a)3' PPset) | % inhibition (hAPO(a)12kB PPset) |
| 144387 | 38 | 60 |
| 144388 | 0 | 57 |
| 144389 | 52 | 39 |
| 144390 | 12 | 0 |
| 144391 | 73 | 57 |
| 144392 | 43 | 50 |
| 144393 | 83 | 82 |
| 144394 | 40 | 76 |
| 144395 | 80 | 84 |
| 144396 | 53 | 72 |
| 144397 | 23 | 64 |
| 144398 | 7 | 33 |
| 144399 | 43 | 44 |
| 144400 | 70 | 75 |
| 144401 | 87 | 72 |

Several antisense oligonucleotides were selected for further testing in a dose response assay.

The selected antisense oligonucleotides were tested in human primary hepatocytes with 25 nM, 50 nM, 150 nM, or 300 nM concentrations of antisense oligonucleotide, as specified in Table 2 below. After a treatment period of approximately 16 hours, RNA was isolated from the cells and apo(a) mRNA levels were measured by quantitative real-time PCR. Human apo(a) primer probe set hAPO(a)3' was used to measure mRNA levels. Apo(a) mRNA levels were normalized to GAPDH mRNA expression. Results are presented as percent inhibition of apo(a), relative to untreated control cells.

TABLE 2

| Dose-dependent antisense inhibition of human apo(a) in human primary hepatocytes, as measured with hAPO(a)3' | | | | |
|---|---|---|---|---|
| ISIS No | 25 nM | 50 nM | 150 nM | 300 nM |
| 144367 | 52 | 78 | 76 | 74 |
| 144370 | 64 | 74 | 68 | 66 |
| 144385 | 0 | 15 | 43 | 5 |
| 144393 | 0 | 9 | 39 | 25 |
| 144395 | 17 | 9 | 8 | 32 |

ISIS 144367 demonstrated better efficacy and dose-dependency than the other antisense oligonucleotides. Hence, ISIS 144367 was considered the benchmark antisense oligonucleotide to compare the potency of newly designed antisense oligonucleotides disclosed herein.

Example 2: Antisense Inhibition of Human Apo(a) in Transgenic Mouse Primary Hepatocytes Antisense oligonucleotides were newly designed targeting an apo(a) nucleic acid and were tested for their effects on apo(a) mRNA in vitro. The antisense oligonucleotides were tested for potency in a series of parallel experiments that had similar culture conditions. Primary hepatocytes from human apo(a) transgenic mice (Frazer, K. A. et al., Nat. Genet. 1995. 9: 424-431) were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12kB was used to measure mRNA levels. Apo(a) mRNA levels were adjusted according to total RNA content, as measured by RIBOGREEN®. The results for each experiment are presented in separate tables shown below. ISIS 144367 from was used as a benchmark for the new antisense oligonucleotides and also included in the studies. Results are presented as percent inhibition of apo(a), relative to untreated control cells. A total of 1,511 gapmers were tested under these culture conditions. Only those antisense oligonucleotides that were selected for further study are presented in the table below with each table representing a separate experiment.

The newly designed chimeric antisense oligonucleotides were designed as 5-10-5 MOE gapmers. The gapmers are 20 nucleosides in length, wherein the central gap segment comprises often 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to one or more regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 3

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 494157 | 238 | 257 | CCTGTGACAGTGGTGGAGTA | 95 | 21199 | 21218 | 12 |
| | 580 | 599 | | | 26690 | 26709 | |
| | 922 | 941 | | | 32237 | 32256 | |
| | 1606 | 1625 | | | 43330 | 43349 | |

TABLE 3-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1948 | 1967 | | | 48874 | 48893 | |
| | 2290 | 2309 | | | 54420 | 54439 | |
| | 3316 | 3335 | | | 72037 | 72056 | |
| 494158 | 239 | 258 | TCCTGTGACAGTGGTGGAGT | 95 | 21200 | 21219 | 13 |
| | 581 | 600 | | | 26691 | 26710 | |
| | 923 | 942 | | | 32238 | 32257 | |
| | 1607 | 1626 | | | 43331 | 43350 | |
| | 1949 | 1968 | | | 48875 | 48894 | |
| | 2291 | 2310 | | | 54421 | 54440 | |
| | 3317 | 3336 | | | 72038 | 72057 | |
| 494159 | 241 | 260 | CTTCCTGTGACAGTGGTGGA | 97 | 21202 | 21221 | 14 |
| | 583 | 602 | | | 26693 | 26712 | |
| | 925 | 944 | | | 32240 | 32259 | |
| | 1609 | 1628 | | | 43333 | 43352 | |
| | 1951 | 1970 | | | 48877 | 48896 | |
| | 2293 | 2312 | | | 54423 | 54442 | |
| | 3319 | 3338 | | | 72040 | 72059 | |
| | 4663 | 4682 | | | 94404 | 94423 | |
| | 5005 | 5024 | | | 115515 | 115534 | |
| 494160 | 242 | 261 | CCTTCCTGTGACAGTGGTGG | 97 | 21203 | 21222 | 15 |
| | 4664 | 4683 | | | 94405 | 94424 | |
| | 5006 | 5025 | | | 115516 | 115535 | |
| 494161 | 243 | 262 | TCCTTCCTGTGACAGTGGTG | 96 | 21204 | 21223 | 16 |
| | 4665 | 4684 | | | 94406 | 94425 | |
| | 5007 | 5026 | | | 115517 | 115536 | |
| 494162 | 244 | 263 | GTCCTTCCTGTGACAGTGGT | 95 | 21205 | 21224 | 17 |
| | 3664 | 3683 | | | 77585 | 77640 | |
| | 4666 | 4685 | | | 94407 | 94426 | |
| | 5008 | 5027 | | | 115518 | 115537 | |
| 494163 | 245 | 264 | GGTCCTTCCTGTGACAGTGG | 96 | 21206 | 21225 | 18 |
| | 4667 | 4686 | | | 94408 | 94427 | |
| 494164 | 246 | 265 | AGGTCCTTCCTGTGACAGTG | 93 | 21207 | 21226 | 19 |
| | 4668 | 4687 | | | 94409 | 94428 | |
| 494165 | 247 | 266 | CAGGTCCTTCCTGTGACAGT | 91 | 21208 | 21227 | 20 |
| | 4669 | 4688 | | | 94410 | 94429 | |
| 494166 | 248 | 267 | GCAGGTCCTTCCTGTGACAG | 89 | 21208 | 21228 | 21 |
| 494167 | 250 | 269 | TGGCAGGTCCTTCCTGTGAC | 92 | 21211 | 21230 | 22 |
| 494168 | 251 | 270 | TTGGCAGGTCCTTCCTGTGA | 89 | 21212 | 21231 | 23 |
| 494169 | 252 | 271 | CTTGGCAGGTCCTTCCTGTG | 92 | 21213 | 21232 | 24 |
| 494170 | 253 | 272 | GCTTGGCAGGTCCTTCCTGT | 88 | 21214 | 21233 | 25 |

TABLE 4

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91<br>84 | 21210 | 21229 | 11 |
| 494283 | 584 | 603 | TCTTCCTGTGACAGTGGTGG | 93 | 26694 | 26713 | 26 |
| | 926 | 945 | | | 32241 | 32260 | |
| | 1610 | 1629 | | | 43334 | 43353 | |
| | 1952 | 1971 | | | 48878 | 48897 | |
| | 2294 | 2313 | | | 54424 | 54443 | |
| | 3320 | 3339 | | | 72041 | 72060 | |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494284 | 585 | 604 | TTCTTCCTGTGACAGTGGTG | 95 | 26695 | 26714 | 27 |
| | 927 | 946 | | | 32242 | 32261 | |
| | 1611 | 1630 | | | 43335 | 43354 | |
| | 1953 | 1972 | | | 48879 | 48898 | |
| | 2295 | 2314 | | | 54425 | 54444 | |
| | 3321 | 3340 | | | 72042 | 72061 | |
| 494285 | 586 | 605 | GTTCTTCCTGTGACAGTGGT | 95 | 26696 | 26715 | 28 |
| | 928 | 947 | | | 32243 | 32262 | |
| | 1612 | 1631 | | | 43336 | 43355 | |
| | 1954 | 1973 | | | 48880 | 48899 | |
| | 2296 | 2315 | | | 54426 | 54445 | |
| | 3322 | 3341 | | | 72043 | 72062 | |
| 494286 | 587 | 606 | GGTTCTTCCTGTGACAGTGG | 95 | 26697 | 26716 | 29 |
| | 929 | 948 | | | 32244 | 32263 | |
| | 1613 | 1632 | | | 43337 | 43356 | |
| | 1955 | 1974 | | | 48881 | 48900 | |
| | 2297 | 2316 | | | 54427 | 54446 | |
| 494287 | 588 | 607 | AGGTTCTTCCTGTGACAGTG | 95 | 26698 | 26717 | 30 |
| | 930 | 949 | | | 32245 | 32264 | |
| | 1614 | 1633 | | | 43338 | 43357 | |
| | 1956 | 1975 | | | 48882 | 48901 | |
| | 2298 | 2317 | | | 54428 | 54447 | |
| 494288 | 589 | 608 | CAGGTTCTTCCTGTGACAGT | 91 | 26699 | 26718 | 31 |
| | 931 | 950 | | | 32246 | 32265 | |
| | 1615 | 1634 | | | 43339 | 43358 | |
| | 1957 | 1976 | | | 48883 | 48902 | |
| | 2299 | 2318 | | | 54429 | 54448 | |
| | 2983 | 3002 | | | 66500 | 66519 | |
| 494290 | 592 | 611 | TGGCAGGTTCTTCCTGTGAC | 90 | 26702 | 26721 | 32 |
| | 934 | 953 | | | 32249 | 32268 | |
| | 1618 | 1637 | | | 43342 | 43361 | |
| | 1960 | 1979 | | | 48886 | 48905 | |
| | 2302 | 2321 | | | 54432 | 54451 | |
| | 2986 | 3005 | | | 66503 | 66522 | |
| 494291 | 593 | 612 | TTGGCAGGTTCTTCCTGTGA | 89 | 26703 | 26722 | 33 |
| | 935 | 954 | | | 32250 | 32269 | |
| | 1619 | 1638 | | | 43343 | 43362 | |
| | 1961 | 1980 | | | 48887 | 48906 | |
| | 2303 | 2322 | | | 54433 | 54452 | |
| | 2987 | 3006 | | | 66504 | 66523 | |
| 494292 | 594 | 613 | CTTGGCAGGTTCTTCCTGTG | 94 | 26704 | 23723 | 35 |
| | 936 | 955 | | | 32251 | 32270 | |
| | 1620 | 1639 | | | 43344 | 43363 | |
| | 1962 | 1981 | | | 48888 | 48907 | |
| | 2304 | 2323 | | | 54434 | 54453 | |
| | 2988 | 3007 | | | 66505 | 66524 | |
| 494294 | 596 | 615 | AGCTTGGCAGGTTCTTCCTG | 90 | 26707 | 26725 | 36 |
| | 938 | 957 | | | 32253 | 32272 | |
| | 1622 | 1641 | | | 43346 | 43365 | |
| | 1964 | 1983 | | | 48890 | 48909 | |
| | 2306 | 2325 | | | 54436 | 54455 | |
| | 2990 | 3009 | | | 66507 | 66526 | |
| 494299 | 626 | 645 | ACTATGCGAGTGTGGTGTCA | 91 | 26736 | 26755 | 37 |
| | 968 | 987 | | | 32283 | 32302 | |
| | 1310 | 1329 | | | 37830 | 37849 | |
| | 1652 | 1671 | | | 43376 | 43395 | |
| | 1994 | 2013 | | | 48920 | 48939 | |
| | 2336 | 2355 | | | 54466 | 54485 | |
| | 2678 | 2697 | | | 60021 | 60040 | |
| | 3020 | 3039 | | | 66537 | 66556 | |
| 494300 | 627 | 646 | GACTATGCGAGTGTGGTGTC | 93 | 26737 | 26756 | 38 |
| | 969 | 988 | | | 32284 | 32303 | |
| | 1311 | 1330 | | | 37831 | 27850 | |
| | 1653 | 1672 | | | 43377 | 43396 | |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1995 | 2014 | | | 48920 | 48940 | |
| | 2337 | 2356 | | | 54467 | 54486 | |
| | 2679 | 2698 | | | 60022 | 60041 | |
| | 3021 | 3040 | | | 66538 | 66557 | |
| 494301 | 628 | 647 | CGACTATGCGAGTGTGGTGT | 93 | 26738 | 26757 | 39 |
| | 970 | 989 | | | 32285 | 32304 | |
| | 1312 | 1331 | | | 37832 | 37851 | |
| | 1654 | 1673 | | | 43378 | 43397 | |
| | 1996 | 2015 | | | 48922 | 48941 | |
| | 2338 | 2357 | | | 54468 | 54487 | |
| | 2680 | 2699 | | | 60023 | 60042 | |
| | 3022 | 3041 | | | 66539 | 66558 | |
| 494302 | 629 | 648 | CCGACTATGCGAGTGTGGTG | 94 | 26739 | 26758 | 40 |
| | 971 | 990 | | | 32286 | 32305 | |
| | 1313 | 1332 | | | 37833 | 37852 | |
| | 1655 | 1674 | | | 43379 | 43398 | |
| | 1997 | 2016 | | | 48923 | 48942 | |
| | 2339 | 2358 | | | 54469 | 54488 | |
| | 2681 | 2700 | | | 60024 | 60043 | |
| | 3023 | 3042 | | | 66540 | 66559 | |
| 494303 | 630 | 649 | TCCGACTATGCGAGTGTGGT | 93 | 26740 | 26759 | 41 |
| | 972 | 991 | | | 32287 | 32306 | |
| | 1314 | 1333 | | | 37834 | 37853 | |
| | 1656 | 1675 | | | 43380 | 43399 | |
| | 1998 | 2017 | | | 48924 | 48943 | |
| | 2340 | 2359 | | | 54470 | 54489 | |
| | 2682 | 2701 | | | 60025 | 60044 | |
| | 3024 | 3043 | | | 66541 | 66560 | |
| 494304 | 631 | 650 | GTCCGACTATGCGAGTGTGG | 94 | 26741 | 26760 | 42 |
| | 973 | 992 | | | 32288 | 23207 | |
| | 1315 | 1334 | | | 37835 | 37854 | |
| | 1657 | 1676 | | | 43381 | 43400 | |
| | 1999 | 2017 | | | 48925 | 48944 | |
| | 2341 | 2360 | | | 54471 | 54490 | |
| | 2683 | 2702 | | | 60026 | 60045 | |
| | 3025 | 3044 | | | 66542 | 66561 | |
| 494305 | 632 | 651 | GGTCCGACTATGCGAGTGTG | 93 | 26742 | 26761 | 43 |
| | 974 | 993 | | | 32289 | 32308 | |
| | 1316 | 1335 | | | 37836 | 37855 | |
| | 1658 | 1677 | | | 43382 | 43401 | |
| | 2000 | 2019 | | | 48926 | 48945 | |
| | 2342 | 2361 | | | 54472 | 54491 | |
| | 2684 | 2703 | | | 60027 | 60046 | |
| | 3026 | 3045 | | | 66543 | 66562 | |
| 494306 | 633 | 652 | GGGTCCGACTATGCGAGTGT | 92 | 26743 | 26762 | 44 |
| | 975 | 994 | | | 32290 | 23209 | |
| | 1317 | 1336 | | | 37837 | 37856 | |
| | 1659 | 1678 | | | 43383 | 43402 | |
| | 2001 | 2020 | | | 48927 | 48946 | |
| | 2343 | 2362 | | | 54473 | 54492 | |
| | 2685 | 2704 | | | 60028 | 60047 | |
| | 3027 | 3046 | | | 66544 | 66563 | |
| 494307 | 1190 | 1209 | CTGCTCAGTCGGTGCTTGTT | 91 | n/a | n/a | 45 |
| | 2558 | 2577 | | | | | |
| 494310 | 1193 | 1212 | CCTCTGCTCAGTCGGTGCTT | 90 | n/a | n/a | 46 |
| | 2561 | 2580 | | | | | |
| 494311 | 1194 | 1213 | GCCTCTGCTCAGTCGGTGCT | 88 | 37714 | 37733 | 47 |
| | 2562 | 2581 | | | 59905 | 59924 | |
| 494334 | 1267 | 1286 | CTTCCAGTGACAGTGGTGGA | 90 | 37787 | 37806 | 48 |
| | 2635 | 2654 | | | 59978 | 59997 | |
| 494336 | 1269 | 1288 | TTCTTCCAGTGACAGTGGTG | 90 | 37789 | 37808 | 49 |
| | 2637 | 2656 | | | 59980 | 59999 | |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494337 | 1270<br>2638 | 1289<br>2657 | GTTCTTCCAGTGACAGTGGT | 95 | 37790<br>59981 | 37809<br>60000 | 50 |
| 494338 | 1271<br>2639 | 1290<br>2658 | GGTTCTTCCAGTGACAGTGG | 91 | 37791<br>59982 | 37810<br>60001 | 133 |
| 494521 | 6393 | 6412 | GACCTTAAAAGCTTATACAC | 82 | 140049 | 140068 | 51 |
| 494525 | 6397 | 6416 | GTCAGACCTTAAAAGCTTAT | 84 | 140053 | 140072 | 52 |
| 494530 | 6402 | 6421 | TGTCAGTCAGACCTTAAAAG | 82 | 140058 | 140077 | 53 |
| 494535 | 6407 | 6426 | GAATTTGTCAGTCAGACCTT | 85 | 140063 | 140082 | 54 |
| 494536 | 6408 | 6427 | AGAATTTGTCAGTCAGACCT | 83 | 140064 | 140083 | 55 |
| 494544 | 6417 | 6436 | CCTTAATACAGAATTTGTCA | 82 | 140073 | 140092 | 56 |

TABLE 5

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 84 | 21210 | 21229 | 11 |
| 494371 | 3900 | 3919 | GCTCCGTTGGTGCTTGTTCA | 93 | n/a | n/a | 57 |
| 494372 | 3901 | 3920 | TGCTCCGTTGGTGCTTGTTC | 93 | n/a | n/a | 58 |
| 494373 | 3902 | 3921 | TTGCTCCGTTGGTGCTTGTT | 83 | n/a | n/a | 59 |
| 494374 | 3903 | 3922 | TTTGCTCCGTTGGTGCTTGT | 89 | n/a | n/a | 60 |
| 494375 | 3904 | 3923 | CTTTGCTCCGTTGGTGCTTG | 85 | n/a | n/a | 61 |
| 494386 | 3977 | 3996 | TCCTGTAACAGTGGTGGAGA | 86 | 81985 | 82004 | 62 |
| 494387 | 3978 | 3997 | TTCCTGTAACAGTGGTGGAG | 82 | 81986 | 82005 | 63 |
| 494388 | 3979 | 3998 | CTTCCTGTAACAGTGGTGGA | 86 | 81987 | 82006 | 64 |
| 494389 | 3980 | 3999 | CCTTCCTGTAACAGTGGTGG | 92 | 81988 | 82007 | 65 |
| 494390 | 3981 | 4000 | TCCTTCCTGTAACAGTGGTG | 92 | 81989 | 82008 | 66 |
| 494391 | 3982 | 4001 | GTCCTTCCTGTAACAGTGGT | 84 | 81990 | 82009 | 67 |
| 494392 | 3983 | 4002 | TGTCCTTCCTGTAACAGTGG | 81 | 81991 | 82010 | 68 |

TABLE 6

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 86 | 21210 | 21229 | 11 |
| 498369 | 3203 | 3222 | TGGAGCCAGAATAACATTCG | 91 | 70667 | 70686 | 69 |
| 498379 | 3213 | 3232 | CCTCTAGGCTTGGAGCCAGA | 85 | 70677 | 70696 | 70 |
| 498408 | 3323 | 3342 | AGTTCTTCCTGTGACAGTGG | 86 | 72044 | 72063 | 71 |

TABLE 6-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 498433 | 3367 | 3386 | GTCCGACTATGCTGGTGTGG | 87 | 72088 | 72107 | 72 |
| 498434 | 3368 | 3387 | GGTCCGACTATGCTGGTGTG | 86 | 72089 | 72108 | 73 |
| 498435 | 3369 | 3388 | GGGTCCGACTATGCTGGTGT | 83 | 72090 | 72109 | 74 |

TABLE 7

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 498229 | 2871 | 2890 | CCTCTAGGCTTGGAATCGGG | 90 | 65117 | 65136 | 75 |
| 498238 | 2883 | 2902 | GTTCAGAAGGAGCCTCTAGG | 93 | 65129 | 65148 | 76 |
| 498239 | 2884 | 2903 | TGTTCAGAAGGAGCCTCTAG | 94 | 65130 | 65149 | 77 |
| 498240 | 2887<br>4573 | 2906<br>4592 | GCTTGTTCAGAAGGAGCCTC | 98 | n/a | n/a | 78 |
| 498241 | 2888<br>4574 | 2907<br>4593 | TGCTTGTTCAGAAGGAGCCT | 94 | n/a | n/a | 79 |
| 498242 | 2889<br>4575 | 2908<br>4594 | GTGCTTGTTCAGAAGGAGCC | 96 | n/a | n/a | 80 |
| 498243 | 2890<br>4576 | 2909<br>4595 | GGTGCTTGTTCAGAAGGAGC | 97 | n/a | n/a | 81 |
| 498244 | 2891<br>4577 | 2910<br>4596 | TGGTGCTTGTTCAGAAGGAG | 92 | n/a | n/a | 82 |
| 498251 | 2898 | 2917 | GCTCAGTTGGTGCTTGTTCA | 90 | n/a | n/a | 83 |
| 498252 | 2899 | 2918 | TGCTCAGTTGGTGCTTGTTC | 90 | n/a | n/a | 84 |

TABLE 8

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498517 | 3548 | 3567 | GCTTGGATCTGGGACCACCG | 89 | 76233 | 76252 | 85 |

TABLE 9

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 94 | 21210 | 21229 | 11 |
| 498833 | 4900 | 4919 | GCCTCCATGCTTGGAACTGG | 94 | 114205 | 114224 | 86 |
| 498859 | 4926 | 4945 | GCTCAGTTGGTGCTGCTTCA | 92 | n/a | n/a | 87 |

TABLE 9-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 498868 | 4978 | 4997 | CCTCGATAACTCTGGCCATT | 94 | 115488 | 115507 | 88 |
| 498875 | 5003 | 5022 | TCCTGTGACAGTGGTGGAGA | 94 | 115513 | 115532 | 89 |

TABLE 10

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 92 | 21210 | 21229 | 11 |
| 499020 | 6257 | 6276 | GTAGGTTGATGCTTCACTCT | 91 | 139913 | 139932 | 90 |
| 499041 | 6318 | 6337 | CGTTTGATTGCTGTCTATTA | 90 | 139974 | 139993 | 91 |

TABLE 11

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498523 | 3554 | 3573 | CTCTGTGCTTGGATCTGGGA | 94 | 76239 | 76258 | 92 |
| 498524 | 3555 | 3574 | CCTCTGTGCTTGGATCTGGG | 96 | 76240 | 76259 | 93 |
| 498525 | 3556 | 3575 | GCCTCTGTGCTTGGATCTGG | 94 | 76241 | 76260 | 94 |
| 498529 | 3560 | 3579 | AGAAGCCTCTGTGCTTGGAT | 89 | 76245 | 76264 | 95 |
| 498535 | 3566 | 3585 | TTCAGAAGAAGCCTCTGTGC | 89 | 76251 | 76270 | 96 |
| 498550 | 3582 | 3601 | GCTCCGTTGGTGCTTCTTCA | 90 | n/a | n/a | 97 |
| 498553 | 3585 | 3604 | TTTGCTCCGTTGGTGCTTCT | 87 | n/a | n/a | 98 |
| 498555 | 3587<br>3905 | 3606<br>3924 | GCTTTGCTCCGTTGGTGCTT | 90 | n/a | n/a | 99 |
| 498556 | 3588<br>3906 | 3607<br>3925 | GGCTTTGCTCCGTTGGTGCT | 89 | 77509<br>81914 | 77528<br>81933 | 100 |
| 498557 | 3589<br>3907 | 3608<br>3926 | GGGCTTTGCTCCGTTGGTGC | 89 | 77510<br>81915 | 77529<br>81934 | 101 |
| 498579 | 3662 | 3681 | CCTTCCTGTGACAGTGGTAG | 87 | 77583 | 77602 | 102 |
| 498580 | 3663 | 3682 | TCCTTCCTGTGACAGTGGTA | 92 | 77584 | 77603 | 103 |
| 498581 | 3665<br>5009 | 3684<br>5028 | TGTCCTTCCTGTGACAGTGG | 94 | 77586<br>115519 | 77605<br>115538 | 104 |

TABLE 12

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 100 | 21210 | 21229 | 11 |
| 494230 | 477 | 496 | CCTCTAGGCTTGGAACCGGG | 95 | 25380 | 25399 | 105 |
| | 819 | 838 | | | 30927 | 30946 | |
| | 1161 | 1180 | | | 36471 | 36490 | |
| | 1503 | 1522 | | | 42020 | 42039 | |
| | 1845 | 1864 | | | 47564 | 47583 | |
| | 2187 | 2206 | | | 53110 | 53129 | |
| | 2529 | 2548 | | | 58662 | 58681 | |
| 494243 | 494 | 513 | TGCTTGTTCGGAAGGAGCCT | 92 | n/a | n/a | 106 |
| | 836 | 855 | | | | | |
| | 1178 | 1197 | | | | | |
| | 1520 | 1539 | | | | | |
| | 1862 | 1881 | | | | | |
| | 2204 | 2223 | | | | | |
| | 2546 | 2565 | | | | | |
| 494224 | 495 | 514 | GTGCTTGTTCGGAAGGAGCC | 95 | n/a | n/a | 107 |
| | 837 | 856 | | | | | |
| | 1179 | 1198 | | | | | |
| | 1521 | 1540 | | | | | |
| | 1863 | 1882 | | | | | |
| | 2205 | 2224 | | | | | |
| | 2547 | 2566 | | | | | |

TABLE 13

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 96 | 21210 | 21229 | 11 |
| 494466 | 4208 | 4227 | GCTTGGAACTGGGACCACCG | 95 | 85138 | 85157 | 108 |
| 494470 | 4212 | 4231 | CTGTGCTTGGAACTGGGACC | 94 | 85142 | 85161 | 109 |
| 494472 | 4214 | 4233 | CTCTGTGCTTGGAACTGGGA | 92 | 85144 | 85163 | 110 |

Example 3: Dose-Dependent Antisense Inhibition of Apo(a) in Transgenic Mouse Primary Hepatocytes Gapmers from the studies described above exhibiting significant in vitro inhibition of apo(a) mRNA were selected and tested at various doses in transgenic mouse primary hepatocytes in a series of parallel studies with similar culture conditions. Cells were plated at a density of 35,000 per well and transfected using electroporation with 0.0625 μM, 0.125 μM, 0.25 μM, 0.500 μM, or 1.000 μM concentrations of antisense oligonucleotide. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration ($IC_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide ISIS 144367.

TABLE 14

| ISIS No | 0.0625 μM | 0.125 μM | 0.250 μM | 0.500 μM | 1.000 μM | $IC_{50}$ (μM) |
|---|---|---|---|---|---|---|
| 144367 | 11 | 27 | 46 | 62 | 80 | 0.31 |
| 494157 | 11 | 47 | 53 | 76 | 87 | 0.23 |
| 494158 | 19 | 57 | 75 | 84 | 88 | 0.13 |
| 494159 | 41 | 65 | 77 | 84 | 92 | 0.07 |
| 494160 | 44 | 69 | 76 | 85 | 91 | 0.06 |
| 494161 | 40 | 64 | 74 | 85 | 91 | 0.08 |
| 494162 | 36 | 63 | 76 | 87 | 88 | 0.09 |
| 494163 | 20 | 59 | 75 | 85 | 92 | 0.13 |
| 494164 | 3 | 45 | 62 | 74 | 90 | 0.21 |
| 494165 | 25 | 39 | 57 | 71 | 75 | 0.19 |
| 494166 | 17 | 30 | 47 | 59 | 76 | 0.31 |
| 494167 | 30 | 43 | 55 | 72 | 80 | 0.18 |
| 494168 | 25 | 36 | 44 | 59 | 75 | 0.28 |
| 494169 | 19 | 39 | 51 | 61 | 81 | 0.25 |

TABLE 15

| ISIS No | 0.0625 μM | 0.125 μM | 0.250 μM | 0.500 μM | 1.000 μM | $IC_{50}$ (μM) |
|---|---|---|---|---|---|---|
| 144367 | 23 | 40 | 58 | 76 | 88 | 0.19 |
| 494170 | 38 | 34 | 60 | 76 | 84 | 0.13 |
| 494230 | 55 | 71 | 89 | 95 | 97 | 0.03 |
| 494243 | 47 | 73 | 87 | 92 | 97 | 0.05 |
| 494244 | 58 | 73 | 86 | 92 | 96 | 0.03 |
| 494283 | 54 | 70 | 84 | 93 | 94 | 0.05 |
| 494284 | 45 | 62 | 83 | 92 | 95 | 0.07 |
| 494285 | 56 | 70 | 84 | 92 | 95 | 0.04 |
| 494286 | 51 | 70 | 87 | 93 | 95 | 0.05 |
| 494287 | 32 | 60 | 67 | 87 | 91 | 0.11 |
| 494288 | 26 | 41 | 61 | 79 | 88 | 0.17 |
| 494290 | 30 | 43 | 64 | 81 | 87 | 0.15 |
| 494291 | 29 | 40 | 56 | 75 | 85 | 0.18 |

TABLE 16

| ISIS No | 0.0625 μM | 0.125 μM | 0.250 μM | 0.500 μM | 1.000 μM | $IC_{50}$ (μM) |
|---|---|---|---|---|---|---|
| 144367 | 10 | 38 | 62 | 68 | 84 | 0.23 |
| 494292 | 17 | 36 | 74 | 85 | 90 | 0.17 |
| 494294 | 10 | 34 | 53 | 80 | 91 | 0.22 |
| 494299 | 32 | 29 | 56 | 77 | 88 | 0.16 |
| 494300 | 34 | 46 | 76 | 86 | 90 | 0.12 |
| 494301 | 44 | 56 | 72 | 86 | 89 | 0.09 |
| 494302 | 42 | 59 | 78 | 88 | 89 | 0.08 |
| 494303 | 37 | 58 | 70 | 86 | 89 | 0.10 |
| 494304 | 46 | 71 | 78 | 89 | 90 | 0.05 |
| 494305 | 39 | 58 | 62 | 85 | 87 | 0.10 |
| 494306 | 31 | 52 | 65 | 79 | 88 | 0.13 |
| 494307 | 23 | 23 | 39 | 65 | 78 | 0.34 |
| 494310 | 14 | 29 | 62 | 70 | 88 | 0.25 |

TABLE 17

| ISIS No | 0.0625 μM | 0.125 μM | 0.250 μM | 0.500 μM | 1.000 μM | $IC_{50}$ (μM) |
|---|---|---|---|---|---|---|
| 144367 | 0 | 29 | 45 | 73 | 92 | 0.27 |
| 494311 | 28 | 53 | 65 | 85 | 95 | 0.13 |
| 494334 | 20 | 44 | 66 | 86 | 96 | 0.16 |
| 494336 | 15 | 38 | 54 | 84 | 97 | 0.20 |
| 494337 | 28 | 50 | 77 | 90 | 98 | 0.12 |
| 494338 | 21 | 40 | 68 | 91 | 98 | 0.15 |
| 494371 | 19 | 0 | 71 | 89 | 97 | 0.15 |
| 494372 | 33 | 44 | 77 | 91 | 97 | 0.12 |
| 494373 | 15 | 36 | 65 | 83 | 95 | 0.19 |
| 494374 | 3 | 17 | 51 | 83 | 90 | 0.24 |
| 494375 | 1 | 34 | 56 | 80 | 93 | 0.23 |
| 494386 | 13 | 26 | 46 | 73 | 91 | 0.25 |
| 494387 | 17 | 27 | 45 | 67 | 88 | 0.28 |

TABLE 18

| ISIS No | 0.0625 μM | 0.125 μM | 0.250 μM | 0.500 μM | 1.000 μM | $IC_{50}$ (μM) |
|---|---|---|---|---|---|---|
| 144367 | 35 | 42 | 62 | 70 | 91 | 0.15 |
| 494537 | 19 | 34 | 54 | 79 | 90 | 0.21 |
| 494544 | 10 | 38 | 73 | 86 | 94 | 0.17 |
| 498229 | 36 | 58 | 80 | 92 | 97 | 0.10 |
| 498238 | 41 | 57 | 75 | 91 | 97 | 0.09 |
| 498239 | 56 | 71 | 79 | 90 | 94 | 0.03 |
| 498240 | 91 | 94 | 98 | 99 | 100 | <0.06 |
| 498241 | 75 | 84 | 91 | 96 | 98 | <0.06 |
| 498242 | 11 | 27 | 42 | 47 | 63 | 0.49 |
| 498243 | 91 | 93 | 96 | 98 | 99 | <0.06 |

TABLE 18-continued

| ISIS No | 0.0625 μM | 0.125 μM | 0.250 μM | 0.500 μM | 1.000 μM | $IC_{50}$ (μM) |
|---|---|---|---|---|---|---|
| 498244 | 4 | 0 | 0 | 13 | 43 | >1.00 |
| 498251 | 30 | 30 | 42 | 73 | 89 | 0.26 |
| 498252 | 37 | 33 | 58 | 80 | 92 | 0.20 |
| 498369 | 22 | 22 | 10 | 22 | 34 | >1.00 |

TABLE 19

| ISIS No | 0.0625 μM | 0.125 μM | 0.250 μM | 0.500 μM | 1.000 μM | $IC_{50}$ (μM) |
|---|---|---|---|---|---|---|
| 144367 | 15 | 32 | 54 | 75 | 90 | 0.22 |
| 498379 | 29 | 48 | 71 | 80 | 95 | 0.13 |
| 498408 | 38 | 57 | 77 | 88 | 96 | 0.09 |
| 498433 | 29 | 36 | 70 | 88 | 96 | 0.15 |
| 498434 | 49 | 43 | 50 | 78 | 90 | 0.19 |
| 498435 | 27 | 39 | 57 | 78 | 93 | 0.18 |
| 498517 | 64 | 72 | 82 | 93 | 98 | <0.06 |
| 498721 | 77 | 84 | 88 | 96 | 97 | <0.06 |
| 498833 | 73 | 78 | 91 | 95 | 99 | <0.06 |
| 498859 | 7 | 24 | 37 | 62 | 75 | 0.36 |
| 498868 | 7 | 14 | 39 | 63 | 81 | 0.36 |
| 498875 | 16 | 21 | 33 | 55 | 81 | 0.39 |
| 499020 | 7 | 24 | 23 | 55 | 78 | 0.36 |
| 499041 | 6 | 16 | 33 | 64 | 83 | 0.35 |

TABLE 20

| ISIS No | 0.0625 μM | 0.125 μM | 0.250 μM | 0.500 μM | 1.000 μM | $IC_{50}$ (μM) |
|---|---|---|---|---|---|---|
| 144367 | 14 | 47 | 64 | 79 | 91 | 0.14 |
| 498523 | 36 | 50 | 80 | 87 | 95 | 0.11 |
| 498524 | 43 | 79 | 87 | 93 | 97 | 0.01 |
| 498525 | 32 | 49 | 75 | 86 | 96 | 0.12 |
| 498529 | 21 | 49 | 57 | 78 | 90 | 0.17 |
| 498535 | 20 | 34 | 55 | 76 | 86 | 0.21 |
| 498550 | 12 | 50 | 69 | 84 | 96 | 0.11 |
| 498553 | 8 | 43 | 55 | 77 | 91 | 0.21 |
| 498555 | 13 | 35 | 68 | 86 | 94 | 0.19 |
| 498556 | 27 | 37 | 71 | 85 | 91 | 0.15 |
| 498557 | 18 | 42 | 75 | 89 | 95 | 0.16 |
| 498579 | 16 | 38 | 67 | 89 | 95 | 0.16 |
| 498580 | 36 | 57 | 81 | 91 | 96 | 0.10 |
| 498581 | 34 | 64 | 75 | 93 | 97 | 0.05 |

TABLE 21

| ISIS No | 0.0625 μM | 0.125 μM | 0.250 μM | 0.500 μM | 1.000 μM | $IC_{50}$ (μM) |
|---|---|---|---|---|---|---|
| 144367 | 0 | 9 | 26 | 49 | 77 | 0.47 |
| 494388 | 0 | 0 | 21 | 33 | 55 | 0.89 |
| 494389 | 0 | 15 | 22 | 50 | 79 | 0.46 |
| 494390 | 5 | 20 | 37 | 68 | 81 | 0.33 |
| 494391 | 7 | 20 | 32 | 54 | 68 | 0.46 |
| 494392 | 18 | 24 | 40 | 57 | 76 | 0.35 |
| 494466 | 33 | 45 | 58 | 69 | 82 | 0.16 |
| 494470 | 45 | 58 | 68 | 79 | 87 | 0.08 |
| 494472 | 37 | 50 | 60 | 69 | 83 | 0.13 |
| 494521 | 0 | 0 | 0 | 15 | 54 | 0.17 |
| 494525 | 0 | 0 | 2 | 28 | 65 | 0.85 |
| 494530 | 0 | 6 | 27 | 51 | 80 | 0.46 |
| 494535 | 0 | 7 | 24 | 53 | 74 | 0.49 |
| 494536 | 0 | 2 | 15 | 42 | 67 | 0.63 |

TABLE 22

| ISIS No | 0.0625 μM | 0.125 μM | 0.250 μM | 0.500 μM | 1.000 μM | $IC_{50}$ (μM) |
|---|---|---|---|---|---|---|
| 144367 | 0 | 4 | 16 | 26 | 77 | 0.65 |
| 498379 | 12 | 18 | 27 | 32 | 63 | 0.81 |
| 498408 | 0 | 11 | 46 | 50 | 77 | 0.41 |
| 498433 | 22 | 30 | 46 | 60 | 83 | 0.27 |
| 498434 | 39 | 29 | 25 | 47 | 78 | 0.40 |
| 498435 | 21 | 28 | 26 | 43 | 73 | 0.50 |
| 498517 | 44 | 48 | 63 | 70 | 84 | 0.11 |
| 498721 | 54 | 54 | 66 | 75 | 89 | <0.06 |
| 498833 | 44 | 51 | 58 | 67 | 83 | 0.11 |
| 498859 | 0 | 29 | 14 | 35 | 66 | 0.69 |
| 498868 | 0 | 12 | 9 | 26 | 60 | 1.07 |
| 498875 | 0 | 30 | 31 | 53 | 78 | 0.40 |
| 499020 | 0 | 27 | 19 | 45 | 74 | 0.51 |
| 499041 | 0 | 12 | 10 | 37 | 65 | 0.77 |

As presented in the Tables above, ISIS 494157 (SEQ ID NO: 12), ISIS 494158 (SEQ ID NO: 13), ISIS 494159 (SEQ ID NO: 14), ISIS 494160 (SEQ ID NO: 15), ISIS 494161 (SEQ ID NO: 16), ISIS 494162 (SEQ ID NO: 17), ISIS 494163 (SEQ ID NO: 18), ISIS 494164 (SEQ ID NO: 19), ISIS 494165 (SEQ ID NO: 20), ISIS 494167 (SEQ ID NO: 22), ISIS 494168 (SEQ ID NO: 23), ISIS 494169 (SEQ ID NO: 24), ISIS 494170 (SEQ ID NO: 25), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494288 (SEQ ID NO: 31), ISIS 494290 (SEQ ID NO: 32), ISIS 494291 (SEQ ID NO: 33), ISIS 494292 (SEQ ID NO: 35), ISIS 494294 (SEQ ID NO: 36), ISIS 494299 (SEQ ID NO: 37), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO:43), ISIS 494306 (SEQ ID NO: 44), ISIS 494311 (SEQ ID NO: 47), ISIS 494334 (SEQ ID NO: 48), ISIS 494336 (SEQ ID NO: 49), ISIS 494337 (SEQ ID NO: 50), ISIS 494338 (SEQ ID NO: 133), ISIS 494371 (SEQ ID NO: 57), ISIS 494372 (SEQ ID NO: 58), ISIS 494373 (SEQ ID NO: 59), ISIS 494374 (SEQ ID NO: 60), ISIS 494375 (SEQ ID NO: 61), ISIS 494386 (SEQ ID NO: 62), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 494521 (SEQ ID NO: 51), ISIS 494530 (SEQ ID NO: 53), ISIS 498229 (SEQ ID NO: 75), ISIS 498238 (SEQ ID NO: 76), ISIS 498239 (SEQ ID NO: 77), ISIS 498240 (SEQ ID NO: 78), ISIS 498241 (SEQ ID NO: 79), ISIS 498243 (SEQ ID NO: 81), ISIS 498379 (SEQ ID NO: 70), ISIS 498408 (SEQ ID NO: 71), ISIS 498433 (SEQ ID NO: 72), ISIS 498434 (SEQ ID NO: 73), ISIS 498435 (SEQ ID NO: 74), ISIS 498517 (SEQ ID NO: 85), ISIS 498523 (SEQ ID NO: 92), ISIS 498524 (SEQ ID NO: 93), ISIS 498525 (SEQ ID NO: 94), ISIS 498550 (SEQ ID NO: 97), ISIS 498580 (SEQ ID NO: 103), ISIS 498581 (SEQ ID NO: 104), ISIS 498721 (ATGCCTCGATAACTCCGTCC; SEQ ID NO: 134), ISIS 498833 (SEQ ID NO: 86), ISIS 498875 (SEQ ID NO: 89), and ISIS 499020 (SEQ ID NO: 90) were more potent than ISIS 144367 (SEQ ID NO: 11).

Example 4: Dose-dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.049 μM, 0.148 μM, 0.444 μM, 1.333 μM, or 4.000 μM concentrations of antisense oligonucleotide, as specified in Tables below. After a treatment period of approximately 16 hours, RNA was isolated from the cells and apo(a) mRNA levels were measured by quantitative real-time PCR. Apo(a) primer probe set hAPO(a) 12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration ($IC_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide, ISIS 144367. As presented in the Tables below, ISIS 494157 (SEQ ID NO: 12), ISIS 494158 (SEQ ID NO: 13), ISIS 494159 (SEQ ID NO: 14), ISIS 494160 (SEQ ID NO: 15), ISIS 494161 (SEQ ID NO: 16), ISIS 494162 (SEQ ID NO: 17), ISIS 494163 (SEQ ID NO: 18), ISIS 494164 (SEQ ID NO: 19), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494290 (SEQ ID NO: 32), ISIS 494292 (SEQ ID NO: 35), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494310 (SEQ ID NO: 46), ISIS 494311 (SEQ ID NO: 47), ISIS 494337 (SEQ ID NO: 50), ISIS 494371 (SEQ ID NO: 57), ISIS 494372 (SEQ ID NO: 58), ISIS 494375 (SEQ ID NO: 61), ISIS 494388 (SEQ ID NO: 64), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 498238 (SEQ ID NO: 76), ISIS 498239 (SEQ ID NO: 77), ISIS 498433 (SEQ ID NO: 72), ISIS 498434 (SEQ ID NO: 73), ISIS 498435 (SEQ ID NO: 74), ISIS 498523 (SEQ ID NO: 92), ISIS 498524 (SEQ ID NO: 93), ISIS 498525 (SEQ ID NO: 94), ISIS 498580 (SEQ ID NO: 103), and ISIS 498581 (SEQ ID NO: 104) were more potent than ISIS 144367 (SEQ ID NO: 11).

TABLE 23

| ISIS No | 0.049 μM | 0.148 μM | 0.444 μM | 1.333 μM | 4.000 μM | $IC_{50}$ (μM) |
|---|---|---|---|---|---|---|
| 144367 | 0 | 26 | 67 | 89 | 92 | 0.32 |
| 494157 | 23 | 50 | 83 | 96 | 96 | 0.15 |
| 494158 | 26 | 62 | 85 | 96 | 96 | 0.11 |
| 494159 | 42 | 65 | 87 | 95 | 94 | 0.07 |
| 494160 | 51 | 70 | 88 | 94 | 94 | <0.05 |
| 494161 | 36 | 67 | 87 | 95 | 96 | 0.08 |
| 494162 | 40 | 69 | 89 | 94 | 95 | 0.07 |
| 494163 | 41 | 57 | 87 | 95 | 94 | 0.08 |
| 494164 | 15 | 43 | 75 | 93 | 96 | 0.20 |
| 494230 | 39 | 77 | 94 | 99 | 99 | 0.05 |
| 494243 | 39 | 76 | 92 | 98 | 99 | 0.06 |
| 494244 | 58 | 79 | 91 | 97 | 99 | 0.02 |

TABLE 23-continued

| ISIS No | 0.049 μM | 0.148 μM | 0.444 μM | 1.333 μM | 4.000 μM | IC$_{50}$ (μM) |
|---|---|---|---|---|---|---|
| 494283 | 18 | 45 | 80 | 93 | 91 | 0.18 |
| 494284 | 9 | 53 | 80 | 95 | 94 | 0.18 |

TABLE 24

| ISIS No | 0.049 μM | 0.148 μM | 0.444 μM | 1.333 μM | 4.000 μM | IC$_{50}$ (μM) |
|---|---|---|---|---|---|---|
| 144367 | 21 | 40 | 79 | 94 | 93 | 0.18 |
| 494285 | 53 | 68 | 90 | 97 | 97 | <0.05 |
| 494286 | 46 | 69 | 89 | 96 | 97 | 0.05 |
| 494287 | 31 | 38 | 79 | 94 | 95 | 0.15 |
| 494290 | 22 | 53 | 74 | 93 | 94 | 0.16 |
| 494292 | 37 | 51 | 81 | 93 | 95 | 0.11 |
| 494294 | 22 | 40 | 72 | 91 | 94 | 0.19 |
| 494299 | 15 | 43 | 75 | 93 | 95 | 0.20 |
| 494300 | 25 | 38 | 79 | 95 | 95 | 0.17 |
| 494301 | 23 | 48 | 82 | 92 | 95 | 0.15 |
| 494302 | 26 | 59 | 86 | 93 | 94 | 0.12 |
| 494303 | 10 | 58 | 84 | 92 | 91 | 0.16 |
| 494304 | 25 | 62 | 83 | 93 | 93 | 0.12 |

TABLE 25

| ISIS No | 0.049 μM | 0.148 μM | 0.444 μM | 1.333 μM | 4.000 μM | IC$_{50}$ (μM) |
|---|---|---|---|---|---|---|
| 144367 | 23 | 40 | 70 | 90 | 94 | 0.19 |
| 494305 | 20 | 48 | 82 | 93 | 95 | 0.16 |
| 494306 | 26 | 53 | 78 | 91 | 92 | 0.14 |
| 494310 | 36 | 50 | 79 | 88 | 92 | 0.12 |
| 494311 | 38 | 50 | 74 | 93 | 95 | 0.12 |
| 494334 | 20 | 42 | 73 | 90 | 94 | 0.19 |
| 494336 | 5 | 39 | 74 | 92 | 95 | 0.23 |
| 494337 | 23 | 51 | 87 | 96 | 96 | 0.14 |
| 494338 | 12 | 42 | 82 | 93 | 95 | 0.19 |
| 494371 | 28 | 49 | 82 | 94 | 94 | 0.14 |
| 494372 | 28 | 54 | 81 | 93 | 88 | 0.13 |
| 494373 | 21 | 28 | 67 | 86 | 92 | 0.25 |
| 494375 | 26 | 40 | 77 | 85 | 92 | 0.18 |

TABLE 26

| ISIS No | 0.049 μM | 0.148 μM | 0.444 μM | 1.333 μM | 4.000 μM | IC$_{50}$ (μM) |
|---|---|---|---|---|---|---|
| 144367 | 5 | 33 | 65 | 78 | 81 | 0.32 |
| 494388 | 30 | 32 | 60 | 82 | 86 | 0.25 |
| 494389 | 30 | 45 | 69 | 84 | 84 | 0.17 |
| 494390 | 32 | 47 | 67 | 83 | 87 | 0.16 |
| 494392 | 23 | 38 | 54 | 79 | 82 | 0.31 |
| 494466 | 48 | 67 | 86 | 91 | 95 | 0.04 |
| 494470 | 74 | 87 | 92 | 96 | 98 | <0.05 |
| 494472 | 69 | 84 | 92 | 96 | 97 | <0.05 |
| 494544 | 5 | 18 | 49 | 74 | 79 | 0.48 |
| 498238 | 25 | 51 | 76 | 92 | 96 | 0.15 |
| 498239 | 25 | 62 | 83 | 93 | 97 | 0.12 |
| 498379 | 5 | 21 | 53 | 71 | 81 | 0.55 |
| 498408 | 1 | 38 | 63 | 79 | 80 | 0.32 |
| 498433 | 23 | 43 | 70 | 77 | 79 | 0.21 |

TABLE 27

| ISIS No | 0.049 μM | 0.148 μM | 0.444 μM | 1.333 μM | 4.000 μM | IC$_{50}$ (μM) |
|---|---|---|---|---|---|---|
| 144367 | 0 | 40 | 76 | 90 | 93 | 0.26 |
| 498434 | 32 | 44 | 64 | 78 | 84 | 0.20 |

TABLE 27-continued

| ISIS No | 0.049 μM | 0.148 μM | 0.444 μM | 1.333 μM | 4.000 μM | IC$_{50}$ (μM) |
|---|---|---|---|---|---|---|
| 498435 | 24 | 42 | 64 | 77 | 79 | 0.23 |
| 498517 | 28 | 23 | 53 | 81 | 85 | 0.45 |
| 498523 | 50 | 64 | 81 | 90 | 93 | <0.05 |
| 498524 | 53 | 70 | 84 | 93 | 96 | <0.05 |
| 498525 | 38 | 55 | 80 | 92 | 96 | 0.09 |
| 498550 | 12 | 18 | 62 | 81 | 83 | 0.33 |
| 498557 | 13 | 33 | 67 | 79 | 83 | 0.33 |
| 498579 | 6 | 42 | 69 | 80 | 85 | 0.31 |
| 498580 | 6 | 46 | 76 | 82 | 83 | 0.23 |
| 498581 | 5 | 40 | 78 | 81 | 84 | 0.25 |
| 498721 | 40 | 31 | 58 | 78 | 83 | 0.35 |
| 498833 | 21 | 20 | 58 | 80 | 90 | 0.44 |

Example 5: Antisense Inhibition of Human Apo(a) in Transgenic Mouse Primary Hepatocytes Additional antisense oligonucleotides were newly designed targeting an apo(a) nucleic acid and were tested for their effects on apo(a) mRNA in vitro. The antisense oligonucleotides were tested in a series of experiments that had similar culture conditions. Primary hepatocytes from human apo(a) transgenic mice were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12kB was used to measure mRNA levels. Apo(a) mRNA levels were adjusted according to total RNA content, as measured by RIBOGREEN®. The results for each experiment are presented in separate tables shown below. ISIS 144367 was also included in the studies for comparison. Results are presented as percent inhibition of apo(a), relative to untreated control cells. A total of 231 antisense oligonucleotides were tested under these culture conditions. Only those antisense oligonucleotides that were selected for further studies are presented below.

The newly designed chimeric antisense oligonucleotides were designed as 3-10-4 MOE gapmers. The gapmers are 17 nucleosides in length, wherein the central gap segment comprises often 2'-deoxynucleosides and is flanked by wing segments on the 5' direction and the 3' direction comprising three nucleosides and four nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to multiple regions of either the human apo(a) mRNA, designated herein as SEQ ID NO: 1 (GENBANK Accession No. NM_005577.2) or the human apo(a) genomic sequence, designated herein as SEQ ID NO: 2

(GENBANK Accession No. NT_007422.12 truncated from nucleotides 3230000 to 3380000), or both. 'n/a' indicates that the antisense oligonucleotide does not target that particular sequence with 100% complementarity.

TABLE 28

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 64 | 21210 | 21229 | 11 |
| 510542 | 241 | 257 | CCTGTGACAGTGGTGGA | 79 | 21202 | 21218 | 111 |
| | 583 | 599 | CCTGTGACAGTGGTGGA | | 26693 | 26709 | |
| | 925 | 941 | CCTGTGACAGTGGTGGA | | 32240 | 32256 | |
| | 1609 | 1625 | CCTGTGACAGTGGTGGA | | 43333 | 43347 | |
| | 1951 | 1967 | CCTGTGACAGTGGTGGA | | 48877 | 48893 | |
| | 2293 | 2309 | CCTGTGACAGTGGTGGA | | 54423 | 54439 | |
| | 3319 | 3335 | CCTGTGACAGTGGTGGA | | 72040 | 72056 | |
| | 4663 | 4679 | CCTGTGACAGTGGTGGA | | 94404 | 94420 | |
| | 5005 | 5021 | CCTGTGACAGTGGTGGA | | 115515 | 115531 | |
| 510543 | 242 | 258 | TCCTGTGACAGTGGTGG | 75 | 21203 | 21219 | 112 |
| | 584 | 600 | TCCTGTGACAGTGGTGG | | 26694 | 26710 | |
| | 926 | 942 | TCCTGTGACAGTGGTGG | | 32241 | 32257 | |
| | 1610 | 1626 | TCCTGTGACAGTGGTGG | | 43334 | 43350 | |
| | 1952 | 1968 | TCCTGTGACAGTGGTGG | | 48878 | 48894 | |
| | 2294 | 2310 | TCCTGTGACAGTGGTGG | | 54424 | 54440 | |
| | 3320 | 3336 | TCCTGTGACAGTGGTGG | | 72041 | 72057 | |
| | 4664 | 4680 | TCCTGTGACAGTGGTGG | | 94405 | 94421 | |
| | 5006 | 5022 | TCCTGTGACAGTGGTGG | | 115516 | 115532 | |
| 510544 | 243 | 259 | TTCCTGTGACAGTGGTG | 73 | 21204 | 21220 | 113 |
| | 585 | 601 | TTCCTGTGACAGTGGTG | | 26695 | 26711 | |
| | 927 | 943 | TTCCTGTGACAGTGGTG | | 32242 | 32258 | |
| | 1611 | 1627 | TTCCTGTGACAGTGGTG | | 43335 | 43351 | |
| | 1953 | 1969 | TTCCTGTGACAGTGGTG | | 48879 | 48895 | |
| | 2295 | 2311 | TTCCTGTGACAGTGGTG | | 54425 | 54441 | |
| | 3321 | 3337 | TTCCTGTGACAGTGGTG | | 72042 | 72058 | |
| | 4665 | 4681 | TTCCTGTGACAGTGGTG | | 94406 | 94422 | |
| | 5007 | 5023 | TTCCTGTGACAGTGGTG | | 115517 | 115533 | |
| 510545 | 244 | 260 | CTTCCTGTGACAGTGGT | 65 | 21205 | 21221 | 114 |
| | 586 | 602 | CTTCCTGTGACAGTGGT | | 26696 | 26712 | |
| | 928 | 944 | CTTCCTGTGACAGTGGT | | 32243 | 32259 | |
| | 1612 | 1628 | CTTCCTGTGACAGTGGT | | 43336 | 43352 | |
| | 1954 | 1970 | CTTCCTGTGACAGTGGT | | 48880 | 48896 | |
| | 2296 | 2312 | CTTCCTGTGACAGTGGT | | 54426 | 54442 | |
| | 3322 | 3338 | CTTCCTGTGACAGTGGT | | 72043 | 72057 | |
| | 3664 | 3680 | CTTCCTGTGACAGTGGT | | 77585 | 77601 | |
| | 4666 | 4682 | CTTCCTGTGACAGTGGT | | 94407 | 94423 | |
| | 5008 | 5024 | CTTCCTGTGACAGTGGT | | 115518 | 115534 | |
| 510546 | 245 | 261 | CCTTCCTGTGACAGTGG | 74 | 21206 | 21222 | 115 |
| | 3665 | 3681 | CCTTCCTGTGACAGTGG | | 77586 | 77602 | |
| | 4667 | 4683 | CCTTCCTGTGACAGTGG | | 94408 | 94424 | |
| | 5009 | 5025 | CCTTCCTGTGACAGTGG | | 115519 | 115535 | |
| 510547 | 246 | 262 | TCCTTCCTGTGACAGTG | 77 | 21207 | 21223 | 116 |
| | 3666 | 3682 | TCCTTCCTGTGACAGTG | | 77587 | 77603 | |
| | 4668 | 4684 | TCCTTCCTGTGACAGTG | | 94409 | 94425 | |
| | 5010 | 5026 | TCCTTCCTGTGACAGTG | | 115520 | 115536 | |
| 510548 | 247 | 263 | GTCCTTCCTGTGACAGT | 73 | 21208 | 21224 | 117 |
| | 3667 | 3683 | GTCCTTCCTGTGACAGT | | 77588 | 77604 | |
| | 4669 | 4685 | GTCCTTCCTGTGACAGT | | 94410 | 94426 | |
| | 5011 | 5027 | GTCCTTCCTGTGACAGT | | 115521 | 115537 | |
| 510549 | 248 | 264 | GGTCCTTCCTGTGACAG | 67 | 21209 | 21225 | 118 |
| | 4670 | 4686 | GGTCCTTCCTGTGACAG | | 94411 | 94427 | |
| 510595 | 632 | 648 | CCGACTATGCGAGTGTG | 76 | 26742 | 26758 | 119 |
| | 974 | 990 | CCGACTATGCGAGTGTG | | 32289 | 32305 | |
| | 1316 | 1332 | CCGACTATGCGAGTGTG | | 37836 | 37852 | |
| | 1658 | 1674 | CCGACTATGCGAGTGTG | | 43382 | 43398 | |
| | 2000 | 2016 | CCGACTATGCGAGTGTG | | 48926 | 48942 | |
| | 2342 | 2358 | CCGACTATGCGAGTGTG | | 54472 | 54488 | |
| | 2684 | 2700 | CCGACTATGCGAGTGTG | | 60027 | 60043 | |
| | 3026 | 3042 | CCGACTATGCGAGTGTG | | 66543 | 66559 | |
| 510597 | 634 | 650 | GTCCGACTATGCGAGTG | 70 | 26744 | 26760 | 120 |
| | 976 | 992 | GTCCGACTATGCGAGTG | | 32291 | 32307 | |

TABLE 28-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1318 | 1334 | GTCCGACTATGCGAGTG | | 37838 | 37854 | |
| | 1660 | 1676 | GTCCGACTATGCGAGTG | | 43384 | 43400 | |
| | 2002 | 2018 | GTCCGACTATGCGAGTG | | 48928 | 48944 | |
| | 2344 | 2360 | GTCCGACTATGCGAGTG | | 54474 | 54490 | |
| | 2686 | 2702 | GTCCGACTATGCGAGTG | | 60029 | 60045 | |
| | 3028 | 3044 | GTCCGACTATGCGAGTG | | 66545 | 66561 | |
| 510598 | 635 | 651 | GGTCCGACTATGCGAGT | 70 | 26745 | 26761 | 121 |
| | 977 | 993 | GGTCCGACTATGCGAGT | | 32292 | 32308 | |
| | 1319 | 1335 | GGTCCGACTATGCGAGT | | 37839 | 37855 | |
| | 1661 | 1677 | GGTCCGACTATGCGAGT | | 43385 | 43401 | |
| | 2003 | 2019 | GGTCCGACTATGCGAGT | | 48929 | 48945 | |
| | 2345 | 2361 | GGTCCGACTATGCGAGT | | 54475 | 54491 | |
| | 2687 | 2703 | GGTCCGACTATGCGAGT | | 60030 | 60046 | |
| | 3029 | 3045 | GGTCCGACTATGCGAGT | | 66546 | 66562 | |

TABLE 29

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 83 | 21210 | 21229 | 11 |
| 510783 | 6400 | 6416 | GTCAGACCTTAAAAGCT | 75 | 140056 | 140072 | 122 |
| 512944 | 3561 | 3577 | AAGCCTCTGTGCTTGGA | 81 | 76246 | 76262 | 123 |
| 512947 | 3560 | 3576 | AGCCTCTGTGCTTGGAT | 85 | 76245 | 76261 | 124 |
| 512958 | 3559 | 3575 | GCCTCTGTGCTTGGATC | 82 | 76244 | 76260 | 125 |
| 512959 | 3585 | 3601 | GCTCCGTTGGTGCTTCT | 77 | n/a | n/a | 126 |

TABLE 30

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 76 | 21210 | 21229 | 11 |
| 510701 | 4217 | 4233 | CTCTGTGCTTGGAACTG | 78 | 85147 | 85163 | 127 |
| 510702 | 219 | 235 | TGCCTCGATAACTCTGT | 79 | 21180 | 21196 | 128 |
| | 531 | 577 | | | 26671 | 26687 | |
| | 903 | 919 | | | 32218 | 32234 | |
| | 1245 | 1261 | | | 37765 | 37781 | |
| | 1587 | 1603 | | | 43311 | 43327 | |
| | 1929 | 1945 | | | 48855 | 48871 | |
| | 2271 | 2287 | | | 54401 | 54417 | |
| | 2613 | 2629 | | | 59956 | 59972 | |
| | 4299 | 4315 | | | 86472 | 86488 | |
| 510704 | 563 | 579 | TGTGCCTCGATAACTCT | 80 | 26673 | 26689 | 129 |
| | 905 | 921 | | | 32220 | 32236 | |
| | 1247 | 1263 | | | 37767 | 37783 | |
| | 1589 | 1605 | | | 43313 | 43329 | |
| | 1931 | 1947 | | | 48857 | 48873 | |
| | 2273 | 2289 | | | 54403 | 54419 | |
| | 2615 | 2631 | | | 59958 | 59974 | |

TABLE 30-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 4301 | 4317 | | | 86474 | 86490 | |
| | 4985 | 5001 | | | 115495 | 115511 | |
| 510757 | 4929 | 4945 | GCTCAGTTGGTGCTGCT | 74 | n/a | n/a | 130 |

Example 6: Dose-dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.156 µM, 0.313 µM, 0.625 µM, 1.250 µM, 2.500 µM, or 5.000 µM concentrations of antisense oligonucleotide, as specified in the Tables below. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each study represented in a separate table. The half maximal inhibitory concentration ($IC_{50}$) of each oligonucleotide is also presented in the Tables.

TABLE 31

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 28 | 55 | 70 | 83 | 90 | 92 | 0.31 |
| 510542 | 33 | 58 | 75 | 87 | 89 | 90 | 0.27 |
| 510543 | 33 | 45 | 68 | 78 | 89 | 89 | 0.34 |
| 510544 | 33 | 50 | 65 | 78 | 88 | 90 | 0.33 |
| 510545 | 33 | 58 | 76 | 87 | 91 | 90 | 0.26 |
| 510546 | 39 | 62 | 76 | 87 | 89 | 91 | 0.22 |
| 510547 | 36 | 66 | 82 | 84 | 86 | 91 | 0.22 |
| 510548 | 50 | 70 | 82 | 91 | 88 | 90 | 0.13 |
| 510549 | 32 | 59 | 73 | 85 | 86 | 90 | 0.27 |
| 510595 | 26 | 57 | 78 | 88 | 90 | 90 | 0.29 |
| 510597 | 30 | 53 | 76 | 85 | 89 | 89 | 0.30 |

TABLE 32

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 36 | 52 | 78 | 87 | 93 | 94 | 0.26 |
| 510598 | 48 | 58 | 81 | 88 | 93 | 92 | 0.18 |
| 510701 | 45 | 59 | 78 | 87 | 95 | 95 | 0.18 |
| 510702 | 49 | 63 | 75 | 90 | 94 | 95 | 0.15 |
| 510704 | 55 | 67 | 80 | 93 | 94 | 95 | <0.16 |
| 510757 | 34 | 48 | 68 | 79 | 90 | 93 | 0.33 |
| 510783 | 21 | 32 | 51 | 58 | 78 | 84 | 0.69 |
| 512944 | 57 | 72 | 81 | 91 | 96 | 97 | <0.16 |
| 512947 | 64 | 74 | 86 | 92 | 96 | 97 | <0.16 |
| 512958 | 48 | 69 | 83 | 91 | 96 | 97 | 0.13 |
| 512959 | 39 | 59 | 76 | 84 | 93 | 93 | 0.22 |

TABLE 33

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 41 | 58 | 75 | 81 | 88 | 87 | 0.22 |
| 510542 | 38 | 54 | 69 | 74 | 85 | 83 | 0.27 |
| 510545 | 21 | 43 | 73 | 77 | 80 | 78 | 0.39 |
| 510546 | 37 | 58 | 73 | 81 | 83 | 81 | 0.24 |
| 510547 | 38 | 58 | 72 | 79 | 84 | 86 | 0.24 |
| 510548 | 40 | 63 | 77 | 79 | 81 | 84 | 0.21 |
| 510549 | 37 | 47 | 67 | 77 | 81 | 83 | 0.31 |
| 510595 | 34 | 66 | 73 | 81 | 80 | 75 | 0.23 |
| 510597 | 39 | 59 | 74 | 83 | 76 | 77 | 0.23 |

TABLE 34

| ISIS No | 0.156 µM | 0.312 µM | 0.625 µM | 1.250 µM | 2.500 µM | 5.000 µM | $IC_{50}$ (µM) |
|---|---|---|---|---|---|---|---|
| 144367 | 33 | 60 | 72 | 83 | 81 | 81 | 0.26 |
| 510598 | 47 | 62 | 75 | 75 | 76 | 76 | 0.18 |
| 510701 | 41 | 67 | 80 | 87 | 92 | 91 | 0.19 |
| 510702 | 51 | 64 | 77 | 80 | 80 | 83 | 0.13 |
| 510704 | 54 | 61 | 77 | 84 | 89 | 80 | 0.12 |
| 512944 | 71 | 74 | 81 | 88 | 92 | 94 | 0.02 |
| 512947 | 65 | 77 | 86 | 90 | 93 | 95 | 0.03 |
| 512958 | 63 | 73 | 84 | 92 | 93 | 96 | 0.06 |
| 512959 | 39 | 62 | 80 | 82 | 86 | 82 | 0.22 |

Apo(a) mRNA levels were significantly reduced in a dose-dependent manner in antisense oligonucleotide-treated cells. The potency of the newly designed oligonucleotides was compared with the benchmark oligonucleotide, ISIS 144367. As presented in the Tables above, ISIS 510542 (SEQ ID NO: 111), ISIS 510545 (SEQ ID NO: 114), ISIS 510546 (SEQ ID NO: 115), ISIS 510547 (SEQ ID NO: 116), ISIS 510548 (SEQ ID NO: 117), ISIS 510549 (SEQ ID NO: 118), ISIS 510595 (SEQ ID NO: 119), ISIS 510597 (SEQ ID NO: 120), ISIS 510598 (SEQ ID NO: 121), ISIS 510701 (SEQ ID NO: 127), ISIS 510702 (SEQ ID NO: 128), ISIS 510704 (SEQ ID NO: 129), ISIS 512944 (SEQ ID NO: 123), ISIS 512947 (SEQ ID NO: 124), ISIS 512958 (SEQ ID NO: 125), and ISIS 512959 (SEQ ID NO: 126) were more potent than ISIS 144367 (SEQ ID NO: 11).

Example 7: Effect of In Vivo Antisense Inhibition of Human Apo(a) in Human Apo(a) Transgenic Mice Transgenic mice with the human apo(a) gene (Frazer, K. A. et al., Nat. Genet. 1995. 9: 424-431) were utilized in the studies described below. ISIS antisense oligonucleotides that demonstrated statistically significant inhibition of apo(a) mRNA in vitro as described above were evaluated further in this model.

Study 1

Female human apo(a) transgenic mice were maintained on a 12-hour light/dark cycle and fed ad libitum normal lab chow. The mice were divided into treatment groups consisting of 4 mice each. The groups received intraperitoneal injections of ISIS 494159, ISIS 494160, ISIS 494161, ISIS 494162, ISIS 494163, ISIS 494230, ISIS 494243, ISIS 494244, ISIS 494283, ISIS 494284, ISIS 494285, ISIS 494286, ISIS 494301, ISIS 494302, ISIS 494304, ISIS 494466, ISIS 494470, ISIS 494472, ISIS 498239, ISIS 498408, ISIS 498517, ISIS 494158, ISIS 494311, ISIS 494337, ISIS 494372, ISIS 498238, ISIS 498523, ISIS 498525, ISIS 510548, ISIS 512944, ISIS 512947, or ISIS 512958 at a dose of 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of some of the treatment groups, and human apo(a) mRNA was quantitated by RT-PCR. The results are presented in Table 35, expressed as percent inhibition of apo(a) mRNA compared to the PBS control.

TABLE 35

Percent inhibition of human apo(a) mRNA in transgenic mice

| ISIS No | % inhibition |
|---|---|
| 144367 | 98 |
| 494159 | 100 |
| 494160 | 95 |
| 494161 | 98 |
| 494162 | 100 |
| 494163 | 100 |
| 494230 | 96 |
| 494243 | 99 |
| 494244 | 99 |
| 494283 | 100 |
| 494284 | 100 |
| 494285 | 100 |
| 494286 | 98 |
| 494301 | 99 |
| 494302 | 96 |
| 494304 | 94 |
| 494466 | 97 |
| 494470 | 93 |
| 494472 | 98 |
| 498239 | 72 |
| 498408 | 100 |
| 498517 | 98 |

The data demonstrates significant inhibition of apo(a) mRNA by several ISIS oligonucleotides. ISIS 494159 (SEQ ID NO: 14), ISIS 494162 (SEQ ID NO: 17), ISIS 494163 (SEQ ID NO: 18), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494301 (SEQ ID NO: 39), and ISIS 498408 (SEQ ID NO: 71) were more potent than the benchmark ISIS 144367 (SEQ ID NO: 11).

Inhibition of Human Apo(a) Protein

Plasma human apo(a) protein was measured from all treatment groups using an Apo(a) ELISA kit (Mercodia 10-1106-01, Uppsala, Sweden). The results are presented in Table 36, expressed as percent inhibition of apo(a) mRNA compared to the PBS control.

TABLE 36

Percent inhibition of human apo(a) protein in transgenic mice

| ISIS No | % inhibition |
|---|---|
| 144367 | 86 |
| 494159 | 86 |
| 494160 | 0 |
| 494161 | 82 |
| 494162 | 84 |
| 494163 | 82 |
| 494230 | 60 |
| 494243 | 84 |
| 494244 | 87 |
| 494283 | 98 |
| 494284 | 98 |
| 494285 | 89 |
| 494286 | 89 |
| 494301 | 93 |
| 494302 | 88 |
| 494304 | 83 |
| 494466 | 76 |
| 494470 | 73 |
| 494472 | 72 |
| 498239 | 54 |
| 498408 | 84 |
| 498517 | 56 |
| 494158 | 71 |
| 494311 | 83 |
| 494337 | 80 |
| 494372 | 78 |
| 498238 | 58 |
| 498523 | 47 |
| 498525 | 58 |
| 510548 | 74 |
| 512944 | 18 |
| 512947 | 65 |
| 512958 | 72 |

The data demonstrates significant inhibition of apo(a) mRNA by several ISIS oligonucleotides. ISIS 494159 (SEQ ID NO: 14), ISIS 494244 (SEQ ID NO: 82), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494301 (SEQ ID NO: 39), and ISIS 494302 (SEQ ID NO: 40) were as potent as or more potent than the benchmark ISIS 144367 (SEQ ID NO: 11).

Study 2

ISIS 494159, ISIS 494161, ISIS 494162, ISIS 494163, and ISIS 494243 were further evaluated in this transgenic model. ISIS 144367 was included for comparison.

Treatment

Female human apo(a) transgenic mice were divided into treatment groups consisting of 4 mice each. The groups received intraperitoneal injections of ISIS 144367, ISIS 494159, ISIS 494161, ISIS 494162, ISIS 494163, or ISIS 494243 at doses of 1.5 mg/kg, 5 mg/kg, 15 mg/kg, or 50 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 37, expressed as percent inhibition of apo(a) mRNA compared to the PBS control.

TABLE 37

| Dose-dependent inhibition of human apo(a) mRNA in transgenic mice | | | |
|---|---|---|---|
| ISIS No | Dose (mg/kg/wk) | % inhibition | $ED_{50}$ |
| 144367 | 100 | 71 | 31 |
| | 30 | 42 | |
| | 10 | 0 | |
| | 3 | 5 | |
| 494159 | 100 | 91 | 5 |
| | 30 | 67 | |
| | 10 | 48 | |
| | 3 | 39 | |
| 494161 | 100 | 82 | 6 |
| | 30 | 49 | |
| | 10 | 61 | |
| | 3 | 30 | |
| 494162 | 100 | 90 | 5 |
| | 30 | 67 | |
| | 10 | 58 | |
| | 3 | 25 | |
| 494163 | 100 | 83 | 5 |
| | 30 | 66 | |
| | 10 | 58 | |
| | 3 | 21 | |
| 494243 | 100 | 80 | 32 |
| | 30 | 26 | |
| | 10 | 0 | |
| | 3 | 6 | |

The data demonstrates significant inhibition of apo(a) mRNA by several ISIS oligonucleotides. ISIS 494159 (SEQ ID NO: 14), ISIS 494161 (SEQ ID NO: 16), 494162 (SEQ ID NO: 17), and ISIS 94163 (SEQ ID NO: 18) were more efficacious than the benchmark ISIS 144367 (SEQ ID NO: 11). Reduction of human apo(a) protein levels Blood was collected from the treatment groups, and human apo(a) protein levels were quantitated by an Apo(a) ELISA kit (Mercodia 10-1106-01, Uppsala, Sweden). The results are presented in Table 38, expressed as percent reduction of apo(a) protein levels compared to the PBS control.

TABLE 38

| Dose-dependent inhibition of human apo(a) protein in transgenic mice | | | |
|---|---|---|---|
| ISIS No | Dose (mg/kg/wk) | % inhibition | $ED_{50}$ |
| 144367 | 100 | 73 | 71 |
| | 30 | 0 | |
| | 10 | 6 | |
| | 3 | 69 | |
| 494159 | 100 | 88 | 2 |
| | 30 | 88 | |
| | 10 | 85 | |
| | 3 | 36 | |
| 494161 | 100 | 90 | 2 |
| | 30 | 85 | |
| | 10 | 73 | |
| | 3 | 44 | |
| 494162 | 100 | 89 | 3 |
| | 30 | 78 | |
| | 10 | 76 | |
| | 3 | 24 | |
| 494163 | 100 | 90 | 3 |
| | 30 | 86 | |
| | 10 | 60 | |
| | 3 | 37 | |
| 494243 | 100 | 61 | 174 |
| | 30 | 0 | |
| | 10 | 0 | |
| | 3 | 0 | |

The data demonstrates significant reduction of apo(a) plasma protein levels by several ISIS oligonucleotides. ISIS 494159 (SEQ ID NO: 14), ISIS 494161 (SEQ ID NO: 16), ISIS 494162 (SEQ ID NO: 17), and ISIS 494163 (SEQ ID NO: 18) were more efficacious than the benchmark ISIS 144367 (SEQ ID NO: 11).

Study 3

ISIS 494244, ISIS 494283, and ISIS 494284 were further evaluated in this model. ISIS 144367 was included for comparison.

Treatment

Female human apo(a) transgenic mice were divided into treatment groups consisting of 4 mice each. The groups received intraperitoneal injections of ISIS 144367, ISIS 494244, ISIS 494283, or ISIS 494284 at doses of 0.75 mg/kg, 2.5 mg/kg, 7.5 mg/kg, or 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 39, expressed as percent inhibition of apo(a) mRNA compared to the PBS control.

TABLE 39

| Dose-dependent inhibition of human apo(a) mRNA in transgenic mice | | | |
|---|---|---|---|
| ISIS No | Dose (mg/kg/wk) | % inhibition | $ED_{50}$ |
| 144367 | 50 | 75 | 22 |
| | 15 | 60 | |
| | 5 | 0 | |
| | 1.5 | 0 | |
| 494244 | 50 | 73 | 18 |
| | 15 | 41 | |
| | 5 | 34 | |
| | 1.5 | 0 | |
| 494283 | 50 | 74 | 16 |
| | 15 | 52 | |
| | 5 | 24 | |
| | 1.5 | 0 | |
| 494284 | 50 | 73 | 16 |
| | 15 | 58 | |
| | 5 | 17 | |
| | 1.5 | 2 | |

The data demonstrates significant inhibition of apo(a) mRNA by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 40, expressed as percent reduction of apo(a) protein levels compared to the PBS control.

TABLE 40

| Dose-dependent inhibition of human apo(a) plasma protein in transgenic mice | | | |
|---|---|---|---|
| ISIS No | Dose (mg/kg/wk) | % inhibition | $ED_{50}$ |
| 144367 | 50 | 64 | 16 |
| | 15 | 14 | |
| | 5 | 0 | |
| | 1.5 | 0 | |
| 494244 | 50 | 67 | 2 |
| | 15 | 60 | |
| | 5 | 58 | |
| | 1.5 | 0 | |
| 494283 | 50 | 64 | 4 |
| | 15 | 65 | |
| | 5 | 64 | |
| | 1.5 | 69 | |
| 494284 | 50 | 66 | 4 |
| | 15 | 63 | |
| | 5 | 51 | |
| | 1.5 | 54 | |

The data demonstrates significant reduction of apo(a) plasma protein levels by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Study 4

ISIS 494285, ISIS 494286, ISIS 494301, ISIS 494302, and ISIS 494311 were further evaluated in this model.

Treatment

Male human apo(a) transgenic mice were divided into treatment groups consisting of 4 mice each. Each such group received intraperitoneal injections of ISIS 494285, ISIS 494286, ISIS 494301, ISIS 494302, or ISIS 494311 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 41, expressed as percent inhibition of apo(a) mRNA compared to the PBS control. The data demonstrates significant inhibition of apo(a) mRNA by ISIS 494285 (SEQ ID NO: 28), ISIS 494286 (SEQ ID NO: 29), ISIS 494301 (SEQ ID NO: 39), ISIS 494302 (SEQ ID NO: 40) and ISIS 494311 (SEQ ID NO: 47).

TABLE 41

| Dose-dependent inhibition of human Apo(a) mRNA in transgenic mice | | | |
|---|---|---|---|
| ISIS No | Dose (mg/kg/wk) | % inhibition | $ED_{50}$ |
| 494285 | 50 | 98 | 1 |
| | 15 | 97 | |
| | 5 | 79 | |
| 494286 | 50 | 97 | 1 |
| | 15 | 91 | |
| | 5 | 80 | |
| 494301 | 50 | 98 | 3 |
| | 15 | 96 | |
| | 5 | 59 | |
| 494302 | 50 | 98 | 2 |
| | 15 | 88 | |
| | 5 | 72 | |
| 494311 | 50 | 99 | 1 |
| | 15 | 96 | |
| | 5 | 87 | |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 42, expressed as percent reduction of apo(a) protein levels compared to the PBS control. The data demonstrates significant reduction of apo (a) plasma protein levels by ISIS 494285, ISIS 494286, ISIS 494301, ISIS 494302 and ISIS 494311.

TABLE 42

| Dose-dependent inhibition of human apo(a) protein in transgenic mice | | | |
|---|---|---|---|
| ISIS No | Dose (mg/kg/wk) | % inhibition | $ED_{50}$ |
| 494285 | 50 | 88 | 2 |
| | 15 | 88 | |
| | 5 | 72 | |
| 494286 | 50 | 90 | 2 |
| | 15 | 85 | |
| | 5 | 75 | |
| 494301 | 50 | 89 | 5 |
| | 15 | 86 | |
| | 5 | 38 | |
| 494302 | 50 | 90 | 3 |
| | 15 | 82 | |
| | 5 | 61 | |
| 494311 | 50 | 90 | 3 |
| | 15 | 82 | |
| | 5 | 69 | |

Study 5

ISIS 494372, ISIS 498524, ISIS 498581, ISIS 498721, and ISIS 498833 were further evaluated in this model.

Treatment

Female human apo(a) transgenic mice were divided into treatment groups consisting of 4 mice each. The groups received intraperitoneal injections of ISIS 494372, ISIS 498524, ISIS 498581, ISIS 498721, or ISIS 498833 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 43, expressed as percent inhibition of apo(a) mRNA compared to the PBS control. The data demonstrates significant inhibition of apo(a) mRNA by ISIS 494372 (SEQ ID NO: 28), ISIS 498524 (SEQ ID NO: 93), ISIS 498581 (SEQ ID NO: 104), and ISIS 498721 (ATGCCTCGATAACTCCGTCC; SEQ ID NO: 134).

TABLE 43

Dose-dependent inhibition of human Apo(a) mRNA in transgenic mice

| ISIS No | Dose (mg/kg/wk) | % inhibition | $ED_{50}$ |
|---|---|---|---|
| 494372 | 50 | 88 | 18 |
| | 15 | 49 | |
| | 5 | 0 | |
| 498524 | 50 | 83 | 8 |
| | 15 | 74 | |
| | 5 | 34 | |
| 498581 | 50 | 98 | 7 |
| | 15 | 58 | |
| | 5 | 48 | |
| 498721 | 50 | 97 | 14 |
| | 15 | 68 | |
| | 5 | 0 | |
| 498833 | 50 | 61 | 155 |
| | 15 | 0 | |
| | 5 | 17 | |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 44, expressed as percent reduction of apo(a) protein levels compared to the PBS control. The data demonstrates significant reduction of apo (a) plasma protein levels by ISIS 494372 (SEQ ID NO: 28), ISIS 498581 (SEQ ID NO: 104), and ISIS 498721 (ATGCCTCGATAACTCCGTCC; SEQ ID NO: 134).

TABLE 44

Dose-dependent inhibition of human apo(a) protein in transgenic mice

| ISIS No | Dose (mg/kg/wk) | % inhibition | $ED_{50}$ |
|---|---|---|---|
| 494372 | 50 | 68 | 32 |
| | 15 | 25 | |
| | 5 | 12 | |
| 498524 | 50 | 38 | 118 |
| | 15 | 0 | |
| | 5 | 0 | |
| 498581 | 50 | 79 | 9 |
| | 15 | 52 | |
| | 5 | 49 | |
| 498721 | 50 | 81 | 10 |
| | 15 | 63 | |
| | 5 | 29 | |
| 498833 | 50 | 15 | 738 |
| | 15 | 0 | |
| | 5 | 67 | |

Example 8: Tolerability of Antisense Oligonucleotides Targeting Human Apo(a) in Rodent Models Gapmer antisense oligonucleotides targeting human apo (a) were selected from the studies described above for tolerability studies in CD1 mice and in Sprague Dawley rats. Rodents do not express endogenous apo(a), hence these studies tested the tolerability of each human antisense oligonucleotide in an animal rather than any phenotypic changes that may be caused by inhibiting apo(a) in the animal.

Tolerability in CD1 Mice: Study 1

CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male CD 1 mice were injected subcutaneously twice a week for 6 weeks with 50 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six-week old male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 45. ISIS oligonucleotides that caused changes in the levels of any of the liver or kidney function markers outside the expected range for antisense oligonucleotides were excluded in further studies.

TABLE 45

Plasma chemistry markers of CD1 mice

| | ALT (IU/L | AST (IU/L) | Albumin (g/dL) | BUN (mg/dL) | Creatinine (mg/dL) | Bilirubin (mg/dL) |
|---|---|---|---|---|---|---|
| PBS | 38 | 71 | 2.9 | 25.2 | 0.16 | 0.15 |
| ISIS 494159 | 615 | 525 | 2.7 | 23.9 | 0.11 | 0.20 |
| ISIS 494161 | 961 | 670 | 2.6 | 23.7 | 0.15 | 0.14 |
| ISIS 494162 | 1373 | 1213 | 2.7 | 23.7 | 0.14 | 0.18 |
| ISIS 494283 | 237 | 242 | 2.5 | 26.2 | 0.14 | 0.13 |
| ISIS 494284 | 192 | 307 | 2.3 | 27.1 | 0.14 | 0.10 |
| ISIS 494285 | 582 | 436 | 2.3 | 25.4 | 0.16 | 0.11 |
| ISIS 494286 | 191 | 227 | 2.5 | 21.1 | 0.12 | 0.15 |
| ISIS 494301 | 119 | 130 | 2.7 | 26.4 | 0.15 | 0.12 |
| ISIS 494302 | 74 | 96 | 2.8 | 24.8 | 0.14 | 0.15 |
| ISIS 494311 | 817 | 799 | 2.7 | 28.7 | 0.12 | 0.17 |
| ISIS 494337 | 722 | 397 | 2.5 | 20.0 | 0.13 | 0.11 |
| ISIS 494372 | 73 | 164 | 2.6 | 28.5 | 0.16 | 0.11 |
| ISIS 510548 | 2819 | 2245 | 3.1 | 26.0 | 0.15 | 0.15 |

Organ Weights

Liver, spleen and kidney weights were measured at the end of the study, and are presented in Table 46. ISIS oligonucleotides that caused any changes in organ weights outside the expected range for antisense oligonucleotides were excluded from further studies.

TABLE 46

Organ weights of CD1 mice (g)

| | Kidney | Liver | Spleen |
|---|---|---|---|
| PBS | 0.68 | 2.0 | 0.13 |
| ISIS 494159 | 0.68 | 3.0 | 0.21 |
| ISIS 494161 | 0.62 | 3.5 | 0.20 |
| ISIS 494162 | 0.60 | 3.3 | 0.20 |
| ISIS 494283 | 0.65 | 2.8 | 0.24 |
| ISIS 494284 | 0.69 | 2.7 | 0.29 |
| ISIS 494285 | 0.59 | 3.2 | 0.21 |
| ISIS 494286 | 0.64 | 2.8 | 0.25 |
| ISIS 494301 | 0.72 | 3.0 | 0.43 |
| ISIS 494302 | 0.63 | 2.3 | 0.23 |
| ISIS 494311 | 0.61 | 3.2 | 0.19 |

TABLE 46-continued

| Organ weights of CD1 mice (g) | | | |
|---|---|---|---|
| | Kidney | Liver | Spleen |
| ISIS 494337 | 0.56 | 2.3 | 0.17 |
| ISIS 494372 | 0.60 | 2.5 | 0.27 |
| ISIS 510548 | 0.55 | 3.7 | 0.20 |

Tolerability in Sprague Dawley Rats

Sprague-Dawley rats are a multipurpose model used for safety and efficacy evaluations. The rats were treated with ISIS antisense oligonucleotides selected from studies described above and evaluated for changes in the levels of various plasma chemistry markers.

Treatment

Groups of male Sprague Dawley rats were injected subcutaneously twice a week for 8 weeks with 30 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six male Sprague Dawley rats was injected subcutaneously twice a week for 8 weeks with PBS. Rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 47. ISIS oligonucleotides that caused changes in the levels of any of the liver or kidney function markers outside the expected range for antisense oligonucleotides were excluded in further studies.

TABLE 47

| Plasma chemistry markers of Sprague Dawley rats | | | | | | |
|---|---|---|---|---|---|---|
| | ALT (IU/L) | AST (IU/L) | Bilirubin (mg/dL) | Albumin (mg/dL) | BUN (mg/dL) | Creatinine (mg/dL) |
| PBS | 30 | 82 | 0.09 | 3.2 | 19 | 0.28 |
| ISIS 494159 | 182 | 208 | 0.14 | 3.4 | 22 | 0.35 |
| ISIS 494161 | 36 | 86 | 0.13 | 3.4 | 23 | 0.35 |
| ISIS 494162 | 102 | 158 | 0.17 | 2.6 | 28 | 0.32 |
| ISIS 494283 | 53 | 156 | 0.13 | 2.9 | 24 | 0.32 |
| ISIS 494284 | 34 | 113 | 0.08 | 2.0 | 28 | 0.32 |
| ISIS 494285 | 110 | 294 | 0.10 | 1.4 | 110 | 0.52 |
| ISIS 494286 | 40 | 83 | 0.07 | 1.6 | 48 | 0.44 |
| ISIS 494301 | 38 | 132 | 0.08 | 3.0 | 18 | 0.33 |
| ISIS 494302 | 47 | 105 | 0.09 | 3.2 | 19 | 0.34 |
| ISIS 494311 | 93 | 185 | 0.51 | 2.7 | 23 | 0.30 |
| ISIS 494372 | 54 | 119 | 0.12 | 3.0 | 19 | 0.33 |
| ISIS 510548 | 116 | 181 | 0.11 | 1.7 | 65 | 0.66 |

Kidney Function

To evaluate the effect of ISIS oligonucleotides on kidney function, urine levels of total protein and creatinine were measured using an automated clinical chemistry analyzer (Hitachi Olympus AU400e, Melville, N.Y.). Results are presented in Table 48, expressed in mg/dL.

TABLE 48

| Kidney function markers (mg/dL) in Sprague-Dawley rats | | |
|---|---|---|
| | Creatinine | Total protein |
| PBS | 103 | 118 |
| ISIS 494159 | 70 | 279 |
| ISIS 494161 | 105 | 315 |
| ISIS 494162 | 58 | 925 |
| ISIS 494283 | 114 | 1091 |
| ISIS 494284 | 97 | 2519 |
| ISIS 494285 | 38 | 2170 |
| ISIS 494286 | 51 | 625 |
| ISIS 494301 | 62 | 280 |
| ISIS 494302 | 101 | 428 |
| ISIS 494311 | 48 | 1160 |
| ISIS 494372 | 46 | 154 |
| ISIS 510548 | 55 | 2119 |

Organ Weights

Liver, spleen and kidney weights were measured at the end of the study, and are presented in Table 49. ISIS oligonucleotides that caused any changes in organ weights outside the expected range for antisense oligonucleotides were excluded from further studies.

TABLE 49

| Organ weights of Sprague Dawley rats (g) | | | |
|---|---|---|---|
| | Kidney | liver | Spleen |
| PBS | 3.5 | 13.1 | 0.9 |
| ISIS 494159 | 3.1 | 11.7 | 1.6 |
| ISIS 494161 | 2.8 | 12.5 | 2 |
| ISIS 494162 | 3.1 | 14.2 | 1.6 |
| ISIS 494283 | 3.3 | 12.9 | 2.3 |
| ISIS 494284 | 4.1 | 15.8 | 2.7 |
| ISIS 494285 | 3.8 | 13.4 | 0.8 |
| ISIS 494286 | 4.2 | 16.7 | 2.5 |
| ISIS 494301 | 3.2 | 12.1 | 2.3 |
| ISIS 494302 | 3.4 | 13.3 | 2.4 |
| ISIS 494311 | 3.5 | 17.4 | 3.2 |
| ISIS 494372 | 3.6 | 12.9 | 3.2 |
| ISIS 510548 | 6.4 | 21.2 | 1.5 |

The finding from the rodent tolerability studies showed that in general, taking into consideration all the tolerability markers screened, ISIS 494372 was the best tolerated antisense compound in both the CD1 mouse model and the Sprague Dawley rat model.

Example 9: Pharmacokinetics of Antisense Oligonucleotide in CD1 Mice

CD1 mice were treated with ISIS oligonucleotides and the oligonucleotide concentrations in the liver and kidney were evaluated.

Treatment

Groups of four CD1 mice each were injected subcutaneously twice per week for 6 weeks with 50 mg/kg of ISIS 494283, ISIS 494284, ISIS 494286, ISIS 494301, ISIS 494302, or ISIS 494372. The mice were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT- GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT).

The results are presented in Table 50, expressed as g/g liver or kidney tissue. The data indicates that ISIS 494372 was at an acceptable concentration in the liver and kidneys.

TABLE 50

| Oligonucleotide concentration (μg/g tissue) of ISIS oligonucleotides in CD1 mice | | |
|---|---|---|
| ISIS No | Liver | Kidney |
| 494283 | 581 | 549 |
| 494284 | 511 | 678 |
| 494286 | 368 | 445 |
| 494301 | 812 | 347 |
| 494302 | 617 | 263 |
| 494372 | 875 | 516 |

Example 10: Pharmacokinetics of Antisense Oligonucleotide in Sprague Dawley Rats Male Sprague Dawley rats were treated with ISIS oligonucleotides and the oligonucleotide concentrations in the liver and kidney were evaluated.

Treatment

Groups of four rats each were injected subcutaneously twice per week for 3 weeks with 10 mg/kg of ISIS 494283, ISIS 494284, ISIS 494286, ISIS 494301, ISIS 494302, or ISIS 494372. The rats were sacrificed 2 days following the final dose. Livers were harvested for analysis.

Measurement of Oligonucleotide Concentration

The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT).

The results are presented in Table 51, expressed as μg/g liver or kidney tissue. The data indicates that ISIS 494372 was at an acceptable concentration in the liver and kidneys.

TABLE 51

| Oligonucleotide concentration (μg/g tissue) of ISIS oligonucleotides in Sprague Dawley rats | | |
|---|---|---|
| ISIS No | Liver | Kidney |
| 494283 | 220 | 434 |
| 494284 | 178 | 573 |
| 494286 | 234 | 448 |
| 494301 | 279 | 540 |
| 494302 | 205 | 387 |
| 494372 | 288 | 663 |

Example 11: Effect of ISIS Antisense Oligonucleotides Targeting Human Apo(a) in Cynomolgus Monkeys Cynomolgus monkeys were treated with ISIS antisense oligonucleotides selected from studies described above. At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well.

The human antisense oligonucleotides tested are also cross-reactive with the rhesus mRNA sequence (XM_001098061.1; designated herein as SEQ ID NO: 132). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 132 is presented in Table 52. Each antisense oligonucleotide targets more than one region in SEQ ID NO: 132 and has multiple start sites. "Start site" indicates the 5'-most nucleotide to which the gapmer is targeted in the rhesus monkey sequence. 'Mismatches' indicates the number of nucleotides mismatched between the human oligonucleotide sequence and the rhesus sequence.

Antisense oligonucleotide tolerability, as well as their pharmacokinetic profile in the liver and kidney, was evaluated.

TABLE 52

| Antisense oligonucleotides complementary to SEQ ID NO: 132 | | |
|---|---|---|
| ISIS No | Start Site | Mismatches |
| 494283 | 278 | 2 |
| | 620 | 2 |
| | 923 | 2 |
| | 1265 | 2 |
| | 1607 | 1 |
| | 1949 | 1 |
| | 2267 | 1 |
| | 2609 | 1 |
| | 2951 | 1 |
| | 3293 | 1 |
| 494284 | 279 | 1 |
| | 621 | 1 |
| | 924 | 1 |
| | 1266 | 1 |
| | 1608 | 1 |
| | 1950 | 1 |
| | 2268 | 1 |
| | 2610 | 1 |
| | 2952 | 1 |
| | 3294 | 1 |
| 494286 | 281 | 1 |
| | 623 | 1 |
| | 926 | 1 |
| | 1268 | 1 |
| | 1610 | 2 |
| | 1952 | 2 |
| | 2270 | 2 |
| | 2612 | 2 |
| | 2954 | 2 |
| | 3296 | 2 |
| 494301 | 322 | 2 |
| | 664 | 2 |
| | 967 | 2 |

TABLE 52-continued

Antisense oligonucleotides complementary to SEQ ID NO: 132

| ISIS No | Start Site | Mismatches |
|---|---|---|
|  | 1309 | 1 |
|  | 1651 | 2 |
| 494302 | 323 | 2 |
|  | 968 | 2 |
|  | 1310 | 1 |
|  | 1652 | 2 |
| 494372 | 1186 | 2 |
|  | 1870 | 1 |
|  | 2188 | 1 |

Treatment

Prior to the study, the monkeys were kept in quarantine for at least a 30-day period, during which the animals were observed daily for general health. The monkeys were 2-4 years old and weighed between 2 and 4 kg. Seven groups of four randomly assigned male cynomolgus monkeys each were injected subcutaneously with ISIS oligonucleotide or PBS using a stainless steel dosing needle and syringe of appropriate size into the one of four sites on the back of the monkeys. The injections were given in clock-wise rotation; one site per dosing. The monkeys were dosed four times a week for the first week (days 1, 3, 5, and 7) as loading doses, and subsequently once a week for weeks 2-12, with 40 mg/kg of ISIS 494283, ISIS 494284, ISIS 494286, ISIS 494301, ISIS 494302, or ISIS 494372. A control group of 8 cynomolgus monkeys was injected with PBS subcutaneously thrice four times a week for the first week (days 1, 3, 5, and 7), and subsequently once a week for weeks 2-12.

During the study period, the monkeys were observed at least once daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For instance, one animal in the treatment group of ISIS 494302 was found moribund on day 56 and was euthanized. Scheduled euthanasia of the animals was conducted on days 86 and 87 by exsanguination under deep anesthesia. The protocols described in the Example were approved by the Institutional Animal Care and Use Committee (IACUC).

Target Reduction
RNA Analysis

On day 86, RNA was extracted from liver tissue for real-time PCR analysis of apo(a) using human primer probe set ABI Hs00916691_m1 (Applied Biosystems, Carlsbad Calif.). Results are presented as percent inhibition of apo(a) mRNA, relative to PBS control. As shown in Table 53, treatment with ISIS antisense oligonucleotides resulted in significant reduction of apo(a) mRNA in comparison to the PBS control.

The mRNA levels of plasminogen, another kringle-containing protein, were also measured. Treatment with ISIS 494372 did not alter the mRNA levels of plasminogen.

TABLE 53

Percent Inhibition of apo(a) mRNA in the cynomolgus monkey liver relative to the PBS control

| ISIS No | % inhibition |
|---|---|
| 494283 | 91 |
| 494284 | 99 |

TABLE 53-continued

Percent Inhibition of apo(a) mRNA in the cynomolgus monkey liver relative to the PBS control

| ISIS No | % inhibition |
|---|---|
| 494286 | 96 |
| 494301 | 88 |
| 494302 | 89 |
| 494372 | 93 |

Protein Analysis

On different days, one mL of blood was collected from the cephalic, saphenous, or femoral vein of all study monkeys. The blood samples were put into tubes containing K2-EDTA for plasma separation. The tubes were centrifuged at 3,000 rpm for 10 min at room temperature to obtain plasma. Apo(a) protein levels were analyzed by an Apo(a) ELISA kit (Mercodia 10-1106-01, Uppsala, Sweden). Results are presented as percentage change of levels from the baseline. As shown in Table 54, treatment with several ISIS antisense oligonucleotides resulted in significant reduction of apo(a) protein levels in comparison to the PBS control. Specifically, treatment with ISIS 494372 reduced cynomolgous plasma protein levels of apo(a).

The protein levels of apoB were also measured in the study groups. Antisense inhibition of apo(a) had no effect on apoB levels.

TABLE 54

Apo(a) plasma protein levels (% inhibition over baseline values) in the cynomolgus monkey

|  | Day 16 | Day 30 | Day 44 | Day 56 | Day 72 | Day 86 |
|---|---|---|---|---|---|---|
| PBS | 0 | 0 | 10 | 0 | 0 | 0 |
| ISIS 494283 | 78 | 79 | 81 | 66 | 66 | 70 |
| ISIS 494284 | 92 | 95 | 95 | 93 | 93 | 94 |
| ISIS 494286 | 92 | 95 | 96 | 94 | 94 | 94 |
| ISIS 494301 | 41 | 45 | 52 | 20 | 17 | 29 |
| ISIS 494302 | 17 | 0 | 2 | 0 | 0 | 20 |
| ISIS 494372 | 67 | 80 | 83 | 79 | 78 | 81 |

Tolerability Studies
Body and Organ Weight Measurements

To evaluate the effect of ISIS oligonucleotides on the overall health of the animals, body and organ weights were measured at day 86. Body weights were measured and are presented in Table 55. Organ weights were measured and the data is presented in Table 56. The results indicate that treatment with ISIS 494372 was well tolerated in terms of the body and organ weights of the monkeys.

TABLE 55

Body weights (g) in the cynomolgus monkey

|  | Day 14 | Day 35 | Day 49 | Day 56 | Day 70 | Day 84 |
|---|---|---|---|---|---|---|
| PBS | 2637 | 2691 | 2748 | 2733 | 2739 | 2779 |
| ISIS 494283 | 2591 | 2670 | 2698 | 2656 | 2704 | 2701 |
| ISIS 494284 | 2559 | 2661 | 2676 | 2675 | 2662 | 2646 |
| ISIS 494286 | 2693 | 2770 | 2838 | 2800 | 2796 | 2816 |
| ISIS 494301 | 2587 | 2604 | 2627 | 2591 | 2596 | 2604 |
| ISIS 494302 | 2759 | 2760 | 2839 | 2825 | 3113 | 3122 |
| ISIS 494372 | 2719 | 2877 | 2985 | 2997 | 3037 | 3036 |

TABLE 56

| Organ weights (% body weight) in the cynomolgus monkey | | | | | |
|---|---|---|---|---|---|
| | Spleen | Kidneys | Liver | Heart | Lungs |
| PBS | 0.14 | 0.38 | 2.2 | 0.33 | 0.51 |
| ISIS 494283 | 0.24 | 0.95 | 2.8 | 0.33 | 0.49 |
| ISIS 494284 | 0.19 | 0.60 | 2.6 | 0.36 | 0.55 |
| ISIS 494286 | 0.22 | 0.63 | 2.7 | 0.38 | 0.55 |
| ISIS 494301 | 0.38 | 0.81 | 3.0 | 0.36 | 0.61 |
| ISIS 494302 | 0.17 | 0.95 | 2.5 | 0.39 | 0.57 |
| ISIS 494372 | 0.18 | 1.16 | 2.6 | 0.36 | 0.56 |

Liver Function

To evaluate the effect of ISIS oligonucleotides on hepatic function, monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. Levels of various liver function markers were measured using a Toshiba 200FR NEO chemistry analyzer (Toshiba Co., Japan). Plasma levels of ALT and AST were measured and the results are presented in Table 57, expressed in IU/L. Bilirubin, a liver function marker, was similarly measured and is presented in Table 57, expressed in mg/dL. The results indicate that treatment with ISIS 494372 was well tolerated in terms of the liver function in monkeys.

TABLE 57

| Liver function markers in cynomolgus monkey plasma | | | |
|---|---|---|---|
| | ALT (IU/L) | AST (IU/L) | Bilirubin (mg/dL) |
| PBS | 33 | 43 | 0.20 |
| ISIS 494283 | 75 | 73 | 0.12 |
| ISIS 494284 | 115 | 79 | 0.17 |
| ISIS 494286 | 67 | 73 | 0.13 |
| ISIS 494301 | 129 | 90 | 0.15 |
| ISIS 494302 | 141 | 75 | 0.15 |
| ISIS 494372 | 46 | 75 | 0.17 |

C-reactive Protein Level Analysis

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 494372 did not cause any inflammation in monkeys.

TABLE 58

| C-reactive protein levels (mg/L) in cynomolgus monkey plasma | |
|---|---|
| | CRP |
| PBS | 1.4 |
| ISIS 494283 | 14.7 |
| ISIS 494284 | 7.7 |
| ISIS 494286 | 4.4 |
| ISIS 494301 | 3.5 |

TABLE 58-continued

| C-reactive protein levels (mg/L) in cynomolgus monkey plasma | |
|---|---|
| | CRP |
| ISIS 494302 | 2.4 |
| ISIS 494372 | 10.2 |

Complement C3 Analysis

To evaluate any effect of ISIS oligonucleotides on the complement pathway in cynomolgus monkeys, blood samples were taken for analysis on day 84 (pre-dose) and day 85 (24 hours post-dose). Approximately 0.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 was measured using a Toshiba 200FR NEO chemistry analyzer (Toshiba Co., Japan). The results indicate that treatment with ISIS 494372 did not cause any effect on the complement pathway in monkeys.

TABLE 59

| Complement C3 levels (mg/dL) in cynomolgus monkey plasma | | |
|---|---|---|
| | Pre-dose | Post-dose |
| PBS | 140 | 139 |
| ISIS 494283 | 127 | 101 |
| ISIS 494284 | 105 | 75 |
| ISIS 494286 | 84 | 38 |
| ISIS 494301 | 118 | 76 |
| ISIS 494302 | 98 | 58 |
| ISIS 494372 | 123 | 109 |

Hematology

To evaluate any effect of ISIS oligonucleotides in cynomolgus monkeys on hematologic parameters, blood samples of approximately 0.5 mL of blood was collected on day 87 from each of the available study animals in tubes containing $K_2$-EDTA. Samples were analyzed for red blood cell (RBC) count, white blood cells (WBC) count, as well as for platelet count, using an ADVIA120 hematology analyzer (Bayer, USA). The data is presented in Table 60.

The data indicate that treatment with ISIS 494372 was well tolerated in terms of the hematologic parameters of the monkeys.

TABLE 60

| Blood cell counts in cynomolgus monkeys | | | |
|---|---|---|---|
| | WBC ($\times 10^3/\mu L$) | RBC ($\times 10^6/\mu L$) | Platelet ($\times 10^3/\mu L$) |
| PBS | 15 | 6.3 | 329 |
| ISIS 494283 | 16 | 5.3 | 456 |
| ISIS 494284 | 13 | 6.3 | 330 |
| ISIS 494286 | 14 | 5.5 | 304 |
| ISIS 494301 | 15 | 6.0 | 392 |
| ISIS 494302 | 12 | 6.3 | 305 |
| ISIS 494372 | 11 | 6.1 | 447 |

Example 12: Characterization of the Pharmacological Activity of ISIS 494372 in Cynomolgus Monkeys The pharmacological activity of ISIS 494372 was characterized by measuring liver apo(a) mRNA and plasma apo(a) levels in monkeys administered the compound over 13 weeks and allowed to recover for another 13 weeks.

Treatment

Five groups of 14 randomly assigned male and female cynomolgus monkeys each were injected subcutaneously with ISIS oligonucleotide or PBS using a stainless steel dosing needle and syringe of appropriate size into the one of four sites on the back (scapular region) of the monkeys. The monkeys were dosed four times a week for the first week (days 1, 3, 5, and 7) as loading doses, and subsequently once a week for weeks 2-13 as maintenance doses, as shown in the table below. The loading dose during the first week is expressed as mg/kg/dose, while the maintenance doses on weeks 2-13 are expressed as mg/kg/week.

TABLE 61

Dosing groups in cynomolgus monkeys

| | | | Number of animals for necropsy | | |
|---|---|---|---|---|---|
| Group | Test Article | Dose | Interim | Terminal | Recovery |
| 1 | PBS | — | 4 | 6 | 4 |
| 2 | ISIS 494372 | 4 | — | 6 | — |
| 3 | | 8 | — | 6 | — |
| 4 | | 12 | 4 | 6 | 4 |
| 5 | | 40 | 4 | 6 | 4 |

Liver samples from animals were taken at the interim, terminal and recovery phases of the study for the analyses of apo(a) mRNA. In addition, plasma samples were collected on different days to measure apo(a) protein levels. This non-clinical study was conducted in accordance with the United States Food and Drug Administration (FDA) Good Laboratory Practice (GLP) Regulations, 21 CFR Part 58.

RNA Analysis

Liver samples were collected from monkeys on days 30, 93, and 182, and frozen. Briefly, a piece (0.2 g) of frozen liver was homogenized in 2 mL of RLT solution (Qiagen). The resulting lysate was applied to Qiagen RNeasy mini columns. After purification and quantification, the tissues were subjected to RT-PCR analysis. The Perkin-Elmer ABI Prism 7700 Sequence Detection System, which uses real-time fluorescent RT-PCR detection, was used to quantify apo(a) mRNA. The assay is based on a target-specific probe labeled with fluorescent reporter and quencher dyes at opposite ends. The probe was hydrolyzed through the 5'-exonuclease activity of Taq DNA polymerase, leading to an increasing fluorescence emission of the reporter dye that can be detected during the reaction. A probe set (ABI Rhesus LPA probe set ID Rh02789275_ml, Applied Biosystems, Carlsbad Calif.) targeting position 1512 of the rhesus monkey apo(a) mRNA transcript GENBANK Accession No XM_001098061.2 (SEQ ID NO: XXX) sequence was used to measure cynomolgus monkey liver apo(a) mRNA expression levels. Apo(a) expression was normalized using RIBOGREEN®. Results are presented as percent inhibition of apo(a) mRNA, relative to PBS control.

As shown in Table 62, treatment with ISIS 494372 resulted in a dose-dependent reduction of apo(a) mRNA in comparison to the PBS control. At day 30, hepatic apo(a) mRNA expression was reduced in a dose-dependent manner by 74% and 99% in the 12 mg/kg/week and 40 mg/kg/week dosing cohorts, respectively. These reductions are statistically significant by one-way ANOVA (Dunnett's multiple comparison test, $P<0.05$).

Apo(a) mRNA levels were also measured during the recovery phase. Liver expression levels at day 88 after the last dose were still reduced 49% and 69% in the 12 mg/kg/week and 40 mg/kg/week dosing cohorts, respectively.

TABLE 62

Percent inhibition levels of liver apo(a) mRNA in the dosing phase in cynomolgus monkeys treated with ISIS 494372

| Day | Dose (mg/kg/wk) | % inhibition |
|---|---|---|
| 30 | 12 | 73 |
| | 40 | 99 |
| 93 | 4 | 44 |
| | 8 | 43 |
| | 12 | 53 |
| | 40 | 93 |

Protein Analysis

Approximately 20 µl of plasma was analyzed using a commercially available apo(a) ELISA kit (Mercodia 10-1106-01, Uppsala, Sweden). The assay protocol was performed as described by the manufacturer. The results are presented in Tables 63 and 64 as percentage change from Day 1 pre-dose apo(a) plasma protein concentrations. Statistically significant differences from Day 1 baseline plasma apo(a) using the Dunnett's multicomparison test are marked with an asterisk.

Maximal reduction in plasma apo(a) protein was observed in all dosing cohorts by Day 93. In the recovery phase, apo(a) plasma protein levels in the 40 mg/kg/week dosing cohort were at 22% and 93% of the baseline after 4 and 13 weeks (Days 121 and 182) of recovery, respectively. The rate of recovery in the 12 mg/kg/week cohort was similar to that seen in the 40 mg/kg/week cohort.

TABLE 63

Apo(a) plasma protein levels as a percent of Day 1 levels in the dosing phase in cynomolgus monkeys treated with ISIS 494372

| Day | Dose (mg/kg/wk) | % |
|---|---|---|
| 30 | 4 | 93 |
| | 8 | 70 |
| | 12 | 49 |
| | 40 | 15* |
| 93 | 4 | 73 |
| | 8 | 56 |
| | 12 | 32* |
| | 40 | 11* |

TABLE 64

Apo(a) plasma protein levels as a percent of Day 1 levels in the recovery phase in cynomolgus monkeys treated with ISIS 494372

| Day | Dose (mg/kg/wk) | % |
|---|---|---|
| 121 | 12 | 38* |
| | 40 | 22* |
| 182 | 12 | 84 |
| | 40 | 93 |

Example 13: Measurement of Viscosity of ISIS Antisense Oligonucleotides Targeting Human Apo(a)

The viscosity of select antisense oligonucleotides from the studies described above was measured with the aim of screening out antisense oligonucleotides which have a viscosity more than 40 cP. Oligonucleotides having a viscosity greater than 40 cP would have less than optimal viscosity.

ISIS oligonucleotides (32-35 mg) were weighed into a glass vial, 120 µL of water was added and the antisense oligonucleotide was dissolved into solution by heating the vial at 50° C. Part (75 µL) of the pre-heated sample was pipetted to a micro-viscometer (Cambridge). The temperature of the micro-viscometter was set to 25° C. and the viscosity of the sample was measured. Another part (20 µL) of the pre-heated sample was pipetted into 10 mL of water for UV reading at 260 nM at 85° C. (Cary UV instrument). The results are presented in Table 65 and indicate that most of the antisense oligonucleotides solutions are optimal in their viscosity under the criterion stated above. Those that were not optimal are marked as 'viscous'. Specifically, ISIS 494372 was optimal in its viscosity under the criterion stated above.

TABLE 65

Viscosity and concentration of ISIS antisense oligonucleotides targeting human Apo(a)

| ISIS No | Motif | Viscosity (cP) | Concentration (mg/mL) |
|---|---|---|---|
| 494158 | 5-10-5 MOE | 9.0 | 350 |
| 494159 | 5-10-5 MOE | 11.7 | 325 |
| 494161 | 5-10-5 MOE | 12.0 | 350 |
| 494162 | 5-10-5 MOE | 25.8 | 350 |
| 494163 | 5-10-5 MOE | Viscous | 275 |
| 494243 | 5-10-5 MOE | 28.4 | 325 |
| 494244 | 5-10-5 MOE | 19.2 | 300 |
| 494283 | 3-10-4 MOE | 13.4 | 300 |
| 494284 | 5-10-5 MOE | 13.4 | 350 |
| 494285 | 5-10-5 MOE | 23.1 | 350 |
| 494286 | 5-10-5 MOE | 16.5 | 275 |
| 494301 | 5-10-5 MOE | 17.1 | 325 |
| 494302 | 5-10-5 MOE | 24.3 | 350 |
| 494304 | 5-10-5 MOE | 49.3 | 275 |
| 494311 | 5-10-5 MOE | 10.8 | 325 |
| 494337 | 5-10-5 MOE | 29.5 | 325 |
| 494372 | 5-10-5 MOE | 12.5 | 350 |
| 494466 | 5-10-5 MOE | Viscous | 275 |
| 494470 | 5-10-5 MOE | 16.7 | 350 |
| 494472 | 5-10-5 MOE | 23.6 | 350 |
| 498408 | 5-10-5 MOE | 31.5 | 300 |
| 510548 | 5-10-5 MOE | 9.0 | 350 |
| 512947 | 3-10-4 MOE | 6.8 | 350 |
| 512958 | 5-10-5 MOE | 26.0 | 350 |

The invention claimed is:

1. A method of treating, slowing the progression of, or ameliorating a symptom of hyperlipidemia in a subject, comprising:

administering to said subject a compound comprising a modified oligonucleotide, wherein:

the modified oligonucleotide consists of 14 to 25 linked nucleosides and comprises a nucleobase sequence comprising a portion of at least 14 contiguous nucleobases complementary to an equal length portion of nucleobases 3900 to 3923 of SEQ ID NO: 1, wherein the nucleobase sequence of the modified oligonucleotide is at least 95% complementary to SEQ ID NO: 1, including any salt thereof, whereby the administration treats, slows the progression of, or ameliorates a symptom of hyperlipidemia in the subject.

2. The method of claim 1, wherein the subject has elevated apo(a) and/or Lp(a) levels.

3. The method of claim 1, wherein apo(a) mRNA and/or protein levels are lowered.

4. The method of claim 1, wherein the modified oligonucleotide consists of 18 to 24, 19 to 22, 15 to 25, 16 or 20 linked nucleosides.

5. The method of claim 1, wherein the modified oligonucleotide comprises a nucleobase sequence comprising a portion of at least 16, at least 18, at least 19, or at least 20 contiguous nucleobases complementary to an equal length portion of SEQ ID NO: 1.

6. The method of claim 1, wherein the nucleobase sequence of the modified oligonucleotide is at least 96%, 97%, 98% or 99% complementary to SEQ ID NO: 1, or is 100% complementary to SEQ ID NO:1.

7. The method of claim 1, wherein the modified oligonucleotide consists of 14 to 25 linked nucleosides and comprises a nucleobase sequence comprising at least 14, at least 15, at least 16, at least 17, at least 18, at least 19, or 20 contiguous nucleobases of the nucleobase sequence of SEQ ID NO: 58.

8. The method of claim 1, wherein the modified oligonucleotide is single-stranded.

9. The method of claim 1, wherein at least one internucleoside linkage is a modified internucleoside linkage.

10. The method of claim 9, wherein at least one internucleoside linkage is a phosphorothioate internucleoside linkage.

11. The method of claim 1, wherein the modified oligonucleotide comprises at least one modified sugar.

12. The method of claim 11, wherein at least one modified sugar is a bicyclic sugar.

13. The method of claim 11, wherein at least one modified sugar comprises a 2'-O-methoxyethyl, a constrained ethyl, a 3'-fluoro-HNA or a 4'-$(CH_2)_n$—O-2' bridge, wherein n is 1 or 2.

14. The method of claim 1, wherein at least one nucleoside comprises a modified nucleobase.

15. The method of claim 14, wherein the modified nucleobase is a 5-methylcytosine.

16. The method of claim 1, wherein the modified oligonucleotide consists of 14 to 25 linked nucleosides and comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

17. The method of claim 16, wherein the modified oligonucleotide consists of 20 linked nucleosides and comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

18. The method of claim 16, wherein the modified oligonucleotide consists of 20 linked nucleosides.

19. The method of claim 1, wherein the modified oligonucleotide consists of 20 contiguous linked nucleosides of SEQ ID NO: 58 and the modified oligonucleotide further comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethy sugar, wherein at least one internucleoside linkage is a modified internucleoside linkage and wherein each cytosine residue is a 5-methylcytosine.

20. The method of claim 1, wherein a therapeutically effective dose of the modified oligonucleotide is administered, whereby hyperlipidemia in the subject is treated, the progression slowed or a symptom ameliorated.

21. The method of claim 20, wherein the subject has or has had aneurysm, angina, arrhythmia, atherosclerosis, cerebrovascular disease, coronary artery disease, coronary heart disease, myocardial infarction, peripheral vascular disease, peripheral artery disease, peripheral artery occlusive disease, retinal vascular occlusion, or stroke.

22. The method of claim 1, wherein the subject is a human subject.

23. The method of claim 1, wherein the compound is a first agent and is co-administered with one or more secondary agents or therapy.

24. The method of claim 1, wherein the modified oligonucleotide has a viscosity of less than 40 cP.

25. The method of claim 23, wherein the one or more secondary agents or therapy is/are selected from among an apo(a) lowering agent, a Lp(a) lowering agent, an agent to reduce thromboembolism formation, a glucose-lowering agent, a LDL lowering agent, a triglyceride lowering agent, a cholesterol lowering agent, a HDL raising agent, an anti-inflammatory agent, an Alzheimer Disease drug, a non-steroidal anti-inflammatory drug (NSAID), fish oil, niacin, nicotinic acid, an apoB inhibitor, a CETP inhibitor, a thyroid hormone analog, a HMG-CoA reductase inhibitor, a fibrate, a microsomal triglyceride transfer protein inhibitor and Lp(a) apheresis.

* * * * *

SEQUENCE LISTING

```
<160> NUMBER OF SEQ ID NOS: 134

<210> SEQ ID NO 1
<211> LENGTH: 6489
<212> TYPE: DNA
<213> ORGANISM: Homo sapiens

<400> SEQUENCE: 1

aggtaccttt ggggctggct ttctcaagga agcccagctc cctgtgattg agaatgaagt     60

gtgcaatcgc tatgactggg attgggacac actttctggg cactgctggc cagtcccaaa    120

atggaacata aggaagtggt tcttctactt cttttatttc tgaaatcagc agcacctgag    180

caaagccatg tggtccagga ttgctaccat ggtgatggac agagttatcg aggcacgtac    240

tccaccactg tcacaggaag gacctgccaa gcttggtcat ctatgacacc acatcaacat    300

aataggacca cagaaaacta cccaaatgct ggcttgatca tgaactactg caggaatcca    360

gatgctgtgg cagctcctta ttgttatacg agggatcccg gtgtcaggtg ggagtactgc    420

aacctgacgc aatgctcaga cgcagaaggg actgccgtcg cgcctccgac tgttaccccg    480

gttccaagcc tagaggctcc ttccgaacaa gcaccgactg agcaaaggcc tggggtgcag    540

gagtgctacc atggtaatgg acagagttat cgaggcacat actccaccac tgtcacagga    600

agaacctgcc aagcttggtc atctatgaca ccacactcgc atagtcggac cccagaatac    660

tacccaaatg ctggcttgat catgaactac tgcaggaatc cagatgctgt ggcagctcct    720

tattgttata cgagggatcc cggtgtcagg tgggagtact gcaacctgac gcaatgctca    780

gacgcagaag ggactgccgt cgcgcctccg actgttaccc cggttccaag cctagaggct    840

ccttccgaac aagcaccgac tgagcaaagg cctggggtgc aggagtgcta ccatggtaat    900

ggacagagtt atcgaggcac atactccacc actgtcacag gaagaacctg ccaagcttgg    960

tcatctatga caccacactc gcatagtcgg accccagaat actacccaaa tgctggcttg   1020
```

-continued

```
atcatgaact actgcaggaa tccagatgct gtggcagctc cttattgtta tacgagggat   1080
cccggtgtca ggtgggagta ctgcaacctg acgcaatgct cagacgcaga agggactgcc   1140
gtcgcgcctc cgactgttac cccggttcca agcctagagg ctccttccga acaagcaccg   1200
actgagcaga ggcctggggt gcaggagtgc taccacggta atggacagag ttatcgaggc   1260
acatactcca ccactgtcac tggaagaacc tgccaagctt ggtcatctat gacaccacac   1320
tcgcatagtc ggaccccaga atactaccca aatgctggct tgatcatgaa ctactgcagg   1380
aatccagatg ctgtggcagc tccttattgt tatacgaggg atcccggtgt caggtgggag   1440
tactgcaacc tgacgcaatg ctcagacgca gaagggactg ccgtcgcgcc tccgactgtt   1500
accccggttc caagcctaga ggctccttcc gaacaagcac cgactgagca aaggcctggg   1560
gtgcaggagt gctaccatgg taatggacag agttatcgag gcacatactc caccactgtc   1620
acaggaagaa cctgccaagc ttggtcatct atgacaccac actcgcatag tcggacccca   1680
gaatactacc caaatgctgg cttgatcatg aactactgca ggaatccaga tgctgtggca   1740
gctccttatt gttatacgag ggatcccggt gtcaggtggg agtactgcaa cctgacgcaa   1800
tgctcagacg cagaagggac tgccgtcgcg cctccgactg ttaccccggt tccaagccta   1860
gaggctcctt ccgaacaagc accgactgag caaaggcctg gggtgcagga gtgctaccat   1920
ggtaatggac agagttatcg aggcacatac tccaccactg tcacaggaag aacctgccaa   1980
gcttggtcat ctatgacacc acactcgcat agtcggaccc cagaatacta cccaaatgct   2040
ggcttgatca tgaactactg caggaatcca gatgctgtgg cagctcctta ttgttatacg   2100
agggatcccg gtgtcaggtg ggagtactgc aacctgacgc aatgctcaga cgcagaaggg   2160
actgccgtcg cgcctccgac tgttaccccg gttccaagcc tagaggctcc ttccgaacaa   2220
gcaccgactg agcaaaggcc tggggtgcag gagtgctacc atggtaatgg acagagttat   2280
cgaggcacat actccaccac tgtcacagga agaacctgcc aagcttggtc atctatgaca   2340
ccacactcgc atagtcggac cccagaatac tacccaaatg ctggcttgat catgaactac   2400
tgcaggaatc cagatgctgt ggcagctcct tattgttata cgagggatcc cggtgtcagg   2460
tgggagtact gcaacctgac gcaatgctca gacgcagaag ggactgccgt cgcgcctccg   2520
actgttaccc cggttccaag cctagaggct ccttccgaac aagcaccgac tgagcagagg   2580
cctggggtgc aggagtgcta ccacggtaat ggacagagtt atcgaggcac atactccacc   2640
actgtcactg gaagaacctg ccaagcttgg tcatctatga caccacactc gcatagtcgg   2700
accccagaat actacccaaa tgctggcttg atcatgaact actgcaggaa tccagatcct   2760
gtggcagccc cttattgtta tacgagggat cccagtgtca ggtgggagta ctgcaacctg   2820
acacaatgct cagacgcaga agggactgcc gtcgcgcctc caactattac cccgattcca   2880
agcctagagg ctccttctga acaagcacca actgagcaaa ggcctggggt gcaggagtgc   2940
taccacggaa atggacagag ttatcaaggc acatacttca ttactgtcac aggaagaacc   3000
tgccaagctt ggtcatctat gacaccacac tcgcatagtc ggaccccagc atactaccca   3060
aatgctggct tgatcaagaa ctactgccga aatccagatc ctgtggcagc cccttggtgt   3120
tatacaacag atcccagtgt caggtgggag tactgcaacc tgacacgatg ctcagatgca   3180
gaatggactg ccttcgtccc tccgaatgtt attctggctc caagcctaga ggcttttttt   3240
gaacaagcac tgactgagga aacccccggg gtacaggact gctactacca ttatggacag   3300
agttaccgag gcacatactc caccactgtc acaggaagaa cttgccaagc ttggtcatct   3360
atgacaccac accagcatag tcggacccca gaaaactacc caaatgctgg cctgaccagg   3420
```

aactactgca ggaatccaga tgctgagatt cgcccttggt gttacaccat ggatcccagt 3480
gtcaggtggg agtactgcaa cctgacacaa tgcctggtga cagaatcaag tgtccttgca 3540
actctcacgg tggtcccaga tccaagcaca gaggcttctt ctgaagaagc accaacggag 3600
caaagccccg gggtccagga ttgctaccat ggtgatggac agagttatcg aggctcattc 3660
tctaccactg tcacaggaag gacatgtcag tcttggtcct ctatgacacc acactggcat 3720
cagaggacaa cagaatatta tccaaatggt ggcctgacca ggaactactg caggaatcca 3780
gatgctgaga ttagtccttg gtgttatacc atggatccca atgtcagatg ggagtactgc 3840
aacctgacac aatgtccagt gacagaatca agtgtccttg cgacgtccac ggctgtttct 3900
gaacaagcac caacggagca aagccccaca gtccaggact gctaccatgg tgatggacag 3960
agttatcgag gctcattctc caccactgtt acaggaagga catgtcagtc ttggtcctct 4020
atgacaccac actggcatca gagaaccaca gaatactacc caaatggtgg cctgaccagg 4080
aactactgca ggaatccaga tgctgagatt cgcccttggt gttataccat ggatcccagt 4140
gtcagatggg agtactgcaa cctgacgcaa tgtccagtga tggaatcaac tctcctcaca 4200
actcccacgg tggtcccagt tccaagcaca gagcttcctt ctgaagaagc accaactgaa 4260
aacagcactg gggtccagga ctgctaccga ggtgatggac agagttatcg aggcacactc 4320
tccaccacta tcacaggaag aacatgtcag tcttggtcgt ctatgacacc acattggcat 4380
cggaggatcc cattatacta tccaaatgct ggcctgacca ggaactactg caggaatcca 4440
gatgctgaga ttcgcccttg gtgttacacc atggatccca gtgtcaggtg ggagtactgc 4500
aacctgacac gatgtccagt gacagaatcg agtgtcctca caactcccac agtggccccg 4560
gttccaagca cagaggctcc ttctgaacaa gcaccacctg agaaaagccc tgtggtccag 4620
gattgctacc atggtgatgg acggagttat cgaggcatat cctccaccac tgtcacagga 4680
aggacctgtc aatcttggtc atctatgata ccacactggc atcagaggac cccagaaaac 4740
tacccaaatg ctggcctgac cgagaactac tgcaggaatc cagattctgg gaaacaaccc 4800
tggtgttaca caaccgatcc gtgtgtgagg tgggagtact gcaatctgac acaatgctca 4860
gaaacagaat caggtgtcct agagactccc actgttgttc cagttccaag catggaggct 4920
cattctgaag cagcaccaac tgagcaaacc cctgtggtcc ggcagtgcta ccatggtaat 4980
ggccagagtt atcgaggcac attctccacc actgtcacag gaaggacatg tcaatcttgg 5040
tcatccatga caccacaccg gcatcagagg accccagaaa actacccaaa tgatggcctg 5100
acaatgaact actgcaggaa tccagatgcc gatacaggcc cttggtgttt taccatggac 5160
cccagcatca ggtgggagta ctgcaacctg acgcgatgct cagacacaga agggactgtg 5220
gtcgctcctc cgactgtcat ccaggttcca agcctagggc ctccttctga acaagactgt 5280
atgtttggga atgggaaagg ataccggggc aagaaggcaa ccactgttac tgggacgcca 5340
tgccaggaat gggctgccca ggagccccat agacacagca cgttcattcc agggacaaat 5400
aaatgggcag gtctggaaaa aaattactgc cgtaaccctg atggtgacat caatggtccc 5460
tggtgctaca caatgaatcc aagaaaactt tttgactact gtgatatccc tctctgtgca 5520
tcctcttcat ttgattgtgg gaagcctcaa gtggagccga agaaatgtcc tggaagcatt 5580
gtaggggggt gtgtggccca cccacattcc tggccctggc aagtcagtct cagaacaagg 5640
tttggaaagc acttctgtgg aggcacctta atatccccag agtgggtgct gactgctgct 5700
cactgcttga agaagtcctc aaggccttca tcctacaagg tcatcctggg tgcacaccaa 5760
gaagtgaacc tcgaatctca tgttcaggaa atagaagtgt ctaggctgtt cttggagccc 5820
acacaagcag atattgcctt gctaaagcta agcaggcctg ccgtcatcac tgacaaagta 5880
atgccagctt gtctgccatc cccagactac atggtcaccg ccaggactga atgttacatc 5940
actggctggg gagaaaccca aggtaccttt gggactggcc ttctcaagga agcccagctc 6000
cttgttattg agaatgaagt gtgcaatcac tataagtata tttgtgctga gcatttggcc 6060
agaggcactg acagttgcca gggtgacagt ggagggcctc tggtttgctt cgagaaggac 6120
aaatacattt tacaaggagt cacttcttgg ggtcttggct gtgcacgccc caataagcct 6180
ggtgtctatg ctcgtgtttc aaggtttgtt acttggattg agggaatgat gagaaataat 6240
taattggacg ggagacagag tgaagcatca acctacttag aagctgaaac gtgggtaagg 6300
atttagcatg ctggaaataa tagacagcaa tcaaacgaag acactgttcc cagctaccag 6360
ctatgccaaa ccttggcatt tttggtattt ttgtgtataa gcttttaagg tctgactgac 6420
aaattctgta ttaaggtgtc atagctatga catttgttaa aaataaactc tgcacttatt 6480
ttgatttga 6489

<210> SEQ ID NO 2
<211> LENGTH: 150001
<212> TYPE: DNA
<213> ORGANISM: Homo sapiens

<400> SEQUENCE: 2
atctttcagc ctctatatta ttttattgtg atttttaatt tccttgaatt ggattttgcc 60
attgtgctaa atcttgatga tcttcatttg tatccgtagt ctgaattata tttctgtcat 120
ttgagttagc tcagtcttgt taagaaccct tgttggaaaa ctggtgcagt tgtttggagg 180
acatatgacc ttctggccat ttgatttatt ggagttctta cgttggttct ttctcatgtc 240
tctgtgtggg tgtttcttta actgcagtgt agattgagta cagccaatag acttcttctt 300
tggaggtttt cacagggcca aggccttgta cagggtcttt atttgtagct gacttcttgt 360
ctttggtttc atagtggggc atgttagcaa aatagttttg ctgttgaagt tttggggtgt 420
gatccatttt ttattttaat gattgtgtat ttcctttata cctaaaacaa gcagaaaacc 480
agtaaaggtc tttgagtctc tgaattcata actccagcat tcatattgct tcctcaggta 540
agtggggttt tcacccagcc cttaagggtg ttagattatt ttttatgtga aattagccag 600
attgtatttc taaacatgat gtaaaacaat aatgacaaaa gttataataa actagccttc 660
ttaccaaatc cacatgtcta atgtgtgtgg gagggtgtta ggcaggggac ctgcagctaa 720
gggagaggca gacaggcccc atggccccaa atctaggata gtatttggta ttggttgatg 780
ggtgagagaa agagagggaa catctgtgca ggatgtggta tcagcacctg gactacatct 840
tagggattcc ttcttcattt ttcagtatgc cctgacaata attatatcta tcagacttac 900
ccccttgacc actggaacac taagactgtt ttgggatctc tgcctgactt tctcagaggt 960
gctggtgagg acattatgag tctggaacct agaaaagcgt tctgactctg ctgactttct 1020
cagaggtgct ggtgaggaca ttatgagtct ggagccctag aaaagcgttc tgactctgcc 1080
actagccaga cagacctgga ctaggcacgt taactctttg tatgacttga ctccaacccc 1140
tcatttgtaa aaccagcatt ttcaagtggt gttttccaca tcagcctttt gcataagctg 1200
tcatttgaag aaaggttttt gtttgtttgt tttttgttta acaaaaaggt taaaaaccac 1260
tggtctagat aattgcaaag tttgctttcc tttttctgtg ctttttctac tatttttaaa 1320
atgtcatcct ccttggtttc ttgatccccc tttctgcact cctgagtctg ggaacactga 1380

-continued

```
ggccaactaa aaggaaactt ggcaaaagag gaacaccttt gggtgtgcca ggctgctccc   1440
agtgttttgc acttataaaa atttaaatgc tgcaaacctc taagacttag atattattgt   1500
tcctatttta caagtgagga acctgaggct cagagaaggt gcaggatggc acagggagac   1560
ctgaattgga accctggttc ccacttactg gctgtcggga cttagaaaag tcatgaactc   1620
tcattgattg ttttcttata tgaaatgggg gctgcagggt tgtcggggga gaaacaataa   1680
gaatgtgcat caagtgtcga gcacgtgcta cgcactccat catggcagct cctactaata   1740
tacagaatag agttgtatct aacatgactc tttcttgcaa gtgacagaaa atccaactta   1800
agatggatta agcaaaaaag gggaattctt gttgagctga aaagtcttta ggctcacatg   1860
atggccccag ggcccaggcc ctgtccagcc atgcagtagg catcatcctt gggcacaaag   1920
gtgagattct tgtggtggca gatgctgtgg cagctcttgc tttgccagga aagactgagg   1980
aaggccactg tccccattaa gtgaacaata gttggccagg tctgagaggt tgaacttggg   2040
tcacaggcct gtccctgaac ccatcactga ttggctccaa cctgcatcag ctattacatg   2100
ctagaggtgg aggcaggacc ccactcatac ccagaagggc aaagggtgga tccctcaaca   2160
ggattatggg atgtagggtg atagactgct gggcagccag aaagcaaaca gatcctctcc   2220
aatacctcaa ctgatgaaag caccaagcta aaatcataag gatctgggtg tgaattctgg   2280
ctctaccatc ttccatgtga cattgggcag ttatttaatc tcttttagcc ttggctttct   2340
tacctgtact aacatataag gtgattgtga tgagcatcat catcgtcaac atcatcatca   2400
ccatccacat tgccaccacc actcccatta tcatcttcat caacatcatc accaccgcca   2460
ccatcaccat tatcattacc accaccgcta tcactattat catcaccctc aacatcatca   2520
ccatcatcac tatcatcacc accaccatca tcgttactac cactaccacc accatcatca   2580
ccacagccac caccaccatc accatcatta ctactcagca ccaccatcat cattccacca   2640
ccatcaccat cattccacca tcaccattat cattaccacc accactgtca ctattatcat   2700
caccctcaac atcatcacca ccaccatcat cattactacc accaccacca ccatcaccat   2760
catcatcatt ctaccaccat caccattatc atcaccatca ccatcaccac cgctatcatc   2820
atgataatca ttatcattac caccaccatt agcattatca ttaccaccac catcactatc   2880
actatcacca tcaccacgac cactaccacc atcaccaaca ccatcattac tacccaccac   2940
caccatcatc atcattccac caccatcaca attattacca ccaccaccat caccaccacc   3000
accaccatca ctatcatcat cagtagacat catataacca gtttgtagct ggcccagagc   3060
ctacttgctg tttcttctgc cccacaacca tccacacatt tctaaccacc atcccccact   3120
aggcttctgc ctcgcctggt ctcacctgca ggtccactga gaaaatgatt ctcagaacac   3180
taactagacc atgaggtgcc acaaaacata actcaggcct gttcatcaat tttctacatg   3240
tcaataatga catcaggtca attggcgttc tcagcctctg agagggaggt caaagttttc   3300
ctgctctccc cttcatgttt ccaggtgttc cctgacttgg atcaaatgca gagtttggag   3360
gtgttgaggc caaggggatt ttccaggtca gtcgtcatcc acaatcaatg gactgatcct   3420
gccgctggac ttaccctgct gccctctccc caaggcccca tcagggaggg cttcaatcct   3480
cttgtcacct gtggcctacc tgccctcaga gatgacatct ctatgtcggc cactggatgg   3540
cagcacctac tcgcagacca catcaacttt cctggcaact tgcggtaggt tttcaccatt   3600
atcaggatgt ttgccttgct caaatagcag attctagaga acggtgctcc ctcacacaac   3660
tatgtagtcc aggtgatgca ccctctgccc gatgcttggt agtcagaaac ttccatcatg   3720
```

-continued

```
cagctctgcc cagattgagc tgagctggcc tctggagtga ggtgctggga caaacatctt   3780
ccatgctgct catgtcaact ccagatgcag tcaggtttct gaaccaaagt caatgatcta   3840
agtgcagtca aaggctctgg gggaagaaag agagagtgcc tcatctcttg cctgtgccat   3900
gctcgcaaag caaggatttt tgcaaaattc taatgaaagc tgggcttgca aaattagaaa   3960
actggattat ttgtgagaac actgaaacat ccctgggtgt gtccatctgg aaaaacagca   4020
tttcctctgg caattttgca accgttctat ttgaatttgg caaagaaaat aaagcagttt   4080
ttcacaaaag aataaacaca accaggagaa tcttcactct cccaaattgt caaagaagta   4140
taaattagaa aatgaatcag gacaatttca acctgttaga ttagctaata tttaaaaatt   4200
gaacactcat acaagtgtgg tgaagtgatt gttttctagt gacattttac actgtcataa   4260
ccttctagaa aataaattgg cagtgttatt gggagacaga aatatgtcta tataatttat   4320
gggaacttag gctcagaaaa tattaaggaa taagaatgaa ctttatgaac aaagatgtgg   4380
agggttggaa gcaagagggg ggccaacgcg cacggggagg aagcatttgg gcagtgactc   4440
cgcagaccca ggctcaggtt gaactagaca acctccttac acctcagttt ccttaactgt   4500
agagcaggag tgatggaact gcctgtttca taggactgtt gtgaggatga agtgagatac   4560
accacattat aagcttgtgc ctggaaagga taatgcttag taaatgatga ctattctttt   4620
ttattgcaat aaaatgtaca cagcgtaaga gttactattt taaccatttt tgcagggtac   4680
caccaagtgg catttagtac attcacagtg gtgtgcaacc atcatcatat ttccagaata   4740
ttttcctcat ccccaaagga aacctcatgc tcattaatca gtagctctcc tttaaaatat   4800
tagttatgaa gatcatagca ctatacaaaa ctcattatgt aatgttgagt gaaaaaatca   4860
gggtgtgaaa ttttgtgata tgatgtaatt agtgaaagaa gcatacaaaa agtctgaaaa   4920
tataaaaaca atagcaattg catttctcag actctacatt taaacattat tctttatggt   4980
tttaaaagca aagaaaaagg taaagaaaca acaaccaacc gcaaagcacc atgacaaagc   5040
tcagattgtt aaatccaggt ttttggaaca tagactctta tatgacgttt acactctcca   5100
gggttcagag agtctggcag cattgggagc tgccttgtgt tctacagcct cacggacaga   5160
caggaggtcc atcaccactg ctctgttctt ctggagtttc cttgtgaaca tgttgtggac   5220
gtagttacca tttctttcat ctttttaaac acaggtacct ttggggctgg ctttctcaag   5280
gaagcccagc tccctgtgat tgagaatgaa gtgtgcaatc gctatgagtt tctgaatgga   5340
agagtcaaat ccactgagct ctgtgctggg catttggctg gaggcattga cagttgcaag   5400
gtaagaaaag atcaagagac caaagttagt cttgtgctct cctgtctcag tctcagtccc   5460
ttagacttga gtcccaaagt agcgaattca agtaggattt aatcaatgga agaccccagt   5520
ctaagtgttg ctcagaaact ccctagatct gtcccaaatg tatattcaga tcatccaagg   5580
ggacttcttg gggcttgagt tccagatcag cagcaaggga gccataagtg ccataactac   5640
ctcagaccac tcaccctcct ggggtgtccc ggtggccagg gactaaagtg gtgatttttc   5700
tggtagggaa ggaggtagag ggtacaggac agagactaac tgcacacaat atctgagact   5760
ggagctcaga tattgctgat gatcagagtt ggcgtgtctc cccaattgat ttacaactgg   5820
ggcttggata ctgttttaaa cgggaggagc ctcctaacca tcttgacaca accactgacg   5880
tgactacact agagatagac tctttccact taattctacc actcttgctt tacttcatga   5940
gaacgaaaat gtaagattgc accatgaatt catttgcgga aagattgata ctatgctttt   6000
attttatttt attttatttt attttatttt attttatttt attgagactc tcaccccggt   6060
tgaagtgcac tgacgtgatt ttggctcact gcaacttcca cctcctgggt tcaagtgaat   6120
```

actccagcct ccctagtagc tgggattaca ggtgcccacc accacgcctg gctaattttt 6180
gtatttttag tagagatggg gtttcaccac attggcctgg ctggtctcaa actcctgacc 6240
ttgtgatcca cctgtcttgg cctcccaaag tgctgggatt acagagttga gccaccgcac 6300
tcgaccctat gttttatttt taaaaatatt tatttattta tttaagccac aactactaga 6360
ataggaagga ttgatatttt attaatttta tttggtattt attatttttt tttctttcct 6420
gagacattct tgctctgtca cccaggctgg agtgcagtgg cacattcttg gctcactgca 6480
acctccatct cctgtgttca agcaattcta gtgcctcagc ctacttagta gctgggatga 6540
ctggcatgtg cctccacacc cagctaattt ttgtattttt tgtagagaca gggttttggc 6600
atgttgccca ggcttgtctc aaactcctgg cctcaggtga tccatctgcc gtggcctccc 6660
aaaatgctgg gattataggc atgagccacc accccctcct ggaaggattg atatcttata 6720
acataattta taattacaga aaacatgtga gttcactagg aataaataaa ttttgaagat 6780
aataaaagat tttcacttat gttgtcattt cggcacagtt tggtatagga tgtggagatg 6840
ttaacattta tacctagctt gctcgtaaac taagacctga aagggttgtg tctatcagct 6900
gcacccctgg gtagcgacac aacctcggga aggcctcagc cccctcctcg tacagcactg 6960
cctgttggaa agcttgaggg aggctatgga tgtgcagcac ttggcagagg gtctggtcat 7020
ggaagttacc agcaaatatg agctactttt atgattttat tttatccaaa agaaagagaa 7080
tgaaagaaga ggggaggaaa caagactaat caggaaagat gaaggtctag ggtgaggga 7140 aggagtaagg agacataaag gcaatgtgga gcagctgagg ggggaaatgg ctttcaccac 7200
ttcccagcat ctattgacat tgcactctca aatattttat aagactctat attcaaggta 7260
atgtttgaac cctgctgagc cagtggcatg ggtctctgag agaatcatta acttaatttg 7320
actatctggt ttgtgggtgc gtttactctc atgtaagtca acaatgtcct gggattggga 7380
cacactttct gggcactgct ggccagtccc aaaatggaac ataaggaagt ggttcttcta 7440
cttcttttat ttctgaaatc aggtaagaca tagttttttt aaattataag aattattttt 7500
tctcccacaa tgtagtaaaa atacatatgc catggcttta tgtgcaattc atttaatttt 7560
tgattcatga aattcccagt tcaaaatctt gtatatgatt gaaaaattct taaaaaaata 7620
agtttaattt ccccgtgaag actgtcacgg tgctggaatg aatgggcaga aaaaataatg 7680
gttgattttt ctaatctaaa agagtgtgcc tacatgatgg ccagtctggc tgaaaaataa 7740
atagccattg tagctaacta tgcaaaggat ggctaagctc ttcgcttggt tctcagtttc 7800
attaatttat atcatctctg ttcaggtgcc atgctcccct cactagcaag ttgaaacaat 7860
gaaataactc tttgaatatg tttggttcct tgacctgttc atggagtggg actcagcatt 7920
tctctctttg ttatggcctg agtaaggctt tccatcggta tacatttgct tcttatccct 7980
ggagaaatta tacacatcca tttgccagat gatatacgca tataatgatt caacaaatac 8040
tcagggtatt tgttgagtgg gttaggtccc cacattttta tacatacata cacacataca 8100
caccgtgtgt gattgtgaat gtaagtgtgt gtcctttaca aatactagct tatttagctc 8160
atggtatagg tagggtagca tagtcatccc cattttataa acaaagaaat ctagacttag 8220
gaaaatcatg ttatttgtct cgtgaccaaa ttcccaaatc aaggaaataa agaaacctgg 8280
atttaagcca gatttccaag aaaaaatcta gggctcttct cactttttca tctttgttcc 8340
aacatttgaa aaaataaatc taaacacatt ccaatgtaac tgaagagcag gttaattgtt 8400
tgccacttgc agaatccaat taagaagaga gaagtctggt ataaagaaag tgatttgctt 8460

-continued ccaaagctag cttaggggaa gaaatgcagc agtcctgccg tactacttca ctttaggagc 8520
agaaagtggc acttttaaaa ggcaacagag gaggcgagca aggattcagg ggtccatgct 8580
agcttgggca ccttatccac caggtagttg agcagttgcc tgctggtgcc tttgtgagca 8640
gggtgttgtc ccttgaggca aatctctgga gggtgagagt tttgtagtgg gcatgctttg 8700
gtttataaat cacctgtgaa ctcaggagtt ccatcttgaa gcacatacat agttagatga 8760
acttgccctg cagggagagt ctgatgaaag ggaggtagat gcttgcaatt taatctataa 8820
attaccagat aaaattttac aagttgactt taaagtcaaa cacatttgaa tttagtggaa 8880
gccattcaag aaaatatcaa agaaaataca gagcaggaga agattaagca aagagttttt 8940
tggggaaatt ggtgtctatg tctgtgtgtg tagggagtgc aggggatatg aatattctat 9000
ttcagcccat ggaaactagg atgtagatca ctgtgaactt attcagcagg ctacacccaa 9060
aggctagaac aaacttctct gccacaggat taacatatgt tttaatcgac ctggggggca 9120
cattctctga taagctcttt tggaaagcca ggctttctgt ggacgtgtta tctttccaat 9180
gtgtgctgga atgcccgggg agaggaaaaa gtttctttta cagccatgct cagtgagaag 9240
cggagaaaca tcttctattc acaaattgct aagtctttta cacatgcaaa tatgcataca 9300
cattcacaca ccacagtgag gaagaaattc tcacaccatt aataaaatac atttacttca 9360
gtagcaatat acatctacat tttgcctata atataaaagt atttttccta ttaaaagatt 9420
tgtttaatgt ttcttcacca acaaataaac cctattaaat ccccattgcc atatgagccc 9480
tggaggtgaa tcagagaaac aaaaggattg tggaaaaatc atcaggttaa aaaaagaaaa 9540
attgattctg ttttgggata tttcctagca acatgagctg gggaggggat ctcagcagtg 9600
atgctctatg aagcataata aaatgacaca gttacaggta acttagttaa aggggggaaat 9660
aaatggaagt ttcctctttt tgaatatcaa ttgtagcctg ctctgctaca tttcaaaaac 9720
actcttcaaa atgtttaact gaactcactg taggaagcac cttattaatt tattgtgtgt 9780
tttgaagtca cactgtgagc tatagaattt acccaagcac aactcttcct ggaaaagaga 9840
gttcaaatga gaaacagtgc ggggtgaaga catggatatg ggcctaaaat atctatttct 9900
caatgatatt ttgatatatc tatcaagtgc tttttagtgg attaggttca gaatgcatca 9960
gccaatgcct gttcaataat ccagttttcc agcatagagc atattaaatt gaggaaggac 10020
aaagtcacag aggtggggag caggtggact gtggccaagg actttgcatg aaacagtgag 10080
cgtgcatcct cctccttgcc ctgccctcat ggtctgtgta ctctcaggag gtcaggacag 10140
gcctttctga gaatgagaat ctgttcatct gcctttctac tggatacttg tcatcggcat 10200
acaaacacat gttctctgca gtgtgtcatc tttcagaacc tcccctgacc ctgtattccc 10260
tagaagtctc gctgctttca gagccaggct tctctcctgc tgccaccccc actgctcttc 10320
tagtcactct ttaacccact ccatctgcat gtggccccca ccacacccct caaagtggtc 10380
aaggttgtcc tgttgcttaa ttccatggaa gcttggctat cttcatttta ttagcctctt 10440
ttggcctctc accctgtgaa aatcactaca ttttgtgcca gagatggagc tggcatctcc 10500
aggcttggaa gagggctgct gaagctcagc caggtgtcct aaggagcctc aggacagggg 10560
atgctcagta gccttgcaat gggaacacag ctgagcccca cttggccacc ctttgccaca 10620
accaggcaga aagcagcttt tgaacagatt tgttgcctca gatttgatct caaagaaaaa 10680
tcgtgggcag tattggtccc aggttctgct tttttacaat ttcctctgaa atctggatgc 10740
ctatcaacac cttggaaaaa ctgaattctc cccaactaat agtggtgtgt cactgtagta 10800
agcctagtac aaaaatggcc ttctttgtgg aggagcttca tatcctccat tttttttttg 10860

-continued

```
cttaattttt gcccaagatg agaacataat ttagttcact ttttatttat tcccaacatc  10920
atccatgcac caacattttt gtaactaaag gagggaccat tcagaagatg cttatcaact  10980
gtcaaagtga cagtgttaca accaatgcac atattgtaag aaatcaaaca atggcctcca  11040
aggttcattt ctacacaggg attagcagat caacatcaat cttggcaaca cagttgccac  11100
tgatggtgtc ttattttttt tatcatgaca tggcaatcaa gagcaaacat gatttattct  11160
tatttaagat tttatggtta gactaggcag atagctagat atgagcagga ggtggaagcc  11220
cctgagagaa tggaggtctg gagaatctga aaccccagag attacccaag tcctgcatgc  11280
tagacatgag tggaggaggg ggaataccta ggtagaaaag aatgcccctt aagatgccca  11340
gcagtcgctc actgtgcagt taacttttca gaatgctgct agatacatgc tgatagggag  11400
ggaagagggc aaaggagaaa ttcctaagag atacacggtt gcagttagta tacatctgag  11460
tgctatacaa ccttctttgg gtggtggcaa gaagcaatgc agccattacg tagaattcat  11520
atcaaacacc tgtatcacag gtgttaaaga aacaagaaac attgtacttc ttgtattctt  11580
aataatgatt tgcaatattg tctttagtat cactgcaaac ctctataaat atgattttta  11640
aaaagtattt ctttaggttg gaattacttc tacgcattga cttatcttcc tgggtttcat  11700
tagccgtacc cgttgtactt tcttccttac cactgtttat ctcaaactct tgagattaaa  11760
gtatgggctc aggagggagc gaggagcttc aggactctca cggacctcca gcacagtgta  11820
gctgccttat ggaaaagtgg ccacactgtt ttctgcactg gtccctgccc ctactattcc  11880
tcactgggca gagcacagcc accctggccc tgcctgaaca ttttagtcag tgttggctct  11940
gtgcttctct ggggaggaaa tccaagagac aacccacagc cctctgcca tttcagctgc  12000
agcagtacca ccgttaatgc ccttgggctt gagaaagaag ggacctggcc acttccctga  12060
cacctccagc acacagcagg gaaagaattc cagtttctct ttcttgtgag ctttcacctg  12120
ctactcttca ccaggcaagg ctcctggctt gggcccacag tgcaggcacc tcgaactcag  12180
ttgaacattt ccactggctg cactctgtgt ttttgtgggg tgaagctccc agaggtgact  12240
gaaagtcctt ctgccactaa cactgcagtc atactgccct tgctgtactt ggactaggga  12300
aggaaaaaag atcctgagtg ctttactcac accccagtgt gccccagcca ccctatggaa  12360
aagaggccag tgtgtcatcc ctgcaagcac cctgaggccc ctgcccctgc tgcccccaag  12420
ctgtagagcc agaatataaa gctggcagaa aaatgtaaaa aggctagact ggcttagcct  12480
cccagcctac atctttctcc tgtgctggat ccttcctgct cttgaacatc ggactccaag  12540
ttcttcagct gtgggacttg gactgtcttc cttgctcctc agattgcagg tggcctatta  12600
tgggaccttg taatcttgtg agttaatacc acttaataag ctccccttttg tgtgagtata  12660
tctatatcta tagatagata taggtatact cactatatat acacatatat acatatactc  12720
tctctctctc tctctcatat atatatatat ataatctcct attagttctg tccctctaga  12780
gaaccccgac taatacagat tttcatacca gaagtggttc ttgaggaaca gaatattaag  12840
gatggaattc tttcattggt tttgggactt ctggtgttgg ctgattaata tgattagacc  12900
aaaaaatgct aaggactcta cttctaatag tatggagaac actgatagta cttggcctga  12960
attgtttaga gagttatgca aaataaatgc atttgacact actgattcat cacttatgag  13020
aggcaaggag tttagtgact ctatacataa tacctttgac tatatgtgga gaaccaagga  13080
acataatgaa gttggttgat tgctcctaag ttctctggag aaagagatga aagaaaatga  13140
tgatctcagg ggatctgtct cccaccttca gaagcagata ctgagccaca aatctgctaa  13200
```

-continued

```
gattgccctg aatgagagtt ttaactcctg tagagaaaga gttgaaattg tgaaaaaaca  13260
gagacaagct gttatcatgc gagtagctga tctgcaacaa gaggtgcatg cacagccttg  13320
ccaggtgttt actgttaaag tgagggcatt gactggaaaa aaatgggacc ctggaacttg  13380
gagtggggat gtgtgggaga accctgatga agctgaggac actgagtttg tgaactctga  13440
tgaaactttt ttgccagaag aaacagtttc cccatcccca gtagtggtaa catcccctcc  13500
ctgacccgtg ctgccattag cctttccacc tttgtctgag gatgtaaacc ctgcactgct  13560
tgaggcaaca gtgatggcct tccctgaggc agctgccagg caagataatg ttgattctcc  13620
tcaagaggca cccctaatgc ccctgaatgc ttctagacct ataactaggc taaattcctt  13680
gcgggcccca gaggtgaggt tcagagtgtg acccatgagg aggtgcatta tactctaaaa  13740
gaactgctta agctttctaa tttatattgg cagaaatctg gagaacaggc atgggaatgg  13800
atattaaggg taagggataa tggtggaagg gacatagagt tggatcaagc tgaatttatt  13860
ggtttggccc tactaagtag ggattctgca tttaatgttg cagctcgggg acttagaaaa  13920
ggttctgata gggccgggag cagtggctca cgcctgtaat cccagcacct tgggaggcgg  13980
gggcgggcag atcacgagat caggagattg agacaattct ggctaaaatg gtgaaacccc  14040
atctctgcta aaaatacaaa aattagctgg gcatggtgat gcgtaactgt aatctcatct  14100
acttgggagg ctgaggcaag agaactgctt gaacctgtga ggcagagatt gcagtgagcc  14160
aagatcgccc cactgcattc cagcctggta acagagcaag actccatttc caaaaaaaaa  14220
aaaaaaaaag ttataatagt ttatttgctt ggttagctga aatatggatt aaaagatggt  14280
ccaatgttag tgagctggaa atgccttggt ttaatgtaga ggaagtgatc caaaggctta  14340
gggagattag gatggtggag tggattagtc actttagacc tactcatccc agctgggagg  14400
gtccagaaga tacacccttg gccgaagctt tgtgaaatag atttgtgaga gcagcacctg  14460
tatttttgaa gagcccgtaa ttgctcttct ctgtatgtca gatctaacag taggaaccac  14520
agtcactcaa ctacaaaatt taaatacaat gggaataatt ggatcctgag gtggcagggg  14580
ccaagtgttg gcactgaacc atcaaaggca aggtgggcat aactaccata atagacagca  14640
gaggcaaagc agccatcaga atagtctgac tcatgtagag ctctggcatt ggctaattaa  14700
tcatggtgtt cctagaagtg aaattgatgg gaaacctact gtattcctac ttgatttata  14760
taaacaaaaa actgccaggt agaatggact aaagactaat ctgaattata aaaacagaga  14820
atcatgggcc ctcaatcaat ttccagactc gaacctgtta cagttccaga acccactgaa  14880
tgaaggggag gctggatccc cttgaggaag gacaccacta ggctactgac aacttatgct  14940
gttactcttt ctcccatcct tccctaagga gacctctggc cttttaccag ggtaactgtg  15000
tgtactggag aaagggaagt aatgagacat ttcagaaagt actggacact ggctctgagc  15060
tgacgttgat tccagggtac ccaaaacgtt attgtggttc cccagttaaa gtaggggctt  15120
atggaggtta ggtaattaat ggagttttag ctcatttctg acttacagtg gttccagtgg  15180
gtccctggac ttatcctctg gtcattttcc cagtgccaaa atgcataatt tgtatagaca  15240
tacttattag ctggcagaaa tgccacattg gctccctgac tggtaggatg agggctatta  15300
tggtgggaaa ggccaaacag aagccattag agctgtctct acctagaaaa ataaaaaaat  15360
caaaaacaat atcccatccc tggagggact gaagtgatta gtgtcaccat caaggacttg  15420
aaagacgcag gggtggtgat tcccaccaca tccctgttca actctcccat ttgacctgtg  15480
cagaggacag atggatcttg gaaaatgatg gtggattatt ttaagcttaa ccaagtggtg  15540
actccaattg cagctgctct accagttgtg gttttgttgc ttgagcaaat taacacatct  15600
```

-continued

```
cctggtgcct ggtatgcagc cattggcttg gcaagtggct ttttctccat tcctgtccat  15660
aagacccacc agaagcaatt tgccttcagc tgacaaggcc agcattatac ctttaccacc  15720
ctacctcagg ggtgtatcaa ctctccagct ttgtgtcata atcttatttg gagagacctt  15780
gctcgctttt cacttccacg agatataaca ctggtccatt acattcatga cattatgatg  15840
attggataca gtgagcaaga agtagcaaac acactgaact tattggtgag acatttgtat  15900
gccagaggat gggaaataaa tccagctaaa atttagggac tttctacctc ggtaaaattt  15960
ctagggttcc agtggcatga gacctatgga gatattcctt ctaaggtgaa gcataacttg  16020
ctgcgtttgg cccctcttac aaccaagaaa gaggcacaat gcctggtggg cctatttgga  16080
ttttggaggc aacacattcc tcgtttgggt gtgttactct ggcccattta tcgagtgacc  16140
tgaaaggctg ccagatttaa gtgcagtcta gaacaaaaga aggctctgaa acaggtccag  16200
gctgctgtga aagctgctct gccatttggg ccacatgacc ccgcagatcc aatggtgctt  16260
gaggtgtcag tggcagatag ggatgctgtt tggagccttt ggcaggcccc cataggtgaa  16320
tcacagtgga gacctctagg attttggagc aaggccctgc cacttctgca gataactact  16380
ctccttttga gagacagcta ttggtctgtt attgggcttt ggtggtaact gaacgtttga  16440
ctgtgggtca taaagtcacc atgctacctg aacctgccta tcatgaactg gttgctttct  16500
gacccatcta gccatgaagt gggtcagcac agcggcattt catcatcaaa ttgaagtggt  16560
gtgtatgtga tcgggcttga gcaggtcctg aaggcacaag taagttacat aaggaagtgg  16620
ctcaaatgcc catgttctcc actcatgcca ccctgccttc cctcccccag cctgcaccaa  16680
tggcctcatg gggagttccc tatgatcagt tgacagagga agggaagact aaggactggt  16740
tcatagatgg ttctgcacga tatgcaggca ccacccgaaa gtggacagct gcagcactat  16800
atccactttc taaatgcatg tgtacacttg tgctaagaaa atatctttat tttatttcct  16860
ttatttttcc tttatcatgt gaccttagat ttatggactt cacatcagca tttaagcatt  16920
taagtgttgt tcatatcagc atttaaatat tgttaacctt atgtaataac ttttggtttg  16980
gggattggtg cgtttctggt tgtatgagga tagttgtatt atattaggca taattatgac  17040
cttattattg tctttatttg aagattatgt atgatttcag gatgtgtgta tgggttcaag  17100
ttgacaagga gttggacttg tgatggttaa tactgtcaac ttgattggat tgaaagatgc  17160
aaagtattaa tctcggttat gtctgtgagg gtgtggcaaa aggagattaa catttgagtc  17220
agtgggctgg gaaggcagac ccacccttaa tctgggtaca caccatctaa tcaagttcca  17280
gtgtggccag attgtaaagc agggagaaaa atgtgaaaag actagactga attagcttcc  17340
cagcctacat ctttctcctg tgccaaatgc ttcctgctct tgaacatcgg actccaagtt  17400
cttcagcgtt gggagttgga ctggctttct tgctcctcag cttgcagagg gcctgttgtg  17460
gaaccttgtg atccgctgag ttaatactac ttaataagat ccccttttata tacatataat  17520
atattatatt atatataata tatataatat atattatata taatatatat aatatattat  17580
atattatata taatatatat tatatattat atataatata tattatatat aatatatatt  17640
atatattata tattatatat aatatatatt atatataata tatataaaat atatatatat  17700
cctattagtt ctgtccctct agagaaccct gactaataca atttatgtca ttaatctcat  17760
ttattgattt gtatacattg aaccaacctt atatcccagg aataaaacct acttgattgt  17820
ggtggattag ctttttgatg tactcttgga ttcaattgct ggtattttat tgagaatttt  17880
tgcatctgtg ttcatcaagg atattggctt gaagttttct ttttttgttg ttccatatca  17940
```

-continued

```
gaatgatgac gacctcatag aatgagttag tctgtcctct tttatctttt ggaattgttt  18000
caggaggctt gatatcagct cttctttata tgactggtat actttggcta ggaatctctc  18060
tggtccaggg gtttttctgg tgtaggtttt taattactga ttcaacttca gaactcatta  18120
ctcattattg agttctaaaa ctcactttca tgtactcttc aaaagactgt cttcttctgt  18180
tgttgagcgg ggtgttctct caaggtcgtt taggtgaagg tggttgctgg tgttcttctg  18240
tatccttact gcttgtcttt ctcttttttt attgactact gaggattaat ggtgatgtgt  18300
ccaactttaa ctctagatta gtctatttct cttttagatt gtaactctgt tttatatatt  18360
ttgaagctct gttgttaggc atgtgtattt ggattgttag gtcttcttga tgatgacctt  18420
tatcattatg taatgtttct tcttatctct ggaagtattc gttgttctga agtctatttg  18480
tgctgatatg aatacagcct tcacagctct attttcacta gtatttgtat atctttttct  18540
cagcttttaa attgagatgt tcagaccatt tgcattaaag tagttgttaa taggattaaa  18600
tttaaatcta ccattaagtt ggttatttct ctttgtccca tttaaacttt gttccttttt  18660
tcatattttt ctgccttcat ttatattgag tttatctcca cgacttactt attaaattaa  18720
tttttaatgg ttttagtatt ttccacaatg tttataatat atactttgat tttttcacat  18780
tccaccttca aatgacagaa ttatactgga tatatagaaa tcttacatca ttgcacttct  18840
ccttcctccc tctcaaaatg ttgtgctatt gctctttgta atagaggctt acttctatta  18900
tgttatagct ctcataatac attgacacta tttttaccct gaataatcag ttgtttttta  18960
aagtgattat gactacaaat attttgaata atttctttat tttaccattt ctggtgctcc  19020
ttatctttta cagtagatcc caatttccat ctggagtcac attctttctg tgaaaaacaa  19080
cctttagcat ttcttatagc acgggactgc tgttgctgtt gtctttcagc ttttctttgt  19140
ctgaagaagt ctttattttg ccttcagttt ttaaaagtga ttttgctgag tatagatact  19200
gggttgagag tttcattcct tgtatcattt taacaatgat gttccattat attccgtttt  19260
gaatagtttc tgactagaaa tctgatcttt gtttctttgt attcaatagt tccttttttct  19320
ctgactgcct ttaagatatt ctcatctttg tttttcaaca gtttgactat aatttgttta  19380
ttattaactt tttgtattta ttctgcttga ggtttcctga gctccttgga tttgcagatt  19440
gttgattttt attgttttttg taaaattcat agccattatc tattctactg ttttgttttt  19500
tttttcactt ctctctctct gtattcttct ttttggactg taagtattca aatgttagat  19560
cattcatatt gcttcataaa ccttatatgc ttcttctgct tttttttttt tgtcaggaac  19620
tctttttttg tatctgtgtt ggtttggata agttctagta gactatgttc aagtttatgg  19680
attattttgt tagttgtgtc taattgactc ctcagtgcat tcagagaatt cttcatctct  19740
gatattataa atctcttcct agcattttca tgttactctt ttctatagtt tccatctctt  19800
tgctgaaatt ctccccctat ccatggatat tgtccacctt taccacaaga ttctttaaca  19860
tattaacata ggtatcatac aaacccaaac tgatagtttc cagatggtgt cttttctgag  19920
tctgtctgtc ttgattgctt tattatttaa cagtgactta tcttccctct tcagcttttg  19980
gtgtgtcttg taattgttta atcaaacact gggtatcata aatggaggaa cagtagagat  20040
tgcagtaaat attatttatg ctttgaaatg ggcacccatc ttctgttgaa aatatgtttt  20100
gtggtcaatt gagtcaacct agtaactggt tgaactgaat ttggcatttg tgcttgttgc  20160
ttttatctta aatgcaccac aggtttaaat tcctccagtg atgggttgct gctatctttt  20220
gcttagagtg gggcctgggg tgtggaagaa ttttctcagt gttcctatct attattagat  20280
tttagcagtc actgcatgcc tgcactacag aggggatatc ttcatacaca taatctaacc  20340
```

ccattgaaac tgctgtttct tcttaatgaa tgctcaatct ttggtggaaa taaacaaatg 20400
ctgtatctcc tggagccact tcagtcttag tcaggttctg cagggctttg aagggaatgc 20460
attctcagta ttcttgtgcc ttatttggat ggaacttgaa cctgtggtgg gtttggagag 20520
aaagagtagc agacgtctgc tatgttgcaa tgcaggatgc tgggcacaag aaaatttcca 20580
gtctctcctc caaggaaata agatttgatc atctacctat ccctgagaag tgaagggctt 20640
tgcctgcggt gctagatgca aaaccatttt tctcccccca ttgcccagaa acttaaggct 20700
ttggcttttc tgagcagtgg tctagggaat tgtgcaaggt tttcatattt gaccctgaca 20760
gcccatcacc acctacagct tgcagtgcca aatgtatctc cctctgatct ctcctgtcct 20820
gtggtcctca tgaacattaa gaagagattt ctaaaaaaga gcttgcacat gagcatagtt 20880
tctggtgaga agaattctga tatgttaact tcctctaaac ttttaaataa aatatttcta 20940
agaattaaat aaagttctag aatgatatga atctattcct ttggtttttt gcacgtctgt 21000
ctgcctgcta atcaagagaa gagaatggtc gtaattctca gagacttttt cctgtttgtg 21060
tcataaatga cttcacattt ttttctgttc taagaactat tcagcttgat ttcttctgtt 21120
ttaattttag cagcacctga gcaaagccat gtggtccagg attgctacca tggtgatgga 21180
cagagttatc gaggcacgta ctccaccact gtcacaggaa ggacctgcca agcttggtca 21240
tctatgacac cacatcaaca taataggacc acagaaaact acccaaatgc gtatgtcatt 21300
aatcttacag taagcaaaac aaggtccaag taaaatttgt cttagaaaag gtgtgcgtca 21360
agctaacttc ttatgattaa atttttctca cacatagaat gcatggcaaa atgtctgaga 21420
aacattactt tgagcaaaga gtatgataga agagaaatgt taagctggct ctctttcctg 21480
agagtttgat aaaatcagga gaatatctgg cggtggtgag gccacaataa tggaaaatca 21540
gaatgtttag acagagtcag cttcaacaac actcactaaa ggtcaatgtg atctttaccc 21600
cttgaaattc tataattcta atctccaatt cctgaagtga aggttgtgtt ggccttttct 21660
gtcttggctc acaagtaaat gatatgtgca tatctatgga aaggcgaatc tatctttttc 21720
tatatctatg tctattccaa cgggtagaaa caccctgggt cctgagcacc agtggtctga 21780
aggaatacgg gttgccagga agagagaagc aaaggcagga aggcagatga aagtaagaaa 21840
tgagacagat gctaaacaat aaaaagtgcg ggaagataga cagaagctgg ggtctgacca 21900
caccatggcc agtctttcac acataagtga ctaccaaaga caagaaaaaa tgatttccgc 21960
ttgttggaca atagatggta gaggaccaag ggaattgcga gagagagaac aatgagatca 22020
actcaacaga tgcactggtt ttcttcctgg agacccttcc tgcactgaag ggcaggagat 22080
ggagcccaaa aaaaactgta gccatcttgc tgaacagagg agggacattg gagtttggga 22140
ttattcaggt ggctaggatt ttctaggcct gctaacaatg agaacagatt tgtggaggaa 22200
aggagttcta gaaatatgca tagaaatctc ctcgagtcat tggctaaaca tgaagctgca 22260
tgtacacaga aaatagatcc acaagaaagt agggcaaaga acatctacgg aagagcagca 22320
actacaatgg aacagtgagc tcaataaaca tgacagagct caaatagcac taagggatat 22380
tggagtttgg accacacaga ggagagagac ttcactgaac atcttgggca ttcagtagag 22440
acccaggaaa agccatactt taggagtaga attagtatat tcttagaata aaggcagctc 22500
cacacaaaca atagcaaaac tgaaaaggaa gtctccaagc atcagaatga tgtccaagtc 22560
aatgaactgc ctctgagagg aaaactcaac catctttaga ggtaaacatc aaagtcaagt 22620
ggctcagcta tgcagtatcc acagtgtgag gcctaaatat aaaacttgac tacacataga 22680

-continued

```
aacctttttag tgtgacccac aagcaggagg aaaatcagcc aatacaaaca gacccagaag  22740
agacagaaat gattagaatg gcataaaaat ttgacatatc actatataat aattgagttc  22800
taggatttaa gaaaacatga atatagaatg caacagacac cttatccaga gacagtaaga  22860
gtataaagag ccaaatcgaa gaactactaa gagatatgtc ttaaatgaaa aaattactag  22920
atggcctccc catctagtta gacatttcag aagaaaatac caaatgaaaa ataattgcat  22980
agaacctaca gaaccagata cacacataca aaacacacgc atgcatacac acacactcaa  23040
acatgtataa gcttacaaac acacacacac atccacaaat gctgaaaaat gaaatcaacc  23100
gagccacaca gacataaagg aaaacataaa aagatttcct acatgtggga agcaagtcac  23160
agaaaggggg aaggagattg gaacagaaat atatactgaa agcaaggatg gctgaaaatt  23220
ttccaaatat aaagaagatt aaaaaatcac ggactcaaga agctcaatgg atcagaaaaa  23280
taatttctaa aatgacaatt ataggatgcc actgggtaca tagcagttca actgtcagag  23340
ggcaaagaca taatacacag aaaaatctcg taaggaacgg gaaaaacaaa aagctgtgtc  23400
ttgctagagg aacagtgata caagtgacta atgtgttccc atcagaaaca ctgcaacctg  23460
gacacaaaag aataacatta aagtaataaa cgtaagaaag aagagctcaa ctgagaaggc  23520
tacatccagc aataaaatgc cttgaagttc atccatgttg gaggaatgca cattgtgcac  23580
tcccctaaac aaagaaaccg gaaactgtaa gactttggaa tcagcaggct tatgtaacaa  23640
aagaggtgac cctaaggaat taaggagaag aagaatagaa caagaaggga actttctgca  23700
gcctatataa tgaagaacct agcaattggc aaatgtagat gaaaatgcta catgttttct  23760
tgatcaaacg tttatatctt tttaaatgag agttgacgag ttgaagcaaa atgataccaa  23820
tatatttaac tttaccatat gtagaagtaa aaatttgaac atgtagcata aatcatgtag  23880
ggattaattg gaagtgtacc actgtaagtt tcttacctca tgcacgatag tatgtaatac  23940
taataaaagg ttaatgtgtg ggttcaaagg gatattgcaa atcctagagc aatcacaaag  24000
tttttaactc tgaggtttgt tgtataataa caatatttta tgtattcaaa agagggaagc  24060
caaggaagaa aaaaaagtct ttaaagagct ctggctctta gtacatccag ttgctcattg  24120
aatgagcttc ctggaatgga gggtctggga ctgagactag gccacatgtg tagagccact  24180
agagacacaa tgttggatcc ccatggccca taatacattt cccattttct caggcagcca  24240
caggtcatga atgtgaggat actgagaggt tggagcaacg ttcttgggag gcataaggaa  24300
gagcgaatgc ttcaagatcc ccgcagccca aactcctcag ctgctttgcc tcctaattca  24360
ttgtttttttg ctcctccata gctgtccgac ctcttcagat ctcttagtct tcctgccatc  24420
ttcctttatg ccatgggacc cactgttctt tcaactcatc ccccagttct ggagtggctg  24480
tggacagcag aggatagact gagagcagga gagaaggtcc tgcccaggaa cccattctag  24540
agatactgca ttctgcctgg gagcaagttt tccagggcag ctttgagaag tcttgcagaa  24600
acaaacctac ttgaccgaca tgatatggga atgacagaca gtaatactat ttgcacaatg  24660
cttttccatg ggaaaggtag agccttttca ctaggttttg agtacatgga gtgtgagagt  24720
tgacctggaa aggttatcct ccttgatgcc atgttttctc tgaagaacta catgttcgtt  24780
gcaactccca cattagaata tgaagtccta ccgagagaga tacggagact agacagatac  24840
agatgcattt gcatgtgaat acacaatccc acaatacaga cgtcaaaacc cataccagtt  24900
attccagaga gatggattgg gcagaaggca gaaggagaat actctgatcg tttttcggcc  24960
acgtgtgtgt gttatctcag tgtttctaag aagcgtttgc tactttagat tttttattta  25020
aaaaaaatag taataatcta ttaagtatga gagatgtgca gagaggatta gtgatcgaga  25080
```

-continued

```
gccatttttg ctggtggcaa tcatatggta cttttaatgg gaatattaga aaggcaccgg  25140
taatgacctt gttgcagcac aaaggagaga gtgtggggtg cccctgcatg ttgtcccacc  25200
tcttgtgacg tgtatcgttt tggaatttcc agtggcttga tcatgaacta ctgcaggaat  25260
ccagatgctg tggcagctcc ttattgttat acgagggatc ccggtgtcag gtgggagtac  25320
tgcaacctga cgcaatgctc agacgcagaa gggactgccg tcgcgcctcc gactgttacc  25380
ccggttccaa gcctagaggc tccttccgaa caaggtaagg agtctgtggc cagacatcta  25440
cacgcttcga tgctgggatg aaaagccatg gaaattccca ctgatgcagc cgccttcaat  25500
ggtaaacgga tgctcgagtg ttgcctgagt tctaccatgt aggaggaagc ctccgtgcac  25560
tctctggggg agccagcgga gtgatttctg gtgcaacgtg gttgggcttt gtctttagga  25620
tgggcacaaa ccctccaggg ggatcgactt caaaattcac cttgttgtaa aacgggctac  25680
ctcagtgtcc cagccaaaat ttttattgta acatgctgtc aggtgtgtca ctctttccaa  25740
gccagtaagc ttttccgggg atttcttcaa gtagccagca ttcagagcaa tcttcagcat  25800
tgcagattct gagaaatgtg gctctggagc ctgtcaccct cgagaaacct aagagggctg  25860
cattgattcc atgtggccct gggtctatgg agcagtacat gagctcccag tgctctaagg  25920
ctcttcagcc ctaggctttg aagggagtga tttctcagta ttcttaaacc tctttctgat  25980
gacacttgta cctgtgaggg gtctagagag aaagagtagt agactcctac tttactacaa  26040
ttcaggatgc agggcatgag aggattccct ctctcctcca agggaagaag cttttggcgt  26100
gcacacatcc ctgagaagca aagtgtcttt gtcttcagtc agatacatag gaccgttttc  26160
tgccccatgg cccggaagcc aaaggccttg gctttcatga tcaacggtct agggaaacat  26220
gcaaaatttc catgtctgtc ccaaactctg cccccgacag ccaattacca cctgcagccc  26280
gcattgccaa atgcggtgcc gtttgcatga agattcagta gagtttccta gaaaggtgct  26340
acctcgtgag ctcactttcc aatgaggaat ctgatctgtt gtgtttctct aaggtgtcag  26400
gtgaaatatt tccaagaact tactacagtt ctagaatggg aggaatctgt tgctttggtg  26460
tttgtttgtt ggtcggtttt ctcacatcca tctgcctatg gataaggaaa agagaacggt  26520
cgtaattctc atagactcct ttctggttgt gtcacaaatg gcttcacatg tttctctatg  26580
ctcagagata ctcagcttga tttcccgtgt tttcatttca gcaccgactg agcaaaggcc  26640
tggggtgcag gagtgctacc atggtaatgg acagagttat cgaggcacat actccaccac  26700
tgtcacagga agaacctgcc aagcttggtc atctatgaca ccacactcgc atagtcggac  26760
cccagaatac tacccaaatg cgtatgtctt tgttctttac cataagagaa gaaagggcca  26820
agtgaagttt ctgttacaag agatgtgtct caagctgagt tctccgaact caacttgtga  26880
cagatgcaga tggcgtagca aaatgtctca ggatgattgc cttggagcta agggtctgag  26940
agaagggaaa tgttaagctc cctctccttc ctcctagttc tattgagcag aagggaaatc  27000
tggaggtgag gagatcacat tatgaagaaa gtcagaatga caaaggacca gacacttaga  27060
ttacccttcc acaacaccaa ctaaacgtca atggagactt tccagttgga attccgttat  27120
tctggcttcc acttcctgaa gggaaggttg cgtttgcctt ttctctctgg gttcaagagg  27180
aaagaatagg tgcttattta tggacaggtg aattgatctg tttctatatc tacgtatatt  27240
ccgattgtca gaaaaacact cgttcctaag taccagtggc ctgaagggat acaggttccc  27300
agcaagagaa gatccaagga aggaaggcag atgagagtca gcacagagag ggatgctgaa  27360
aagtaaaagg gatgggtgga tggagagaag cccgggtctg accacccaat ggccaatatt  27420
```

-continued

```
ttggccacaa gcgactacca gagacatgga aaaatggttt ctacatgtgg gacaacagat  27480
ggtagaggac ctagagaatt gagagagggg caatgatggg ctccactccg cagatgcctt  27540
ggctttcttc ctggataccc ttcctgcact gaatagcaag gagatggagc ccaagcagac  27600
tgtagccatc ttgctgaatg gaggagaggg attggagttt gggatgactg tggtagctga  27660
aatttttcta ggtctgctag aaataagaac tggtttgtgt ggaggaaaag agctctacaa  27720
atacgcatag aagtctcctc cagtcgttgg cctgacatga cgctgcctgt gcacaggaaa  27780
tggttccacg agaaagtgtg gcaaagaaca tttactgaga aacagcaagt acaagagcac  27840
aggaagctca ataaagaaga gagagatcac atagcactct gggatactgg agttcttccc  27900
agctagacca gagagtcctc acggagcaca ttgccaattc agtggagacc ccagaacagc  27960
cgtaatttaa aggtacactt agtatattac tagaataaag tcagctgcag acaacccctt  28020
gcacagctgg aaagcaagtg tccaagcatc aaatcggttt ccaatcaatg aagtgcctgt  28080
gagaggaaat ctcaactctc tttagaagta aacaacaaag tcgattgcct cagctatgcg  28140
gtatccgcag agtgagtcct aaatttaaaa tctgactaca tgtagaaaag cgtttcgtgt  28200
gacccatgac caggaaataa atcgggtaat acaaacaggc tcaggaatga gagaaatgat  28260
tagaattgcg tgaaaatttg acatatcagt atgataactg atttcaaata tttaaaaaaa  28320
caacatgcaa gaaagcagat atcatatcaa gagaaattaa cagtacagaa tagccaaatt  28380
aaattaaaga ggtagtataa aaaaagtatg tcttaattga aaaaaattac tgtatggccg  28440
gctgatcaat ttagacgttt cagaggaaaa cattacccaa cacacaattc tagagaacct  28500
acagaatgag ctacacacac acacacacac acacacacac acactgaaaa cacacccata  28560
ctcacacaca cgcagaaact cacaagttct aacacacaca gacacgcgca cccctgaaga  28620
aacagtgaaa tataaaatta agcgagcctc acagacatgt aggaaaatat gaaaagattt  28680
cctgcatgtg ggaagcaagt cacagtaaag agcaagggag tttataatag aaacaaatac  28740
cagaatcaag gatggctgat aacttttcaa ttacgaagaa cattaaaaaa aatcacagaa  28800
tcgtgaaact caagggatca tatagggaat ttcggaaaaa aaacccaacc tgtatgatgt  28860
acttttgtac atcacagttc gaaggtaaca aggcaaagat gtaataagaa gaaacctgtc  28920
acgagaaact ggaggaaaaa gagctgtgtc ttcctacaag tacactgata caaattgcca  28980
atgtgttcac ctcagaaaca ctggaagcca gataccaggg aatattgtta aaatgataat  29040
caggaacaaa aagagatcaa ccgggaatgc tgaatccagc aataaaatgc cttgaaggtc  29100
atccatgtcg gataaatgca tattgtgcac tgccccaaag aaagaaaccg gaaactgtaa  29160
gaattggaaa tcagcaggct tatgtaacaa gagaggtgac ccgaaggaat taggtagaag  29220
aagaattgaa caagaaagga actttctgca gcccacgtaa tgaagaatcc agcaattggc  29280
aaatgtagat agatgtaaat gcaaaatatt ttcttgatca aatttctata tctttgtaaa  29340
tgagagttga ctacttgaaa caaaatgata gcaagatatt taacttcagc atatgtagag  29400
gtaagaattt gaaatggtag cataaatcac gaagggatta attcgaagtg taccgttgta  29460
agtttcttta cctcatgcac gatggtgtgt catattaata aaagggtact gtgcgggttc  29520
gaagggatat tgcaaatcct agagcaatca caaaggtttg aactctgagg tttttggtat  29580
aataagaata gtccatgcat tcaaaagagg gaagccaagg aagaactaga agtctttcaa  29640
gagctcaggc tcttatacat ccagttgctc attgaaccag cttcctggaa tggagggtct  29700
ggggttgaga ctaggccaca agtctagagt ctctagagag acagtgttgg aaccccatgg  29760
cccataatac atttcccatt ttctcaggca gccagaggtc atgaatgtga ggatactggg  29820
```

-continued

```
aggttggagc aacgttcttg ggaggcataa ggaagagcga atgcttcaag atccccgcag  29880
cccaaactac tcgcctgctt tgccccctaa tgcatttttc tctgctgctc cgtagctgtc  29940
cgacctcttc agatctctta gtccaccctg ccgtcttcct ttatgccatg ggtcccactg  30000
ttctttcaac tcatccccct ttccctcagt cccggagtag ctgcggccag cagagggtag  30060
actgagagca ggagagaagg acctgcctag gaaccccttc tagagatact gcatcctgcc  30120
tgggagcaag ttttccaggg cagctttgag aagtcttgga gaaacaaacc tactaaacct  30180
gacagacagt aatactattt gcacaatgct tttctgtggg aaaggtagag ccttttcact  30240
acgtattgag tacatagagt gtgagggttg acctggaacg gctatcctcc tggatgacgt  30300
gtgttttctg aagaactaca tgttcgttgc aactcccaca ttagaatatg aagtcctacc  30360
gagagagata cggagactag acagatacag atgcatttgc atgtgaatac acaatcccac  30420
aatacagacg tcaaaaccca taccagttat tccagagaga tggattgggc agaaggcaga  30480
aggagaatac tctgatcgtt tttcggccac gtgtgtgtgt tatctcagtg tttctaagaa  30540
gcgtttgcta ctttagattt tttatttaaa aaaatagtaa taatctatta agtatgagag  30600
atgtgcagag aggattagtg atcgagagcc atttttgctg gtggcaatca tatggtactt  30660
ttaatgggaa tattagaaag gcaccggtaa tgaccttgtt gcagcacaaa ggagagagtg  30720
tggggtgccc ctgcatgttg tcccacctct tgtgacgtgt atcgttttgg aatttccagt  30780
ggcttgatca tgaactactg caggaatcca gatgctgtgg cagctcctta ttgttatacg  30840
agggatcccg gtgtcaggtg ggagtactgc aacctgacgc aatgctcaga cgcagaaggg  30900
actgccgtcg cgcctccgac tgttaccccg gttccaagcc tagaggctcc ttccgaacaa  30960
ggtaaggagt ctgtggccag acatctacac gcttcgatgc tgggatgaaa agccatggaa  31020
attcccactg atgcagccgc cttcaatggt aaacggatgc tcgagtgttg cctgagttct  31080
accatgtagg aggaagcctc cgtgcactct ctgggggagc cagcggagtg atttctggtg  31140
caacgtggtt gggctttgtc tttaggatgg gcacaaaccc tccaggggga tcgacttcaa  31200
aattcacctt gttgtaaaac gggctacctc agtgtcccag ccaaaatttt tattgtaaca  31260
tgctgtcagg tgtgtcactc tttccaagcc agtaagcttt tccggggatt tcttcaagta  31320
gccagcattc agagcaatct tcagcattgc agattctgag aaatgtggct ctggagcctg  31380
tcaccctcga gaaacctaag agggctgcat tgattccatg tggccctggg tctatggagc  31440
agtacatgag ctcccagtgc tctaaggctc ttcagcccta ggctttgaag ggagtgattt  31500
ctcagtattc ttaaacctct ttctgatgac acttgtacct gtgaggggtc tagagagaaa  31560
gagtagtaga ctcctacttt actacaattc aggatgcagg gcatgagagg attccctctc  31620
tcctccaagg gaagaagctt ttggcgtgca cacatccctg agaagcaaag tgtctttgtc  31680
ttcagtcaga tacataggac cgttttctgc cccatggccc ggaagccaaa ggccttggct  31740
ttcatgatca acggtctagg gaaacatgca aaatttccat gtctgtccca aactctgccc  31800
ccgacagcca attaccacct gcagcccgca ttgccaaatg cggtgccgtt tgcatgaaga  31860
ttcagtagag tttcctagaa aggtgctacc tcgtgagctc actttccaat gaggaatctg  31920
atctgttgtg tttctctaag gtgtcaggtg aaatatttcc aagaacttac tacagttcta  31980
gaatgggagg aatctgttgc tttggtgttt gtttgttggt cggttttctc acatccatct  32040
gcctatggat aaggaaaaga gaacggtcgt aattctcata gactcctttc tggttgtgtc  32100
acaaatggct tcacatgttt ctctatgctc agagatactc agcttgattt cccgtgtttt  32160
```

```
catttcagca ccgactgagc aaaggcctgg ggtgcaggag tgctaccatg gtaatggaca  32220
gagttatcga ggcacatact ccaccactgt cacaggaaga acctgccaag cttggtcatc  32280
tatgacacca cactcgcata gtcggacccc agaatactac ccaaatgcgt atgtctttgt  32340
tctttaccat aagagaagaa agggccaagt gaagtttctg ttacaagaga tgtgtctcaa  32400
gctgagttct ccgaactcaa cttgtgacag atgcagatgg cgtagcaaaa tgtctcagga  32460
tgattgcctt ggagctaagg gtctgagaga agggaaatgt taagctccct ctccttcctc  32520
ctagttctat tgagcagaag ggaaatctgg aggtgaggag atcacattat gaagaaagtc  32580
agaatgacaa aggaccagac acttagatta cccttccaca acaccaacta aacgtcaatg  32640
gagactttcc agttggaatt ccgttattct ggcttccact tcctgaaggg aaggttgcgt  32700
ttgccttttc tctctgggtt caagaggaaa gaataggtgc ttatttatgg acaggtgaat  32760
tgatctgttt ctatatctac gtatattccg attgtcagaa aaacactcgt tcctaagtac  32820
cagtggcctg aagggataca ggttcccagc aagagaagat ccaaggaagg aaggcagatg  32880
agagtcagca cagagaggga tgctgaaaag taaaagggat gggtggatgg agagaagccc  32940
gggtctgacc acccaatggc caatattttg gccacaagcg actaccagag acatggaaaa  33000
atggtttcta catgtgggac aacagatggt agaggaccta gagaattgag agaggggcaa  33060
tgatgggctc cactccgcag atgccttggc tttcttcctg gatacccttc ctgcactgaa  33120
tagcaaggag atggagccca agcagactgt agccatcttg ctgaatggag gagagggatt  33180
ggagtttggg atgactgtgg tagctgaaat ttttctaggt ctgctagaaa taagaactgg  33240
tttgtggagg aaaagagctc tacaaatacg catagaagtc tcctccagtc gttggcctga  33300
catgacgctg cctgtgcaca ggaaatggtt ccacgagaaa gtgtggcaaa gaacatttac  33360
tgagaaacag caagtacaag agcacaggaa gctcaataaa gaagagagag atcacatagc  33420
actctgggat actggagttc ttcccagcta gaccagagag tcctcacgga gcacattgcc  33480
aattcagtgg agaccccaga acagccgtaa tttaaaggta cacttagtat attactagaa  33540
taaagtcagc tgcagacaac cccttgcaca gctggaaagc aagtgtccaa gcatcaaatc  33600
ggtttccaat caatgaagtg cctgtgagag gaaatctcaa ctctctttag aagtaaacaa  33660
caaagtcgat tgcctcagct atgcggtatc cgcagagtga gtcctaaatt taaaatctga  33720
ctacatgtag aaaagcgttt cgtgtgaccc atgaccagga aataaatcgg gtaatacaaa  33780
caggctcagg aatgagagaa atgattagaa ttgcgtgaaa atttgacata tcagtatgat  33840
aactgatttc aaatatttaa aaaaacaaca tgcaagaaag cagatatcat atcaagagaa  33900
attaacagta cagaatagcc aaattaaatt aaagagctag tataaaaaaa gtatgtctta  33960
attgaaaaaa attactgtat ggccggctga tcaatttaga cgtttcagag gaaaacatta  34020
cccaacacac aattctagag aacctacaga atgagctaca cacacacaca cacacacaca  34080
cacaaactga aaacacaccc atactcacac acacgcagaa actcacaagt tctaacacac  34140
acagacacgc gcacccctga agaaacagtg aaatataaaa ttaagcgagc ctcacagaca  34200
tgtaggaaaa tatgaaaaga tttcctgcat gtgggaagca agtcacagta aagagcaagg  34260
gagtttggaa tagaaacaaa taccggaatc aaggatggct gataactttt caattacgaa  34320
gaacattaaa aaaaatcaca gaatcgtgaa actcaaggga tcacataggg aatttcggaa  34380
aaaaaaccca acctgtatga tgtacttttg tacatcacag ttcgaaggta acaaggcaaa  34440
gatataataa gaagaaacct gtcacgagaa actggaggaa aaagagctgt gtcttcctac  34500
aagtacactg atacaaattg ccaatgtgtt cacctcagaa acactggaag ccagatacca  34560
```

gggaatattg ttaaaatgat aatcaggaac aaaaagagat caaccgggaa tgctgaatcc 34620
agcaataaaa tgccttgaag atcatccatg tcggataaat gcatattgtg cactgcccca 34680
aagaaagaaa ccggaaactg taagaattgg aaatcagcag gcttatgtaa caagagaggt 34740
gacccgaagg aattaggtag aagaagaatt gaacaagaaa ggaactttct gcagcccacg 34800
taatgaagaa tccagcaatt ggcaaatgta gatagatgta aatgcaaaat attttcttga 34860
tcaaatttct atatctttgt aaatgagagt tgactacttg aaacaaaatg atagcaagat 34920
atttaacttc agcatatgta gaggtaagaa tttgaaatgg tagcataaat cacgaaggga 34980
ttaattcgaa gtgtaccgtt gtaagtttct ttacctcatg cacgatggtg tgtcatatta 35040
ataaaagggt actgtgcggg ttcgaaggga tattgcaaat cctagagcaa tcacaaaggt 35100
ttgaactctg aggtttttgg tataataaga atagtccatg cattcaaaag agggaagcca 35160
aggaagaact agaagtcttt caagagctca ggctcttata catccagttg ctcattgaac 35220
cagcttcctg gaatggaggg tctggggttg agactaggcc acaagtctag agtctctaga 35280
gagacagtgt tggaacccca tggcccataa tacatttccc attttctcag gcagccagag 35340
gtcatgaatg tgaggatact gggaggttgg agcaacgttc ttgggaggca taaggaagag 35400
cgaatgcttc aagatccccg cagcccaaac tactcgcctg ctttgccccc taatgcattt 35460
ttctctgctg ctccgtagct gtccgacctc ttcagatctc ttagtccacc ctgccgtctt 35520
cctttatgcc atgggtccca ctgttctttc aactcatccc cctttccctc agtcccggag 35580
tagctgcggc cagcagaggg tagactgaga gcaggagaga aggacctgcc taggaacccc 35640
ttctagagat actgcatcct gcctgggagc aagttttcca gggcagcttt gagaagtctt 35700
ggagaaacaa acctactaaa cctgacagac agtaatacta tttgcacaat gcttttctgt 35760
gggaaaggta gagccttttc actacgtatt gagtacatag agtgtgaggg ttgacctgga 35820
acggctatcc tcctggatga cgtgtgtttt ctgaagaact acatgttcgt tgcaactccc 35880
acattagaat atgaagtcct accgagagag atacggagac tagacagata cagatgcatt 35940
tgcatgtgaa tacacaatcc cacaatacag acgtcaaaac ccataccagt tattccagag 36000
agatggattg ggtaggaggc agaaggagaa tactctgatc gtttttcggc cacgtgtgtg 36060
tgttatctca gtgtttctaa gaagcgtttg ctactttaga ttttttattt aaaaaaaata 36120
gtaataatct attaagtatg agagatgtgc agagaggatt agtgatcgag agccattttt 36180
gctggtggca atcatatggt acttttaatg ggaatattag aaaggcaccg gtaatgacct 36240
tgttgcagca caaaggagag agtgtggggt gcccctgcat gttgtcccac ctcttgtgac 36300
gtgtatcgtt ttggaatttc cagtggcttg atcatgaact actgcaggaa tccagatgct 36360
gtggcagctc cttattgtta tacgagggat cccggtgtca ggtgggagta ctgcaacctg 36420
acgcaatgct cagacgcaga agggactgcc gtcgcgcctc cgactgttac cccggttcca 36480
agcctagagg ctccttccga acaaggtaag gagtctgtgg ccagacatct acacgcttcg 36540
atgctgggat gaaaagccat ggaaattccc actgatgcag ccgccttcaa tggtaaacgg 36600
atgctcgagt gttgccggag ttctgccatg ttgggggaag cctccgtgta ctctctgggg 36660
gagccagcgg agtgatttct ggtgcaactt gggtgggctt tgtctttaga atgggcacaa 36720
accttccagg gtgatgggct tcacaactca cctccttcta aaatgggcta tctcagtgtc 36780
ttagccaaaa tttttattgt aacgtgctgt caggtgtgtg attctttctg tcgcagtaag 36840
cttttctggg gatttcttca agtagccagc agtcagtgca atcttcagca ttgcagattt 36900

-continued

```
caaaaaatgt ggctctggag cctgtcatcc tcgagaaacc taacagggct gcattaattc  36960
catatggtcc tgggtctatg gagcagtata tgagctccca atgctctaag gctcttcagt  37020
cctaggcttt gaagggagtg atttctcagt gttcttaaac ctctttctga tggcacttgt  37080
acctgtgagg ggtctagaga gaaaggttag tagacttctc ctttactgca attcaggatg  37140
cagggcatga gaagattccc tccctcctcc aagggaagaa ggttttggcg tgcacacatc  37200
cttgagaagc aaagtgtctt tgccttcagt cagatatata ggatcgtttt ctgccccatg  37260
gcctggaagc cagaggcctt ggctttcatg atcaacgatc tagggaaaca tgcaaaattt  37320
ccatgtcttt cccctcctct gccctcgaca gccaattacc acctgcatcc tgcattgcca  37380
aatgcagtgc cctttgtatg aacattcagt agagtttcat agaaaggtgc tacttcgtga  37440
gcgcactttg cagtgagaag gagtctgttc tgttctgttt ttctaaggat ttcaggtgaa  37500
atatttccta gaacttacta cagttctaga ttggtaggaa tctgtaggtt tgctgtatgt  37560
tttttggttg gttttctccc atccatctgc ctacaggtaa gggaaagata acgttcgtaa  37620
ttctcataga ctcctttctg gttgtgtcat aaatggcttc acatatttcg ttattctcag  37680
agatactcag tttatttctt gtgttttcat ttcagcaccg actgagcaga ggcctggggt  37740
gcaggagtgc taccacggta atggacagag ttatcgaggc acatactcca ccactgtcac  37800
tggaagaacc tgccaagctt ggtcatctat gacaccacac tcgcatagtc ggaccccaga  37860
atactaccca aatgcgtatg tctttgttct ttaccataag agaagaaagg gccaagtgaa  37920
gtttctgtta caagagatgt gtctcaagct gagttctccg aactcaactt gtgacagatg  37980
cagatggcgt agcaaaatgt ctcaggatga ttgccttgga gctaagggtc tgagagaagg  38040
gaaatgttaa gctccctctc cttcctccta gttctattga gcagaaggga aatctggagg  38100
tgaggagatc acattatgaa gaaagtcaga atgacaaagg accagacact tagattaccc  38160
ttccacaaca ccaactaaac gtcaatggag actttccagt tggaattccg ttattctggc  38220
ttccacttcc tgaagggaag gttgcgtttg ccttttctct ctgggttcaa gaggaaagaa  38280
taggtgctta tttatggaca ggtgaattga tctgtttcta tatctacgta tattccgatt  38340
gtcagaaaaa cactcgttcc taagtaccag tggcctgaag ggatacaggt tcccagcaag  38400
agaagatcca aggaaggaag gcagatgaga gccagcacag agagggatgc tgaaaagtaa  38460
aagggatggg tggatggaga gaagcccggg tctgaccacc caatggccaa tattttggcc  38520
acaagcgact accagagaca tggaaaaatg gtttctacat gtgggacaac agatggtaga  38580
ggacctagag aattgagaga ggggcaatga tgggctccac tccgcagatg ccttggcttt  38640
cttcctggat acccttcctg cactgaatag caaggagatg gagcccaagc agactgtagc  38700
catcttgctg aatggaggag agggattgga gtttgggatg actgtggtag ctgaaatttt  38760
tctaggtctg ctagaaataa gaactggttt gtggaggaaa agagctctac aaatacgcat  38820
agaagtctcc tccagtcgtt ggcctgacat gacgctgcct gtgcacagga aatggttcca  38880
cgagaaagtg tggcaaagaa catttactga gaaacagcaa gtacaagagc acaggaagct  38940
caataaagaa gagagagatc acatagcact ctgggatact ggagttcttc ccagctagac  39000
cagagagtcc tcacggagca cattgccaat tcagtggaga ccccagaaca gccgtaattt  39060
aaaggtacac ttagtatatt actagaataa agtcagctgc agacaacccc ttgcacagct  39120
ggaaagcaag tgtccaagca tcaaatcggt ttccaatcaa tgaagtgcct gtgggaggaa  39180
atctcaactc tctttagaag taaacaacaa agtcgattgc ctcagctatg cggtatccgc  39240
agagtgagtc ctaaatttaa aatctgacta catgtagaaa agcgtttcgt gtgacccatg  39300
```

-continued

```
accaggaaat aaatcgggta atacaaacag gctcaggaat gagagaaatg attagaattg  39360
cgtgaaaatt tgacatatca gtatgataac tgatttcaaa tatttaaaaa aacaacatgc  39420
aagaaagcag atatcatatc aagagaaatt aacagtacag aatagccaaa ttaaattaaa  39480
gagctagtat aaaaaaagta tgtcttaatt gaaaaaaatt actgtatggc cggctgatca  39540
aattagacgt ttcagaggaa aacattaccc aacacacaat tctagagaac ctacagaatg  39600
agctacacac acacacacac acacacacac acacactgaa aacacaccca tactcacaca  39660
cacgcagaaa ctcacaagtt ctaacacaca cagacacgcg cacccctgaa gaaacagtga  39720
aatataaaat taagcgagcc tcacagacat gtaggaaaat atgaaaagat ttcctgcatg  39780
tgggaagcaa gtcacagtaa agagcaaggg agtttggaat agaaacaaat accggaatca  39840
aggatggctg ataacttttc aattacgaag aacattaaaa aaaatcacag aatcgtgaaa  39900
ctcaagggat catataggga atttcggaaa aaaaacccaa cctgtatgat gtacttttgt  39960
acatcacagt tcgaaggtaa caaggcaaag atataataag aagaaacctg tcacgagaaa  40020
ctggaggaaa aagagctgtg tcttcctaca agtacactga tacaaattgc caatgtgttc  40080
acctcagaaa cactggaagc cagataccag ggaatattgt taaaatgata atcaggaaca  40140
aaaagagatc aaccgggaat gctgaatcca gcaataaaat gccttgaaga tcatccatgt  40200
cggataaatg catattgtgc actgccccaa agaaagaaac cggaaactgt cagaattgga  40260
aatcagcagg cttatgtaac aagagaggtg acccgaagga attaggtaga agaagaattg  40320
aacaagaaag gaactttctg cagcccacgt aatgaagaat ccagcaattg gcaaatgtag  40380
atagatgtaa atgcaaaata ttttcttgat caaatttcta tatctttgta aatgagagtt  40440
gactacttga aacaaaatga tagcaagata tttaacttca gcatatgtag aggtaagaat  40500
ttgaaatggt agcataaatc acgaagggat taattcgaag tgtaccgttg taagtttctt  40560
tacctcatgc acgatggtgt gtcatattaa taaaagggta ctgtgcgggt tcgaagggat  40620
attgcaaatc ctagagcaat cacaaaggtt tgaactctga ggtttttggt ataataagaa  40680
tagtccatgc attcaaaaga gggaagccaa ggaagaacta gaagtctttc aagagctcag  40740
gctcttatac atccagttgc tcattgaacc agcttcctgg aatggagggt ctggggttga  40800
gactaggcca caagtctaga gtctctagag agacagtgtt ggaaccccat ggcccataat  40860
acatttccca ttttctcagg cagccagagg tcatgaatgt gaggatactg ggaggttgga  40920
gcaacgttct tgggaggcat aaggaagagc gaatgcttca agatccccgc agcccaaact  40980
actcgcctgc tttgcccccct aatgcatttt tctctgctgc tccgtagctg tccgacctct  41040
tcagatctct tagtccaccc tgccgtcttc ctttatgcca tgggtcccat tgttctttca  41100
actcatcccc ctttccctca gtcccggagt agctgcggcc agcagagggt agactgagag  41160
caggagagaa ggacctgcct aggaacccct tctagagata ctgcatcctg cctgggagca  41220
agttttccag ggcagctttg agaagtcttg gagaaacaaa cctactaaac ctgacagaca  41280
gtaatactat ttgcacaatg cttttctgtg ggaaaggtag agccttttca ctacgtattg  41340
agtacataga gtgtgagggt tgacctggaa cggctatcct cctggatgac gtgcgttttc  41400
tgaagaacta catgttcgtt gcaactccca cattagaata tgaagtccta ccgagagaga  41460
tacggagact agacagatac agatgcattt gcatgtgaat acacaatccc acaatacaga  41520
cgtcaaaacc cataccagtt attccagaga gatggattgg gcagaaggca gaaggagaat  41580
actctgatcg tttttcggcc acgtgtgtgt gttatctcag tgtttctaag aagcgtttgc  41640
```

-continued

```
tactttagat tttttattta aaaaaaatag taataatcta ttaagtatga gagatgtgca  41700
gagaggatta gtgatcgaga gccatttttg ctggtggcaa tcatatggta cttttaatgg  41760
gaatattaga aaggcaccgg taatgacctt gttgcagcac aaaggagaga gtgtggggtg  41820
cccctgcatg ttgtcccacc tcttgtgacg tgtatcgttt tggaatttcc agtggcttga  41880
tcatgaacta ctgcaggaat ccagatgctg tggcagctcc ttattgttat acgagggatc  41940
ccggtgtcag gtgggagtac tgcaacctga cgcaatgctc agacgcagaa gggactgccg  42000
tcgcgcctcc gactgttacc ccggttccaa gcctagaggc tccttccgaa caaggtaagg  42060
agtctgtggc cagacatcta cacgcttcga tgctgggatg aaaagccatg gaaattccca  42120
ctgatgcagc cgccttcaat ggtaaacgga tgctcgagtg ttgcctgagt tctaccatgt  42180
aggaggaagc ctccgtgcac tctctggggg agccagcgga gtgatttctg gtgcaacgtg  42240
gttgggcttt gtctttagga tgggcacaaa ccctccaggg ggatcgactt caaaattcac  42300
cttgttgtaa aacgggctac ctcagtgtcc cagccaaaat tttattgtaa acatgctgtc  42360
aggtgtgtca ctctttccaa gccagtaagc ttttccgggg atttcttcaa gtagccagca  42420
ttcagagcaa tcttcagcat tgcagattct gagaaatgtg gctctggagc ctgtcaccct  42480
cgagaaacct aagagggctg cattgattcc atgtggccct gggtctatgg agcagtacat  42540
gagctcccag tgctctaagg ctcttcagcc ctaggctttg aagggagtga tttctcagta  42600
ttcttaaacc tctttctgat gacacttgta cctgtgaggg gtctagagag aaagagtagt  42660
agactcctac tttactacaa ttcaggatgc agggcatgag aggattccct ctctcctcca  42720
agggaagaag cttttggcgt gcacacatcc ctgagaagca aagtgtcttt gtcttcagtc  42780
agatacatag gaccgttttc tgccccatgg cccggaagcc aaaggccttg gctttcatga  42840
tcaacggtct agggaaacat gcaaaatttc catgtctgtc ccaaactctg cccccgacag  42900
ccaattacca cctgcagccc gcattgccaa atgcggtgcc gtttgcatga agattcagta  42960
gagtttccta gaaaggtgct acctcgtgag ctcactttcc aatgaggaat ctgatctgtt  43020
gtgtttctct aaggtgtcag gtgaaatatt tccaagaact tactacagtt ctagaatggg  43080
aggaatctgt tgctttggtg tttgtttgtt ggtcggtttt ctcacatcca tctgcctatg  43140
gataaggaaa agagaacggt cgtaattctc atagactcct ttctggttgt gtcacaaatg  43200
gcttcacatg tttctctatg ctcagagata ctcagcttga tttcccgtgt tttcatttca  43260
gcaccgactg agcaaaggcc tggggtgcag gagtgctacc atggtaatgg acagagttat  43320
cgaggcacat actccaccac tgtcacagga agaacctgcc aagcttggtc atctatgaca  43380
ccacactcgc atagtcggac cccagaatac tacccaaatg cgtatgtctt tgttctttac  43440
cataagagaa gaaagggcca agtgaagttt ctgttacaag agatgtgtct caagctgagt  43500
tctccgaact caacttgtga cagatgcaga tggcgtagca aaatgtctca ggatgattgc  43560
cttggagcta agggtctgag agaagggaaa tgttaagctc cctctccttc ctcctagttc  43620
tattgagcag aagggaaatc tggaggtgag gagatcacat tatgaagaaa gtcagaatga  43680
caaaggacca gacacttaga ttacccttcc acaacaccaa ctaaacgtca atggagactt  43740
tccagttgga attccgttat tctggcttcc acttcctgaa gggaaggttg cgtttgcctt  43800
ttctctctgg gttcaagagg aaagaatagg tgcttattta tggacaggtg aattgatctg  43860
tttctatatc tacgtatatt ccgattgtca gaaaaacact cgttcctaag taccagtggc  43920
ctgaagggat acaggttccc agcaagagaa gatccaagga aggaaggcag atgagagtca  43980
gcacagagag ggatgctgaa aagtaaaagg gatgggtgga tggagagaag cccgggtctg  44040
```

accacccaat ggccaatatt ttggccacaa gcgactacca gagacatgga aaaatggttt 44100
ctacatgtgg gacaacagat ggtagaggac ctagagaatt gagagagggg caatgatggg 44160
ctccactccg cagatgcctt ggctttcttc ctggataccc ttcctgcact gaatagcaag 44220
gagatggagc ccaagcagac tgtagccatc ttgctgaatg gaggagaggg attggagttt 44280
gggatgactg tggtagctga aatttttcta ggtctgctag aaataagaac tggtttgtgg 44340
aggaaaagag ctctacaaat acgcatagaa gtctcctcca gtcgttggcc tgacatgacg 44400
ctgcctgtgc acaggaaatg gttccacgag aaagtgtggc aaagaacatt tactgagaaa 44460
cagcaagtac aagagcacag gaagctcaat aaagaagaga gagatcacat agcactctgg 44520
gatactggag ttcttcccag ctagaccaga gagtcctcac ggagcacatt gccaattcag 44580
tggagacccc agaacagccg taatttaaag gtacacttag tatattacta gaataaagtc 44640
agctgcagac aacccccttgc acagctggaa agcaagtgtc caagcatcaa atcggtttcc 44700
aatcaatgaa gtgcctgtga gaggaaatct caactctctt tagaagtaaa caacaaagtc 44760
gattgcctca gctatgcggt atccgcagag tgagtcctaa atttaaaatc tgactacatg 44820
tagaaaagcg tttcgtgtga cccatgacca ggaaataaat cgggtaatac aaacaggctc 44880
aggaatgaga gaaatgatta gaattgcgtg aaaatttgaa atatcagtat gataactgat 44940
ttcaaatatt taaaaaaaca acatgcaaga aagcagatat catatcaaga gaaattaaca 45000
gtacagaata gccaaattaa attaaagagc tagtataaaa aaagtatgtc ttaattgaaa 45060
aaaattactg tatggccggc tgatcaattt agacgtttca gaggaaaaca ttacccaaca 45120
cacaattcta gagaacctac agaatgagct acacacacac acacacacac acacacaaac 45180
tgaaaacaca cccatactca cacacacgca gaaactcaca agttctaaca cacacagaca 45240
cgcgcacccc tgaagaaaca gtgaaatata aaattaagcg agcctcacag acatgtagga 45300
aaatatgaaa agatttcctg catgtgggaa gcaagtcaca gtaaagagca agggagtttg 45360
gaatagaaac aaataccaga atcaaggatg gctgataact tttcaattac gaagaacatt 45420
aaaaaaaatc acagaatcgt gaaactcaag ggatcacata gggaatttcg gaaaaaaaac 45480
ccaacctgta tgatgtactt ttgtacatca cagttcgaag gtaacaaggc aaagatataa 45540
taagaagaaa cctgtcacga gaaactggag gaaaaagagc tgtgtcttcc tacaagtaca 45600
ctgatacaaa ttgccaatgt gttcacctca gaaacactgg aagccagata ccagggaata 45660
ttgttaaaat gataatcagg aacaaaaaga gatcaaccgg gaatgctgaa tccagcaata 45720
aaatgccttg aagatcatcc atgtcggata aatgcatatt gtgcactgcc ccaaagaaag 45780
aaaccggaaa ctgtaagaat tggaaatcag caggcttatg taacaagaga ggtgacccga 45840
aggaattagg tagaagaaga attgaacaag aaaggaactt tctgcagccc acgtaatgaa 45900
gaatccagca attggcaaat gtagatagat gtaaatgcaa aatattttct tgatcaaatt 45960
tctatatctt tgtaaatgag agttgactac ttgaaacaaa atgatagcaa gatatttaac 46020
ttcagcatat gtagaggtaa gaatttgaaa tggtagcata aatcacgaag ggattaattc 46080
gaagtgtacc gttgtaagtt tctttacctc atgcacgatg gtgtgtcata ttaataaaag 46140
ggtactgtgc gggttcgaag ggatattgca aatcctagag caatcacaaa ggtttgaact 46200
ctgaggtttt tggtataata agaatagtcc atgcattcaa aagagggaag ccaaggaaga 46260
actagaagtc tttcaagagc tcaggctctt atacatccag ttgctcattg aaccagcttc 46320
ctggaatgga gggtctgggg ttgagactag gccacaagtc tagagtctct agagagacag 46380

-continued

```
tgttggaacc ccatggccca taatacattt cccattttct caggcagcca gaggtcatga  46440
atgtgaggat actgggaggt tggagcaacg ttcttgggag gcataaggaa gagcgaatgc  46500
ttcaagatcc ccgcagccca aactactcgc ctgctttgcc ccctaatgca tttttctctg  46560
ctgctccgta gctgtccgac ctcttcagat ctcttagtcc accctgccgt cttcctttat  46620
gccatgggtc ccactgttct ttcaactcat ccccctttcc ctcagtcccg gagtagctgc  46680
ggccagcaga gggtagactg agagcaggag agaaggacct gcctaggaac cccttctaga  46740
gatactgcat cctgcctggg agcaagtttt ccagggcagc tttgagaagt cttggagaaa  46800
caaacctact aaacctgaca gacagtaata ctatttgcac aatgcttttc tgtgggaaag  46860
gtagagcctt ttcactacgt attgagtaca tagagtgtga gggttgacct ggaacggcta  46920
tcctcctgga tgacgtgtgt tttctgaaga actacatgtt cgttgcaact cccacattag  46980
aatatgaagt cctaccgaga gagatacgga gactagacag atacagatgc atttgcatgt  47040
gaatacacaa tcccacaata cagacgtcaa aacccatacc agttattcca gagagatgga  47100
ttgggcagaa ggcagaagga gaatactctg atcgtttttc ggccacgtgt gtgtgttatc  47160
tcagtgtttc taagaagcgt ttgctacttt agattttta tttaaaaaaa atagtaataa  47220
tctattaagt atgagagatg tgcagagagg attagtgatc gagagccatt tttgctggtg  47280
gcaatcatat ggtactttta atgggaatat tagaaaggca ccggtaatga ccttgttgca  47340
gcacaaagga gagagtgtgg ggtgcccctg catgttgtcc cacctcttgt gacgtgtatc  47400
gttttggaat ttccagtggc ttgatcatga actactgcag gaatccagat gctgtggcag  47460
ctccttattg ttatacgagg gatcccggtg tcaggtggga gtactgcaac ctgacgcaat  47520
gctcagacgc agaagggact gccgtcgcgc ctccgactgt taccccggtt ccaagcctag  47580
aggctccttc cgaacaaggt aaggagtctg tggccagaca tctacacgct tcgatgctgg  47640
gatgaaaagc catggaaatt cccactgatg cagccgcctt caatggtaaa cggatgctcg  47700
agtgttgcct gagttctacc atgtaggagg aagcctccgt gcactctctg gggagccag  47760
cggagtgatt tctggtgcaa cgtggttggg ctttgtcttt aggatgggca caaaccctcc  47820
agggggatcg acttcaaaat tcaccttgtt gtaaaacggg ctacctcagt gtcccagcca  47880
aaatttttat tgtaacatgc tgtcaggtgt gtcactcttt ccaagccagt aagcttttcc  47940
ggggatttct tcaagtagcc agcattcaga gcaatcttca gcattgcaga ttctgagaaa  48000
tgtggctctg gagcctgtca ccctcgagaa acctaagagg gctgcattga ttccatgtgg  48060
ccctgggtct atggagcagt acatgagctc ccagtgctct aaggctcttc agccctaggc  48120
tttgaaggga gtgatttctc agtattctta aacctctttc tgatgacact tgtacctgtg  48180
aggggtctag agagaaagag tagtagactc ctactttact acaattcagg atgcagggca  48240
tgagaggatt ccctctctcc tccaagggaa gaagcttttg gcgtgcacac atccctgaga  48300
agcaaagtgt ctttgtcttc agtcagatac ataggaccgt tttctgcccc atggcccgga  48360
agccaaaggc cttggctttc atgatcaacg gtctagggaa acatgcaaaa tttccatgtc  48420
tgtcccaaac tcttccccg acagccaatt accacctgca gcccgcattg ccaaatgcgg  48480
tgccgtttgc atgaagattc agtagagttt cctagaaagg tgctacctcg tgagctcact  48540
ttccaatgag gaatctgatc tgttgtgttt ctctaaggtg tcaggtgaaa tatttccaag  48600
aacttactac agttctagaa tgggaggaat ctgttgcttt ggtgtttgtt tgttggtcgg  48660
ttttctcaca tccatctgcc tatggataag gaaaagagaa cggtcgtaat tctcatagac  48720
tcctttctgg ttgtgtcaca aatggcttca catgtttctc tatgctcaga gatactcagc  48780
```

ttgatttccc gtgttttcat ttcagcaccg actgagcaaa ggcctggggt gcaggagtgc 48840
taccatggta atggacagag ttatcgaggc acatactcca ccactgtcac aggaagaacc 48900
tgccaagctt ggtcatctat gacaccacac tcgcatagtc ggaccccaga atactaccca 48960
aatgcgtatg tctttgttct ttaccataag agaagaaagg gccaagtgaa gtttctgtta 49020
caagagatgt gtctcaagct gagttctccg aactcaactt gtgacagatg cagatggcgt 49080
agcaaaatgt ctcaggatga ttgccttgga gctaagggtc tgagagaagg gaaatgttaa 49140
gctccctctc cttcctccta gttctattga gcagaaggga aatctggagg tgagaagatc 49200
acattatgaa gaaagtcaga atgacaaagg accagacact tagattaccc ttccacaaca 49260
ccaactaaac gtcaatggag actttccagt tggaattccg ttattctggc ttccacttcc 49320
tgaagggaag gttgcgtttg ccttttctct ctgggttcaa gaggaaagaa taggtgctta 49380
tttatggaca ggtgaattga tctgtttcta tatctacgta tattccgatt gtcagaaaaa 49440
cactcgttcc taagtaccag tggcctgaag ggatacaggt tcccagcaag agaagatcca 49500
aggaaggaag gcagatgaga gtcagcacag agagggatgc tgaaaagtaa aagggatggg 49560
tggatggaga gaagcccggg tctgaccacc caatggccaa tattttggcc acaagcgact 49620
accagagaca tggaaaaatg gtttctacat gtgggacaac agatggtaga ggacctagag 49680
aattgagaga ggggcaatga tgggctccac tccgcagatg ccttggcttt cttcctggat 49740
acccttcctg cactgaatag caaggagatg gagcccaagc agactgtagc catcttgctg 49800
aatggaggag agggattgga gtttgggatg actgtggtag ctgaaatttt tctaggtctg 49860
ctagaaataa gaactggttt gtgtggagga aaagagctct acaaatacgc atagaagtct 49920
cctccagtcg ttggcctgac atgacgctgc ctgtgcacag gaaatggttc cacgagaaag 49980
tgtggcaaag aacatttact gagaaacagc aagtacaaga gcacaggaag ctcaataaag 50040
aagagagaga tcacatagca ctctgggata ctggagttct tcccagctag accagagagt 50100
cctcacggag cacattgcca attcagtgga gaccccagaa cagccgtaat ttaaaggtac 50160
acttagtata ttactagaat aaagtcagct gcagacaacc ccttgcacag ctggaaagca 50220
agtgtccaag catcaaatcg gtttccaatc aatgaagtgc ctgtgagagg aaatctcaac 50280
tctctttaga agtaaacaac aaagtcgatt gcctcagcta tgcggtatcc gcagagtgag 50340
tcctaaattt aaaatctgac tacatgtaga aaagcgtttc gtgtgaccca tgaccaggaa 50400
ataaatcggg taatacaaac aggctcagga atgagagaaa tgattagaat tgcgtgaaaa 50460
tttgacatat cagtatgata actgatttca aatatttaaa aaaacaacat gcaagaaagc 50520
agatatcata tcaagagaaa ttaacagtac agaatagcca aattaaatta aagaggtagt 50580
ataaaaaaag tatgtcttaa ttgaaaaaaa ttactgtatg gccggctgat caatttagac 50640
gtttcagagg aaaacattac ccaacacaca attctagaga acctacagaa tgagctacac 50700
acacacacac acacacacac acaaactgaa aacacaccca tactcacaca cacgcagaaa 50760
ctcacaagtt ctaacacaca cagacacgcg cacccctgaa gaaacagtga aatataaaat 50820
taagcgagcc tcacagacat gtaggaaaat atgaaaagat ttcctgcatg tgggaagcaa 50880
gtcacagtaa agagcaaggg agtttggaat agaaacaaat accggaatca aggatggctg 50940
ataacttttc aattacgaag aacattaaaa aaaatcacag aatcgtgaaa ctcaagggat 51000
cacataggga atttcggaaa aaaaacccaa cctgtatgat gtacttttgt acatcacagt 51060
tcgaaggtaa caaggcaaag atataataag aagaaacctg tcacgagaaa ctggaggaaa 51120

```
aagagctgtg tcttcctaca agtacactga tacaaattgc caatgtgttc acctcagaaa  51180
cactggaagc cagataccag ggaatattgt taaaatgata atcaggaaca aaaagagatc  51240
aaccgggaat gctgaatcca gcaataaaat gccttgaagg tcatccatgt cggataaatg  51300
catattgtgc actgccccaa agaaagaaac cggaaactgt aagaattgga aatcagcagg  51360
cttatgtaac aagagaggtg acccgaagga attaggtaga agaagaattg aacaagaaag  51420
gaactttctg cagcccacgt aatgaagaat ccagcaattg gcaaatgtag atagatgtaa  51480
atgcaaaata ttttcttgat caaatttcta tatctttgta aatgagagtt gactacttga  51540
aacaaaatga tagcaagata tttaacttca gcatatgtag aggtaagaat ttgaaatggt  51600
agcataaatc acgaagggat taattcgaag tgtaccgttg taagtttctt tacctcatgc  51660
acgatggtgt gtcatattaa taaaagggta ctgtgcgggt tcgaagggat attgcaaatc  51720
ctagagcaat cacaaaggtt tgaactctga ggtttttggt ataataagaa tagtccatgc  51780
attcaaaaga gggaagccaa ggaagaacta gaagtctttc aagagctcag gctcttatac  51840
atccagttgc tcattgaacc agcttcctgg aatggagggt ctggggttga gactaggcca  51900
caagtctaga gtctctagag agacagtgtt ggaaccccat ggcccataat acatttccca  51960
ttttctcagg cagccagagg tcatgaatgt gaggatactg ggaggttgga gcaacgttct  52020
tgggaggcat aaggaagagc gaatgcttca agatccccgc agcccaaact actcgcctgc  52080
tttgcccccct aatgcatttt tctctgctgc tccgtagctg tccgacctct tcagatctct  52140
tagtccaccc tgccgtcttc ctttatgcca tgggtcccac tgttctttca actcatcccc  52200
ctttccctca gtcccggagt agctgcggcc agcagagggt agactgagag caggagagaa  52260
ggacctgcct aggaacccct tctagagata ctgcatcctg cctgggagca agttttccag  52320
ggcagctttg agaagtcttg gagaaacaaa cctactaaac ctgacagaca gtaatactat  52380
ttgcacaatg cttttctgtg ggaaaggtag agccttttca ctacgtattg agtacataga  52440
gtgtgagggt tgacctggaa cggctatcct cctggatgac gtgcgttttc tgaagaacta  52500
catgttcgtt gcaactccca cattagaata tgaagtccta ccgagagaga tacggagact  52560
agacagatac agatgcattt gcatgtgaat acacaatccc acaatacaga cgtcaaaacc  52620
cataccagtt attccagaga gatggattgg gcagaaggca gaaggagaat actctgatcg  52680
tttttcggcc acgtgtgtgt gttatctcag tgtttctaag aagcgtttgc tactttagat  52740
tttttattta aaaaaaatag taataatcta ttaagtatga gagatgtgca gagaggatta  52800
gtgatcgaga gccatttttg ctggtggcaa tcatatggta cttttaatgg gaatattaga  52860
aaggcaccgg taatgacctt gttgcagcac aaaggagaga gtgtggggtg cccctgcatg  52920
ttgtcccacc tcttgtgacg tgtatcgttt tggaatttcc agtggcttga tcatgaacta  52980
ctgcaggaat ccagatgctg tggcagctcc ttattgttat acgagggatc ccggtgtcag  53040
gtgggagtac tgcaacctga cgcaatgctc agacgcagaa gggactgccg tcgcgcctcc  53100
gactgttacc ccggttccaa gcctagaggc tccttccgaa caaggtaagg agtctgtggc  53160
cagacatcta cacgcttcga tgctgggatg aaaagccatg gaaattccca ctgatgcagc  53220
cgccttcaat ggtaaacgga tgctcgagtg ttgcctgagt tctaccatgt aggaggaagc  53280
ctccgtgcac tctctggggg agccagcgga gtgatttctg gtgcaacgtg gttgggcttt  53340
gtctttagga tgggcacaaa ccctccaggg ggatcgactt caaaattcac cttgttgtaa  53400
aacgggctac ctcagtgtcc cagccaaaat ttttattgta acatgctgtc aggtgtgtca  53460
ctctttccaa gccagtaagc ttttccgggg atttcttcaa gtagccagca ttcagagcaa  53520
```

tcttcagcat tgcagattct gagaaatgtg gctctggagc ctgtcaccct cgagaaacct 53580
aagagggctg cattgattcc atgtggccct gggtctatgg agcagtacat gagctcccag 53640
tgctctaagg ctcttcagcc ctaggctttg aagggagtga tttctcagta ttcttaaacc 53700
tctttctgat gacacttgta cctgtgaggg gtctagagag aaagagtagt agactcctac 53760
tttactacaa ttcaggatgc agggcatgag aggattccct ctctcctcca agggaagaag 53820
cttttggcgt gcacacatcc ctgagaagca aagtgtcttt gtcttcagtc agatacatag 53880
gaccgttttc tgccccatgg cccggaagcc aaaggccttg gctttcatga tcaacggtct 53940
agggaaacat gcaaaatttc catgtctgtc ccaaactctg cccccgacag ccaattacca 54000
cctgcagccc gcattgccaa atgcggtgcc gtttgcatga agattcagta gagtttccta 54060
gaaaggtgct acctcgtgag ctcactttcc aatgaggaat ctgatctgtt gtgtttctct 54120
aaggtgtcag gtgaaatatt tccaagaact tactacagtt ctagaatggg aggaatctgt 54180
tgctttggtg tttgtttgtt ggtcggtttt ctcacatcca tctgcctatg gataaggaaa 54240
agagaacggt cgtaattctc atagactcct ttctggttgt gtcacaaatg gcttcacatg 54300
tttctctatg ctcagagata ctcagcttga tttcccgtgt tttcatttca gcaccgactg 54360
agcaaaggcc tggggtgcag gagtgctacc atggtaatgg acagagttat cgaggcacat 54420
actccaccac tgtcacagga agaacctgcc aagcttggtc atctatgaca ccacactcgc 54480
atagtcggac cccagaatac tacccaaatg cgtatgtctt tgttctttac cataagagaa 54540
gaaagggcca agtgaagttt ctgttacaag agatgtgtct caagctgagt tctccgaact 54600
caacttgtga cagatgcaga tggcgtagca aaatgtctca ggatgattgc cttggagcta 54660
agggtctgag agaagggaaa tgttaagctc cctctccttc ctcctagttc tattgagcag 54720
aagggaaatc tggaggtgag gagatcacat tatgaagaaa gtcagaatga caaaggacca 54780
gacacttaga ttacccttcc acaacaccaa ctaaacgtca atggagactt tccagttgga 54840
attccgttat tctggcttcc acttcctgaa gggaaggttg cgtttgcctt ttctctctgg 54900
gttcaagagg aaagaatagg tgcttattta tggacaggtg aattgatctg tttctatatc 54960
tacgtatatt ccgattgtca gaaaaacact cgttcctaag taccagtggc ctgaagggat 55020
acaggttccc agcaagagaa gatccaagga aggaaggcag atgagagtca gcacagagag 55080
ggatgctgaa aagtaaaagg gatgggtgga tggagagaag cccgggtctg accacccaat 55140
ggccaatatt ttggccacaa gcgactacca gagacatgga aaaatggttt ctacatgtgg 55200
gacaacagat ggtagaggac ctagagaatt gagagagggg caatgatggg ctccactccg 55260
cagatgcctt ggctttcttc ctggataccc ttcctgcact gaatagcaag gagatggagc 55320
ccaagcagac tgtagccatc ttgctgaatg gaggagaggg attggagttt gggatgactg 55380
tggtagctga aatttttcta ggtctgctag aaataagaac tggtttgtgt ggaggaaaag 55440
agctctacaa atacgcatag aagtctcctc cagtcgttgg cctgacatga cgctgcctgt 55500
gcacaggaaa tggttccacg agaaagtgtg gcaaagaaca tttactgaga aacagcaagt 55560
acaagagcac aggaagctca ataaagaaga gagagatcac atagcactct gggatactgg 55620
agttcttccc agctagacca gagagtcctc acggagcaca ttgccaattc agtggagacc 55680
ccagaacagc cgtaatttaa aggtacactt agaatattac tagaataaag tcagctgcag 55740
acaacccctt gcacagctgg aaagcaagtg tccaagcatc aaatcggttt ccaatcaatg 55800
aagtgcctgt gagaggaaat ctcaactctc tttagaagta aacaacaaag tcgattgcct 55860

-continued

```
cagctatgcg gtatccgcag agtgagtcct aaatttaaaa tctgactaca tgtagaaaag  55920
cgtttcgtgt gacccatgac caggaaataa atcgggtaat acaaacaggc tcaggaatga  55980
gagaaatgat tagaattgcg tgaaaatttg acatatcagt atgataactg atttcaaata  56040
tttaaaaaaa caacatgcaa gaaagcagat atcatatcaa gagaaattaa cagtacagaa  56100
tagccaaatt aaattaaaga gctagtataa aaaaagtatg tcttaattga aaaaaattac  56160
tgtatggccg gctgatcaaa ttagacgttt cagaggaaaa cattacccaa cacacaattt  56220
tagagaacct acagaatgag ctacacacac acacacacac acacacacac acacaaactg  56280
aaaacacacc catactcaca cacacgcaga aactcacaag ttctaacaca cacagacacg  56340
cgcacccctg aagaaacagt gaaatataaa attaagcgag cctcacagac atgtaggaaa  56400
atatgaaaag atttcctgca tgtgggaagc aagtcacagt aaagagcaag ggagtttata  56460
atagaaacaa ataccagaat caaggatggc tgataacttt tcaattacga agaacattaa  56520
aaaaaatcac agaatcgtga aactcaaggg atcatatagg gaatttcgga aaaaaaaccc  56580
aacctgtatg atgtactttt gtacatcaca gttcgaaggt aacaaggcaa agatgtaata  56640
agaagaaacc tgtcacgaga aactggagga aaaagagctg tgtcttccta caagtacact  56700
gatacaaatt gccaatgtgt tcacctcaga aacactggaa gccagatacc agggaatatt  56760
gttaaaatga taatcaggaa caaaaagaga tcaaccggga atgctgaatc cagcaataaa  56820
atgccttgaa ggtcatccat gtcggataaa tgcatattgt gcactgcccc aaagaaagaa  56880
accggaaact gtaagaattg gaaatcagca ggcttatgta acaagagagg tgacccgaag  56940
gaattaggta gaagaagaat tgaacaagaa aggaactttc tgcagcccac gtaatgaaga  57000
atccagcaat tggcaaatgt agatagatgt aaatgcaaaa tattttcttg atcaaatttc  57060
tatatctttg taaatgagag ttgactactt gaaacaaaat gatagcaaga tatttaactt  57120
cagcatatgt agaggtaaga atttgaaatg gtagcataaa tcacgaaggg attaattcga  57180
agtgtaccgt tgtaagtttc tttacctcat gcacgatggt gtgtcatatt aataaaaggg  57240
tactgtgcgg gttcgaaggg atattgcaaa tcctagagca atcacaaagg tttgaactct  57300
gaggtttttg gtataataag aatagtccat gcattcaaaa gagggaagcc aaggaagaac  57360
tagaagtctt tcaagagctc aggctcttat acatccagtt gctcattgaa ccagcttcct  57420
ggaatggagg gtctggggtt gagactaggc cacaagtcta gagtctctag agagacagtg  57480
ttggaacccc atggcccata atacatttcc cattttctca ggcagccaga ggtcatgaat  57540
gtgaggatac tgggaggttg gagcaacgtt cttgggaggc ataaggaaga gcgaatgctt  57600
caagatcccc gcagcccaaa ctactcgcct gctttgcccc ctaatgcatt tttctctgct  57660
gctccgtagc tgtccgacct cttcagatct cttagtccac cctgccgtct tcctttatgc  57720
catgggtccc actgttcttt caactcatcc ccctttccct cagtcccgga gtagctgcgg  57780
ccagcagagg gtagactgag agcaggagag aaggacctgc ctaggaaccc cttctagaga  57840
tactgcatcc tgcctgggag caagttttcc agggcagctt tgagaagtct tggagaaaca  57900
aacctactaa acctgacaga cagtaatact atttgcacaa tgcttttctg tgggaaaggt  57960
agagcctttt cactacgtat tgagtacata gagtgtgagg gttgacctgg aacggctatc  58020
ctcctggatg acgtgcgttt tctgaagaac tacatgttcg ttgcaactcc cacattagaa  58080
tatgaagtcc taccgagaga gatacggaga ctagacagat acagatgcat ttgcatgtga  58140
atacacaatc ccacaataca gacgtcaaaa cccataccag ttattccaga gagatggatt  58200
gggcagaagg cagaaggaga atactctgat cgtttttcgg ccacgtgtgt gtgttatctc  58260
```

-continued

```
agtgtttcta agaagcgttt gctactttag attttttatt taaaaaaaat agtaataatc  58320
tattaagtat gagagatgtg cagagacgat tagtgatcga gagccatttt tgctggtggc  58380
aatcatatgg tacttttaat gggaatatta gaaaggcacc ggtaatgacc ttgttgcagc  58440
acaaaggaga gagtgtgggg tgcccctgca tgttgtccca cctcttgtga cgtgtatcgt  58500
tttggaattt ccagtggctt gatcatgaac tactgcagga atccagatgc tgtggcagct  58560
ccttattgtt atacgaggga tcccggtgtc aggtgggagt actgcaacct gacgcaatgc  58620
tcagacgcag aagggactgc cgtcgcgcct ccgactgtta ccccggttcc aagcctagag  58680
gctccttccg aacaaggtaa ggagtctgtg gccagacatc tacacgcttc gatgctggga  58740
tgaaaagcca tggaaattcc cactgatgca gccgccttca atggtaaacg gatgctcgag  58800
tgttgcctga gttctaccat gtaggaggaa gcctccgtgc actctctggg ggagccagcg  58860
gagtgatttc tggtgcaacg tggttgggct ttgtctttag gatgggcaca aaccctccag  58920
ggggatcgac ttcaaaattc accttgttgt aaaacgggct acctcagtgt cccagccaaa  58980
atttttattg taacatgctg tcaggtgtgt cactctttcc aagccagtaa gcttttccgg  59040
ggatttcttc aagtagccag cattcagagc aatcttcagc attgcagatt ctgagaaatg  59100
tggctctgga gcctgtcatc ctcgagaaac ctaacagggc tgcattaatt ccatatggtc  59160
ctgggtctat ggagcagtat atgagctccc aatgctctaa ggctcttcag tcctaggctt  59220
tgaagggagt gatttctcag tgttcttaaa cctctttctg atggcacttg tacctgtgag  59280
gggtctagag agaaaggtta gtagacttct cctttactgc aattcaggat gcagggcatg  59340
agaagattcc ctccctcctc caagggaaga aggttttggc gtgcacacat ccttgagaag  59400
caaagtgtct ttgccttcag tcagatatat aggatcgttt tctgccccat ggcctggaag  59460
ccagaggcct tggctttcat gatcaacgat ctagggaaac atgcaaaatt tccatgtctt  59520
tcccctcctc tgccctcgac agccaattac cacctgcatc ctgcattgcc aaatgcagtg  59580
ccctttgtat gaacattcag tagagtttca tagaaaggtg ctacttcgtg agcgcacttt  59640
gcagtgagaa ggagtctgtt ctgttctgtt tttctaagga tttcaggtga aatatttcct  59700
agaacttact acagttctag attggtagga atctgtaggt ttgctgtatg tttttggtt  59760
ggttttctcc catccatctg cctacaggta agggaaagat aacgttcata attctcatag  59820
actcctttct ggttgtgtca taaatggctt cacatatttc gttattctca gagatactca  59880
gtttatttct tgtgttttca tttcagcacc gactgagcag aggcctgggg tgcaggagtg  59940
ctaccacggt aatggacaga gttatcgagg cacatactcc accactgtca ctggaagaac  60000
ctgccaagct tggtcatcta tgacaccaca ctcgcatagt cggaccccag aatactaccc  60060
aaatgcgtat gtctttgttc tttaccataa gagaataaag ggccaactga agtttctgtg  60120
acaagagaca tgcttcaagc tgagttctcc gaactcaact tgtgtcagat tcagatggtg  60180
tagcaaaatg tctcaggatg atttccttgg agctaagggt ctgagagaag agaaatgtta  60240
agctgcctca ccttcctcct agttttgtgg agcagaaggg aaatgaggag gcgaggagat  60300
caccttatga agaaagtcag aatgacgaac caccaaacac ttagattacc cttgcccaac  60360
acccactaag cgtcaatgaa gactttccag ttggaattcc gttattctga cttccaattc  60420
ctgaagggaa gattgtgttt gccttttctg tctgggctca tgaggaaagt tttatgtgctt  60480
acttatggac aggtgaattg atctgtttct atttctacct gtattccaat agggagaaaa  60540
tctcttggtc ctaagtacca gtggcctgaa aggatagagg ttcccagcaa gagaagatcc  60600
```

aaggaaggaa ggcagatgag agtcagcaca gagagggatg ctgaaaagta aaagggatgg 60660
gtagatggat agaagccctg gtctgaccac cccatggcca atcatttggc cataatcaac 60720
aaccaaagac atggaaaaat ggtttctaca tgtgggacaa cagatggtag aggacctaga 60780
gaattgagag agggccaatg atgagctcaa ctccatagat gccttggctt tcttcctgga 60840
tacccttcct gcactgaata gcaaggagat ggagctcaag cagcctgtag ccatctagct 60900
gagcagagga gagggattgg agtttgggat gactctggta ttttctaggt ccgctacaaa 60960
taagaactgg tttgtggagg aaaggagctc tacaaatacg catagaagtc tcctccagta 61020
gttggcctca catgacactg catgtgcaca gaaaatggtt ctacagaaag tgtggcaaag 61080
aacatttact gagaaacagc aactacaaga gaacagcaag ctcaattaag aagatagaga 61140
tcacatagca ctctgtgtta ttggagttct taccagctag atgagagagt gctcacggaa 61200
cacattgcca attcagtgga gaccccagaa cagccataat ttcaaagtac aattagtata 61260
ttactagaat aaaggcagct gcagacaacc ccttgcacag ctgaaaagca agtgtccaag 61320
catcaaatgg gtttccaatc aatgaagtgc ctgtgagagg aaatctcaac tctcttcaga 61380
agtaaacaac aaagtcaatt gcctcagcta tgcggtatcc ccagagtgag tcctaaatta 61440
aaaatttgac tacgtgtaga aaagaatttc gtgtgatcca tgaccagaaa ataaatcagg 61500
caatacaaac aggctcagaa atgacatcga taattagaat tgcatgaaaa tttgacatat 61560
cagtatgata actgatttca gatatttaaa aaaagtgcaa caaagcaggt atcatatcaa 61620
gacaaattaa tagtatagaa tagccaaatc aaattaaaga actattatac aaaaagtatg 61680
tcttaaatga agaaattact gtatgtccgc ctgaaaaatt tagatgtttc agaagaaaaa 61740
attaaccaaa aacaattctg cagaacctac agaatgagcc acacacacac acattcaaaa 61800
cacacccata cacacacaca tgcaaaaact cacaagttct aacacacaca caaacacaca 61860
cacacatgca catccctaaa gaaataggga aatataaaat taaccgaccc tcagagacat 61920
gcaggaaaat ataagaagat ttcctgcatg tgggaagcaa gtcacagtaa agagcaaggg 61980
agtttggagt agatacaaat accggaatca cggatggctg ataacttttc aattatgaag 62040
aacgttagaa aaatcacaga ttcatgaaac taaagggatc aaataggaaa tttcgagaaa 62100
aaaaactaca tgatgcactt ctctacatca cagttcaaag gtaacaaggc aaggatataa 62160
gaagaagaaa catctcacga gaaactggag aaaaaagagc tgtgtcttcc tagagtacag 62220
tgatacaaat tgctaatgcg ttcacctcag aaacactgga agccagatac cagggaatat 62280
tattaaaatg ataatgagga acaagaagag atcaaccgag aatgctgaat ccagcaataa 62340
aatgccttga agatcatcca tgttggataa atgcatattg tgcactgccc aaaacaaaga 62400
aactggaaag tgtaagactt tggaatcagc aggcttatgt agcaacagag gtgacccgaa 62460
agaattaggt ataagaagaa tagaagaatt gcatgaaaat ttgacatatg actaagataa 62520
ctatttcaaa tatttaaaaa aagatgaata tgtaataaaa cagataaaat atcaaaagaa 62580
agtaacagta ttgactagcc aaatcaaatt aaagacttag tgtaaaaagc tatgtcttaa 62640
aagaaaaaat tactggatgg ctgcctgatc aatttagaca tttctgaata ggaaactaac 62700
caaaaatcaa ttctacagaa ccaactacac acatatatac acatacaaca cacccataca 62760
cacccacgca aaaactcaca agttcacaca cacacacaca cacacacaac cctcaagaaa 62820
tagtgaaata gaaaaccaac cgaacctcac agacatgttg caaaatagga aaagatttcc 62880
tgcatatggg aagcaagtca cagaaaagag aacgggagat tggaaacaga aacaaatacc 62940
ggaatcaagg atggccgaaa acttttcatt gatcaagaat attaacaaaa tcgcaaaaac 63000
acgaaattca atgcatcaaa taggcgtttc gaaaaaaaga aaaaatctgg tatgatgcac 63060
ttttgtactt cacattttca cggtaagaag acaaagatat aataacaaga aacttcttat 63120
gagaaactgg ggaaaaacaa gctgtttctt gctagaagaa cagtgataca aattgctaat 63180
gcattctcgt caaaaacact ggaagccaga taccgggaat gttattaatg tggtaaacag 63240
gaacaagaag agatcaacca agaatgctaa atccagcaat aaaatgcctt gaagatcatc 63300
catgctgcat aaatgtatgt tgtgcactgc cccaaacaaa gaaaccggaa actgtaagaa 63360
tttggaatca gcaggctgat gtaacaagag aggtgaccca aaggaattag gtagaagaag 63420
aatagtacaa gaagggaact ttctgcagcc catgtaatga agaacccagc aattggcaaa 63480
tgtagatgta aatgcaaaat attttcttga ccaaatttct atatattttt aaatgagcgt 63540
tgactactgg aaacaaaatg atagcaatat atttaatttt agcatatgta gaggtaagaa 63600
tttgaacaag tagcgtaaat catgtaggga ataattagaa gtgtaccatt gtaagtttct 63660
tacctcatgc acaatggtat gtaatattaa taaaatgtta ctgtgtgggt tcaaggagat 63720
attgcaaatc ctagagcaat cacaaagttt tgaactctga ggtatattgt ataataagaa 63780
tattccatgt attcaaaaga gagaagccaa ggaagaaaga aatttgtcac gagtttgggc 63840
tcttagtaca tcctgtagct cattgaacca gcttcctgga atggagggtc tgggattgac 63900
actaggccac atgtatagag tctctagaga gacagtgttt catccccatg gcccgtaata 63960
catttcccat tttctcaggc agccacaggt catgaatgtg aggatagaga gaggttggag 64020
caacgttctt gggaggcata aggaagagca aatgcttcaa gatccccgca gcccaaactc 64080
ctacctgctt tgccccctaa tgcagtgttc ctccgtagct gtccgacctc ttcagatctc 64140
ttagtctacc ctgccatctt cctttatgcc atgggtccca ctgttctttc aactcatccc 64200
cctttccctc agtgcagagt agctgcggcc agcagagggt agactgagag caggagagaa 64260
ggtcctgccc aggaacccat tctagagatg ctgcattctg cctgggagca agtttttccag 64320
ggcagctttg agaagtcttg cagaaacaaa cctatttgac ccacatgata tgggaatgac 64380
agaaagtaat acaatttgca cagtgctttt ccatgggaaa agtagagcct tttcgcgagg 64440
ttttgagtac atagagagtg aaggttgacc tggaaaggtt atcctcctgg atcccatgtt 64500
ttttctgaag aactacctgt tagttgcaac ttgcacatta gaatatgaag tcctaccgag 64560
agagatacgg agaactagat aaatacagat acttttgtat gtgaataaac gattccacaa 64620
tacacacatc aaaatccata ccagttattc cagagagatg gattgggcag aaggcagaag 64680
gagaatactc tgatcgtttt ttgcccacgt gtatgtatta tctcagtgtt tctaagaagc 64740
gtttgctact ttagattttt ttttataata ataatctttt aagtatgaga aatgtgcaga 64800
caggattagt gattgagagc catttgtgct tgtggcaatc atatggtact tttatgggaa 64860
tattagaaag gcactggtaa tgaccttgtt gcagcacaaa ggagagggtg tggggtgccc 64920
ctgcatattg tcccacctct tgtgacgtgt atcgttttgg aatttccagt ggcttgatca 64980
tgaactactg caggaatcca gatcctgtgg cagcccctta ttgttatacg agggatccca 65040
gtgtcaggtg ggagtactgc aacctgacac aatgctcaga cgcagaaggg actgccgtcg 65100
cgcctccaac tattaccccg attccaagcc tagaggctcc ttctgaacaa ggtaaggagc 65160
ctgtggccag aaacctacac gtttcgatgc tgggatgaaa agccatggaa attcccactg 65220
atgcagcagc ctccaatggt aaacggatgc tcgagtgttg actgagttct gtcatgtagg 65280
aggaagcctc cgtgcactct ctgggggagc cagcggattg atttctggta caacgttggg 65340
tgggctgtgt ctttagaatt ggcacaaacc ctccagggtg atcgacttca caactcacct 65400
cgttgaaaaa tgggctatct cagtgtctta gccaaaattt ttattgtaac atgctgtcag 65460
atgtgtgact ctttccaagc cagtaagctt ttcctgggac ttcttcaatt agccagcatt 65520
cagtgcaatc ttcagcattg cagattcaga gaaatgtggc tctggagcct gtcacccttg 65580
agaaacaggg ctaacagggt tgcattaatt ccaaatcacc ctggttctat ggagcagtac 65640
atgaactccc aatgatctat gtttcaggac ttcctcagtc ataggtgggc tctgcagccc 65700
taggttttta agtgagtgac tgccccgtgt tctggtggca gttgtacctg tgagcggtct 65760
ggatagaaag agtcggagac ttctgtatta ttgcaactca ggatgtgggt catgagagga 65820
tttcatctct cctgcagggg agtaagctgt tcgcctccac ccatccctga taactgaagt 65880
gtctttgtct gcagtcctag acgaaggact gttgtctctc ccatggccca gaagctgaag 65940
accttgcctt ttgttatgaa acgttcattg ttttcatgtc tgtccgtttc tctgccccta 66000
acacccaatc accatgtatg gcctgtaccc ccaaatgcat cgtgctttgc tgtttgctgc 66060
cccatagtcc tcatgaacat tcagtagaaa ttcccataaa tgtgcttgca cgtgagcaca 66120
gtttccattg agaagccctc tcatttgtcc tttttttcta agcttttatg tgaaatattt 66180
ctaagaactt actacagttc taaagtgtta ggaatttgtt tctttggtgt ttttgtttgt 66240
tggttggttg ttgcttttct caagtccatc tgcctacaaa taaagaaaca agaatgttac 66300
ttgtcatatt ctcctgaggt cataattctc agagactttt ttctggtttg tgccataagt 66360
ggcttcacat gtttgtctct tcttggaaac actcagtttg atttcttttc ttttcatttc 66420
agcaccaact gagcaaaggc ctggggtgca ggagtgctac cacggaaatg gacagagtta 66480
tcaaggcaca tacttcatta ctgtcacagg aagaacctgc caagcttggt catctatgac 66540
accacactcg catagtcgga ccccagcata ctacccaaat gcgtatgtct attttcttta 66600
ccataagtga aggaagggtc agtggaaatt tctgttagta gagtcatgct tcaagctgag 66660
tgttcaggac tcaagttgtc tcagatgaac agtgcatagc aaaatgtctc aggaacattg 66720
tctttgagca aagagtctaa gagaagacaa atgttaatct ggctctcctt cctcctagtt 66780
taatggagca gaaaggtatc tggaggcaag gatatcacat taagaaacaa gtcaagatga 66840
caaatgatga aactcttaga gtacccttcc acaacaccca ctaaggttca atgcagcctt 66900
ttctccttgg aattctatta aactaaactc caattcctga agtgaaggtt ctgttggggt 66960
tttctgtttt ggcttacaag gaaagtatat atgtatatct atggagaggc aaatctatct 67020
ctttctatat ctacgtctat tccaatatgt agaaacacag tcggttctga ccaccagtgg 67080
tctgaaggga tactggttgt tagagaataa aaatggcagg aaggcagatg agagtcagca 67140
aagagagaga tcctgtaaag taaaagggtg gatagatgga cagaagccca ggtctgacca 67200
gcccatggcc aggctttagg ccataagtga caccaaagac atggaaaaat ggtttctaca 67260
tgttggacaa cagacagtag tggaccaaaa gaatagtgac agggggaaca atgagatcaa 67320
ctccatagat accttggctt tcttcctgga ggcccttctt gcactgaaga gcaaggtgat 67380
ggagcccaga tggactgtag ccatcttcct gaatgcagga gagagattgg aatttgggac 67440
tactgtggta gctaggattt tataggcctg ctgagaatga gaatggattt gtggatgaaa 67500
ggagctccag gggcacgcat agtagtctcc tcgaatcttt ggctaaacat gacgttgcat 67560
gtgcccagaa aaaggttcca caagaaagta gagaaaagaa tatatcctga ggaatagcaa 67620
ctgcgattga acagtgagct caataaagag gacagagccc tcatagcatt ctgggatact 67680
ggagttctga ccagctggag gagagacctc actgaacctc ttgggaatac agtagagact 67740
ccagaaaagt catactttag gagtagaatt agtaaatttc tagaaaaaaa ggcagctcta 67800
gacaaaccct ggcaaaactg aaaagcaagt ctccaagcat taaaatcatt tccaagtcaa 67860
ttaactgcct gggagaggaa aaccctcttt agaggtaaac aacaaagtca agtggctcag 67920
ctatgtggtg ttcacagtgt gagttctaaa tttaaaactt gactacacat agagaagctt 67980
ttagtatgaa ccatgaccag gtgaaaaatc agtcaataca aatagaccta gaaatgacag 68040
aaatgattag aatggcaaaa aatttgacat atcaatatgt caactgagtt ttaggtttta 68100
agaaaacatg aatacggaat gaagcagata ccatatcaag agacagtaac agtatagaag 68160
agccaaatta aattaaagaa ctagtataag aaggtatgtc ttaaatgaaa aaattactgg 68220
atgtattccc aatggagtga gatgtttcag aagtaaaaac taactgaaaa acaattttat 68280
accacctaca gaaccagcta cacatacaca aatgacacac acatatacac acatactcac 68340
acatgcacag gcttagaaac atgcacgcac acacacacac acacacacac acacctccac 68400
aaatactaaa aaatgaaatc cactgatcct cacagacagg cgggaaaata taaaaagatt 68460
tcctgcatgt gggtaggaag tcacagaagg agaggaagga gagattgcta caggaacaaa 68520
tactggaagc aaggatagct aaaaactttt caaataagaa gaatattaaa aaccacagat 68580
tcaagaagct gaatgaatca gacagggaat ttccaaaaaa aaaaaaaaaa aaactgtatg 68640
attcactttt gtacatcacc gttcaacagt cagaaggcaa agatataata acaagaaaca 68700
tctcatgaga aactggagga aaaagagctg tgtcttgcta gaagaacagt gatacaaatt 68760
gctaatgcat tctcatcaga aacactggaa cccagttaac aggggatatc attaaaatga 68820
taaactagaa aaaaaagaga tcaaatgaga atgctacatc cagcaataaa atgccttgaa 68880
gatcatccat gttggataaa tgcatattgt gcactgcccc aaataaataa accaaaaact 68940
aataatttgg aatcagcagg cttgtgtaac aagagatgtt gcccaaagaa aattagctag 69000
aagaagaata gttcaagagg agaactttct gcagcccacg taatgaagaa cccagcaaat 69060
ggcaaatgta gatgtaaatg caaaatattt tcttgatcaa atttctatat ctttttaaat 69120
gagagttgac tacttgaagc aaaatgatag caatatattt aactttagca tatgtagagg 69180
taaaaatttg aacatataga ctaaatcatg tggggaataa ttggaagtgt accattgtaa 69240
gtttcttacc ttatccacga tggtatgtaa tattaatgaa aggttgaatt tgtgggtcca 69300
aagggatatt gtaaatccta aagcaatcat aaaattttga attctgaggg atattatata 69360
ataagaattt tccatgtatc caaaagaggg aagccaagga agaaaaagaa gtctttcaag 69420
tactcaagct ctgagcacat ccagttgctc attgaaccag cttcctggaa tggagggtct 69480
gggcttgaga ctaggtcaca tgtgtagagt ctctagagag acagtgttgg atccccatgg 69540
cccataatac atttcccgtt ttcccaggca gccacaggtc acgaatggga ggattctgag 69600
aggttggagc aatgttctta ggaggcataa ggaggagtga atgctctgag atttccccag 69660
cctgaggtcc tccatagctg cccgacctct tcagacctca tagtctgccc agctgtctcc 69720
ctttatgcca tgagtgccac tgttctttca actcatcccc cattccctca gtcccggaat 69780
tgctgtggcc agcagaggat ggactgagag caggagagga agtcctgacc aggaacccat 69840
cctagagata ctgcatcctg cctgaaagct aggtttccag ggcagctttg agaagtcttg 69900
cagaaagaaa cccacttgac ccacctgata cggtatcgac agacaggaat actttttgtg 69960
caatggtttt acatgctgaa catagagcct tttggctaca ttttgagtac attgaatgag 70020
actgctggcc tgggaaggat atcatgctgg atgccatttt tttctctgga gaactatgtg 70080

-continued

```
ttagttccaa ctcgcacatt actatatgaa gtcctacaca gagagatacg gagagctaga  70140
cagatagaga tacttttgta tgtgcataac caattccaca atacacacgt caaaatccat  70200
accagttatt ccagagagat ggattgggca gaaggcagaa ggaggatatt ctgatccctt  70260
tttggccaca tgtatgtata atctcagtgt ttctaggaag tgtgtgctgc attagatttt  70320
ttttctttaa aaaaagtgat aatatattaa gtatgagaaa tgtgcagaga ggattagaga  70380
ttgagagcca tttgtcattg tggcaattgt atggtatctc ttttgggaat atttcaaagg  70440
caccagtaat gaccttgttg tagcaaaata tacagtgttc ctgcatatgt acccattttt  70500
tgtgatgtgt attcttttgg aatttccagt ggcttgatca agaactactg ccgaaatcca  70560
gatcctgtgg cagccccttg gtgttataca acagatccca gtgtcaggtg ggagtactgc  70620
aacctgacac gatgctcaga tgcagaatgg actgccttcg tccctccgaa tgttattctg  70680
gctccaagcc tagaggcttt ttttgaacaa ggtaagaagt tgtgccagac atttacctgc  70740
ttggatgctg ggatgaaaag ccatggatac ccccactgac gcacaaccct tcagtgctac  70800
actggttctc gtgtgttggt tctgggtctg ccatgtggga ggaagcctta gcgcactctc  70860
tgggggagcc agaggtgtga tttttggtgc aacctgtgcg agctgtgtct ttaggatggg  70920
cggaaaccat tctgggtgct cgacttcacc actcccctca ttgtaaaagg ggctatctca  70980
ttgtcctaga caaaattctt attgtaatat gctgtcagat gtgtgtgtct ttccaagcca  71040
gtaaactttt ccagggattt cttcaagtag acagcattca gtgcaatctt cagcattgca  71100
gattccgaga aatgtggctc tagatcctgt tatccttgag aaacctaact gggttgcatt  71160
aattccatat ctccctgggt ctgtggagta gtacatgagc tcccgaagct ctatctctca  71220
ggtctttttc agtccgaggc aggttgtgca gttcttagct ttgaagggag tgatttttc  71280
gtgtgctttt gcctctttct gatggaactt gtacctgcgg ggggtctgga gaaaaagagt  71340
agtagacttt tgctttattg caatgcatta tgctgggcac gagaggattc cctatcttat  71400
tgtaggtgat aagcttttgg cctccactca tccctgagaa gtgaagtgtt gttgcctaca  71460
gttttagctg caggactgtt gtctgcccca tcaccaggag tttaatgctt tcttttttga  71520
gcaatcatct agggacacat gcaaggtttt tatatgtcct tgcctcctcc ccaaaaaacc  71580
attttaatgc ttggagactt gcttttcagc tttgccaaat gcatcaccct ttcttctatg  71640
ctgttccatg tcgtcatgaa cactctgtag agattcctag aaatgagctt ccatgttagt  71700
ggagtttccg atgagaagca atctgatatt tcttttccac taagttttac atgaaatatt  71760
tctaagaact tactacagtt ctagaatggt aggcatctct tactttcgtg tttgtttgtg  71820
tgttttctca tgtccatttg cctattaata aagaatagag aatggttgta aatctcagtg  71880
actctttttt ggtttatgtc ataaatggct tcctgtattt ttctgttcta ggaaataata  71940
agcttgatgt cttctgtttt aatttcagca ctgactgagg aaacccccgg ggtacaggac  72000
tgctactacc attatggaca gagttaccga ggcacatact ccaccactgt cacaggaaga  72060
acttgccaag cttggtcatc tatgacacca caccagcata gtcggacccc agaaaactac  72120
ccaaatgcgt acgtctttgt tctttaccat aagcgaagga agggccaatg gaagtttctg  72180
ttagaagagt catgcttcaa ggtgactgct caggactcaa cttggctcag atgcagagga  72240
acatttcctg tgagcaaaag ttcttagaga agactttgtt tttttgagac agagtcttgc  72300
tttgttgccc aggctggagt gcagtggcat gatctcggct cactgcaagc tccgcctccc  72360
gggttcacac cattctcctg cttcagcctc tctagcagct gggactacag gcacccacca  72420
ccacacccgg ctaatttttt gtatttttag tagagacagg gtttcactgt tctagccagg  72480
```

atggtcttgg tctcctgacc tcgtgatccg cctgcctcag cctcccaaag tgctgggatt 72540
acaggcgtga gccaccgtgc ctggctgaga agacattttt taagctggct ctccttcctc 72600
ctagttttat ggaagcagaa ggatatatgg agttgagaag atcttattaa taaaacagcc 72660
gggatgacaa atgaccaaag agttagagta tccttctaca acatcggctg agggttaata 72720
caacctttc accttggaat tctatcattc taagctctag tccctgaagt gaatgttgtg 72780
ttggcctttt gcatcttggg tcacagggaa ttgatacttg cacatctatg gagaggcaaa 72840
tctttttcta tctacttctt tttcaatggg tacaaacaca cttggtcctg agcaccagtg 72900
gtctgaagag atacggtctg cccagaggag aagaacaaag gcaggaaagc agatgagagt 72960
cagcaaaggg gcgatgctga aaagtaaaag gggcgggtag atggacagaa gccatgatct 73020
ggccattcta tggccagtct ttcggccata agtgactacc aaagacacgg caaaacggtt 73080
tccacatgtt gaacaacaga tgctagagga ccaagagtat tgcaagaggg agaaaatgag 73140
atcaacccat caatgccttg gctttcttca aggagaccct tcctgcactg aagagcaagg 73200
agatggagcc caagctgact gtagccatgt tgctgaacag aggagagtga ttggactttg 73260
ggattactca ggtagttagg attttctagc catgctaaga gtaagaatgg acttgtggag 73320
gataggagct ccaggcatag aagtctcctc aagtgttagt ctaaacataa agcagcactt 73380
gcatagaaga ttttccacaa gaaaatatgg caaaaaaaca ccatatattg aggaacaaca 73440
actacaaggg aacagtgagc ttaataaagg tgacagagct cacatagtgc tctggaatat 73500
tggagttttg accagctaga gagaagagac ctcattgaaa atcttgggca ttcagtagag 73560
acctcagaaa agtcagactt tatgagtaga ctttgtatat tcctagaata aaggcagctc 73620
cagaaaaaac ctagcaaagc tgaaaagcaa atctccaagc attaaaatgg tgtcctagtc 73680
aattaactgc cttctagaag aaaactcaac actctttaca ggtgaacaac aaagttaagt 73740
tgctgagcta tgcaatatcc acagtgtgag tcctaaattt ataactttac tacacataaa 73800
aaagcattta gtgtgaacca taaccaggaa aataatcagt caataaaaat agaaccagga 73860
atgatagaaa tgatttaaat ggcatgagaa tttgacatat tagtatcata actgcattgc 73920
tggatttaag aaaacataaa catggaacgt aacagatatc atatcaaggg aaagtaaaag 73980
gataaaagag tcaaatcaaa ttaaaggact attaaaaggt atatcttaaa tgaaaaattc 74040
actggatggt ctcccaatca ggttagttgt ttccagggaa aaaattaact gaaaaataat 74100
tcaatagaat ctacagaaat agctgcacat atatacacac aatggcacac gtgcacacac 74160
ccacacccac acaggtgtga atcctagagc cacacgagca ttgaaacata gagaagtaaa 74220
aattgttcat tgaggaatat gtagcaatgc tcaatgtgtt ttaccctaat aagagctttt 74280
gtgatgtatg attgaaaaac tgacacaact gaagagagaa atagataagc ccacactctg 74340
agttagagat ttccttgatt ctctcactat ggttataaat ctttcccaaa cacaacaggc 74400
tagaacaaat atgcagaaaa ttagacatag tatctttgtt ctcaataaaa acgtcgacct 74460
atttaacatt ataccgaact accgagtaca cattaaagtg tgcatggagc attcactgag 74520
gtgtactcta cacatgacct tccagcaagt ctccatagat ttaaaagaat taaagtcata 74580
cagagtgtgt cactttattc tcccagaata aagtgagata tgaataatga gaagtttgcc 74640
agcttctcaa atatttggga gtcatacggt gcatttcaaa atactctttg ggacaaagaa 74700
aacatcacta aggaatttag aaaagttttg aactgagtaa gaatataaca caatttatcc 74760
aaacttagga gatgcagtga atgtctttag gcttttacat aattttagat gctcttaggg 74820

-continued

```
aaaaacagaa gcatgtaata atcaagattt caaactgcaa ttctcaaagt gtagtctaga  74880
gaaacctgag gacctttgag taccttcaga gacagtccat gaggttaaag gactttgcta  74940
cgtgaaaagt aagatgctat tggccctttt tactttcatt ttccaacaag agaagagggg  75000
agttttccag cagttacata atatgtaatg gcatcatgtc tctgatggct aagaaaatgg  75060
gcaattgttg actttgtgtg ttaaaaaaat tctcagtgtt ggtttcttat actataaata  75120
ttcatcttgt gttttgaaaa agaaaagctc tttggaatcc cctatgaaca aagactttga  75180
cagttgttga tctaagacca cagcttaaat atctacacaa gaaaaaaaaa aaaagcaaat  75240
aagagccaag gaaagcagat ggaaggaagt agtccaaacc agtgacattc agtgaacaag  75300
aaaagagacc aacaagggag taaactcttg aaacagaaag ttgattcttt gaaaagatcc  75360
atatgattga acacagtctg gctaaacaaa tgacagacca atgagggtgc acaaccatca  75420
ccatctggag taacagagga gaggtgccat tactatagca tcttccagtt ctgaaagctg  75480
aaaagaagat tttgagaaca attgtatgtg aataaattca ggaatgttaa tcatgtgggc  75540
caattcctga ggaagacaac aaatcagcaa accagatgct gaatagttag tgtagtcctg  75600
tagagagaca tacagagagg ctgacagaga aatatttgta tgtgcataaa acaatctaca  75660
agacacactt caaaatcaat ctcagttaat ctggaggaac atatttcaca gaaggtggaa  75720
ggagggtatt ctgatcctct tgtacattgt acaacattgt acaatgtaca gagtataatt  75780
gtacaagtac aattgaagtt gtacaagtac aagtgcaact tgcacaatgt acagagtaaa  75840
cattgatgtt tactctcaat tttcttatgg agcacagatg actttggatg tgttacaata  75900
tgaatgataa tttgtctttg agatgttcgc agttgtttag aagttgagga ccatttgtgc  75960
atattatggg acctttagtg aaaatatttc aaagtctctt tttacacttt gttacagcaa  76020
aatgtagagg gcgctaagtg cccttgaatc ttctcccatc tctggtgacc tgtgttgttt  76080
tgaaatttgc agtggcctga ccaggaacta ctgcaggaat ccagatgctg agattcgccc  76140
ttggtgttac accatggatc ccagtgtcag gtgggagtac tgcaacctga cacaatgcct  76200
ggtgacagaa tcaagtgtcc ttgcaactct cacggtggtc ccagatccaa gcacagaggc  76260
ttcttctgaa gaaggtagga agtctatggc cagacaacca caccctagga cgttgggatg  76320
aaaagagttg caaaatctta gtgatataga agccttccat gctcacacaa ttccaagtag  76380
aatgtggact cagggtcagc cactgggaag gaacactcag cgccttctct gggagaacca  76440
gagctgtgat gtttggtacc ctgtgaaagg gtggtatcta taggaagggt gcagaccctc  76500
tagggcactg gacttaccac tcccctggtt attcaaagga tcattttagt gtcttagcca  76560
gaagaatatt ctaacatttt gccaaatttg tgaagattta ccaagctcat gataagcctt  76620
tcatggtatt tcttcaagta gtcagtgttc attgcatctt tggctttgcg gtttcggagg  76680
aatgcggttt ttgagtctgt catccttgag aaacctaata tgacttttct tagttccata  76740
tacttctggg tccaggtagc agtacatagc caacaaatgc tccatcgttc tggcctatct  76800
ccatcttaag ccagtcctgc acaactaggc tttgatggga gggatctctc agtgttcttg  76860
cccctccttc tcatggaaca tatatctgtg ttggtctctg agaagaagag tagtggatat  76920
ctactttgtt gcaatgcaga atcctgggcc aaagatacca gccatccctc caagggaata  76980
aaattttggc cagtagccct ctctgagaga caatttgtct ttgcctacga gtcctagatg  77040
caggaccgct tcctgcccca tcttcaagaa gctgaaggct ttggctttgg aggatcagca  77100
gtctagggaa atgtgtgacg gtttcatgtc tgtccccact gacagtcaat caccacctac  77160
aacctgcaca gcctgatgca tagcagtcta gtttcctgcc ttattctcag gaacacccag  77220
```

-continued

```
aagatgtcta tattaaagag catgcacatg agtgcaattt tgactgatag gcactctgat  77280
ctttcctttg gtgcctgtgt tttaaaggaa atctttctaa gaactcgtta aagttctaga  77340
atgctatgaa tctttgggtt ttattattgg tatgtccatc tgcctgctag tacagaacag  77400
agcatggtag tctttctcag agacaatgat cctgtttcag tcacagattt cttctgatgc  77460
ttctgtgttc tagaaattac tcagcttgat ttctcctctt tgaatttcag caccaacgga  77520
gcaaagcccc ggggtccagg attgctacca tggtgatgga cagagttatc gaggctcatt  77580
ctctaccact gtcacaggaa ggacatgtca gtcttggtcc tctatgacac cacactggca  77640
tcagaggaca acagaatatt atccaaatgg gtacaacctt gagttttctt caaagacaga  77700
cagcagcccc cttacatttc tcttggaagg gccatgcttc caactaactt cttatgacaa  77760
atttatctca gatctggaat gttgggtaga atgtctcagg cttctttctt caggcacagt  77820
gtctgaaagg agagaaatgt caggccagct ctcttttctc atagttgaca gaagcaggag  77880
gatatttgaa ggtggtgagt tctcatgaat agaaagctca ggacacatgg ccacgtgctt  77940
agaaatagca ccattccaca atgcccacta aagaccaatg caatagttca accagggatt  78000
tctgtcattc taatctccaa gtcctgaagt gaaggttgta ttagccatgt tcatcttggg  78060
caacaaataa aggatatcta tgttgacatc cagatcttcc aatcactttc tcctctaacc  78120
tgtacctggg ttctgagaac aaggtatctg aagagctatg tgttgccagc acatgagggg  78180
caaaagtagg aaggcagctg agagtcagga agtataaaga ttctgaagag ttacacatgc  78240
aggaagatgg acagaaaccc agttcagacc acgtcagcgt ttctgccatg aaggactatc  78300
aaatacatag gaaaagtgtt ttcataggtt ggacaacaga catgacaggc ctgagaaaat  78360
tcagaaaggg aatcaaagga gatcaacctt atcatgtccc tggcatcctt ccttgagacc  78420
cttgaagggc aagcagatgg agcccagctg accacagcag tcttgcttaa ctgaggagag  78480
agactggagt ttgtgatgcc tcaggcatct gacgtattct aggctggcta agaatgagag  78540
gggatttgtg gaggaaagga gctccaagaa tacacaccga agtcttctca aggctttggc  78600
taaatacaaa gctgcgtatg cacaaggaga gttttcacaa agaaagaaca ataaagaaaa  78660
gctactgggg aaagaacaac tgcaagggaa cagtgagctc aatggagatg ctagagctca  78720
catagcactg ggggatattt gagttctgac cactcagagg agagacacct cactgaacat  78780
cttgggcatt cagtagaggt caaagaaagc cataatttgg gagtaggatc ttcggattcc  78840
tagaaataag gtgactccag aaacactcca gcaacccttc ttccaagcca gtctaaaagg  78900
atccaaatga tttccaagta aattaactgc cttccagaaa aaagtaaact caaccctcct  78960
tagaggtaag gaacgaatac aagtttctca gttatatgac atccccagag tgcaacttgc  79020
atttaaaaat ttactagaca caaaagaagt tttcactgtg atccataact gggagaaaaa  79080
tcactcaaca caaataggcc cagaaataat agaaattatg gcattggcaa gaacatttaa  79140
aatgcacctc tgagaactgt gtttcaggaa aatgtcagca aaagctgacc atgagagaaa  79200
tgaatgcata atatcagaaa agaaaagaat tgaagagcca aatggaaatt taaaaactga  79260
gaaaagttat atctgtaatg aggaattcac tggatggcct tataaccagt ttagatatta  79320
tggtaggaaa aggtgaacga gaaaatgatt caattaaagc tagacaaacc acaagacaga  79380
cagacagaca caaatacaca tacacacaat gactgaacca attaatcaac agagcctcaa  79440
ggacatctag gaaaacatcc acacatttaa tatatgtgtt aggcaagtca cagaaagaga  79500
ggaaaaagat aatgtgacag aagttatact tgaagccatg acggctgaca aatttccaaa  79560
```

catacagaaa atgagaaatt catagtcatg aagctcaatg actcaggtat agatttttaa 79620
agagcaaaac tctgatttac tggggtacat catagttaaa ttgtctgatt tcaaagctaa 79680
gaagaaaaaa agggggttcc tatgaacaaa cattttgaca gttgatctaa gaccacagct 79740
taaatatcta ggcaaggaaa agcaaataag acacaaggaa aggggatgga tggaaatagt 79800
ccaaaccaat gacattcagt gaacaagaaa atagaccaac aaaggagtaa atccatgaaa 79860
cagaaagttg gttctttgaa aagattcatg tgattgacca cagtctggct gaacagatga 79920
cagaccaagg agggagtaca accatcacca tttgaagtaa caggggagag gagccattgc 79980
tataccatac tccaggtctg aaagctgaca agaagatatc aagaaaaact gtatgtgaat 80040
aaattcatga atgtagatca tgtggatcaa ttccttaggt aaacaacaaa tcagcaaacc 80100
agatactgaa tagattgggt actcctatag aaagacatac agatagccag acagagaaac 80160
atttgtacgt gcataaaaca atctacaaga ctcacttcaa aatctctcag ttaatccaaa 80220
gtaacatatt tggcagaagg tggaaggagg gtattctgat cctttcttgt acacattgat 80280
gttttctctc ggtttcttta tggagtatag acgagtttgg atgtgttaca ataagaatga 80340
taatctgtct ttgaaatgtt cacagttgtt tagaagttga ggacgatttg tgattgttac 80400
aggaccttta gtgagaatat ttcaaagtca ctttttacca ctttgttaca acaaaatgta 80460
gaggatgtct ggtgcccttg tatcttctcc catctctggt gaactgtatt gttttgtaat 80520
ttgcagtggc ctgaccagga actactgcag gaatccagat gctgagatta gtccttggtg 80580
ttataccatg gatcccaatg tcagatggga gtactgcaac ctgacacaat gtccagtgac 80640
agaatcaagt gtccttgcga cgtccacggc tgtttctgaa caaggtaaga agtctctggc 80700
cagacaacca cacccttgga cgttgggata aaaagagttg caaaatctta gtgatacaga 80760
agccttccat gctgcacggg aatctgaatg tggactcagg gtcagccaat gggaaggaag 80820
cctcagcgcc ttctctgggg gaaccagggc tgagattttt ggcaccccgt gacagggtgg 80880
tgtctttagg aagcgtgcag accttctagg gcactggatt taccactccc ctggttattc 80940
aatagattat ttcagtgtcc tagtgaaaat ggatattcta acatcctgcc aaatttgtga 81000
tgatttacca agctcatcat gagcctttcc tggtatttct tcaagtagac agtactcatt 81060
gcaaacttca gctttacagt ttcagaggaa tgtggttttt gagtctgtca tccttgagaa 81120
acctgatatg actttactta gttccatatc ctcctgggtc taggtaacag tacatagcca 81180
gcaaatgctc tatctccctg tctaccttaa tcttaggcag gtgctgcaca cctaggcttt 81240
gatggaaggg atttcttagt gttcttgccc ctccttctca tggaacacgt atctgtgttg 81300
ctgtttgtga agaagagtag tggatgtcta ctttgttgca atgcaggatc ctgggcccaa 81360
gatttcccgc cgtccctcca agggaataaa attttggcca gtacccctct ctgagagaca 81420
atgtgtcttt gcctggaagt cctagatgga ggaccacttc ctgccccatc ttccagaaac 81480
ttaaggcttt ggctttggag gatcagtgct ctggagaaat gtgtgacggt ttcatgtctg 81540
cccccactga caaccaccac ctacagcctg caccgcctga tgcatggcac tctggtctcc 81600
tgccttgttc tcaggaacac ccaaaagaga tctttgccaa agaacaggca catgagtgca 81660
attttgactg ataggcactc tgatctgtcc tttggtgccc aggttttaaa gaaaatcttt 81720
ctaaaaactc attgaagttc cagaatgcta tgaatctttg agctttgtta ttggcatgtc 81780
catctgccta ctaatgtaga acagagcatg gtcgtcattt tcagagatga tgtcctgttt 81840
ctatcatgga tttttttct catgcttctg tgttctggaa attactcagt ttgttttctc 81900
ctctttgaat ttcagcacca acggagcaaa gccccacagt ccaggactgc taccatggtg 81960
atggacagag ttatcgaggc tcattctcca ccactgttac aggaaggaca tgtcagtctt 82020
ggtcctctat gacaccacac tggcatcaga gaaccacaga atactaccca aatgggtatg 82080
tctttgagtt ttctcccaag agaaacagcc acccacttaa atttctcctg gaagagccat 82140
gcttccagct aacttcttat gacccaattt ctctcagacc cagaatgttg gacagaatgt 82200
ctcaggcttc ttgctttggg cacagggtct gagaggagag aaatgtcagg ccagctctct 82260
tttctcatag ttgatagaag taggaggata cttggaggtg gtgaggtctc atgaatagaa 82320
agctcagaag aacatatgac catgtgctta gaaatagcac cattccacaa tgcccactaa 82380
agaccagtga aatagttcaa ccagggaatt ctgtcattct aatctccaag ccctggagtg 82440
aaggttgtgt ttgccatgtt tgtcttgggt aacaagtgaa ggatatctat attgacttcg 82500
agatcttccg atcactttct cctctaacct gtataaacac attgggttct gagaacaagg 82560
tgtctgaaaa gctatgtgtt gccagcccat gaggggcaaa aggaggaagg cagctgagag 82620
tcaggaagta tagagatgct gaagagttac acattcagga agatggacag aaacccatgt 82680
ctggctatgc cagcctttct gccatgaagg actatcaaat acatgagaaa acagttttca 82740
caggttggac aacagatatg gtaggcttga gagaactgag aaagggaatc aaaggagatc 82800
aacttcatca ttaacctgtc ttccttcctg gacacagtgt tggattgaag gacaagcaga 82860
tggagcccag ctgaccacag cagtcttgct taactgagga gagagactgg agtctgcgat 82920
gcctcaggca gctgatgtgt tctaggctgg ctaagaatga gaagggattt gtggaagaaa 82980
ggagctccag gaatacacac agaagtctcc tcaaggcttt ggctaaatac aaagctgcgt 83040
atgcacaggg agagttttca taaagaaaga acaacaaaga aaagctactt gggaaagaac 83100
aactgcaggg gaacagtaag ctcaatggag atgccagagc tcacatagca ctgggggata 83160
tttgaattct gaccactcag aggagaaaca cctcactaca ttttgggcat tcagtagaga 83220
ccaaagaaag ctgtattttg ggattgggat catcttattc ctagaatcaa ggtgactcca 83280
gaaaaactcc aacaaccctt cttccaagcc agtctaaaag gatccaaatg atctccaagt 83340
aaattaactg cattccacaa gaaaaaaaaa actcaacccc ccttagaggc aagggacaaa 83400
tacaagttgc tcagttatat ggcattccta ttgcgttact tctatttaaa aatttaatag 83460
agacacaaga agctttcact gtgatacata actgggagaa aaaatcactc aacacaaaca 83520
ggcccagaaa ttatagaatt gatgacattg gtgagaacat ttaaaatgca cctctgagaa 83580
ctgtgtttca ggaaaatgtc agcaaaagct gaccatgaga gaaacaaaag cagaatagca 83640
agagaaaaga aaagaaccgg agagccaaat gaaaattaaa gaactgagaa aaggtacatc 83700
tctaatgaag aactcactgg atggccttat catcacttta gacattacgg taggaaaggt 83760
gacctagaaa ataattcaat aggagctaca caaatcacag gacagacaga cagaccaaca 83820
gacagaaaca cacacacaca cacacacaca cacacacaca cacacacaca cacacaaaga 83880
ctgaacctat taatcaacag agcctcaagg gcatctagga aaaatccaca catttaatat 83940
atgtgttagg caagtcacag aaggagaaga aaaagatatc atgacagaca ttatacttga 84000
agcgatgatg gctcgcaaca cgccaaatat acagaaaaca agaaactcat agtcaagaag 84060
ctaaatgact caggtataga attttaaaga gcaaaactct atgatttact gggatatatc 84120
atagttaagt tgcctcaatt caaagctaaa aagaaaaaaa gggggttcct atgaacaaca 84180
gctttgacag ctgttgatct aagaccacag cttaaatatc taggcaagga aaagcaaata 84240
aggcacaagg aaagaggatg gaaggaaata gtccaaacca atgacattca gtggaaaaga 84300

-continued

```
aaatagacca acaaaggagt aaatccatga aacagaaagt taggttcttt gaaaagtcta  84360
tatgattggc caaagtctgg ctaaacagat gacagaccaa ggagggagca tatccatcac  84420
catcatgagt aacaggagag agatgccatt gctatagcat cctccaggtg tgaaagctga  84480
gaagtagata ttgagatcaa ctgtatgtaa ataaattcat gaatgtagat catgtggatg  84540
gattgcttag gtaaataaca aatcagcaaa tcaaacactg aatagatcat gcagttttat  84600
agagacttac agacagcctg acagataaac atttgtatgt acgtgaaaca atctccaaga  84660
cacacttcaa aatccctctc ggttaatcca aaggaatgta tttggcagaa ggtagaagga  84720
gggtattctg atcctttctg gtacacattg atgttttctc tcagttttct tataaagcat  84780
agattacttt gaatgtgtta caataagaat cataagctgt ctttgaaatg ttgacagttg  84840
tttagaagtt gaggaccatt tgtgagtgtt atgggacttt agtgagaata tttcaaattt  84900
gcttgtttac actttgttac aagaaaacat agagggtgcc aggtggtgct gtatcttctc  84960
caatctctgg tgacctgtat tgttttggaa tttgcagtgg cctgaccagg aactactgca  85020
ggaatccaga tgctgagatt cgcccttggt gttataccat ggatcccagt gtcagatggg  85080
agtactgcaa cctgacgcaa tgtccagtga tggaatcaac tctcctcaca actcccacgg  85140
tggtcccagt tccaagcaca gagcttcctt ctgaagaagg taagaagcct gcagtcagac  85200
aaccataccc tcggacattg ggataaaaag atttgcaaaa tctttgtgat gcagaaaact  85260
tccatgctgc acaggaagtc gaaggtgaag tcatggacag ccaatgggaa ggaagcttca  85320
gtgccttctc tgggggggacc agagctggga tgttgagtgc cttgtgaggg atggtgtctt  85380
taaaaggggc acagaccctc taggacactg gatttatcac ttccctgtta tcaaacgaat  85440
catattagtg tcctagccaa gatggatatt ctaacatcct gccaaacttg tgaagatata  85500
ccaagctcct aagcctgtcc agccctttct tcaagtaggc agtgtttatt gcagtcttca  85560
gctttaccat tttgaaggaa tgccattttt gaggctgttg ttcttgagaa acctaacatg  85620
tcttcattag atccgtattg tcctgagact ttgaagcagt acatagccac caaattgttt  85680
atctccccag cctaccttca tcttgggcat gccttccaca cctaggattt gagggaaggg  85740
atttctcagt gttctcatcc ctgcttctca tggaacattt atctccgttg tttttgaga  85800
agaagagtag tggatgtcag ctttcttgta atgagggatc ctgggcccaa gattccctgt  85860
ctcccctcct aggctataaa attttggcct gtactccttc tccctgagag gcaatgtgtc  85920
tttacctaca agtcctagat gcaagatcct tttctgcccc acaccccaga atctgaaggc  85980
ttttgctttg gaggagcagt ggtctagtgt gcaagggttt catgtatacc ccccactaac  86040
agccaatcac cacctatagc ctgaacagct tgatgcatgg caccctggtc tcctgccttg  86100
ttctcatgaa cacccagaag aggtgtaagc aaaagaccat tcacatgagt gtaattttga  86160
agtataggca ctctgatctg tttttgttt gtttctttgt ttgtttgttt tccagggttg  86220
aattaaaata tttatgacta cttattaaat ttctagaatc ctataagtct atttgtattt  86280
ttattctaca tttcaatttg catgctaata tagaagagtg taaattgtta atcctcagat  86340
tattccactt tgtgtgtcat aattttttc acatttccct tttctaggca atactgagct  86400
tgattttctc ttttaatttc agcaccaact gaaaacagca ctggggtcca ggactgctac  86460
cgaggtgatg gacagagtta tcgaggcaca ctctccacca ctatcacagg aagaacatgt  86520
cagtcttggt cgtctatgac accacattgg catcggagga tcccattata ctatccaaat  86580
gcgtatgtct atcatgttag ccataaaagg aacaatagtc aactaaaatt tctcttagct  86640
ggcccatgct acaagctcac ttcctaggtc caaatttctc atagactcag agtttgtagc  86700
```

-continued

```
aaaatgtctc aggaaactta cttttgagca aaaggtctga atgaagagaa gttttaggat  86760
tgctatcttt cataacaatt tgatggaagc agcaggatat atggaggtgg tgaagtctca  86820
ttaatgtaaa gctaaggaga tcaaatgacc aaatgctgag acaaagtatc attccacaat  86880
gcccactaaa ggtccatgca gtctttcaac catgcaattc tatcattcta tcctccattc  86940
cctgaagtga aatttgtgtt tgccattttt gacacgaatc agaagtaaca aattcaggct  87000
gggtgcagtg gctcaggcct gtgatcccaa cactttggga ggacaagacg ggcagatcac  87060
cagaggtcag gagttcaaga ccagcctggc taacatggca aaaccccatc tctacgaaaa  87120
attaaaaaat tagccggtca tggtggtggg tacctgtaat tccaactact tgggaggctg  87180
aggcaggaga aacacttgag cctgggattc agagtttgct gtgagccgag aacatgccac  87240
tgcactccag cctgggtgac agagcaagac tcaatctcaa aaaaaaaaaa aaagaagaag  87300
aagaagaaaa gaagaagagg aagaagaaga agaggaagaa gaagaagaag aagaagagga  87360
agaggaagag gaggaggagg aggaggagga agaagaagaa gaagaagaag aagaagaaga  87420
agaagaagaa gaagaagaag aagaagaaga agaagaaaat agaaatgagt gcatatattt  87480
atatatgagt actagcctgt atgaacacac tgggttctaa gcaccagttt tctgaaggga  87540
tatgggttgt caggcagagt aaaagcagga atgcagatga gagtcaggaa gtaaacagat  87600
gtggtgatta aaatgggcag gtacatggac aaaaaaatgc atgtctgaca aaaactggcc  87660
tcttgccata agtgagtatg aataatatgg aaaaactgtt tgcacatgtt gaacagcaga  87720
cagtacaacc tgagatagtt tagaaaggga aacaaataag atcaacccca taattaccct  87780
tcctagactt aagggcaaag agttttaacc aaagcattcc acagcagtct tgctaaactg  87840
gggagagaga ctggagtttt gtttactaat aaaaccgaga ttttctaggt taggtaataa  87900
tgagaaagta tttgtggaga aaaggagctc caggaataca cacagaagtc tcttcaagtc  87960
tctggctgaa cagaaagctg tgtatgcaca gaaagagttt ccagagagaa aggagaacaa  88020
agaacagcta ctggggaaag aacaactgct ggggaacagt gagctcaatg aagatgccag  88080
agctcacata gcactgggag gtatttgagc tctgaccagc ctgaggagag acacttcatt  88140
gaacatcttg ggcattcagc aaagacccca aaaaaccata cttcaggagt agaattaatg  88200
cattcctaga ataaagtcta ctccagaaac accctagaaa agcttagaaa ccaagtctaa  88260
aaagatccaa atgatctcca agtaaattaa ttgcctgtca gaagaaaaca acctcttcag  88320
aggtaaacaa caaaattaaa ttgctcaatt atatagtatg cacaatgtgt ggcatacatt  88380
taaaaatttg ctaaacatac aaaaagcatt tagtgtgacc cataaccagg agaaaaatca  88440
gtcaatacaa atagacccaa aaatgataaa aataacagaa ttggcaagga gatttaaaat  88500
gtatgtatca taattgtgtt caaggattta aagaaagcgt ggacaagaaa taaataaatg  88560
gataatatca acagaaagaa aaattgtaaa aggaccaaat ggagagtcaa gaactgaaaa  88620
aaaagacatc tctttaatga gaaaatcact acatggcctt ataatcatat tagatagtac  88680
agatgataaa gctaactaga aaatattagg gtggtgcaaa ccatagcacg cttatacaaa  88740
gcctgagaag ataaacagag cctcaaggac atctatgaaa atatcaaaat atttaatatt  88800
tgtttaaagc aagtcacaga ggaagggaaa gagatattgg aacagaaaaa atacttgaag  88860
cagtgatggc tgatgacttt ctaaatatgg aaaaaatgat aaactcacat agtcaagaag  88920
ctcaatggat cagatatagg attttaaaaa gtaaagctgt atgatttatt tggacacatc  88980
ataattaaat tgtccataat caaagataga aagtaaaatc ttatttgaag cccaagggaa  89040
```

-continued

```
aaaacatacc tttacataga gtaacagtga cacaaatgac tgatgccttc tcatcagaaa  89100
caacacaaat cagaaacaat agaataacac ctttagagtg gtaagaagaa aaaaagatca  89160
aatcagaaac aacaaaataa cacgtttaga gtggtaagga ggaaaacaag atcaaatcag  89220
aaacaatgga ataacacctt tagagtgtaa gaaagaaaaa aagatcaaat caggaacaac  89280
agaataacgc cttcagagtg gtaagaagga aaacaagata aaatcagaaa caatgaaata  89340
acacctttag agtagtaaga agaagaaaag atcaggtcag aaaaaatgga ataatatgct  89400
aagaagaaaa aaaaagatca agtcagaaac aatggaataa cacctttaga gtgaaaagaa  89460
ggaaaaaaac ccagcaagct taaacgctat gcacagcaaa caattccact gaaaatgaat  89520
gttacgtaag tacatattct gtcctcctaa aaacaaagaa caaataaaag aatgtttcat  89580
cagcaggatt atgtaataaa agatgtgaaa gaatgctatg taagtagaag aaaaataata  89640
ccatatggga attggcatca aaaccacaaa atactatcaa aacaaaaaaa ctttattgat  89700
aaatttaaca caatatgcaa aagaactata ccatgtatac tacataacat tggtgagaag  89760
aaaattagaa gatctaaata aagacacatc atgcttatag attaaaaaat ccaatgtcac  89820
ttttcacaaa actgatcttt agtttcaacc cacacccaag cagaattcct gcagtctttt  89880
cttgaaaacc taacagaatg tatatgctag aatcaccaag acaatcttta aaaagaataa  89940
aaaacttgga ataaaatcac aagtttgtgg gatagatgca tatggtaata tggaaattct  90000
cataaagaca cagtaatcaa gacatgtggt attggctggg acgcttggct gtaatcctaa  90060
cactttggga ggccaagatg agaggattgc ctgagatgag gagttgcaga caagcctggg  90120
caacatagca agaccctcat ctctacaaat atttaaaaaa attagccagg tttggtgcca  90180
tgtgcctgta gtcccagcta ttcaggaagc tgaggtggga ggatcactgg agcccatgag  90240
gtggaggctg aaatgagcca tgattgtgct actgaacttt agcctgggag acagattaaa  90300
accttccctc tctctctcaa acaaacaaac aaaaaaataca tagtattggg caaaacatat  90360
gcaaacaaaa acagaaaagg gtcagcataa atttacatat atggtcaatt tattttcaat  90420
acaggtagca aagcaattta atgaggaaat ttttttccaa aattggtctg aaacaactgg  90480
atagccatag aaaaaaacta taacaaatgt gacgcttgaa tcctactgta tgactcaaat  90540
taaattaatt tgagatagct cttagacctc aatgtaacag ctaattctga ggctgaaata  90600
taagactgct atgaaaaagt atagtatctt ataaccttgg agaaggaaaa attttttgag  90660
ggaagaacca gaaaacacta actgtaaaag aaaacaaatg ataatgtgga cattcattga  90720
ataaaaactt atgctcacca aatatgactg ttaagaaaat aaataagtaa gtaacacact  90780
ggaagaaaaa cactctcatc catatatctg acaaatggcc tgtatccaga gtatagaaac  90840
atttctccca ctcactaatc agaggacaaa caacctaatc aaaatgggca acaggcttga  90900
atagtcattt cttaggagaa gatgcacaca gagccaacaa tcacctgaaa aagtgcacaa  90960
catcttagcc atcaaaaatc aagagttata accctcataa gatgacactg aacatccagt  91020
gtacatggat atcattaaga agacacaata ataagtggtg tcaccgattt ggagctagaa  91080
tgtgccactc tctcatatgc tggtggaagt tcaaaatcat acaacaaatt aaaaaatcag  91140
tctgatgctt tcttataaag ttcgataaat atgcatctat cctacaaacc tgtaattcta  91200
ttcttgaata tttacccccc aaaatgaaaa cataagtcca caaaaatcta tataaatatt  91260
catagcagct ttatgtttta taaactcaaa ataaaaacta tttcaatgtt ttcatcaaaa  91320
gaaaatgaaa actatttaaa tggtttcatc aaaagaaaat gaaaaaagaa tttccagtat  91380
atttatacaa aggaatacta ttcatcaaca aggaacaagt tactgatagt ctcagaagca  91440
```

tgaacaaacc tcaaaaatat attaaggaaa gaagccagac gtcaaagtgt atagtctgta 91500
tgagtccatt catgtgagtt tatagaaaac acaatttatg gtgaaagaaa ccaatagcat 91560
ttgacactgg ccgtgggaag agggtagcag agattgattg agcagccaca caagggagtt 91620
tctggggtgg tgaaaatgtt ctgcattgtg agggcagtgt gggctacaca agtatatgta 91680
tttatcaaat ctcatccagc tacatttaag atctgtgcat ctcactctat gtgaaaatat 91740
actcaactga aaaacagagc aggtatctgt ttcaggtgct acatcacttg atacgtccag 91800
ttgtgttaaa aaccactgcc taacatcctc aaatgggga tctgggcttg agactaggtc 91860
acatgtgtag agtctctaca gagaccgtgt tggattccca tgctccataa tacgttccaa 91920
gttttctcag acagccacag gtcatgaatg tgaggattct gagaggttgg agcaacgttc 91980
ttgggaggca taatggggaa ggcattctcc aagattcctc cagcctgggg tcttcacctg 92040
ctgtgcctct tactgcattg ttttctgact catccatagc cacttgaccc cttcagatcc 92100
catagtctac ctagccgtct ccctttatgc cttgggtccc gctgttcttt caactcatca 92160
cccattcctt cagtcccaga gtggctgcag ccagcagagg atggactgag agcaggagag 92220
gaggtcgtgc ccatgaaccc atcctagaga agcagcatcc tgcctgggag ctagttttcc 92280
agggaagctt ttataagtcc tgtagaccca aacccacttg ctctaccaga tacagtattt 92340
atagtaatac tattttcatg attattttat attgcaaatg tagagcattt atgctacact 92400
atgagtaaat agagtaaggg ggctggcatg ggaattatat aatcttggat gccacttctt 92460
ccttggggaa atgtatttga gttccaactt acatattact atatagtctt atagagagag 92520
agacaaagag ctagacagac agagatatct ttgtatgtgc attaaaaaat ctaagataca 92580
tatttcaaaa tctgtgtcat ttattctgga ggaaagtatt tggcagaagg tgaaaggaag 92640
atattctgat cctttcttgt acagacatgt attatctcag ttttcataga gagcatatac 92700
tacttttgat gttttaaaac aaaaattata atctgtgatg tgtccacagt tgtttaaaag 92760
ttgaagctga agaccatttg tgcttgtggc aatattattg tggtataatg ggaatatttc 92820
aaaggcactt gttaacactt tgttacagca aaatgtagag ggcgctaagt gcccttgaat 92880
attctcccat ctctggtgac ctgtgttgtt ttgaaatttg cagtggcctg accaggaact 92940
actgcaggaa tccagatgct gagattcgcc cttggtgtta caccatggat cccagtgtca 93000
ggtgggagta ctgcaacctg acacgatgtc cagtgacaga atcgagtgtc ctcacaactc 93060
ccacagtggc cccggttcca agcacagagg ctccttctga acaaggtaag aaatttgtgg 93120
ttagacatct atatactggg atgaaaaacc atggaaaatc ttactgatgc agaagccttc 93180
agtggtacac tggagggttg gttgagggtc tgcaatgtgg aggaaagcct cagcgccctc 93240
tctgggggat ccagaactgt gatttttggc acgctgtgag gaggcagtgt ctttaggaag 93300
ggcacggtgt ctttaggaag ggcacagacc cgccagggca ctggacttac cactcccctg 93360
gttattaaat gggtcatttc agtgtcctag ccaaaatgga tattctaaca gcctgccaaa 93420
tatgtgaaga tttccaagcc aataagcctt tccagtgatt taaagtagac ttttttcatt 93480
gcaatctaca gtttgcagtt tcttaagaac atggcctttg agtatgatat cctagagaaa 93540
cctaaggaga ctgcattatt tttctattgt cctggggctg catagcagga ggtaaccaac 93600
gaatgctgtc tctccctggc ctatctcagt ctttcacagg ctctgttcac ctcagctttg 93660
aagttagaaa tttctaggtg ttcttgcctc ttcttctcat gaaacctgca ttggcagtga 93720
gtctacagaa gaagaggaag agaattctgc tttgttacaa ttcaggactc tgggcactag 93780
aagattccct atctctcctc caagggaata agttgtttgt ctctaaccct ccttgagaaa 93840
caatgagtct ttgcctgcac tcctaaatgt aggatgattt cctgcccaaa ttttcaaaag 93900
attaagcctt ttgccttggt atgagcaatg gtctagggaa atgcgcaagg gtcttgtgtc 93960
ggcccctgac tgaccaccag tcacctccta cagcctgcac caaggaatgc attgcattct 94020
ggtcttctgc cctgtggttc tcatgaaaac cagcagagat tcatatgatg gagctgcaca 94080
tgaatgtaat ttccaatgtc cagcattctc ctctgttctt tatctttaga tttaaaaata 94140
atgtttctat gaacttatta aaattctaga atactatgaa tctactgggt cttttcacat 94200
ccttttgcta ctagtagaaa aaagaatagt aataattttc agaggctact gtccagtatg 94260
tgacataaat tgtctcccat gtttctctgc tcatgcaatt actgagtatg atttatttta 94320
ttttaatttc agcaccacct gagaaaagcc ctgtggtcca ggattgctac catggtgatg 94380
gacggagtta tcgaggcata tcctccacca ctgtcacagg aaggacctgt caatcttggt 94440
catctatgat accacactgg catcagagga ccccagaaaa ctacccaaat gcgtatgtat 94500
ttgattaaaa ccataagagg agcaacagcc aactcaaata ttggttagaa gacccatgct 94560
ttaagctcac ttcctaggga caaatttctc ttagactcac attttggcaa aatgtctcag 94620
gacctttgct tttgagcaaa gagtctaaga gaagagaaat tttaggcctg ctatttttcc 94680
taatagtttt atggaaggag tagaatatac ggaagtggcg aagtcatatt aatgtaaagc 94740
tcagaagata aatgaccaaa gcttaaacac agcaccattc cacaatgccc actaaaaatc 94800
aatgtcatct ttcactcgtg caattctgtc attctaaatt tcaattcccg aaggtttgtt 94860
tgccattttt gtcatgggta ataagtaaaa aaaaaaaaat taagatgtgt atatatatat 94920
atatatatat atatatacac acacacacac acacacaaac atctgaatat ttatatatat 94980
gtctgaatat ttatatactt gtgtataaaa cttatattta aatttttgca taaatttata 95040
tatttttaat atttcattaa aaattatatt gtttcactat gtatgtctga gtatttttat 95100
atattttaat ataacatttt aaatatttat atataaatat tcaggtatgt aactgaatat 95160
tcatttacac acacaaatat atgtgtgcat gtgtgtatat atatatatac ccatatatat 95220
atatatatat atatatacat atatatatat atatatatat gtatatatat atatatatat 95280
atatatacac acacacacac acacacatac atacaggtat aaacacactg ggcctgaagc 95340
accagtggtc tgaaaggaca tgtgttgcca ggacttgaag agcaaaagca ggaaggcgga 95400
tgagagtcag gaggtacaca aacgctgaaa agtaaaatgg acaagtacat ggacaaaaag 95460
caggtataag cataacagcc ttttggaagt aaatgactat aaaatatatg aaaatactgt 95520
tttcacaagt tgcacaacag atagtagtgt attgagataa tttagaacag aaaacaaatg 95580
tgatcaaccc cataagtgtg ctgtatttca tcatggattg aaggaaaaag agatggagcc 95640
caagaagacc acagcagtct tgatgaactg agagacacca gagtttggga ttacaaaggc 95700
agctgggatt ttctacactt ggtaataatg agaaagaatt tgtggagata aagagctaca 95760
gtcatgtacc tagaagtcac ctcagtgtaa tataaatctg catatgcaca gggagtgatt 95820
ccacaatgaa agtaggacaa agaacagcta ctggggaaag aataactaca agggaacaat 95880
gagttcaatg gagatggcag agctcacaaa gcactggggg atatttgagt tcttaccagc 95940
tagaaaagag acctcattgc aaatcttggg cattcagtag agaccccaga aaagccactc 96000
tttggaaaca gagttgatgt attttaagag caaaatctac tccacaaaaa tcctagcaaa 96060
attgaaaagc aagtcagaaa gaccaaaatc ctctcaacat aaattagttg cccatcagaa 96120
gaaagcttaa cctcttcata ggtaaacaat aaaatcaaat tgctcagtta tctggcatcc 96180
acaatatgtg acataaattt aaaaatttac tagacataca agaagcattt agtgtgatcc 96240
ataaccagga gaaaaatcat tcaatacaaa tagacccaga aatgacagaa atgatagaat 96300
tagcaaaaac atttaaaata tacatatgat catttgatct tgtgatcaga tatcacaaga 96360
gaagaaagag atacttgaac agaaaaaatg cctgaagcaa tgatggctga aaactttcca 96420
aatatgaaga aaaaaaagct cacagattca agaaaactaa tcaatcagaa atatgatttt 96480
gaaaagtaaa aatgtatgat ttactttggc aaatcttctt ggttaaattg tctaaaatca 96540
aagaaagcta ggaaaatttt ataagccaga ggaaaaaaga ttgtttatat aaaggaacag 96600
ttacacaaat gactgatgcc ttctcatcag aaacaatgaa agtcagaaac aataaagtaa 96660
catctttaaa gtaatagaag aaaaacccaa gaggtgaggg atcgtggcag acaggaggca 96720
ggactagatt gcagctctgg acagagcagc atgcagaggc tcatattgtg aattttagcc 96780
ccatattgac tgcaagaaca gaccagcaat cctgagagga cccacagacc gtgtgaagga 96840
agcagactgc tcctgcagga taagggagac accccaaata ctgtgagttc cccaactgca 96900
gaagtggaaa agggaggcct tactccctca aacacacccc acaactggag aagctgaaag 96960
tctgtttgca ggagaagttc ccaactttac ctgggcctca gtaaatttag agagctgagc 97020
caagcaaaat ataggggtag aggaagcagc agagaagacc tcagagcttg ctggatcccc 97080
aagcagctca ttcctgcctg gcaccacaga gatccatcag aagtgtggcc aaaggaacag 97140
agggtaaaac tccacatgga ggactgctct acctgaactt tctaacaatt tgaacagggg 97200
gagaagcctc ctggccagaa cttgggggag ggcatgaatc tggtttgcag acttcacagg 97260
tgggggaagg actaaagccc ttttctttca cagctgggag gtggaaagcc tcaggcaagt 97320
tttcaagcct gactttcccc ccacctggaa acagacttgg agctgttgcg gggttggggg 97380
catggtggga gtaagaccag cccttcagtt tgcatgggtg ctgggtgagg cctgtgactg 97440
acagcttccc tccacttccc cgacaactca gatgactcag cagaggcagc cataatcctc 97500
ctaggtacac aactccagtg acctgggaac ttcacccccca caccatacag aagcttcagt 97560
aagacgtgcc caaggaaagt ctgagctcag acacgcctag tcccaccccc aactgatggt 97620
ccttccctac ccaccctggt agcagaagac aaagagcata taatctttgg agttctaggg 97680
cccacccacc tctagtccct ctccacacta gtatagctga tgcaggaggc caaccagcac 97740
aaaaatagag cattaaacca ccaaagctag gaacccctat ggagtccatt gcaccctcct 97800
ccacctccac cagaacaggc actggtatcc acagctgaga gacccataga tggttcacat 97860
cacaggactc tgtacagaca gtccccagta ccagcccaga gctgggtaga cttgctaggt 97920
ggcaagaccc agaagacagg caataatcac tgcagttcag ctcacaggaa gccacatcca 97980
taggaaaaga gggagagtac tacatcaagg gaacacccca tgggataaaa acatctgaac 98040
aacagccttc agccctacct tccctctgac acagtctacc caaatgagaa ggaaccagaa 98100
aaccaaccct ggtaatatga caaaacaagg ctcatcacac tcccagttca ccagcaatgg 98160
atccaaacca agaagaaatc cctgatttac ctgaaagaga attcaggagg ttagttatta 98220
agctaatcag ggagggacca gagaaaggca aagcccaatg caaggaaatc caaaaaaaaa 98280
aaggtataag aagtaaaagg tgaaatattc aacaaaatag atagcttaat aaaaaaacaa 98340
taaaaaattc agtagacttt ggacacacct ttggaaatgt gacatgctct ggaaagtctc 98400
agcaatagaa ctgaacaagt agaaaaaata aattcagagc tcaaagacaa ggacttcaaa 98460
ttaacccaat ccaacaaaga caaagaataa aggataagaa aatatgaaca aagccttcaa 98520
gatgtctggg attatgttaa atgaccaaat ataagaataa tcgtggctcc tgaggaaaaa 98580
gacaatacta aaagcttgga aaacatattt gggggaataa ctggggaaaa cttacctggc 98640
cttgctggac acctagacat gcaaatacaa gaaacacaaa gaacatgtaa atacaagcag 98700
cacaaagaac acctgggaaa ttcatcacaa aaagatctta gcctaggcac attctcatca 98760
ggttatgcaa agttaagacg aaggcaagaa tcttaagagc tgtgagacag aagcaccagg 98820
taatgtataa aggaaaccct atcagattaa cagccagttt ttcagcagga actgtacaag 98880
ctataaagga ttggagccct atcatagcct cctcaaacaa aacaattatc agtcaagaat 98940
tttgtatcca gcgaaagtaa gcatcatata tgaaggaaag atacagtcgt ttttggacaa 99000
acaaatgcta agagaattca ccattaccaa gtcaccacta gaagaactgc taaaaggagc 99060
tctaaatctt gaaacaaatc ctagaaacac atgaaaacag aatctcttta aagcataaat 99120
cacacaggac ctataaaaca aaagtacaag ttaaaaaaca aaaacaaaaa acaaaaccaa 99180
agtacggagg caataaagaa tatgatgaat gcagtggcac ctcacatttc aatgctaaaa 99240
ttgaatctaa atggcctaaa tgctccactt aaaggataca aaaagagttg gtggctggca 99300
agatggctga ataggaacag ctccagtctg ccgctccccg tgagatcaac acatagggtg 99360
ggtcatttct gcatttccaa ccaaggtacc cggctcatct cattgggact ggttagacag 99420
tgggtgcagc ccacagaggg tgacctgaag cagggtgggg tgtcacctca cctgggaagt 99480
ggaaggggtc agggaactcc ctcccctagc caaaggaagc cgtgagggac tgtgccgtga 99540
agaccagtgc attctggcac aaatactatg cttttcccac ggtctttgca acctgaagac 99600
caggagattc ccttgggtgc ctacaccacc agggccctgg atttcaagcc caaaactggg 99660
ctggcatttg ggcagacact aagctagctg caggagtttt ttttcatacc ccagtggtcc 99720
ctggaatgcc agcaagacag aaccattcac ccccgtgaag aaagggctga agccagggag 99780
ctaagtggtc tttctcagtg gatcccaccc ccatggagcc cagcaagcta agctccactg 99840
gcttgaaatt cttgctgcca gcacagcagt ctgaagttga cctgggacgc tcaagcttgg 99900
tgggaggagg ggtatccaca aatactgggg cttgagtagg aggttttccc ctcacagtgt 99960
aagcaaaacc gctaggaagt ttgaactggg cagggtgcac tgcagcttgg caaagccatt 100020
gtagcaagag tgcctctcta gattcctcct ctctgggcag ggcatctctg aaagaaaggc 100080
agcagcccca gtcagaagct tatagataaa actcccatct ccctgggaca gagcaactgg 100140
aggaaggggt ggctgtgagt gcagctccag cagacttagt ttcctgcctg ccagctctga 100200
aaagagcacc agatccccca acacagcact agagctctga taagggacag actgcctcct 100260
caagtgggtc ctggtttcag aagataataa gaaactcctc tgagctaaag gagcatgttc 100320
taacacaatg caaggaagct aagaaccttg aaaaaggtca gaggaattgc taactacagt 100380
aagcagttta gagaagaaca taaatgacct tagggagctg aaaaacacag cacgagaact 100440
tcatgacaca tacacaagta tcaatagcaa aatcgatcaa gtggaagaaa ggatatcaga 100500
gattgaaaat caacttaatg aagtaaagcg tgaaaacaag attaaggaat aaagaatgaa 100560
aaggaatgaa caaatcctcc aagtatggga ctatgtgaaa agattgaacc tacgtttgat 100620
tggtgtacct gaaagtgatg ggagaatgga accaagttgg aaaacactct tcaggatatt 100680
atccaggaga acttccccaa cctagcaaga caggccaaca ttcaaattaa ggaaatacag 100740
agaataccac attcaaattc aggaaataca gagaacacca caaagatact cctcaagaag 100800
agcaacctga agacacataa tcgtcagatt caccaaggtt gaaatgaagg aaaaaaatgt 100860
tgagggcagc cagagagaaa gtttgggtta cccacaaagg gaaccccatc agactaacag 100920
tggatcttcc tgcagaaact ctacaagcca gaagagagtg ggaggccaat attcaacatt 100980
cttttttact attattatac tttaagttct agggtacatg tgcacaaggt gcaggtttgt 101040
tacatatgta tacatgtgcc atgttggtgt gctgcaccca ttaactcttc atttacatta 101100
ggtatatctc ctaatactat ccctccccac tccccccatc ccatgacagg ccccggtgtg 101160
tgatgttccc cactctgtgt ccatgtactc tcattgttca attcccacct atgagtgaga 101220
acattcggtg tttggatttc tgtccttgtg atagtttgct gagaatgatg gtttccagct 101280
tcatccacat ccctacaaag gacatgaagt catccttctt tatggctgca tagtattcca 101340
tggtgtatat gtgccacatt ttcttaatcc agtctaccat tgatggacgt ttgtgttggt 101400
tccaagtctt tgctattgtg aatagtgccg caataaacat atgtgtgcat gtgtctttat 101460
agcagcatga tttataatcc tttagatata tatccagtaa ttgtatggct gtgtcaaatg 101520
gtatttctag ttctaaatcc ttgaggaatc accgcactgt cttccacaat ggttgaacta 101580
gtttacagtc ccaccaccag tgtaaaaatg ttcctatttc tccacatcct ctctagcatc 101640
tgttgtttcc tgacttttta atgatcacca ttctaactgg tatgagatgg tatctcattg 101700
tggttttgat ttgcatttct ctgatggcca gtgatggtga gcacttttttc atgtgtctct 101760
tgactgcata aaagttttct tttgagaatt gtctgttaat atcctttgcc aactttttga 101820
tggggttgtt tgattttttt tcttgtaaat ttgtttatgt tctttgtaga ttctggatat 101880
tagccctttg tcagatgggt agattgtaaa aattttctcc cattctgtag cttgcctgtt 101940
cattctgagg gtagtttctt ttgctgtgca gaagctcttt agtttaatta gatcccattg 102000
gtcaattttg gcttttgttg ctattgcttt tggtgattta gtcatgaagt ccttgcccat 102060
gcctatgtcc tgaatggtat tgcttaggtt ttcttctagg gtttatatgg ttttaggtct 102120
aacatttaag tctttaatcc atcttgaatt aatttttata taaggtgtaa ggaagggatc 102180
cagtttcagc tttctacata tggctaggca gttttcccag caccatgtat taaataggga 102240
aacctttccc tatttcttgt ttttgtcagg tttgtcatag atcagatggt tgtagatgtg 102300
tggtattatt tctgagggct ctgttctgtt ccattggtct atatctctgt tttggtacca 102360
gtaccatgct gttttggtta ctgtagcctt gtaatgtagt ttgaagtcag gcagagtgat 102420
gcctccagct ttgctttttt ggcttaggat tgtcttggca atgcatgctc tttttgttc 102480
catatgaact ttaaagtagt tttttccaat tctgtgaaga aagtcattgg tagcttgatg 102540
gggatggcat tgaatctata aattacctta ggcagtatgg ccattttcac aatattgatt 102600
cttcctatcc atgagcatgg aatgttcttc catttgtttg tgtcctcttt tatttcatta 102660
agcagtggtt tgtagttctc cttgaagagg tccttcccat cccttgtaag ttggattcct 102720
aggtatttta ttctctttga agcaattgtg aatgggagtt catccatgtc cctacaaagg 102780
acatgaagtc atgtatggga atgcttgtga tttttgcaca ttgattttgt atcttgagac 102840
tttgctgaag ttgcttatca gcttaaggag attttggtct gagaagatgg ggttttctaa 102900
atatacaatc atgtcatctg caaacaggga caatttaact tcctcttttc ctaactgaat 102960
accctttatt tccttctcct gcctaattgc cctggccaga acttccaaca ctatgttgaa 103020
taggagtggt gagagagggc atccctgtct tgtgccagtt ttcaaaggga atgcttccag 103080
tttttgccca ttcagtatga tattggctat gggtttgtca taaatagctc ttattatttt 103140
gagatatgtc ccatcaatac atagtttatt gagagttcag catggagagc tgttgaattt 103200
tgtcaaaggc cttttctgca tctattgaga taatcatgtg gtttttgtct ttggttctgt 103260

-continued ttatatgatg gattacattt attgatttgc atatgttgaa ccagccttgc atcccaggga 103320
taaagccaac ttgatcatgg tggataagct ttttgatgtg ctgctggatt cggtttgcca 103380
gtattttatt gaggattttt gcatcaatgt tcatcatgga tgttggtcta aaattctcat 103440
ttttgttgtg tctctgccag gatttggtat caggatgatg ctggcctcat aaaatgagtt 103500
agggaggatt ccctcttttt ctatgattgg aatagtttca gaagaattgg taccagctcc 103560
tctttgtatc tgtggtagaa ttcggctatg aatctctcct ggactttttt tggttggtag 103620
gctcttaatt attgcctcaa tttcagagcc tgttattggt ctattcaagg attcaatttc 103680
tttctggttt agtcttggta gggtgtatgt gtccaggaat tttccattt cttctagatt 103740 ttctagttta tttgcacaga ggtgtttata atattctctg atggtagttt gtatttctgt 103800
gggattggta gtgatatccc ctttatcatt ttttattgca tctatttgat tcttctctct 103860
tttcttcttt attagtcttg ctagtggtct atcaattttg ttgatctttt caaaaaacca 103920
gctcctggat tcattgatgt tttgaaggtt tttttgtgtc tctatctcct tcagttctgc 103980
tctggtctta gttatttctt gccttctgct agctttttaa tgtgtttgct cttgcttctc 104040
tagttctttt aatggtgatg ttagggtgtc aattttagat ctttcctgct ttctcttgtg 104100
ggcatttagt gctgtaaatc tccccctaca cactgcttta aatgtgtccc agagattctg 104160
gtatgttgtg tctttgttgt cattggtttc aaagaatatc tttatttctg ccttcatttc 104220
gttacatacc cagtagtcac tcaggtgcag gttgttcagt ttccatatag ttgagcagtt 104280
tttaatgagt ttcttaatcc tgagtcctag tttgattgca ctgtggtctg agagacagtt 104340
tgttataatt tctgttcttt tacatttgct gaggaatgcc tcacttccaa ctatctggtc 104400
aatttcagaa taagtgcgat gtggtgctga gaagaatgta tattctgttg atttggggtg 104460
gagagttctg tagatgtcta ttaggtctgc ttggtgcaga gctgagttca attcctggat 104520
atccatgtta actttctgtc tcattgatct gtctaatgtt gacagtgggg tgttaaagtc 104580
tcccattatt attgtgtggg agtctaagtc tctttgtagg tctctaagga cttgctttat 104640
gaatctaggt gctcctgtat tgggtgcata tatatttagg atagttagct cttcttgtta 104700
aattggtccc tttaccatta tgtaatggcc ttctttgtct cttttgatct ttgttagttt 104760
aaagtctgtt ttatcagaga ctaggattgc aacccctgct ttttttgttg ttttccattt 104820
gcttggtaga tcttcctcca tccctttatt ttgagcctat gtgtgtctct gcacgtgaga 104880
tgtgtcttca gaatacagca cactgatgga tcttgactct ttatccaatt ttccagtctg 104940
tgtcttttaa ttggagcatt tagcccattt acatttaagg ttaatatttt tatgtgtgaa 105000
tttgatcctg tcatcatgat gttcgctggt tattttgctc attagttgat gcagtttctt 105060
cctagcatcg atggttttta caatttggca tgtttgtgca gtggctgata ccgattgttt 105120
ctttccatgt ttagtgcttc cttcaggagc tcttgtaagg caggcctggt ggtgacaaaa 105180
tctctcagca tttgcttgtc tgtaaaggat tttatttctc cttcacttat gaagcttagt 105240
ttggctggat atgatattct cagttgaaaa ttcttttctt taagaatgtt gaatattggc 105300
tgccactctc ttctggcttg tagagtttct gctgagagat ctgctgttag tctgatgggc 105360
ttccctttgt gggtaacccg acctttctgg tgaatctgac aattatgtgt cttggagtta 105420
ctcttctcga ggagtatttt tgtggcattc tctgtatttc ctgaatttga atgttggcct 105480
gcctttgtag gttggggaag ttctcctgga taatatcctg aagagtgttt tccaacttgg 105540
ttccattctc ctcgtcactt tcaggtacac caagcagatg tagatttggt cttttcacat 105600
agtcccatat ttattggagg ctttgttcat ttctttttac tcctttttt ctctaaactt 105660

-continued

```
ctcttctcgc ttcatttcat tcatttgatc tttaatcact gatacccttt cttccacttg 105720
attgaatcaa ctactgaaac ttgttcatgt gtcacgtagt tctcgtgcca tggttttcag 105780
ctccattaga tcatttaagg tcttctctat gctgtttatt ttagtctgcc attcatctaa 105840
actttttcaa ggtttttagc ttctttgcaa tgggttcgaa catccttctt tagctcggag 105900
aaatttgtta ttacagatcg tctgaagcct tcttctctca actcatcaaa gtcattctct 105960
gtccagcttt gttctgttgc tcgtgaggag ctgcgttcct tcggaggaga agaggcaccc 106020
tgatttttag aattttcagc tgttctgctc tggtttctcc ccatctttgt ggtttatcta 106080
cctttggttc ttgatgatgg tgatgtacag atggggtttt ggtgtggatg tcttttctgt 106140
ttgttagttt tccttctaac agtcaggacc ctcagctgca ggtctgttgg agtttgctgg 106200
aggtccactc cagtccctgt ttgcctgggt attaccagtg gaggctgcag aacagcaaat 106260
attacagaac agcaaatgtt gctgcctgat tcttcctctg gaagcttcat ctcagagggg 106320
cacccagctg tatgaggtgt cagttggccc ctactgggag gtgtccccca gttaggctac 106380
tcgggggtca cggacccact tgaggaggca gtctgtccat tctcagatct caaactctct 106440
gctgggagaa ccactactct cttcaaagct gtcagacagg gatgtttaag tctgcagaag 106500
tttctgctgc cttttgttca gctatgccct gcccccagag gtggagtcta cagaggcagg 106560
caggtctcct tgagctgtgg tgggctccac ccagtttgag cttcctggtc gctttgttta 106620
cctactcaag tctcagcaat ggcagacgcc cctcccccag ctttgctgcc gccttgcagt 106680
tcggtctcag actactgtgc tagcagttca atctcagact gctgtactag cagtgagcaa 106740
ggctctgtgg gcatgggacc ctctgagcca tgtgcaggat ataatctcct ggtgtgccgt 106800
ttgctaagac cattggaaaa gtgcaatatt agggtgggag tgtcccgatt ttccgggtac 106860
atctgtcatg gcttcccttg gctaggaaag ggaattccct gacccettac acttcccggg 106920
tgaggcaata tcccgccttg cttcggctca ctctccgtgg gctgcaccca ctgtctgaca 106980
agccccggtg agatgaaccc agtacctcag ctggaaatgc agaaaccacc catcttctgc 107040
tttgctcatg ctgggaactg tggactggag ctgttcctat tcggccatct tgaaacctcc 107100
cctctctcac gatcacaagg tcccacaata ggccgtctgc aggctgagga gcaagaaaag 107160
ccagtctgaa ttccaaaact gaagaaattg gagtctgatg ttcaagggca ggaaacatcc 107220
agtgccaaag aaagatgtag aatattcaac attcttaaag aaaataattt tcaacctaga 107280
atttcatatc cagccaaact aagctttata acaaaggaga agtaaaatcc tttacaaaca 107340
agcaaatgct gaggaatttt gtcaacacca ggcctgcctt acaagaggtc ctgaagaaaa 107400
cactaaatat ggaaaggaaa aaccagtaac agctactgca aaaacatacc aaattgtaaa 107460
caccatcaac actataaaga aactgcatca actaatgggc aaaatagcca gctagcatca 107520
taatgacagg atcaaattca cacataacaa tattaacctt aaatgtaaat gggctaaatg 107580
ccccaattaa aagacacaga ctgggaaatt gaataaagag tcaagaccca ttggtttgct 107640
gtgttcagaa gacccatctc agggtgaaaa gacatacatg ggctcaaaat aaagaaatga 107700
aggaatattt accaagcaaa tggaaagaaa aaaaaagcag cggttgcaat cttagtcttt 107760
gatgaaacag actttaaacc atcaaagatc aaaagagaca aaggagggca ttacctaatg 107820
gtaaaagtat caatgcaaca agaagatctg actgtcctac ttatatatgc acccaataca 107880
ggagcaccca gattaataaa gcaagttctt agagacctac aaagagactt agacttccac 107940
acaaaaatag tgggagactt taacacccca cagccaatat tagatcgacg tgacagaaaa 108000
```

-continued ttaacaagga tattcaggac gtgaattcag ctctggacca agctgaccta atagacatct 108060
acagaactcg acaccacaaa tcaacagaat atacattctt ctcagcacca cattgcactt 108120
attctaaaat tgaccacata attggaagta aaacacttct cagcaaatgc cgtagaatgg 108180
aaatcataac aaacagtctc tcagaccaaa gtgcaatcaa actagaactc aggattaata 108240
aactcactca aaaccacaca actatatgga aactgaacaa cctgctcctg aattactact 108300
gggtaaataa caaaattaag gcagaagtag ataagttctt agaaaccaaa gagaacaaag 108360
acacaatgtg ccagaatctc tggtacacag ctaaagccat gtttagaggg aaatttatag 108420
cactaaatgc ccacaggaga aagcgggaaa gatctaaaat caacacccta acatcacaat 108480
tcaaagaacc agagaagcaa gagcaaacaa atacaaaagc tagcagaaga caagaaataa 108540
ctaagatcag agcagaactg aaggggataa agacacgaaa accctttaaa aaattaataa 108600
atccaagagc tggttttttg aaaagattaa caaaatacat agaagcctag ccagactaat 108660
aaagaagaaa atagagaaga atcaaataga cacaataaag aataataaag gggatatcac 108720
caatgatgcc acagaaatac aaactaccat cagagaatac tttaaacacc tctatgcaaa 108780
taaaatagaa aatctaaaag aaatggataa attcctggac acatacaccc tcccaagact 108840
aaaccaggaa gaagtcaaat ccctgaatag accaataaca agttctgaaa tcgaggcagt 108900
aattaatagc ttaccaacca aaaaaagccc agaccagagg gattaacagt caaatcctaa 108960
cagaggtaca aagaagagct agtactattc cttctgaaac tattccacac aatagaaaaa 109020
gagggactcc tgcctaactc attttatgag gccagcatca ttctgatacc aaaacctggc 109080
agagacacaa caagaaaaga aaatttcagg ccaacatccc tgatgaacat caatgtgaaa 109140
atcctcaata aaatactggc aaactgaatc cagcagcaca tcaaaaagct tatccaccat 109200
gatcaagttg gcttcatccc tgggatgcaa ggctggttca acatattcaa atcaataaac 109260
ataatccatc acataaacag aaccaatgac aaaaaccgta tgattatcgc aatagacgca 109320
gaaaaggcct ttgataaaat tcaataccca atcatgctaa aaactcttaa taaactaggt 109380
attgatggag catgtctcaa aataataaga gctacttatg acaaatgcat agccaatatc 109440
atactgaatg agcagaagct ggaagcattc cctttgaaaa ccagcacaag acaaggatgc 109500
cctctctcac cactcctatt caacatagta ttggaaattc tgtccagggc aatcaggcaa 109560
gagaaagaaa taaaggtatt caagtgggaa gagagggagt caaattattt ctctttgcag 109620
atgacatgat tgtatattta gaaaactcta tcatctcagc ccaaaatctc cttaagctga 109680
taagcaactt cagcaaagtc tcaggataca aaatcaatgt gcaaaaatca caagcattcc 109740
tatacaccaa taagagacac agagccaaat cctgagtgaa ttcccattca caattgctac 109800
aaagagaata aaatatacct aggaatccaa cttacaaggg atgtgaagga cctcttcaag 109860
gagaactaca aaccactgct caaggaaata agataggaca caaacaaatg gaaaaacatt 109920
ccatgctaat ggattggaag aatcaatatt gtgaaaattg ccatactgcc caaagtgatt 109980
tatagattca atgttatccc catcaagcta ccattgattt cttcacataa ttagaaaaaa 110040
ctactttcaa tttcatatgg aatagaaaaa gggcctgtat atccaagaca acctaagcaa 110100
aaagaacaaa gctggaggca tcatgctatc tgacttcaaa atatactaca aggctacagt 110160
aacaaaaaca gcatggtatg gtactggtac caaaacagat atatagacca atagaacaga 110220
acagaggcct cagaaataac accacacatc tacaactatt ggatctttga caaactggac 110280
aaaaataagc aatggggaaa ggattcccta tttaataaat ggtgttggga aaactggcta 110340
gccatatgca gaaaactgaa actggatccc ttccttacac cttatacaca aattaactca 110400

-continued agatagatta aagaattaaa tgtaagacct aaaaccataa aaaccctaga agacactttg 110460
ggaggccgag gtggatggat cacgaggtca ggagatcgag accatcttgg ctaacacagt 110520
gaaagcccat ctctactaaa aatacaaaaa attagctggg tgtggtcgtg ggcacctgta 110580
gtcccagcta cttgggaggc tgaggcagga gaatggcatg agctgaggag gttgagcttg 110640
cagcaagcca agattgtgcc actgcactcc agcctgggca acagagtgag actccatcaa 110700
aaaaacaaaa acaaaaacaa aaaatcaaac cctagaagaa aacataggca ataccattca 110760
ggacataggc atgggagaag acttcatgac taaaacagca aaaccaatgg caacaaaagc 110820
caaaatttac aaatcagatc taattaaaat aaagagcttc tgcacagcaa aaaactctca 110880
tcagagtgaa aaagcaacct atggagaaaa attctgtggt ctagccatct gacaaagggc 110940
taatgtttag aatgtacaag caacttaaac aaatgtacaa gaaaaaaaaa acaaccccat 111000
caaaaagtgg gcaaaggata tgaacagaca cttctgacag gaagaccttt atgtggctga 111060
caaacatgaa aaaagctcat catcactgtt aattagagaa atgcaaatcg aaaccacaat 111120
gagataccat ctcatgcccg ttagaatggc gatcattaaa aagtcaggaa acaacagatg 111180
ctgaagagga tgtgtggaga aagaggaaca catttacact gttggtggga gtgtaaatta 111240
gttcaaccat tgtggaagac agtgcggtga ttcctcaagg atctagaacc agaagtacca 111300
tttgacccag caatcccatt actgggtata tacccaaagg attataaatc attctacaat 111360
aaagacacat gcacacgtat gtttattgta gcactattca caatagcaaa gacttggaac 111420
caactgaaat gcccatcaat gatagactgg ataaagaaaa tgtggcacat atacactgtg 111480
gaatactatg cagccataaa acaggatgag ttcatgtctt ttgcagggac atggatgaag 111540
ctggaaacca tcattctcag caaactaaca caagaacaga aaaccaaaca ccatatgttc 111600
tcactcataa gtgtgagttg aacaatgaga acacatggac acaggaaggg gaacatcaca 111660
cacaggggcc tgttggggag ttgaggctag ggagggatt ggattaggag aaatacctaa 111720
tgtagatgat gggttgctgg gtgcagcaaa ccaccatgac acgtgtatac ctatgtaaca 111780
aacccacaca ttctacacat gtatctcaga acttaaagta taataataat aagatacaga 111840
actgcagaat gaataagaac tcaccaacca tctgctgcct tcaggagact catttaagac 111900
ataaggactc acataaactt aaagtaaatg ggtggaaata ataataagtg gtgtcactga 111960
tgtggaggta gattataaaa ctcttatcat atgctggtgg aagatcaaaa tgataaaacg 112020
aattaaaaaa tcagtcagat ggtttcttaa aaagttccat caatatgcct ctatcttaca 112080
aacctgcaat tctattcctg aatctttatc ccaaggaaat gaaaaagtaa gtccacaaag 112140
agttctatat gaatatttat aggagcttta tttattataa ttcaaactgt aaaaataatt 112200
tcaatgttca tcaataacaa aatgaaaaaa taatttgcaa cctactggta cacttgaata 112260
ctattcagca ctgagtatct taaatagcat ggatggagct caaaaatata ctcaggaaag 112320
aagccatgta tattctgtat gagttcattt acatgagatc atttacattt cctccaaaag 112380
aggaaaaact aatttctgtt gaaagaaacc aatgtatttg cctctggcag tggtaagggg 112440
gtagcacaga ttaattgggt agggactcaa gagagtttct ggggtcacag aaatgttccg 112500
tgtggtgatg ggagtttggg ctccacaggt ataggtgttg atccaaaatc atcaaaaaaa 112560
caacattgca gatctgtgca tctcactctg tgggaaagta tatctcaact gtaaaaaggg 112620
cagaaattgc ttttaaacgc tcagcctttt agcacatcca gttgcttgga gaaccagctt 112680
actcaaatgg gggtctaggc tggagactag gtcacaggca tagagtctct aaactttccc 112740

-continued

```
atggcacata atacgtttca ggttttctca gagagctgca ggttagtaat ctgaggattc 112800
tgacaagttg ggtcaacgtt cctaggaggc atgaatggga gtgcattctc taagatccct 112860
ccaccccagg gtccttgctt tctgtgcctc ttactccatt gttttctgac tcctctgtag 112920
ccactcgacc tcttcagatc ccattgtcta cccagccatc gccctttatg acttgggtcc 112980
cactgttctt tcatctcatc ctccattccc tcagtttcgg agtggctgcc gctagcagag 113040
gatggactga gagcaggaga ggtggtcctg cccaggaacc catcctagag aaatggcatc 113100
ctgtctggga gctagttttt tagggcaggt tttataagtc ttgtaaagcc agacacactt 113160
gatctacctg gtatgttatt tacagtaata ctattttcat aattgctttt cactctaaaa 113220
gtagagcctt ttagctacac tgtgagtaaa taaaggggct ggcctgggaa tggtatcatg 113280
ttggatgttg tttcttccct gaagtaatat atatcagtta caatttacat gttactgcag 113340
agtcctagag agagacacag agaatgagac agataccaat acattttat gtgcattaaa 113400
aaaatctaag gccaggcgca gtggctcaca cctgtaatcc cagcactttg ggaggccgag 113460
gtgggtggat cacgaggtca ggagattgag accatcctgg ctaacacggt gaaaccctgt 113520
ctctactaaa aatacaaaaa attagccagg cgtggtggcg ggcgcctgta gtcccagcta 113580
ctcaggagac tgaggcagga gaatggcttg aacccaggag gcagaccttg cagtgagccg 113640
agattgcgcc actgcactcc agtctgggcg acagagcgag actccgtcac aaaaaaaaaa 113700
aaaaatctaa aatgcactct tcaaaatcta tgtcatttat tctggaggaa tgcagttggc 113760
agaaggagga agatattccg aatttttctt gtatacattt atgtatgatc tcagtttttt 113820
tatggatcat agaccaattt tgatatttta aaataaaaat tataatctat cttggaaatt 113880
tacatggttc tttagaactt gaggaccgtt tttgcttttc ggaatattat tgtacctaaa 113940
atgggaatat tacaacgtca ctttttaaca ctttgttata acaaagttta gacagcgctg 114000
ggtgcccctg aattttttcc cgcctcttgt gacctgtgtt gttttggaat ttgcagtggc 114060
ctgaccgaga actactgcag gaatccagat tctgggaaac aaccctggtg ttacacaacc 114120
gatccgtgtg tgaggtggga gtactgcaat ctgacacaat gctcagaaac agaatcaggt 114180
gtcctagaga ctcccactgt tgttccagtt ccaagcatgg aggctcattc tgaagcaggt 114240
aagaagtctg tggccagata tctacacatt tgaacattgg gatgaaaaga gatggaaaat 114300
ctgactgatg cagaagcctt ccatgctaca cagaaacttg agggtatggc aggtggaaag 114360
aagcctcagc actctctctg gtggagcaat ttttggcgca acgtgcgtgg gcggtgactt 114420
caggaatggt gcaaacccac ctgggcactt gacttaccac tcactttgtt atgaaagggg 114480
ttatctcggt gttccagaca aaattccaat tctaacatca ggccaaattt gtgccaaatt 114540
tcacactagt gagtgtttcc aggcatttat taaaatggac agtgttcatt gcaatcttca 114600
gcattgcagt tgctgaggta tgtggccgct gagtttgtca tcctggggaa acctaatatg 114660
atgatattta ttccatctaa tcctggggct atttggcagt aaataccaca gaatacacta 114720
tttctctggc ttatttcagt cttaggtagg ctctgcacac ctatgcttgg aaggcaggaa 114780
tttcttggtg ttcttgtgcc ttcttctcat ggaacgtgca tctttggtgt gtgttgagag 114840
gaagggtagt agacttctgc tttgttgcaa tgcaggatgc tggaacaaga ggattccctg 114900
tctctactgt aagggaataa gattttagcc tccatccttc tctaagaagc aatgtgtctt 114960
tgcctccaag tactagatgc aggaccatga actgccccgt ccaccagaag cttaaggctt 115020
tggcttttca ggagcaatca tctagggaac tgtgcagggt tttcatgtct gtcccctact 115080
gacagccaat caccatacag cctgcataac ctaatccatc atcgtctggt ttcctgcctc 115140
```

attgttttca tgaacaacca gtagagagcc atacgaaaga gcttgcacat gagtctttgt 115200
tccaattgta agagcactga taggtccttt tcccaccagg ttttgaatat aaaatttcta 115260
agaacttatt aaaatattag aatgttatta atctattgtt tttgcttcag catgtccttc 115320
tgcttgtgag tatactaaag agaacagtca taattctgaa actactgtcc tgtttgtgtc 115380
ataaattgct tcacatgttt ctgcatacta gtagttactc agcttgattt tgtctatttt 115440
cagcaccaac tgagcaaacc cctgtggtcc ggcagtgcta ccatggtaat ggccagagtt 115500
atcgaggcac attctccacc actgtcacag gaaggacatg tcaatcttgg tcatccatga 115560
caccacaccg gcatcagagg accccagaaa actacccaaa tgagtatgtc tttgatgtta 115620
cttgtaagag gagcaacagc caacttaagt tcctcctaga agagccttgc ttcaagctaa 115680
cttgttagga caaatttccc ttagacccag aaggtgtgtc aaaatgtcca gacaactttg 115740
cttttgatca aagagtctga gagaataggt attttaggct tgctatcttt tctaatagtc 115800
tgatggaagc agaaggctac atggagctga tgaggtcttt ttaatataaa gctcaagaga 115860
tcaaatgatc aaatacttag agtgccattc tacaaggctc ataaaagatc aatgcactct 115920
ttcacccatg caattctatc attctaacct cccttctctg aaatgaaggc tttttgccat 115980
ttttgtcatg ggtcacaagt aaataattca catgtatatg agtatatata taaccaggtg 116040
tgtttattca gactagtatg tatatatata catatatatg ttcatataag ttagtattca 116100
tatatatgtt catatatata tgttcataca gactagtatt catatatata tacatatata 116160
tatacacaca catatatata tatatatata tgttctaggg aaacatgcaa ggtttttatg 116220
tctgtccctg actgatgacc aaatacccta tagcctgcac agctgcaagc tgtatagcca 116280
tacaatttgc aggacacaca cacatacaca cacacacaca cacacacaca cactaacata 116340
taatataata taatataata taatataata taatataata taatataatt aatatatata 116400
aacctgtgtg aacacactgg gttctaagct ccagttttct gaagggatat gggttgccag 116460
gagaggaaga gcaaaagcaa gaatgtagat gagaattagg aagtaaacag atatggagat 116520
taaaatgggc aggtacatgg acaaaaaacc aggtctgaca aaaactggct ttctgccata 116580
aatgactata aaagatatta aaaaacactt tccacatgtt ggacaagaga cagtacagga 116640
ctgagataat ttagaaaagg aaatgaatga gcgcaactcc gtaactatta tgactttctt 116700
cctggagaac cttcctggac tgaagggcaa ggaattggag ccaaagccaa ccacagcagt 116760
cttgctgaac tgaggaaaga gactggagtt tgggatagct aagaaaatgt gtattttcta 116820
tgctaggtaa taatgagaaa gaatttgtgg tgaaaaggag ctgaaggaat atgcatggaa 116880
gtctaatata aactgcatat gcacagggag aaattctaca aagtgggaca gagaaccact 116940
actggggaaa ggacaaattc agggaaacag tgagctcaat ggtgacgcca gagctcacgt 117000
agcactgggg gataccgggg ttctgatcag cccgaggaga gacacctcat tgaacatctc 117060
gggcattcag tagagacccc agaaaagtca tactttagga gtaggattta tgccttctta 117120
gaataaagac taccccagaa acaccctagt aaagcttaaa aaccaagtct aaaaggaccc 117180
aaatgatctc caagtaaatt aactgcctga cagaagaaaa ctcaaccatc actggaggta 117240
aataacatga ttacagtgct ctgtaatgtt gcattcacaa ggagtgacat catttaaaaa 117300
tttatgaggc aggaaaaagc aattagtgtg atccataact aggagaaaaa ccagtcaata 117360
caaatagacc aagaaatagt agaaacgatg gaattgacaa agaaattaaa actgtatata 117420
tgataattgt gttcaaagat ttaaagaaaa catgaacatg agggaaacaa atgcagaata 117480

-continued taaaaaaaag caaatgcgta aaacaaccaa atggaaatta aagaactaca aaaaagtata 117540
accttaataa aatactcact ggatggcctt aatattagtt tatacattac agaagaaaaa 117600
gtgaaccaga agataactca atgaaagcca tacaatctgt aagacacaca cacacgcaca 117660
cgcgcgcgcg cgcacacaca cacacacaca gagagagaga gagagagaaa gagagagaga 117720
gaaaggctga aaaaaataaa tagaacctta aggatatcag tgaaaatagc aaaagattta 117780
atatatgggt aaagcaagtc acagaaggac gggaaggaga tattgggaca gaaaaaaata 117840
ctcaaagcaa tgatggctga agactttaca cgtatgaaga aaatgataaa ctcacagtca 117900
agaagctcaa tgaatcagaa atagtatttt taaaagcaaa actctatgat ttacttgggt 117960
acattataga taaatcgtcc aacatcaaag ataacaagga taatcttata agccagagga 118020
aaacaatatc atttacatag agggacagta atgaaagtga ccgatgcctt ctccttggaa 118080
acaatggcat aacatcttta aagtgataaa gagaaataaa aacagatcaa cctaggacga 118140
catgtccagc caaaacaaac aaataaacaa aaaaaccctt taaaataaac gtgatgtaaa 118200
tacgtattct gccacctcca gaggaaacaa gcaaaaaaac aaaagaatgt ttccaaggca 118260
ggcttctgta ttaaaagatt ttaaggaaag ttattcaggt agaagaaaaa taataccaga 118320
tgggaacttt aatccatact aagtaatgaa gagccctgga aatggcaaat ggcaatgtca 118380
atataaaata ctcttattta tctaattttt aaatgtattt aaaggacaat ttgtgatatt 118440
aattaaaata ataggaatat attgttgttt caacgtatgt agtagtaaaa ttcataaaaa 118500
cagtagcaca aataatgcag atgataactg gaagtatact gttaatgagt tttttgcatt 118560
atccatgaag ttatataata ttaatagatg gttgaatgtg atagtttaag gtgggatatt 118620
ataaatccta ggacaaccaa aaaaatttaa actgagagga atggatagta agaggaatag 118680
tccttttatg caaaagaagg aagaaaaaga ggaataaaga atataaaaga tatggtgtaa 118740
acagaaaata catagcatta ttgtagacac aaactgaact accttatgag tatattaaat 118800
ataaaaggat taagcattac aaataaaagg cagagattgt aaattgaata aaaaccacag 118860
ctaagtgtgt tctttttaga ataaatactc tttaagtgta aagatctact ttaaacacca 118920
aaatatgaaa aaggatatat accatgaaaa cctgaatcat aaataagctg gagtggtgat 118980
taatggatgc aggcactcct aaagactaat aagtgaatgt ggtcaaattg aagaaacaaa 119040
agtatatacg tgctcaatgt gcaaaaactt tttctgtata catgctatga tcctttggaa 119100
aattaaagtt ttaaagcaat atcactgaca atagtatcaa aaccaaaaaa tatttagtga 119160
taaatttcac acactatgct caaggactat acaccttgca ctagaaaaca atgttgagga 119220
aagaattaaa agatctaaat atacaccatg cttatagatt aaaagactcc atatcagttc 119280
tcgtgaaatt gatctttgga tgaaacccac acccaagcac tattgcaaca gtcctttttt 119340
ggaaaaaaaa attggaggac ttatatacct taatataaag acttataaaa gtacaggaat 119400
caagacatgt ggtattggcc tggccccttg gctcatgcct gttaccccaa cattttggga 119460
ggctgagtct ggaggatggc ttgagcccag atgttcaaga ccagccttag caacagagtg 119520
agaccctctc tctacaaaaa ataaacaatt agatcgatgt gatgacttgc acatgtagtt 119580
tcagctactc ggaatgctga ggtgagagga ttgcttgact caggaggtct agccatgagt 119640
gagcattgat catgcctctg cattccagcc tggatgatgg aatgagacac tgtctcaaaa 119700
aaaaaaaaaa aaaaggatat gtgttattgg ccaaaaaagt atgcaaacct aaaaagggat 119760
ggcccaccac cagacccaca tacatatatg gtaaatggat tttccgtata gatggcaaag 119820
caattcaatg gagacaaaaa tgttttacaa aatcattctg aaccatttgg atatccatga 119880

-continued tacaaaacaa aagcagaact tgacttttgc ttttcatctc aaattatttt gatatctctt 119940
ccacctaagt gtcagagcta aaactgaacc tgaaatatga aagttccatg aaaaaatata 120000
aaatcttcac aaccttggag aaggcaaact tttttgaggc aggagtctgt aaacactcac 120060
tataaaataa aacaaattat aatgtgggct ttcatgaaaa ctcatgctta ccaaaagtca 120120
ttgttaagaa aataaatagg caagtaacac atgagaagaa aaatgctctc tgtccatata 120180
tctgacaaat ggcttgtgtc cagaatatag gaacatttct cccactcact aaacagagga 120240
caaacaacta atgggcaaca gattgaatag gcatttcttg gggatagata gatgtacaca 120300
tagccaataa gcacctgaaa aaatgtccag tatctcagcc atgaaaaata aagagttata 120360
atcatcatga gatgtcacca aacacccaat ggacatggat attattaaga agacaccaca 120420
gtaactgatg tcactgatgt agagcaagga tgtgaaactc tctcatatgc tggtgaaagt 120480
gcaaaatgat acaaccactt ttgaaatcag tctgatagtt tctccaaaag ttcaataaat 120540
gcacttttac cctacaaacc tgcaatcctg tttgtgaata tttaccccac agaaatggaa 120600
acataagtcc acgaagacat ctccaagaat attcatagca gctttatttt ttataacccc 120660
aaactgtaga caatttcaat gtcaatcaat aagaaaatga ataaataatt tgtgaactag 120720
tcatacaatg gcatactgtt cagcaataaa agggagcatg tttttgatac tctcaaatag 120780
tatggaagat gctcaaaaat attacattaa agaaagatgc cagataacaa aaatgaacat 120840
tatgtatgag tctattgatg taaggttcca gaaaggtaaa actaatttct ggtgaaagaa 120900
accaatatca tttgcctctg gccatgggaa gagagtagca gagattgatt gagcagtaaa 120960
acgaagtttt tttctggggt gatgtaaatg tcctgtattg tgattgaagt gtgagttaca 121020
caagtgtaca tgttcatcag aagtcatcaa actacatcta agatctgtgc atttgactat 121080
acatgaaaat atacctcagt tgaaaataga tcaataacct ccctcatata ctatacttgc 121140
taacacagcc agctgcttgg agaaccagct tgctggaatg gagaatctgg gcttgagact 121200
gggtcacatg tatagagtct ctacagagac aatgttgcat tcccacggta cataatacat 121260
ttcaaggttt ctcagacagc cacatgtcat gaatgtgagg attctgagag gttggagcaa 121320
cattcctggg aggaacgaag gggagcacat tctccaagat cccccaccac cggggtcctc 121380
accggctgtg cttttttttt tttttttctt gacagagtct cgctctgtcg ccaggcagga 121440
gtgtaatggc ccaatctcgg ctgattgcag cctccaactc cagggttcaa gagattctcc 121500
tgcctcagct tcatgagtag ctgggactac agatgtgcgc cactgcgccc agctaatttt 121560
tgtattttta gtagagacgg ggttttgcca tgttggccaa gatggtctcg ctctgttgac 121620
ctcgtgatcc acccgccttg gcttcccaaa gtgctgggat tacaggcgtg agccaaagca 121680
cccagcctgt gcctctcact tactcaattg tttttctgaa ccctccatag ctggtggacc 121740
ttttcagatc ccatagtcta gccagccctc tcactttatg ccttgggtcc cactgttcct 121800
tcatctcatc cccctctgt cagtcccgca gtggctgtgg ccagtagagg atggactgag 121860
agtaggagag gaggttctgc ccaggaaccc atcctagaga aacagcatcc tgcctgggac 121920
ctagtcttcc aggtcagctt ttataagtct tttagactca aactcacttg acccacctga 121980
agtggtattg acaataatgc tattttcatg gttgttttc actgtaaatg cagagccttt 122040
tagctacacg actagtacag agagtaaggg aggctggcct gggaatgata tcatcttgga 122100
tggcatttcc tccttggaga aatatatgtt agttccaact cacatgttac tatacagtcc 122160
tgtagaaaga gatacagaga gttagacagg tatagacgca tttgtatatg cataacaatc 122220

-continued tataagacac acatcaaaat ccgtataccg gttcctctag gggtatgtgc ttggcagaag 122280
gtagaaggag ggtattctgg ttcctttctt ttgcacattt atgtatgatc tcagtttttta 122340 tatggagcat tgatagggtt tggctatgtc cccacccaaa atctcatctt gacttgtaat 122400
ctctataatc ctgataatcc ccatgtgtca agggcaggac caggtggagg taactggatc 122460
atgggggcag tttctcccag gctgttctca tgacagtgag agagtctcct gagatctgat 122520
ggttttgtaa gtgtctggca tttcccctac ttgcacttac tctgtcctgc cgcctgtgaa 122580
gaaggtgcct gtttctccct tgccttctgc catgactgta aatttccaga ggcctcccca 122640
gcaatgtgga actgtgagtc aattaaaact cttttctttg taacttaccc agtctgtctc 122700
gggtatttcc tcatagcaat gtgagaacgg gctaatacaa gcatatacta cttttgatat 122760
tttaaaataa aaattatcat ctatctttga aaggcatgca caaatgggaa gttgaggaac 122820
atttgtgttg tggcaattgt atgatacctt taatgggaat atttcaaaga cacttgttaa 122880
gactttgtta gaacaaaatg tagagggtgc tggatgtccc tgaatattct tccgcctcct 122940
gtaacttgta ttgctttgga atttccagtg gcctgacaat gaactactgc aggaatccag 123000
atgccgatac aggcccttgg tgttttacca tggaccccag catcaggtgg gagtactgca 123060
acctgacgcg atgctcagac acagaaggga ctgtggtcgc tcctccgact gtcatccagg 123120
ttccaagcct agggcctcct tctgaacaag gtaagaagtc tgtgtcttac cttgtctagc 123180
acatacctct ctatgtgctt ggacaacggg atgaaaagac atgaaaaacc acactgatgc 123240
agaagccttt agtgctacac gggagctcga gtgttggttg aggttctgcc atgaccaagg 123300
aagtctcagt gccgtccctg ggaaagccag agctgtgatt tttggcacaa cttgtgggag 123360
tagtgacttt aggactggcg caaaacctcc agggtgctca acttaaccac tcaccttatt 123420
ctaaaatggg ttatttcagt gtcccagtca aattcctatt ctaacatgct gtcaactgtg 123480
tgattatttc caagccaata agcatttcca gtaatttctt aaaatagtgt tcattgcagt 123540
cttcagcgtt gtggctcctg agggatgtgg cccctgattc tgtcgtccta gagaagcctg 123600
acatgactgc attgattctg tatcgtcctg ggtctatgtg gctgcctggc tgtctgtaat 123660
catctgtttt atttttattt ttttctacag actgtatgtt tgggaatggg aaaggatacc 123720
ggggcaagaa ggcaaccact gttactggga cgccatgcca ggaatgggct gcccaggagc 123780
cccatagaca cagcacgttc attccaggga caaataaatg ggcaggtctg gaaaaaaatg 123840
taagccactt tgatttggac tctttttccc tttgctgaca aatcttttca aacagaagag 123900
gggcagagga aaatactgga aagacttcag gaggctaagc gtaattagcc ttagcatgga 123960
aagtgcaagc agcacaggcc agcaaagccc cacgcgtgtg ggggttctca ggcctcttct 124020
cttttgacat ttctttactg tttccattgt tgggtgctgt ttctcgtttc tagtgcttgt 124080
cctctaagcc aggggtcccc actccagtac tggtactggt actggtactg gaactggtaa 124140
ttatctgtgg cctgttagga actgggctgc acagcaggag gtgagcttcg ggggagcaaa 124200
caaagcttca tctgtatttt ctgctgcttc ccatcactct catagctgcc tgagctctgc 124260
cagctgtcag atcagaggca gcattagatt atcatagcac aaaccctatt gtgaactgca 124320
catgtgagga atctagattg catgctcctt atgagaatct aatgcctgat gatctgtcat 124380
gcttccatca cccccagatg ggaccaccta cttgcaggaa aattagctca gggctcccac 124440
tgattttacc ttatggtgag atgcacattt atttcattat atattacaat gtaataataa 124500
ttgaaataaa gtgcacgata aatggaaggt acttgagtca tcctttaacc atcgcccccct 124560 caccccaggt gcacagaaaa attgcctttt atgaaactgg tctctggtgc caaaaaagtt 124620
ggggaaccac actgctctgg gttctagtag tcagagatgc cctctatgag gcttaagtca 124680
gatttttcta gaaaagattt ggatgggcca tcaggtcacc atgagacttc ccttagcctc 124740
atgcattctc tgtgatggtt tactttgggg cctatgaata gggaagactg agatatagga 124800
aaaaccaaag tgtctgtgtt cccccactct cacacccatg taacataaca cttctcacac 124860
cagatatggg gggatttctc ctcacacccc aagcgagtct ccagcagata ccagctgggt 124920
gtcctacaat gtaactcggt cctgacactc tatctggaga cagtgtcaga tcccacaagt 124980
taaggctcag tcctacaaga ctgccccact gcagatgcca atcccaagtt gcaggctgtg 125040
acctgtactt ctgcccagct ggataaagat ctgtttttct atatgaccct ccatgggttt 125100
gattactttg ctagagtggc tcacagaact cagggaaaca cgttactttt atttacccat 125160
ttattataaa agatattaaa aaggatcctg gtgaacagcc aggtggaaga gatgcacagg 125220
gcaaggcacg tgggaagggg ctcagagcct ctatgccctc tccagtgcac cagtccccag 125280
taccctaagt gttcagcaac ccagaagctc tccaagtgca gtcttgttgg gtttttatgg 125340
aggcttcatt acagaggcac agttgattac atcattggcc atcggtgatc ggctcacctt 125400
cggcccctct tccctccctg gaggttggag ggtggggctg aacagttcca accctcaagt 125460
cacatggttg gttcccttgg caaccagccc ctggggctat ccaggaaccc accaagagtt 125520
gcttcattgc agctcccttc acccaggaaa ctccaaggga tttaggagct ctgtgttaag 125580
aactgggggg cagagaccca atatacattt cttattctat cacaatatca caggaagcta 125640
aggatgatac tgcctttgtg tgtcttggct gtggatggtg cataatgcat ggaagtaagc 125700
atttctgaat caacagcaaa caggctttat caggtagaag acccctcagc gccccaggga 125760
caaagctcat caatgatgtc ccactgtcct ctgaggctct agctctaaga cctccagtgg 125820
gtcaagctcc tggagaagtg gcacattctc caaagaccct tcagggtcac cacaccctgg 125880
ttaagggtgt ggcctcataa ctccttttga ctatgactga tggcttacag catagaaaga 125940
aataactttg tcaaaaaata taataatgat agaaaggaag aaggaacgct cccttttgtc 126000
ttctaagaat agatgtgaaa tgtgtgtgcc ttagaatatc ttctccctct cctgctccac 126060
gtgagctgga gcttacatgc ctgcttgttt tcagtactgc cgtaaccctg atggtgacat 126120
caatggtccc tggtgctaca caatgaatcc aagaaaactt tttgactact gtgatatccc 126180
tctctgtggt aagttgcctt ctgttttggt aaggaaactg cttccttaat atggatttgg 126240
aaaaaaaaaa gcaaaaaaaa cagaaaatgg cttttgagct gagtgcttct ggggaggaga 126300
tggctgccct ctccaccaga gcctgctttt catcatggcc accttgaacc tgccctacta 126360
ttggccccat ttgttaggaa aacacccgcc cctcccacca cacacacata aataaaataa 126420
atgtcaaatt cccaaagggc aaacttagag gtgatctaat cagcccggga tagtcccacc 126480
gaacccttct ttgtctagcg tgggatgcat gaaaaacaaa tttagagtca ttatgatgaa 126540
aaactgtcct cttctgcagc tgagaagaaa aaaaaaatac gagcagcagg aaacagctaa 126600
gcatgtaatg cacattgtaa acctcagatg gccatcctag gaaatcaatg aagggtagtg 126660
cagctcttta gccccagatg gcctttctcg taagattact actcatgagt cccattagcg 126720
acattgctta gagactgctt gttaggttcc ttcctcattg ctctgagact cttattggga 126780
gtatgaggct tggatcaggg gaaggggaat tgacattaga tcttaaatga ttggggtaac 126840
aaatccatgg gggaaaaaaa gccacttgta cttgttccct attttcttcc tgctgaccaa 126900
tcaacttgtc tgtccgagtt acagaacacc accctggact tttcttttgt gtaatttggt 126960

-continued

```
tgcttgtggt tgggtctgcc atgtgaaggg accttgagct gggggaagaa ggttggcctc 127020
caagtccact gaagaccagc atcctgagat tgcctgggga ggtggtacag ggcagtgatg 127080
aagatcatgg gagccacact gcccatcgtc acatttgggc cactcctggg gagagcaaga 127140
gggaagaagg agaggttagg gtgataggaa agattctact tggccaatat tattataatg 127200
tggcattgtg gtctctggat ttagtgtgag ttgatagctg actttttct cgagtgggtg 127260
cttttgttct attttgtcgg tgctattgca gaagcatctt ggtggttcct ctacctcaaa 127320
gtctcttgat ggggtcagtt ccagttctcc gcttctggcc ccatctagta cacgccactg 127380
cctctcactg cctgggctct ctatccttga caggctgcct tgaatttaag cccagtctga 127440
cttacctgcc tcaaacaccc acagtagtgc ctgggactca tgcacctttg actcccatgg 127500
aagggaagtg cagtagcttc ccaggtgcaa ttctgctgtc ctcacccaca ttgaggatgt 127560
atgagaatca ggttcttaga gattggagaa agaaggaaga atgggaacaa gatttcttcc 127620
aatggactgt gaggttcccc accttacttt gatgtaagac aagtgaggtt aaccccaagc 127680
ctggtgagga gggttcccat cagacacttg gaaatcctga ggactgtttc ctgcagaagg 127740
atgtggttgg tgggatattc aggtttgact catgattgag aaagttagag cctctggttg 127800
gagaaagagt ttaataacta tttcatttcc accaacacat tcagtacgaa taataaataa 127860
gtaaaaataa atagaaacat tcagttttat tttgaatagt aggagtaggg tataatttct 127920
gtagttactc ttttagtaca atgatgcatg tttactgtat gtaaggcata ctagcagaaa 127980
ttgagctcag cactagaaaa gatgattgca ttccatgcca tgcttctttt ttacaaaaga 128040
cttctataga tagattctca aaacaaccca cagcaaatga aaagttattt ggaaaactca 128100
ggttccagat tcactggagt gtagaatctc tggttggttg gggaggaatt tcctcttgca 128160
gttgttatta ataattatat gaataattat taactatatt aatatttata gttttgaaga 128220
ccttgaaggg ctggagacaa cagagaagca tttttgaaca ccctctgtag cccctgcact 128280
gttgtaggca ttgatgggtg gtaccaaaga tgggacactt tccctacctc cagagacctt 128340
gtgggcttgc tgcagagaga aggcagggag gaggaaaaga agaatagagg cacatgtgtg 128400
taaattaccc ccacagcagt cagttagtca tgggaggctc cccagaagaa ctgtcctgaa 128460
gctggctgag agaaggcaac atttcaacat aggacagtta tccttgctac ataaaatcac 128520
atacacacat gcacatatgt ccacacacag agactcacat gcaaaagaat cctttgtgcc 128580
tttcagtaaa ctttacatgg tttagaaaga acttatattt ccttgaaagg agagtgtcct 128640
ttgttgttta ctaccacttt ttaaacttag aaagaaaaat ctaaagagtg tttatgattt 128700
taccatttaa tttcaccttt gagatgtgaa aaactagtgc ttggaattcg tcctgaatta 128760
aacgacacaa ttgctaactt ggactcaaat gcgacttctt ttcccacctt gtgccacagc 128820
atcctcttca tttgattgtg ggaagcctca agtggagccg aagaaatgtc ctggaagcat 128880
tgtagggggg tgtgtggccc acccacattc ctggccctgg caagtcagtc tcagaacaag 128940
gtaagaacag gcccagaaac catctatact gtccttccat gtaagcccca caaaaccctt 129000
ctacatttac acagaaccca cacagctgat gcatcaatac ctgcctctct gttttctgaa 129060
ggaggaaaaa atatagaaaa attaaaaaaa gttatattat tataggttct ctacttggaa 129120
aatagccaaa atacaaatct ttttcttgat ctgggcagtt ccatcaaaat ctgtaggcac 129180
agtgatttgc accaagttcc aatacttttg gaaaatattg aagatgctct gagggtttct 129240
atggatatcc attgtctcac tgtcagatga aaagaaaggg aagtttttag aaatgtgaca 129300
ctttgcagtg agggaggaca agagcaaact tacctacagt ctatcacagg cacagatttt 129360
```

-continued tttttacact tttgtgaatc attgaattca atgccgaggc tattcatcta ttcacaaaca 129420
catgaacaaa ttatgggttg tgatccccat aaatgaagag taatcagtcc gaacccacag 129480
aacctggaca ttttgggtat cgtttcagtg gaacatgcaa ttcgtaagtt cagtttgctt 129540
gggtgtctct taggaagaac acataggaca cagacccatc tgcctgcatg ttttgcttcc 129600
tcatctcctt tctacaccag ggcacctgtg ctcaattgct gttctcctct aaagagactt 129660
ccttctgtaa gtttgtgaaa tgccatcgac aaacctgatc gcatcgcatt tcactctgct 129720
gttgagttga tttttcttta ctttatcgtt tgtaacttct tgctctacag agctttcacc 129780
ttccacatat ttcagattca ttctttccta aactgtgtgg tggtctatgt cctcactgac 129840
tatcaacata ctgccatcat gcacttccta tctctattcc tcttcgttgc aatctggctc 129900
caagtggctc acaccattat tctgatctat caactgccta cacagtccta gaaagtaagt 129960
gagtcaagaa acatccccca aaagtaaact tttcaggtaa gatcagaaga ccctcatgag 130020
tcactgctgc tcaggatcgt atctggctcc ttgaagagtg accttgcata gatcttgtca 130080
taaaaaatga aagagacctt gggaaggtct tgggctggtc acttttgtca gagtccaggg 130140
ctgtggggtg aaagccacag ctatagagct tcattctgga gtcacttagc tttgctctcc 130200
tggggacagg ctgtgcctat tcttgcctca ggcatcaaaa aaagtggcac agatgggccc 130260
ttctgaaaaa tctcactact ggagcacagc tcgaagtttc tactatcctg acgttgggcg 130320
gtagtccttt gctttgggaa tatgaacatg atcaaaactg agtgaacttg tcttcctggc 130380
tttctgtaca atgaagtaga acaaaccatc caatttgacc aaagccttgg catgttttct 130440
ttctaggttt ggaaagcact tctgtggagg caccttaata tccccagagt gggtgctgac 130500
tgctgctcac tgcttgaaga agtacgttta agggaaaact gacatggggt cttatcttca 130560
agactttttt cctccctctc ttcctccatc ccttctttct tcccaccctc cccttccttc 130620
ctccccacct ctcttccttt tctggaagga acactaggaa ccagggaatg catgcagaat 130680
cctgaggcag aatttccagg gcaattggat gagagaggag ggaagtgttt ctagagggaa 130740
tctgcagagg gaagacccag tgcaagtgat tttttggacc tgtataaacc gcaggacaga 130800
gctgttcact accagaggca tcaatctgta ttgcattgct ctagagcaat atctgaggct 130860
gaataattta taaagaaaag agtttaattg gcacatgttt ctgcaggctt tacaggaagc 130920
aggatgctgt catctcctct gcttctgtgt gggcctaagg aagattacaa tcatggtgga 130980
gggcaaagtg ggagcaggca tgtcacatgg ccagagcagg agcaagagac agagagagat 131040
ggggtggggg tgctgcacaa taccaaatga ccagactttg caagaactaa gagtgagagc 131100
tcactgatca ccatgaagat gtggcccaag ccattcaaga gggatgcacc tctatgatcc 131160
aaaccccttt cacaggccat agctccatca ctggggacta cagttgaaca cgagatttag 131220
gtggggacaa atatacaaac tatatcacag tctctgatga aacagattga gaacagacct 131280
taactgtcag tttccagcaa attgtgaatt ttgtttcttg ccactcataa gtcactgatt 131340
ctgggtggcc gagggtgtca gagggacagc gccaagttca tggcacagag gatacctgaa 131400
ggggctggac catatttttc tcttgacatc ctcatctttt ctaggtcctc aaggccttca 131460
tcctacaagg tcatcctggg tgcacaccaa gaagtgaacc tcgaatctca tgttcaggaa 131520
atagaagtgt ctaggctgtt cttggagccc acacaagcag atattgcctt gctaaagcta 131580
agcaggtact cgctcacctg tggtcttcac cccacgctgg tgaagatatt tgctttatgt 131640
ctgggtttta tgggccatgg ccactgcatg gcagtgggga ggaactgtct atcacatgaa 131700

-continued aggctcaagg gctttgggga cagcatcaat cttcaacccc agccctgcca catgttagtt 131760
gtgctcttta aaaaggcaga aggattcgtt tcctcacgtg gaaaaagaga taccctgtta 131820
cccgtaaaac ttacttaatg ttcaccagtt catccacatt catgatcagg gaaaggttgt 131880
tattccaggc taactattct cctttcataa taatatgctg gagagaatca aatgagattg 131940
catttcaaag cgcttgaaaa accaccatat cgagccatgc ttagtgtggg cgcctctaat 132000
cactgctatt caggaggctg acgaggaaga attgcttgag cccaggactt caaggctgta 132060
ggcagctatg attgtgccac tgcactccag gctgggtgac agatcaagac cctgtctcaa 132120
caaaagaaaa gaaaacaaaa caaatgaaca gaaatattcc acaatgtcaa aaaaaaaaaa 132180
aacccacaca acatacaatt tacaaatgca aataataata ttattgttgt cttctttgat 132240
tttctctttc ctggtgaaat tttgttttat taagcctgac aaagtgatac ctttgcttac 132300
atcacttaaa gttagtctat ttggacctag gtgacagtac aatcagctaa gaaacagtat 132360
ttgtaggaga ggcaggtttg ggacaggtga caaggcatgt ggggtgctcg ctgtgctggt 132420
ggctctggaa ggcagggtgt caatgcagac agggatgagc atggcctggt tgggaaggca 132480
tggggcaggc aggagcctga gctgctctcc tgggcctggt cacaagccca tggcagcttc 132540
tctgggtctg tgaactgagg ggtgatgtcc tggaatcctc tgacactcta ggaaggagag 132600
aagggccttt ctggctcagc ctttataaac agtagctgat ctccctcttg ctccccaggg 132660
tcctccccac catcccagca aatgtgcaaa tacaagatct ctgctcctca tggtcctcag 132720
agagctgggg tgttctgatg gcttgaacaa gtcacttagg aaatgtgggg ttttggaggc 132780
attctctgat aggctgatac gttttgagtt tagagttccc accgcacatc cccacacccc 132840
tagagtctag ggcatttagt gctccatgag ggaacctgta gagtgaggac atctgcatca 132900
caggctgggc cttctagtgt ccagaagcag aaagtgtgtc tgcttcaaag ttggtgctaa 132960
tgatgatttt tggtcagaat acggcatttc tcatttccat tcctttatcc ccttgaactt 133020
actaaagtag aatcaggtct aaaaaccaga gttctaatct ttaagagtcc ctgggattct 133080
aaggtatatg aatgtccttg gaaaacaata ccatttagtt catgcaaggt gcttatttcc 133140
catcctcttt catttgatgt ctagcatttt actgcattct taccaccacg gtttagtaac 133200
attcacgagg aggaagtgga ggatccagat ggagcaactt gctctgggca cacaaggcat 133260
ttgcaatttt ataccctctt gatgatgtct cagccagaca ttctgcccag tcatcaatgc 133320
cctcttcaat taatatgaaa ggacacactt ggcatgagat tccaatcgtg cacagaatat 133380
acatgagaag tgtgcctttg tcatccctac tttcaaaggc taaggccacc ctcagtttct 133440
tgcatgcaac tgatgccttt caaatgaaac cttacatctg tgtagtccat aggcaaccac 133500
aggcaaatgt gagggtgaaa cgctgtgttc tacattgttc tgtgtcagtg aagcaaggca 133560
gtgccagctc agagggctct ggggcttcaa ggcagggatg cctggttgta ggtactgcca 133620
cttccagctg ggcagtgaaa cataactgct aatactttcc ttacaggcct gccgtcatca 133680
ctgacaaagt aatgccagct tgtctgccat ccccagacta catggtcacc gccaggactg 133740
aatgttacat cactggctgg ggagaaaccc aaggtgagat caattccatt gcccacgtaa 133800
caaattgttt ttgaccttca gtgcatgtta caaaatgagc attttggaga tagttgtaca 133860
aattcctacc catgaatgtg gtctacccac tcctgacttt gcctggacac ctgtctatgt 133920
ctccataatc agtcttcaag ggacttgggc aaggggagcg gtgccatttc cttgagtctc 133980 tctcttttt gttttcagaa tcttttaatt ttttttgtaa tgattgtatg tttcccttac 134040
aacaaaaaca aacaccagta gaggtctttg agtctcttaa tcataatttc agcattcata 134100

-continued ttgcttcccc aggtaagtgg ggttttgacc cagccctcaa gttaagggtg ttagattatt 134160
tttcatgtga aattagacag actgcgtttc taaacatggt gcaaaacagt aacgacaaaa 134220
gttgtaatta aactattctt cttcccaaat acccacatgt ctaatgtgtg tgtgagggtg 134280
ttaggcaggg gacctgaagc tgggggagag gcagacagtt cccatggccc caagtctagg 134340
atggcatttg gtattggttg atgggtgaga gcaagagagg gaatattttt gtgcatgatg 134400
tggtatcagc acctgtacta cattttatgg attccttctt ctctttgcgg tatgccctga 134460
caataattat atccgtcagc cttaccccct tggcagtagg aaaactgaaa ctgtcttaaa 134520
gtctcagctc tactttctca gaggtgcagg caagggcact gggagtctgg ggccctggaa 134580
aactgttctg actctgccac ttgccagata gacctgaact agacacgtta cctctttgta 134640
ccacttggct ctaatccctt atctgtaaaa ccagcatttt caaatggtgc tttgcacatc 134700
agccttttgc ataagctttg atttgataaa atgtttttttg tgtttttaaa aagattaaaa 134760
accacaggtt tagataattt caaagtaggc ttcccttttt ctgtcatttt cctattattt 134820
ttaaaacctc acctccttga ctccttgttc cctttttctg cactgctgag tctgggagca 134880
ctgaggccag gtaaaaggaa acttggcaaa tgaggggcac ctatgggtgt gggaggctgc 134940
tcctggtgtt tgcatatttt aaaatttaaa tgctacaaac cactgtgagt taggtattat 135000
tgttcctatt ttaccattga ggaagctggg gctcagagaa ggtggagggt ggtacagaca 135060
aacctgaatt ggaaccctgg ctcctgccta tgggctgtca ggacttagaa aagtcgtgag 135120
ctctcgctga ttgtttcctc agctgatgtg ggctgcaggg ctgttatggg ggaaataata 135180
agaaagtgca tcaagtgctg agcacatcct aagcactcca tcatggcagc tcctactact 135240
aataaagaat agaattatat ctaacatgat tctttcttgc aagtgacaga aaatccaact 135300
caaattggat taagcaaaac aagggaaatt cttagtgagc tgcaaagttt tcaggctcac 135360
atgatggccc caaatcccag gtcctcccaa tcatggagta ggcactattt gggggcacaa 135420
aggtgacatt cccatggctg cagatgctgt ggtgctgtgg ctgtaccggg aaagaataag 135480
aaaggccact ctcccaatta tgtgaacaat agtctgccca ctctgagaag tcaaacttgg 135540
gtcacagtcc tgcccctgaa cccatcactg actggctctg acctgcacca attgttccat 135600
gttggaggtg aaggcaagac ccccactaata cccataaggg gcaaaagtta gatagatcct 135660
tcaagaggat tatgggaggt agggcaaaaa gctgctgggc agccagaaag caaacagagc 135720
ctctatgata cctcaactga tgaaagcatg aagctaaaat cataaggatc tgggtgtgag 135780
ttctggctct cccatcttcc atgtgacatt gggcagttat ttaatctctt ttagcctccg 135840
ctttctcatc ttacatatga gataattgtg aggattaaga ttacacataa tcatcatcat 135900
caccgtccac cactaccacc atcatcccca tcaacatcat cgccaccact atcatcattc 135960
ttactggcac taccatcacc atcaccacca ttccaccacc atcaccaata tcatcactgt 136020
caacatcatt accaccatca ccatcaccac caccatcatc attactacca ctaccactac 136080
taccaccatc accatcacca ccattccacc accatcacca atatcatcac tctcaacatc 136140
atcaccatca ccatcaccac caccatcatc atcattacta ccactaccac tactaccacc 136200
atcaccatca ccactgtccc actactatca gcatgacatc accatcacca ccaccatcat 136260
cattaccacc gctactacca acatcaccat caccacaatt ctactgccat caccattaac 136320
attaccacca ccatcatcac tatcaccatc accaccatca tcaccactgc cattatcact 136380
gccaccatca tcactatcct ctatatttcc tcatctgtat tatcattact accaccatca 136440

-continued ctatcaccac catcgtcacc atcataatca ccatcaacac catctccaat accaccatca 136500
ctgtaaccat catcaccacc accatgatca ctatcaccat catcacaatg atcactgtaa 136560
ccatcattac tacccaccac catcaccact actccaccac catcaccatt atcattacca 136620
tcaccattat caccaccatc atcatcacca gcaccaccat catcaccagc accaccatca 136680
ccatcaccat cattaacacc atcactatca ccattggttt aatcatcacc accatcatca 136740
taaataaaca tcacataacc agggtgtagc tgggtgttga ccccagagcc cactcactgt 136800
ttcctctctc ccaccccat ccacacattt ctaaccacca tcctgcactg ggctcccagt 136860
ctcctctggt ctcacccaca tgtccactga gaaaaggatt ttcagaacac caactagacc 136920
aggaggagcc acatacataa ctcaggcctg cttatcaact ttctacatgt taataatgac 136980
atcagatcaa tgggtgttct cagcttctca gaaggaggtc aaaattctcc ccctctcccc 137040
ttcatgtgtc cagaccttcc cggatttgga tgtaccaagt gcagagtggt gttgaggcca 137100
aggggctcat ccatgtaagt ctcatctgca atcactgggc tgatcccgtg gccctgtctc 137160
cagggcgcca tcagagaggg cttcaatcct caggttacct gtggcccacc ctgccctcag 137220
aggtgccatc tctacattgg ccacgagatg gcagcacata ctcatagact gcattaattt 137280
cccagcaact cctggtgggt tttccctctt atcaggatgt ttgccttgct cagagagcaa 137340
atctgagagc agtgacacct aacttaactt tcagcaaaat attttgagaa gggtgcccct 137400
ttacacatct gtgcagtcca ggtgatgcat cccatgccca atgctcggta gtcaggagga 137460
gcttcctcca tgcagctctg cggaagagac tcttccacgc tgctcatgta aactccagat 137520
tcggtgtcag ttttctgaca ccgaagacaa tgatctaagt gcagtcaagg gctttgggga 137580
aagcaggaga gagtgcctca gttctagcct gtgccatgct tgcaaagttt tgcaaaattc 137640
taatgagagc tgggcttgca acattggaaa cttggattat ttgtgagagc actgagaaat 137700
ccctgggcat gtccatctgg aaaaacagca tttcctctgg cactttagca gaggttctgt 137760
ttcaatttgg cgaaggaaat taagcagttt ttcacaaaag aagaactaca acgaggagaa 137820
ttgtccctag tatttcttct ccctaattgt caaggaagtg taaattagaa aatgaatcag 137880
gacaatttcc acctactatg ttagctaata ttttaaaaat tgaatatcac aagggtgagg 137940
caaagtaatt gttttccagt gacattttcc actgtcacac ccttttagag aataatttgg 138000
caatgttact gtgagataga aatatgtcta tataattatg ggaactgaga cttcagaaag 138060
taataaggaa taagaatgaa atttatgaac aaacatgtgg aaggttggaa gcaagagtgg 138120
ggccaacacg catggggagg aagcatttgg gcagcgactc cgcagaccca gactcaagct 138180
gagctataca acctccttac gcctcagttt cctcaactga agaacaggaa tgacaagtgc 138240
ctgtttcata ggaccgttgt gaggattaag tgagatatac cacattatga gcttgtgcct 138300
ggaaaggttg attcttagta aatgatgact attctttttt attgcaataa aatttataca 138360
acatagagtt actattttaa ccatttttgc aggtaccact gagtggcatt cagtacattc 138420
acaatggtgt gcaaccgtca ccatatttcc aggacatttt tctcatcccc aaaggaaacc 138480
tcatgcccat taagcagtca ctcctcatta aaatattagt tatgaagact gtagcatttt 138540
tttaaaaact catgatataa cattgattga aaaaatcagt ataggaaatt gtgcattatg 138600
atgtaatagt aaaagaagca tataaaaatc tgaaaaaagt atataaaaag aatagcaatt 138660
gtatttctca gactctcttt acattgtaaa aatcattttg atagcttcaa aagaaaagca 138720
aaaagtacac aaacaacaac caaccccaaa gcagcatgac aaagcccaga ttgttgaatc 138780
caggtcttgg gaacataaaa tcttatatga catttgcact ttaatgggtc agagagtcca 138840
gtggcattgg gagctgcctt gtgttctgca gcctcacgga cagacaggag gtccagctcc 138900
actgctctgt tcttctggaa tttcctcgtg aacaagcttt ggcctcagta accatttctt 138960
tcatcttttt aaacacaggt acctttggga ctggccttct caaggaagcc cagctccttg 139020
ttattgagaa tgaagtgtgc aatcactata agtatatttg tgctgagcat ttggccagag 139080
gcactgacag ttgccaggta agaaaagatc aatagatcaa agtcttgtgc tctcccgtct 139140
cagtctcagt cccttagacg tcagtcccaa agtggcaaat tcaggaaggt tttgtcagtg 139200
gaagacccca gtctaagtgt tgctcagaaa ctccccagat ctgtccctga atgcatattc 139260
agatcatcta aggagacgtc ttggggcttg agttccagat ccatagcaag ggagccgtaa 139320
gtgccataac tacctcaggc cactcacctt cctggtgtgt gctggtcacc agtgactgaa 139380
gtggtggctt ttccagtaga gaggaaggta gagggtacag gaccgagaca aattacacac 139440
acttaacaat gatgtccagg ctagcccagt ctaaaggaaa caccaagtta ggaagcaatg 139500
catgcaggat tcacaaggga ttattttttt tcccaggaaa aaactaagtg atgtggtttt 139560
gttgaataga ctttgctaag tacttaagca ctgcagatgc ttgagtaata tgctcataag 139620
ttcctttctg atttgaatta ctgggaaaat gtacatatgg ataagagaag gatggcatcc 139680
catattaaaa ggttggcagc ttaaagctca catgaatttt cccctacctc tgtttagggt 139740
gacagtggag ggcctctggt ttgcttcgag aaggacaaat acattttaca aggagtcact 139800
tcttggggtc ttggctgtgc acgccccaat aagcctggtg tctatgctcg tgtttcaagg 139860
tttgttactt ggattgaggg aatgatgaga aataattaat tggacgggag acagagtgaa 139920
gcatcaacct acttagaagc tgaaacgtgg gtaaggattt agcatgctgg aaataataga 139980
cagcaatcaa acgaagacac tgttcccagc taccagctat gccaaacctt ggcatttttg 140040
gtatttttgt gtataagctt ttaaggtctg actgacaaat tctgtattaa ggtgtcatag 140100
ctatgacatt tgttaaaaat aaactctgca cttattttga tttgaattaa ttttggtttt 140160
ggtcttcaaa attttcatgc tcttttcatc ccatctattt ttatttttat tttttagact 140220
ttacgtcctg ggtacatgt gcagaatgtg caggtttgtt acatagatgt acacgtgcca 140280
tggtagtttg ctgcacccat caacctgtca tctaattcgg tatttctttt agttctatcc 140340
ctcccctagc cctccacccc ttgacaggcc caggtgtgtg atgttgccct ccctgtgtcc 140400
atgtgttctc attgttcaac tcacacttat gagtgagaac atgccgtgtt tgtttttctg 140460
ttcttgtgtt agtttgctga gaatgatagt ttccagcttc atccatgtcc ctgcaaagga 140520
catgaactca tccttttta tggctgcata gaattccatg gtgtatatgt gccacatttt 140580
atccaatcta acattgatgg gcaattgggt tggttccaac tctttgctat tgtgaatagt 140640
gccacaataa acatacgtgt gcatgtgttt tcatagcaga atgatttata atcctctggg 140700
tatataccca gtaatgggat tgcagggtca aatggtgttt ctggtgctag atctttgagg 140760
aatcaccaca ctgtcttcca caatggttga actaatttat gctcccacca acaatatcaa 140820
ggcattccta tttctccaca tcctctccag catctgttgt ttcctgactt tttaatgatc 140880
gccattctaa ctggcatgag atggtatctc attgtggttt tgatttgcat ttctctaatg 140940
atcagtgatg atgagctttt ctcatatgtt tgttggctgc ataaatgcct tttttggaga 141000
agcatctgtt catatccttt gcccactttt tgatggtgtt gttttttct ggtaaatttg 141060
tttaagttct ttgtagattc tggatattag ccttttgtca gatggataga tggcaaaaat 141120
tttatcctat tatgtaggtt gcctgttcac tccgatgata gtttcttttg ctgtgcagaa 141180

-continued gctctttggt ttaattagat ctcatttgtc tattttggct tttgttacca ttgcttttag 141240
tgttttagtc atgaagtctt ctcccatgct atgtcctgaa tggtattgcc taagttttct 141300
tccagggttt ttatggtttt aggttttgca tttaagtctt taatccatct tgagttaatt 141360
tttgtataag taatgccctt ctttgtctct tttgatcttt gttggcttaa agtatatttt 141420
atcagagact agaattgcaa tccctgcttt ttttttctt tttgctttcc ttttgcttgg 141480
taaatattct tccatccctt tattttgagc ctatgtatgt ctgcacatga gataggtttc 141540
ctgaatacag cacaccaatg ggtcttgact ctttattcaa tttgccagtc tgtgtctttt 141600
aattgggggc atttagtcca tttacattta aggttaatat tgttatgtgt gaatttgatc 141660
ctgtcattat gatgctagcg ggttattttg cccattagtt gatgcagttt cttcatagtg 141720
tggatggcct ttacaatttg gtagtttttg cagtggctgg taccaattgt tcctttccat 141780
gtttagtgct tcgttcagga gctcttgtga ggcaggcctt gtggtgacaa aatctttcag 141840
catttgcttg tctgtaaagg attttatttc tcctttgctt atgaagctta gtttcgctgg 141900
gtatgaaatt ctgggttgaa aattattttc ttttagaatg ttgaatattg gcccccactc 141960
tcttcgggct tgttgggttt ctgcagagag atccactgtt agtctgattg gcttcccttt 142020
ccgggtaacc caacctttct ctctggctgc ccttagaaat ttttccttca tttcaacctt 142080
ggtgaatctg acgattatgt cttgaggtgg ctcttctcga ggagtatctt tgtggtgttc 142140
tctgtatttc ctgaatttga atgttggtct gtcttgctag gttggggaag ctctccttga 142200
taatatcctg aagagtgttt tccaacttgg ttctattctc cccatcactt tcaggtacat 142260
caatcaaatg tagatttggt cttttcacat agtcccatat ttcttggagc ctttgtttat 142320
tccttttcat tctttatcct ctattcttgt cttcttgctt tatttcatta agttgatctt 142380
caatctctga tatcctttct tttgcttgat cgatttggct attgatactt gtatatgctt 142440
cacaaagttc ttatgctgtg tttttcagtc agatcaggtc atttatgttc ttctctaaac 142500
tggttattct acttagcaat tcatgtaacc ttttttcaag gttcttagct tctttgcatt 142560
gggttagaac atgctgcttt agctcggagg attttgttat tatacacctt atataatagc 142620
ctgatataac tataagattt ttttgtaagc accatcgtaa ccacaaagca aaaacctaaa 142680
gtagatatac aaaagataaa aaggaatcaa agcataccac tagagaaaat cacttaatca 142740
caaataaaga tacgaagagt ggaataaagg aacgaagggt ctacaaaaca accagaaagc 142800
aattaacaaa atggtgatag cagatcttac ctataaataa ttatcttgaa tggaaatgga 142860
ttaaattttc caataaaaag acatacagtg gccaaataga ttaaaaaata agatccaact 142920
atatgatgcc tataacacac tcacttcacc tgtaaggact caaacagact gaaagtaaag 142980
ggatggaaaa aatattctat gcaaatggaa acaagaagat agaggggtag ttatacagat 143040
tgagtatcac taatccaaac atctgaaatc tgaaatactc caaaattaaa aatgtttaag 143100
tgccaacatg atgttcaaag gaaatgttct tcggagcatt ttggattttt gtgtttaggg 143160
atgcaaaaac agtaaatata taatttgtat tagtccattc tcacactgct ataaagaata 143220
ctacaaagag actgagtaat tataaaggaa agatgtttaa ttaactcaga gttccacagg 143280
cttaacagga agcatggcta aggaggccac aggaaactta taatcatggc ggaagatgaa 143340
ggagaagcag gcaccttctt cacaaggtgg caggacggag tgtgagtgtg tgaaggagga 143400
actgtcaaac acttataaaa ccatcagatc ttgtgggaac tcactcactc tcacaagaac 143460
agcataggga aaaccgcccc catgatccaa tcccctccca ctgggctcct cccttgacac 143520
atggggatca tgagggttac aattcacgat gagatttggg tgggacacag ccaaaccata 143580
tcataatgca aacattgcaa aaacaattca aaattcaaaa catttctggt ttcaggcatt 143640
ttggataagg gaaactcaac tcaacatgag gtaaagcaga ctttaagtca aaaactgtaa 143700
aaagagacga agaagaatgt aataataagg agatcagttc attacaaata tatagcaatt 143760
ataaatatat attaatatat atacccaaaa ttgtagtacc tacatatagt aactaaaaca 143820
aacattaata gatctcacag gagagctaca ctgtaatata atcatagtag cacacttgaa 143880
tagctccact ttcactaatg gacagatcat ccagacagag aatcaatatg gaaacacgag 143940
acttaaacta cactttagcc aagtagacct aacagaaata tatagaacat tccatccaac 144000
agcagtagaa tacacattat tctcaagtgc acagggaata ttctccagaa tagatcatat 144060
gttaggtcac aaaactagtc aaaaaatgta agaagattga aatcatatca ggtttttttt 144120
ttagatcata atcgtatgaa actagaaatc aataatgggg gaatattgga aaatccacaa 144180
atagatagaa attaatcaat atgctcctga acaatcaatg agtcgaagaa gatattaaaa 144240
gaggaaattt taaaaaatca agacatgagt tcatgtcctt tgcagggaca tgaatgaagc 144300
tggaaaccat cattctcagc aaactatcat aaggacagaa atccaaacac cgcatgttct 144360
cactcatagg taggaattga acaatgagaa cacttggcca cagggcgggg aacatcacac 144420
accagggctt gtcagggggt gggaagctgg tgaagggata gcattaggag aaatatctaa 144480
tgtaaatgac gagttgatgg gtgcagcaaa ccaacacggc acatgtatac ctatgtaaca 144540
aacctgcacg ttgtgcacat gtaccccaga acttaaagta taataataaa aaaagaaata 144600
tttgtttttg atttatatgc caatcagaca aaatgtgaaa agccctactg aaattaagta 144660
tcaccatgaa agataaattc tggataattt tttcaagttt taacaatgta gctttaattg 144720
gagaaagcta tcatttggaa tgagttaatc tatcctatac taaaataagt cacttgcttt 144780
aaaacataat aaatatgatt ttgaattgaa aacaaaaaca actcaagaca aaggaaaatg 144840
gacacactaa cataccaata atttatagta tgcagcaaaa gtggttttaa gagggaagct 144900
tttaccaata aacacttcca ttaaaaaaga agatctcaaa taagcaacct aagattacac 144960
ctcaacaaac tagacaaaga actaactaac ccaaaagtta gtagaaggaa agaaataata 145020
aagatcacat cagaaatagt aaagactaaa aaactgatac caaaaagaaa taaaactact 145080
agttggtttt caataaaata acaaaattga ccaactttta gctagattaa gaaaaacaga 145140
gaatactcaa ataaaaccag aaagaggaga cattacaata gatactacag aagtacaaac 145200
gatcataaga gactactatg aataattaca tgccaacaaa ttggataact tagaagaaat 145260
ggatgaattc ctagagcaaa aaacctacaa agactgactc agaaagaaat agaaaatctg 145320
aacagaccaa taatgtgtac atgattgtat cagtaataac aagtctccca tcaatgaaaa 145380
ggccaggacc taatggcttc actgctgaag cataccaaac attacaaaga ctaatatcaa 145440
ccctcctcaa actcttctta aaaactaaaa agaaggaatg ctttcacatt cattttatga 145500
ggatagcatt acactgatac taaacacaga aaaataatac gctaataaaa gaacattaca 145560
ggcaatatcc ctgataaaca tatgtgcaaa aatccgcaac aaaatactag aaaactgaat 145620
ccagtagcac tttaaaaaga tcattcacca tgatcaagtg cgatttgttt cacgaatgca 145680
agaatagttc aacttacaca aataaataaa tgaaaggatg gatgataaaa atgtgtatct 145740
atatatatat gttttataca cacacacaca cacacacaca cacacacaca cagaggaata 145800
ttattcagcc ttaatgaaga agaaaatcct gcctttgcat caacctggag gacattataa 145860
taagtgaaat aagccagaca cagaaaggca aatactgtgt gatctcgctt acatatggaa 145920

-continued tctaagaaag tcaaattcct agaaatagag agtagcttag tgattgccag agccgtggaa 145980
gggggaaatg gagagatgtt gatcaaagga tacaactgta tagctttgca agataaatag 146040
gttctggaga tctaatgtgc agaatggtga ctagagttaa taatactgta ttgcatactt 146100
gaaatttgct aaaagagttg atcttaagtg tcctcaccat atacacaaaa gtattatgtg 146160
aggtggtgaa tattttaatt agcttatgat aataatttca cagtgtacat ctatattaag 146220
gcattacatt gtacatctta aatatatata atttttattt gtgaagtgta cctcaataaa 146280
actggaaaaa ataattgaaa agtaatgaaa aaaattaaaa gctattatgt gtcaaatgac 146340
attatcaaga aagtgaaaag caacctactg atgaagcaaa cctattgaca aaggcctggt 146400
gtccagaata tattaagatc tctaggctgg gagcagtggc tcacacctgt aatcccagca 146460
cttggggagg ccaaggtggg aggatcactt gagcctggga gttcgacact gcagtgagct 146520
atgattgggc cactgccctc caggctgcgt gacagagtga gactgccatc tcttaaccca 146580
cttcttattt agaaaaagaa aatatgtagc ttgctgcctg catagtattc ttggggcaaa 146640
tgggaaatga gttaaaaaaa aaaaaaagaa ctcttacaac tcaacaataa aaagaaaaac 146700
aagaacgtga atagacattt tttccaaaaa agatatacaa ataggcaata agtacatgaa 146760
atgatggtca acatcattag tcattaagaa aatgccaata aaatcacaat gaaataagac 146820
ttcatatcca ttaaaatgtc tataatttaa aaaatggaaa ataacaagca tttgtgagga 146880
tgtggagaaa ttagaatcct gtatattgct ggtgggaatg tacagggaaa atggtttggc 146940
cactgtggaa aacaatttga cagttcctta aaatgctaaa catagaatta ccatgtgatc 147000
taacaatttt actcttaggt gtatatatac aagaattgaa aacaagtgcc caaacagata 147060
ccttgcatga gaatgttcat agcagcactg ttacaacagc cacacccaaa tgtcaatcaa 147120
tagatgaggg gataaacaaa ttgtggttta tacagctaca aaaaggaatg aagtactggt 147180
atccgctaca tggctgaaac ttgaaagcaa gggctgggat ggggtcatgg aaagtaccag 147240
cttattgggt actgcattgt gctttggggt catgaaaatg ttttggaact ggatggaggt 147300
ggtggttgcc aatgtgaaca tactaaatac aacgcattgt tcactataag actgctactt 147360
ttcttatgag aatttcactt caattaaaaa ataccttcca tgtatccttt ctaaggatga 147420
tactagaata tttgctttgg caaaatgagg aagtaacttt ttttaaaaag gaagatgtgg 147480
gatccatgaa acgggatcaa atatcagaga ggaaaggggg tcttctggat gacagtccat 147540
ggagatccca caactgcaca gcaggccggc tgtgcaccca ggccacacca gagcagagcc 147600
ggtggttccc gaggagctct ctggaagaaa aacgctagat ggcctgattg gtttgggggc 147660
atattgaaaa ggtatataac tgagaatttg gagtggaatt aggaaacaga cataaaagct 147720
tacagaaaag aaaataatga attctaggga gaaatataaa aggatactac aggcctcagt 147780
tacataaaca ctgaatattt acttaaccaa aattacaata taattacata attattttag 147840
gtacatatgg caaaaggatg tgtgggtgta tgtagtatgt acggtgtgtg aagtgtatgt 147900
gtgtggtatg tggacggtat gtgtatgctg tgtatgccaa taaaatcaca atgaaataag 147960
acttcatatc cattaaaatg tctataattt aaatgtctat aattttaaaa atggaaaaca 148020
cttctcatat ggcaggagca ggagcaaggg tgggggaggt accacacaca cttaaacaac 148080
cagatctcct gagaactcac tatcaggaga acagcacctg gagaaggtgc taaaccattc 148140
atgagttact gccctatgag ccaatcacct cccatcagac cccgcctcca cactaaggat 148200
tacaatttga cttgaaattt gggcatgaac acagatcgaa accatatcaa taggtaatga 148260
ctaaaactga aaaaagaagt accacagtca gaaagttatt tagagagctg aaggtaaatg 148320

-continued

```
ccaataggat cagttgaaag aattggaggt ggccgggtgc ggtggctcag gcctgtaatc 148380
ccagcacttt gggaggcgga ggtgggtgga tcgccctgag gtcaggagtt tgagaccagc 148440
ctggccaaca tggtgaaacc cagtctctac taaaaataca aaaattagcc aggcctggtg 148500
gtggacgccg tagtcccagc tactcaagag gctgaggcag gagaatcgct tgaaccaggg 148560
aggtgaaggt tgcagtgaac cgagatcgtg ccactgcact ccagcctggg tgacagagca 148620
aaactccatc tcaaaaataa atgaaataaa gaattggaag tgtttgcctc tggagagaag 148680
gaaacgcagt aattctgtaa aaacagaact ttttactttt tttcttttttt tttttttttt 148740
tgagacagag tctccttctg tcacccaggc tggagtgcag tggtgcagtc ttggctcacc 148800
gcaacctctg cctcttgggt tcaagcaatt cccgtgcctc agcctcccaa gtagctagga 148860
ttacagatat gggctgctat atccagctaa ttttttttta tttttattag agatgaagtt 148920
tcaccatgtt ggccaatctg gtctcaagct cctggactca tgatcctcct gcctcggcct 148980
tccaaattgc tatgattaca ggtgtgagcc accatgcctg gacagaactt tttgactctt 149040
taaactatgt gcatatataa agctgattta aaaaaaacca agtaaaataa ttttaaaatg 149100
ttccaaaaca gattggatgg gtacacactt catcatgagt ggttgaggga gactgggtta 149160
gagatgagga aattccaggg actggggaaa agttaaaatg acaaactgtt cacaattgtt 149220
aactgcaggt tgtgggaaag ttggtaagtt gctacagtgt ttgttccctc tgtaggtttg 149280
catatattta acatttctta aattagcata ataatgaact gtgtaatcag ctgtagagtt 149340
gagggtgtgg agctggcaca ggacagctga gctactggtt taaaataaat gacatttaaa 149400
aaaatggcta tttgtagaat taacagatat aagacaccct gatcaaggga tgataagaaa 149460
ggactccagg gctctgtctc agctgtcttg gcaacacctg gaagacatgg gcctctgcaa 149520
ggtctcatac tttcaggagg tgttgatgaa ggatatggac agatctgaag ctctgggcac 149580
tgcatggtct gagaagagaa gctccggaaa cgcgggagct gagtgcagat gcagaagggc 149640
tgtcatccag cagaggggta ggtgacaact ggcctagcga gtgacccctta tcatggctac 149700
atttgttgat cactttcttt gtatgaggca ctgctgtgat tgcattaaat ttccacttac 149760
ctaaatccaa cgttgtgcac ttgtgaattt ctactcttac aaaaaacaca acggcaacaa 149820
cctcaaacca gtaatctagt caaaaaagca attcccaagg catgacattc agattcatca 149880
gcactcacag agactacagt gattgctgat aacgccaact taatacctgg ccaacagcat 149940
ggatcctgac ctccactttt cttgtgtgtt tacagaacca caaaaaggtg cagtgttttc 150000
a                                                                 150001
```

<210> SEQ ID NO 3
<211> LENGTH: 138001
<212> TYPE: DNA
<213> ORGANISM: Homo sapiens

<400> SEQUENCE: 3

```
ctctcccaaa ttgtcaaaga agtataaatt agaaaatgaa tcaggacaat ttcaacctgt     60
tagattagct aatatttaaa aattgaacac tcatacaagt gtggtgaagt gattgttttc    120
tagtgacatt ttacactgtc ataaccttct agaaaataaa ttggcagtgt tattgggaga    180
cagaaatatg tctatataat ttatgggaac ttaggctcag aaaatattaa ggaataagaa    240
tgaactttat gaacaaagat gtggagggtt ggaagcaaga ggggggccaa cgcgcacggg    300
gaggaagcat ttgggcagtg actccgcaga cccaggctca ggttgaacta gacaacctcc    360
```

-continued

```
ttacacctca gtttccttaa ctgtagagca ggagtgatgg aactgcctgt ttcataggac    420
tgttgtgagg atgaagtgag atacaccaca ttataagctt gtgcctggaa aggataatgc    480
ttagtaaatg atgactattc tttttattg caataaaatg tacacagcgt aagagttact     540
attttaacca tttttgcagg gtaccaccaa gtggcattta gtacattcac agtggtgtgc    600
aaccatcatc atatttccag aatattttcc tcatccccaa aggaaacctc atgctcatta    660
atcagtagct ctcctttaaa atattagtta tgaagatcat agcactatac aaaactcatt    720
atgtaatgtt gagtgaaaaa atcagggtgt gaaattttgt gatatgatgt aattagtgaa    780
agaagcatac aaaaagtctg aaaatataaa aacaatagca attgcatttc tcagactcta    840
catttaaaca ttattcttta tggttttaaa agcaaagaaa aaggtaaaga aacaacaacc    900
aaccgcaaag caccatgaca aagctcagat tgttaaatcc aggtttttgg aacatagact    960
cttatatgac gtttacactc tccagggttc agagagtctg gcagcattgg gagctgcctt   1020
gtgttctaca gcctcacgga cagacaggag gtccatcacc actgctctgt tcttctggag   1080
tttccttgtg aacatgttgt ggacgtagtt accatttctt tcatcttttt aaacacaggt   1140
acctttgggg ctggctttct caaggaagcc cagctccctg tgattgagaa tgaagtgtgc   1200
aatcgctatg agtttctgaa tggaagagtc aaatccactg agctctgtgc tgggcatttg   1260
gctggaggca ttgacagttg caaggtaaga aaagatcaag agaccaaagt tagtcttgtg   1320
ctctcctgtc tcagtctcag tcccttagac ttgagtccca aagtagcgaa ttcaagtagg   1380
atttaatcaa tggaagaccc cagtctaagt gttgctcaga aactccctag atctgtccca   1440
aatgtatatt cagatcatcc aaggggactt cttggggctt gagttccaga tcagcagcaa   1500
gggagccata agtgccataa ctacctcaga ccactcaccc tcctggggtg tcccggtggc   1560
cagggactaa agtggtgatt tttctggtag ggaaggaggt agagggtaca ggacagagac   1620
taactgcaca caatatctga gactggagct cagatattgc tgatgatcag agttggcgtg   1680
tctccccaat tgatttacaa ctggggcttg gatactgttt taaacgggag gagcctccta   1740
accatcttga cacaaccact gacgtgacta cactagagat agactctttc cacttaattc   1800
taccactctt gctttacttc atgagaacga aaatgtaaga ttgcaccatg aattcatttg   1860
cggaaagatt gatactatgc ttttatttta ttttatttta ttttatttta ttttatttta   1920
ttttattgag actctcaccc cggttgaagt gcactgacgt gattttggct cactgcaact   1980
tccacctcct gggttcaagt gaatactcca gcctccctag tagctgggat tacaggtgcc   2040
caccaccacg cctggctaat ttttgtattt ttagtagaga tggggtttca ccacattggc   2100
ctggctggtc tcaaactcct gaccttgtga tccacctgtc ttggcctccc aaagtgctgg   2160
gattacagag ttgagccacc gcactcgacc ctatgtttta tttttaaaaa tatttattta   2220
tttatttaag ccacaactac tagaatagga aggattgata ttttattaat tttatttggt   2280
atttattatt tttttttctt tcctgagaca ttcttgctct gtcacccagg ctggagtgca   2340
gtggcacatt cttggctcac tgcaacctcc atctcctgtg ttcaagcaat tctagtgcct   2400
cagcctactt agtagctggg atgactggca tgtgcctcca cacccagcta atttttgtat   2460
tttttgtaga gacagggttt tggcatgttg cccaggcttg tctcaaactc ctggcctcag   2520
gtgatccatc tgccgtggcc tcccaaaatg ctgggattat aggcatgagc caccaccccc   2580
tcctggaagg attgatatct tataacataa tttataatta cagaaaacat gtgagttcac   2640
taggaataaa taaattttga agataataaa agattttcac ttatgttgtc atttcggcac   2700
agtttggtat aggatgtgga gatgttaaca tttataccta gcttgctcgt aaactaagac   2760
```

ctgaaagggt tgtgtctatc agctgcaccc ctgggtagcg acacaacctc gggaaggcct 2820
cagccccctc ctcgtacagc actgcctgtt ggaaagcttg agggaggcta tggatgtgca 2880
gcacttggca gagggtctgg tcatggaagt taccagcaaa tatgagctac ttttatgatt 2940
ttattttatc caaaagaaag agaatgaaag aagaggggag gaaacaagac taatcaggaa 3000
agatgaaggt ctaggggtga gggaaggagt aaggagacat aaaggcaatg tggagcagct 3060
gaggggggaa atggctttca ccacttccca gcatctattg acattgcact ctcaaatatt 3120
ttataagact ctatattcaa ggtaatgttt gaaccctgct gagccagtgg catgggtctc 3180
tgagagaatc attaacttaa tttgactatc tggtttgtgg gtgcgtttac tctcatgtaa 3240
gtcaacaatg tcctgggatt gggacacact ttctgggcac tgctggccag tcccaaaatg 3300
gaacataagg aagtggttct tctacttctt ttatttctga aatcaggtaa gacatagttt 3360
ttttaaatta taagaattat tttttctccc acaatgtagt aaaaatacat atgccatggc 3420
tttatgtgca attcatttaa tttttgattc atgaaattcc cagttcaaaa tcttgtatat 3480
gattgaaaaa ttcttaaaaa aataagttta atttccccgt gaagactgtc acggtgctgg 3540
aatgaatggg cagaaaaaat aatggttgat ttttctaatc taaaagagtg tgcctacatg 3600
atggccagtc tggctgaaaa ataaatagcc attgtagcta actatgcaaa ggatggctaa 3660
gctcttcgct tggttctcag tttcattaat ttatatcatc tctgttcagg tgccatgctc 3720
ccctcactag caagttgaaa caatgaaata actctttgaa tatgtttggt tccttgacct 3780
gttcatggag tgggactcag catttctctc tttgttatgg cctgagtaag gctttccatc 3840
ggtatacatt tgcttcttat ccctggagaa attatacaca tccatttgcc agatgatata 3900
cgcatataat gattcaacaa atactcaggg tatttgttga gtgggttagg tccccacatt 3960
tttatacata catacacaca tacacaccgt gtgtgattgt gaatgtaagt gtgtgtcctt 4020
tacaaatact agcttattta gctcatggta taggtagggt agcatagtca tccccatttt 4080
ataaacaaag aaatctagac ttaggaaaat catgttattt gtctcgtgac caaattccca 4140
aatcaaggaa ataaagaaac ctggatttaa gccagatttc caagaaaaaa tctagggctc 4200
ttctcacttt ttcatctttg ttccaacatt tgaaaaaata aatctaaaca cattccaatg 4260
taactgaaga gcaggttaat tgtttgccac ttgcagaatc caattaagaa gagagaagtc 4320
tggtataaag aaagtgattt gcttccaaag ctagcttagg ggaagaaatg cagcagtcct 4380
gccgtactac ttcactttag gagcagaaag tggcactttt aaaaggcaac agaggaggcg 4440
agcaaggatt caggggtcca tgctagcttg ggcaccttat ccaccaggta gttgagcagt 4500
tgcctgctgg tgcctttgtg agcagggtgt tgtcccttga ggcaaatctc tggagggtga 4560
gagttttgta gtgggcatgc tttggtttat aaatcacctg tgaactcagg agttccatct 4620
tgaagcacat acatagttag atgaacttgc cctgcaggga gagtctgatg aaagggaggt 4680
agatgcttgc aatttaatct ataaattacc agataaaatt ttacaagttg actttaaagt 4740
caaacacatt tgaatttagt ggaagccatt caagaaaata tcaaagaaaa tacagagcag 4800
gagaagatta agcaaagagt tttttgggga aattggtgtc tatgtctgtg tgtgtaggga 4860
gtgcagggga tatgaatatt ctatttcagc ccatggaaac taggatgtag atcactgtga 4920
acttattcag caggctacac ccaaaggcta gaacaaactt ctctgccaca ggattaacat 4980
atgttttaat cgacctgggg ggcacattct ctgataagct cttttggaaa gccaggcttt 5040
ctgtggacgt gttatctttc caatgtgtgc tggaatgccc ggggagagga aaaagtttct 5100

-continued

```
tttacagcca tgctcagtga gaagcggaga aacatcttct attcacaaat tgctaagtct   5160
tttacacatg caaatatgca tacacattca cacaccacag tgaggaagaa attctcacac   5220
cattaataaa atacatttac ttcagtagca atatacatct acattttgcc tataatataa   5280
aagtattttt cctattaaaa gatttgttta atgtttcttc accaacaaat aaaccctatt   5340
aaatccccat tgccatatga gccctggagg tgaatcagag aaacaaaagg attgtggaaa   5400
aatcatcagg ttaaaaaaag aaaaattgat tctgttttgg gatatttcct agcaacatga   5460
gctggggagg ggatctcagc agtgatgctc tatgaagcat aataaaatga cacagttaca   5520
ggtaacttag ttaaaggggg aaataaatgg aagtttcctc tttttgaata tcaattgtag   5580
cctgctctgc tacatttcaa aaacactctt caaaatgttt aactgaactc actgtaggaa   5640
gcaccttatt aatttattgt gtgttttgaa gtcacactgt gagctataga atttacccaa   5700
gcacaactct tcctggaaaa gagagttcaa atgagaaaca gtgcggggtg aagacatgga   5760
tatgggccta aaatatctat ttctcaatga tattttgata tatctatcaa gtgcttttta   5820
gtggattagg ttcagaatgc atcagccaat gcctgttcaa taatccagtt ttccagcata   5880
gagcatatta aattgaggaa ggacaaagtc acagaggtgg ggagcaggtg gactgtggcc   5940
aaggactttg catgaaacag tgagcgtgca tcctcctcct tgccctgccc tcatggtctg   6000
tgtactctca ggaggtcagg acaggccttt ctgagaatga gaatctgttc atctgccttt   6060
ctactggata cttgtcatcg gcatacaaac acatgttctc tgcagtgtgt catctttcag   6120
aacctcccct gaccctgtat tccctagaag tctcgctgct ttcagagcca ggcttctctc   6180
ctgctgccac ccccactgct cttctagtca ctctttaacc cactccatct gcatgtggcc   6240
cccaccacac ccctcaaagt ggtcaaggtt gtcctgttgc ttaattccat ggaagcttgg   6300
ctatcttcat tttattagcc tcttttggcc tctcaccctg tgaaaatcac tacattttgt   6360
gccagagatg gagctggcat ctccaggctt ggaagagggc tgctgaagct cagccaggtg   6420
tcctaaggag cctcaggaca ggggatgctc agtagccttg caatgggaac acagctgagc   6480
cccacttggc cacccctttgc cacaaccagg cagaaagcag cttttgaaca gatttgttgc   6540
ctcagatttg atctcaaaga aaaatcgtgg gcagtattgg tcccaggttc tgctttttta   6600
caatttcctc tgaaatctgg atgcctatca acaccttgga aaaactgaat tctccccaac   6660
taatagtggt gtgtcactgt agtaagccta gtacaaaaat ggccttcttt gtggaggagc   6720
ttcatatcct ccattttttt tttgcttaat ttttgcccaa gatgagaaca taatttagtt   6780
cactttttat ttattcccaa catcatccat gcaccaacat ttttgtaact aaaggaggga   6840
ccattcagaa gatgcttatc aactgtcaaa gtgacagtgt tacaaccaat gcacatattg   6900
taagaaatca aacaatggcc tccaaggttc atttctacac agggattagc agatcaacat   6960
caatcttggc aacacagttg ccactgatgg tgtcttattt tttttatcat gacatggcaa   7020
tcaagagcaa acatgattta ttcttattta agattttatg gttagactag gcagatagct   7080
agatatgagc aggaggtgga agcccctgag agaatggagg tctggagaat ctgaaacccc   7140
agagattacc caagtcctgc atgctagaca tgagtggagg agggggaata cctaggtaga   7200
aaagaatgcc ccttaagatg cccagcagtc gctcactgtg cagttaactt ttcagaatgc   7260
tgctagatac atgctgatag ggagggaaga gggcaaagga gaaattccta agagatacac   7320
ggttgcagtt agtatacatc tgagtgctat acaaccttct ttgggtggtg gcaagaagca   7380
atgcagccat tacgtagaat tcatatcaaa cacctgtatc acaggtgtta aagaaacaag   7440
aaacattgta cttcttgtat tcttaataat gatttgcaat attgtcttta gtatcactgc   7500
```

-continued

```
aaacctctat aaatatgatt tttaaaaagt atttctttag gttggaatta cttctacgca   7560
ttgacttatc ttcctgggtt tcattagccg tacccgttgt actttcttcc ttaccactgt   7620
ttatctcaaa ctcttgagat taaagtatgg gctcaggagg gagcgaggag cttcaggact   7680
ctcacggacc tccagcacag tgtagctgcc ttatggaaaa gtggccacac tgttttctgc   7740
actggtccct gcccctacta ttcctcactg ggcagagcac agccaccctg gccctgcctg   7800
aacattttag tcagtgttgg ctctgtgctt ctctggggag gaaatccaag agacaaccca   7860
cagcccctct gccatttcag ctgcagcagt accaccgtta atgcccttgg gcttgagaaa   7920
gaagggacct ggccacttcc ctgacacctc cagcacacag cagggaaaga attccagttt   7980
ctctttcttg tgagctttca cctgctactc ttcaccaggc aaggctcctg gcttgggccc   8040
acagtgcagg cacctcgaac tcagttgaac atttccactg gctgcactct gtgtttttgt   8100
ggggtgaagc tcccagaggt gactgaaagt ccttctgcca ctaacactgc agtcatactg   8160
cccttgctgt acttggacta gggaaggaaa aaagatcctg agtgctttac tcacacccca   8220
gtgtgcccca gccaccctat ggaaaagagg ccagtgtgtc atccctgcaa gcaccctgag   8280
gcccctgccc ctgctgcccc caagctgtag agccagaata taaagctggc agaaaaatgt   8340
aaaaaggcta gactggctta gcctcccagc ctacatcttt ctcctgtgct ggatccttcc   8400
tgctcttgaa catcggactc caagttcttc agctgtggga cttggactgt cttccttgct   8460
cctcagattg caggtggcct attatgggac cttgtaatct tgtgagttaa taccacttaa   8520
taagctcccc tttgtgtgag tatatctata tctatagata gatataggta tactcactat   8580
atatacacat atatacatat actctctctc tctctctctc atatatatat atatataatc   8640
tcctattagt tctgtccctc tagagaaccc cgactaatac agattttcat accagaagtg   8700
gttcttgagg aacagaatat taaggatgga attctttcat tggttttggg acttctggtg   8760
ttggctgatt aatatgatta gaccaaaaaa tgctaaggac tctacttcta atagtatgga   8820
gaacactgat agtacttggc ctgaattgtt tagagagtta tgcaaaataa atgcatttga   8880
cactactgat tcatcactta tgagaggcaa ggagtttagt gactctatac ataatacctt   8940
tgactatatg tggagaacca aggaacataa tgaagttggt tgattgctcc taagttctct   9000
ggagaaagag atgaaagaaa atgatgatct caggggatct gtctcccacc ttcagaagca   9060
gatactgagc cacaaatctg ctaagattgc cctgaatgag agttttaact cctgtagaga   9120
aagagttgaa attgtgaaaa aacagagaca agctgttatc atgcgagtag ctgatctgca   9180
acaagaggtg catgcacagc cttgccaggt gtttactgtt aaagtgaggg cattgactgg   9240
aaaaaaatgg gaccctggaa cttggagtgg ggatgtgtgg gagaaccctg atgaagctga   9300
ggacactgag tttgtgaact ctgatgaaac ttttttgcca gaagaaacag tttccccatc   9360
cccagtagtg gtaacatccc ctccctgacc cgtgctgcca ttagcctttc cacctttgtc   9420
tgaggatgta aaccctgcac tgcttgaggc aacagtgatg gccttccctg aggcagctgc   9480
caggcaagat aatgttgatt ctcctcaaga ggcaccccta atgcccctga atgcttctag   9540
acctataact aggctaaatt ccttgcgggc cccagaggtg aggttcagag tgtgacccat   9600
gaggaggtgc attatactct aaaagaactg cttaagcttt ctaatttata ttggcagaaa   9660
tctggagaac aggcatggga atggatatta agggtaaggg ataatggtgg aagggacata   9720
gagttggatc aagctgaatt tattggtttg gccctactaa gtagggattc tgcatttaat   9780
gttgcagctc ggggacttag aaaaggttct gatagggccg ggagcagtgg ctcacgcctg   9840
```

-continued

```
taatcccagc accttgggag gcgggggcgg gcagatcacg agatcaggag attgagacaa   9900
ttctggctaa aatggtgaaa ccccatctct gctaaaaata caaaaattag ctgggcatgg   9960
tgatgcgtaa ctgtaatctc atctacttgg gaggctgagg caagagaact gcttgaacct  10020
gtgaggcaga gattgcagtg agccaagatc gccccactgc attccagcct ggtaacagag  10080
caagactcca tttccaaaaa aaaaaaaaaa aaagttataa tagtttattt gcttggttag  10140
ctgaaatatg gattaaaaga tggtccaatg ttagtgagct ggaaatgcct tggtttaatg  10200
tagaggaagt gatccaaagg cttagggaga ttaggatggt ggagtggatt agtcacttta  10260
gacctactca tcccagctgg gagggtccag aagatacacc cttggccgaa gctttgtgaa  10320
atagatttgt gagagcagca cctgtatttt tgaagagccc gtaattgctc ttctctgtat  10380
gtcagatcta acagtaggaa ccacagtcac tcaactacaa aatttaaata caatgggaat  10440
aattggatcc tgaggtggca ggggccaagt gttggcactg aaccatcaaa ggcaaggtgg  10500
gcataactac cataatagac agcagaggca aagcagccat cagaatagtc tgactcatgt  10560
agagctctgg cattggctaa ttaatcatgg tgttcctaga agtgaaattg atgggaaacc  10620
tactgtattc ctacttgatt tatataaaca aaaaactgcc aggtagaatg gactaaagac  10680
taatctgaat tataaaaaca gagaatcatg ggccctcaat caatttccag actcgaacct  10740
gttacagttc cagaacccac tgaatgaagg ggaggctgga tccccttgag gaaggacacc  10800
actaggctac tgacaactta tgctgttact ctttctccca tccttcccta aggagacctc  10860
tggcctttta ccagggtaac tgtgtgtact ggagaaaggg aagtaatgag acatttcaga  10920
aagtactgga cactggctct gagctgacgt tgattccagg gtacccaaaa cgttattgtg  10980
gttccccagt taaagtaggg gcttatggag gttaggtaat taatggagtt ttagctcatt  11040
tctgacttac agtggttcca gtgggtccct ggacttatcc tctggtcatt ttcccagtgc  11100
caaaatgcat aatttgtata gacatactta ttagctggca gaaatgccac attggctccc  11160
tgactggtag gatgagggct attatggtgg gaaaggccaa acagaagcca ttagagctgt  11220
ctctacctag aaaaataaaa aaatcaaaaa caatatccca tccctggagg gactgaagtg  11280
attagtgtca ccatcaagga cttgaaagac gcaggggtgg tgattcccac cacatccctg  11340
ttcaactctc ccatttgacc tgtgcagagg acagatggat cttggaaaat gatggtggat  11400
tattttaagc ttaaccaagt ggtgactcca attgcagctg ctctaccagt tgtggttttg  11460
ttgcttgagc aaattaacac atctcctggt gcctggtatg cagccattgg cttggcaagt  11520
ggctttttct ccattcctgt ccataagacc caccagaagc aatttgcctt cagctgacaa  11580
ggccagcatt ataccttac  caccctacct caggggtgta tcaactctcc agctttgtgt  11640
cataatctta tttggagaga ccttgctcgc ttttcacttc cacgagatat aacactggtc  11700
cattacattc atgacattat gatgattgga tacagtgagc aagaagtagc aaacacactg  11760
aacttattgg tgagacattt gtatgccaga ggatgggaaa taaatccagc taaaatttag  11820
ggactttcta cctcggtaaa atttctaggg ttccagtggc atgagaccta tggagatatt  11880
ccttctaagg tgaagcataa cttgctgcgt ttggcccctc ttacaaccaa gaaagaggca  11940
caatgcctgg tgggcctatt tggattttgg aggcaacaca ttcctcgttt gggtgtgtta  12000
ctctggccca tttatcgagt gacctgaaag gctgccagat ttaagtgcag tctagaacaa  12060
aagaaggctc tgaaacaggt ccaggctgct gtgaaagctg ctctgccatt tgggccacat  12120
gaccccgcag atccaatggt gcttgaggtg tcagtggcag atagggatgc tgtttggagc  12180
ctttggcagg cccccatagg tgaatcacag tggagacctc taggattttg gagcaaggcc  12240
```

-continued

```
ctgccacttc tgcagataac tactctcctt ttgagagaca gctattggtc tgttattggg  12300
ctttggtggt aactgaacgt ttgactgtgg gtcataaagt caccatgcta cctgaacctg  12360
cctatcatga actggttgct ttctgaccca tctagccatg aagtgggtca gcacagcggc  12420
atttcatcat caaattgaag tggtgtgtat gtgatcgggc ttgagcaggt cctgaaggca  12480
caagtaagtt acataaggaa gtggctcaaa tgcccatgtt ctccactcat gccaccctgc  12540
cttccctccc ccagcctgca ccaatggcct catggggagt tccctatgat cagttgacag  12600
aggaagggaa gactaaggac tggttcatag atggttctgc acgatatgca ggcaccaccc  12660
gaaagtggac agctgcagca ctatatccac tttctaaatg catgtgtaca cttgtgctaa  12720
gaaaatatct ttattttatt tcctttattt ttcctttatc atgtgacctt agatttatgg  12780
acttcacatc agcatttaag catttaagtg ttgttcatat cagcatttaa atattgttaa  12840
ccttatgtaa taacttttgg tttggggatt ggtgcgtttc tggttgtatg aggatagttg  12900
tattatatta ggcataatta tgaccttatt attgtcttta tttgaagatt atgtatgatt  12960
tcaggatgtg tgtatgggtt caagttgaca aggagttgga cttgtgatgg ttaatactgt  13020
caacttgatt ggattgaaag atgcaaagta ttaatctcgg ttatgtctgt gagggtgtgg  13080
caaaaggaga ttaacatttg agtcagtggg ctgggaaggc agacccaccc ttaatctggg  13140
tacacaccat ctaatcaagt tccagtgtgg ccagattgta aagcagggag aaaaatgtga  13200
aaagactaga ctgaattagc ttcccagcct acatctttct cctgtgccaa atgcttcctg  13260
ctcttgaaca tcggactcca agttcttcag cgttgggagt tggactggct ttcttgctcc  13320
tcagcttgca gagggcctgt tgtggaacct tgtgatccgc tgagttaata ctacttaata  13380
agatcccctt tatatacata taatatatta tattatatat aatatatata atatatatta  13440
tatataatat atataatata ttatatatta tatataatat atattatata ttatatataa  13500
tatatattat atataatata tattatatat tatatattat atataatata tattatatat  13560
aatatatata aaatatatat atatcctatt agttctgtcc ctctagagaa ccctgactaa  13620
tacaatttat gtcattaatc tcatttattg atttgtatac attgaaccaa ccttatatcc  13680
caggaataaa acctacttga ttgtggtgga ttagcttttt gatgtactct tggattcaat  13740
tgctggtatt ttattgagaa tttttgcatc tgtgttcatc aaggatattg gcttgaagtt  13800
ttcttttttt gttgttccat atcagaatga tgacgacctc atagaatgag ttagtctgtc  13860
ctcttttatc ttttggaatt gtttcaggag gcttgatatc agctcttctt tatatgactg  13920
gtatactttg gctaggaatc tctctggtcc aggggttttt ctggtgtagg tttttaatta  13980
ctgattcaac ttcagaactc attactcatt attgagttct aaaactcact ttcatgtact  14040
cttcaaaaga ctgtcttctt ctgttgttga gcggggtgtt ctctcaaggt cgtttaggtg  14100
aaggtggttg ctggtgttct tctgtatcct tactgcttgt ctttctcttt ttttattgac  14160
tactgaggat taatggtgat gtgtccaact ttaactctag attagtctat ttctctttta  14220
gattgtaact ctgttttata tattttgaag ctctgttgtt aggcatgtgt atttggattg  14280
ttaggtcttc ttgatgatga cctttatcat tatgtaatgt ttcttcttat ctctggaagt  14340
attcgttgtt ctgaagtcta tttgtgctga tatgaataca gccttcacag ctctattttc  14400
actagtattt gtatatcttt ttctcagctt ttaaattgag atgttcagac catttgcatt  14460
aaagtagttg ttaataggat taaatttaaa tctaccatta agttggttat ttctctttgt  14520
cccatttaaa ctttgttcct tttttcatat ttttctgcct tcatttatat tgagtttatc  14580
```

-continued

```
tccacgactt acttattaaa ttaattttta atggttttag tattttccac aatgtttata  14640
atatatactt tgatttttc acattccacc ttcaaatgac agaattatac tggatatata  14700
gaaatcttac atcattgcac ttctccttcc tccctctcaa aatgttgtgc tattgctctt  14760
tgtaatagag gcttacttct attatgttat agctctcata atacattgac actattttta  14820
ccctgaataa tcagttgttt tttaaagtga ttatgactac aaatattttg aataatttct  14880
ttattttacc atttctggtg ctccttatct tttacagtag atcccaattt ccatctggag  14940
tcacattctt tctgtgaaaa acaaccttta gcatttctta tagcacggga ctgctgttgc  15000
tgttgtcttt cagcttttct ttgtctgaag aagtctttat tttgccttca gtttttaaaa  15060
gtgattttgc tgagtataga tactgggttg agagtttcat tccttgtatc attttaacaa  15120
tgatgttcca ttatattccg ttttgaatag tttctgacta gaaatctgat ctttgtttct  15180
ttgtattcaa tagttccttt ttctctgact gcctttaaga tattctcatc tttgtttttc  15240
aacagtttga ctataatttg tttattatta actttttgta tttattctgc ttgaggtttc  15300
ctgagctcct tggatttgca gattgttgat ttttattgtt tttgtaaaat tcatagccat  15360
tatctattct actgttttgt tttttttttc acttctctct ctctgtattc ttctttttgg  15420
actgtaagta ttcaaatgtt agatcattca tattgcttca taaaccttat atgcttcttc  15480
tgcttttttt tttttgtcag gaactctttt tttgtatctg tgttggtttg gataagttct  15540
agtagactat gttcaagttt atggattatt ttgttagttg tgtctaattg actcctcagt  15600
gcattcagag aattcttcat ctctgatatt ataaatctct tcctagcatt ttcatgttac  15660
tcttttctat agtttccatc tctttgctga aattctcccc ctatccatgg atattgtcca  15720
cctttaccac aagattcttt aacatattaa cataggtatc atacaaaccc aaactgatag  15780
tttccagatg gtgtcttttc tgagtctgtc tgtcttgatt gctttattat ttaacagtga  15840
cttatcttcc ctcttcagct tttggtgtgt cttgtaattg tttaatcaaa cactgggtat  15900
cataaatgga ggaacagtag agattgcagt aaatattatt tatgctttga aatgggcacc  15960
catcttctgt tgaaaatatg ttttgtggtc aattgagtca acctagtaac tggttgaact  16020
gaatttggca tttgtgcttg ttgcttttat cttaaatgca ccacaggttt aaattcctcc  16080
agtgatgggt tgctgctatc ttttgcttag agtggggcct ggggtgtgga agaattttct  16140
cagtgttcct atctattatt agattttagc agtcactgca tgcctgcact acagagggga  16200
tatcttcata cacataatct aaccccattg aaactgctgt ttcttcttaa tgaatgctca  16260
atctttggtg gaaataaaca aatgctgtat ctcctggagc cacttcagtc ttagtcaggt  16320
tctgcagggc tttgaaggga atgcattctc agtattcttg tgccttattt ggatggaact  16380
tgaacctgtg gtgggtttgg agagaaagag tagcagacgt ctgctatgtt gcaatgcagg  16440
atgctgggca caagaaaatt tccagtctct cctccaagga aataagattt gatcatctac  16500
ctatccctga gaagtgaagg gctttgcctg cggtgctaga tgcaaaacca tttttctccc  16560
cccattgccc agaaacttaa ggctttggct tttctgagca gtggtctagg gaattgtgca  16620
aggttttcat atttgaccct gacagcccat caccacctac agcttgcagt gccaaatgta  16680
tctccctctg atctctcctg tcctgtggtc ctcatgaaca ttaagaagag atttctaaaa  16740
aagagcttgc acatgagcat agtttctggt gagaagaatt ctgatatgtt aacttcctct  16800
aaacttttaa ataaaatatt tctaagaatt aaataaagtt ctagaatgat atgaatctat  16860
tcctttggtt ttttgcacgt ctgtctgcct gctaatcaag agaagagaat ggtcgtaatt  16920
ctcagagact ttttcctgtt tgtgtcataa atgacttcac atttttttct gttctaagaa  16980
```

```
ctattcagct tgatttcttc tgttttaatt ttagcagcac ctgagcaaag ccatgtggtc  17040
caggattgct accatggtga tggacagagt tatcgaggca cgtactccac cactgtcaca  17100
ggaaggacct gccaagcttg gtcatctatg acaccacatc aacataatag gaccacagaa  17160
aactacccaa atgcgtatgt cattaatctt acagtaagca aaacaaggtc caagtaaaat  17220
ttgtcttaga aaaggtgtgc gtcaagctaa cttcttatga ttaaattttt ctcacacata  17280
gaatgcatgg caaaatgtct gagaaacatt actttgagca aagagtatga tagaagagaa  17340
atgttaagct ggctctcttt cctgagagtt tgataaaatc aggagaatat ctggcggtgg  17400
tgaggccaca ataatggaaa atcagaatgt ttagacagag tcagcttcaa caacactcac  17460
taaaggtcaa tgtgatcttt accccttgaa attctataat tctaatctcc aattcctgaa  17520
gtgaaggttg tgttggcctt ttctgtcttg gctcacaagt aaatgatatg tgcatatcta  17580
tggaaaggcg aatctatctt tttctatatc tatgtctatt ccaacgggta gaaacaccct  17640
gggtcctgag caccagtggt ctgaaggaat acgggttgcc aggaagagag aagcaaaggc  17700
aggaaggcag atgaaagtaa gaaatgagac agatgctaaa caataaaaag tgcgggaaga  17760
tagacagaag ctggggtctg accacaccat ggccagtctt tcacacataa gtgactacca  17820
aagacaagaa aaaatgattt ccgcttgttg gacaatagat ggtagaggac caagggaatt  17880
gcgagagaga gaacaatgag atcaactcaa cagatgcact ggttttcttc ctggagaccc  17940
ttcctgcact gaagggcagg agatggagcc caaaaaaaac tgtagccatc ttgctgaaca  18000
gaggagggac attggagttt gggattattc aggtggctag gattttctag gcctgctaac  18060
aatgagaaca gatttgtgga ggaaaggagt tctagaaata tgcatagaaa tctcctcgag  18120
tcattggcta aacatgaagc tgcatgtaca cagaaaatag atccacaaga aagtagggca  18180
aagaacatct acggaagagc agcaactaca atggaacagt gagctcaata aacatgacag  18240
agctcaaata gcactaaggg atattggagt ttggaccaca cagaggagag agacttcact  18300
gaacatcttg ggcattcagt agagacccag gaaaagccat actttaggag tagaattagt  18360
atattcttag aataaaggca gctccacaca aacaatagca aaactgaaaa ggaagtctcc  18420
aagcatcaga atgatgtcca agtcaatgaa ctgcctctga gaggaaaact caaccatctt  18480
tagaggtaaa catcaaagtc aagtggctca gctatgcagt atccacagtg tgaggcctaa  18540
atataaaact tgactacaca tagaaacctt ttagtgtgac ccacaagcag gaggaaaatc  18600
agccaataca aacagaccca gaagagacag aaatgattag aatggcataa aaatttgaca  18660
tatcactata taataattga gttctaggat ttaagaaaac atgaatatag aatgcaacag  18720
acaccttatc cagagacagt aagagtataa agagccaaat cgaagaacta ctaagagata  18780
tgtcttaaat gaaaaaatta ctagatggcc tccccatcta gttagacatt tcagaagaaa  18840
ataccaaatg aaaaataatt gcatagaacc tacagaacca gatacacaca tacaaaacac  18900
acgcatgcat acacacacac tcaaacatgt ataagcttac aaacacacac acacatccac  18960
aaatgctgaa aaatgaaatc aaccgagcca cacagacata aaggaaaaca taaaaagatt  19020
tcctacatgt gggaagcaag tcacagaaag ggggaaggag attggaacag aaatatatac  19080
tgaaagcaag gatggctgaa aattttccaa atataaagaa gattaaaaaa tcacggactc  19140
aagaagctca atggatcaga aaaataattt ctaaaatgac aattatagga tgccactggg  19200
tacatagcag ttcaactgtc agagggcaaa gacataatac acagaaaaat ctcgtaagga  19260
acgggaaaaa caaaaagctg tgtcttgcta gaggaacagt gatacaagtg actaatgtgt  19320
```

-continued tcccatcaga aacactgcaa cctggacaca aaagaataac attaaagtaa taaacgtaag 19380
aaagaagagc tcaactgaga aggctacatc cagcaataaa atgccttgaa gttcatccat 19440
gttggaggaa tgcacattgt gcactcccct aaacaaagaa accggaaact gtaagacttt 19500
ggaatcagca ggcttatgta acaaaagagg tgaccctaag gaattaagga gaagaagaat 19560
agaacaagaa gggaactttc tgcagcctat ataatgaaga acctagcaat tggcaaatgt 19620
agatgaaaat gctacatgtt ttcttgatca aacgtttata tctttttaaa tgagagttga 19680
cgagttgaag caaaatgata ccaatatatt taactttacc atatgtagaa gtaaaaattt 19740
gaacatgtag cataaatcat gtagggatta attggaagtg taccactgta agtttcttac 19800
ctcatgcacg atagtatgta atactaataa aaggttaatg tgtgggttca aagggatatt 19860
gcaaatccta gagcaatcac aaagttttta actctgaggt ttgttgtata ataacaatat 19920
tttatgtatt caaaagaggg aagccaagga agaaaaaaaa gtctttaaag agctctggct 19980
cttagtacat ccagttgctc attgaatgag cttcctggaa tggagggtct gggactgaga 20040
ctaggccaca tgtgtagagc cactagagac acaatgttgg atccccatgg cccataatac 20100
atttcccatt ttctcaggca gccacaggtc atgaatgtga ggatactgag aggttggagc 20160
aacgttcttg ggaggcataa ggaagagcga atgcttcaag atccccgcag cccaaactcc 20220
tcagctgctt tgcctcctaa ttcattgttt tttgctcctc catagctgtc cgacctcttc 20280
agatctctta gtcttcctgc catcttcctt tatgccatgg gacccactgt tctttcaact 20340
catcccccag ttctggagtg gctgtggaca gcagaggata gactgagagc aggagagaag 20400
gtcctgccca ggaacccatt ctagagatac tgcattctgc ctgggagcaa gttttccagg 20460
gcagctttga gaagtcttgc agaaacaaac ctacttgacc gacatgatat gggaatgaca 20520
gacagtaata ctatttgcac aatgcttttc catgggaaag gtagagcctt ttcactaggt 20580
tttgagtaca tggagtgtga gagttgacct ggaaaggtta tcctccttga tgccatgttt 20640
tctctgaaga actacatgtt cgttgcaact cccacattag aatatgaagt cctaccgaga 20700
gagatacgga gactagacag atacagatgc atttgcatgt gaatacacaa tcccacaata 20760
cagacgtcaa aacccatacc agttattcca gagagatgga ttgggcagaa ggcagaagga 20820
gaatactctg atcgtttttc ggccacgtgt gtgtgttatc tcagtgtttc taagaagcgt 20880
ttgctacttt agatttttta tttaaaaaaa atagtaataa tctattaagt atgagagatg 20940
tgcagagagg attagtgatc gagagccatt tttgctggtg gcaatcatat ggtactttta 21000
atgggaatat tagaaaggca ccggtaatga ccttgttgca gcacaaagga gagagtgtgg 21060
ggtgcccctg catgttgtcc cacctcttgt gacgtgtatc gttttggaat ttccagtggc 21120
ttgatcatga actactgcag gaatccagat gctgtggcag ctccttattg ttatacgagg 21180
gatcccggtg tcaggtggga gtactgcaac ctgacgcaat gctcagacgc agaagggact 21240
gccgtcgcgc ctccgactgt taccccggtt ccaagcctag aggctccttc cgaacaaggt 21300
aaggagtctg tggccagaca tctacacgct tcgatgctgg gatgaaaagc catggaaatt 21360
cccactgatg cagccgcctt caatggtaaa cggatgctcg agtgttgcct gagttctacc 21420
atgtaggagg aagcctccgt gcactctctg ggggagccag cggagtgatt tctggtgcaa 21480
cgtggttggg ctttgtcttt aggatgggca caaaccctcc agggggatcg acttcaaaat 21540
tcaccttgtt gtaaaacggg ctacctcagt gtcccagcca aaatttttat tgtaacatgc 21600
tgtcaggtgt gtcactcttt ccaagccagt aagcttttcc ggggatttct tcaagtagcc 21660
agcattcaga gcaatcttca gcattgcaga ttctgagaaa tgtggctctg gagcctgtca 21720
ccctcgagaa acctaagagg gctgcattga ttccatgtgg ccctgggtct atggagcagt 21780
acatgagctc ccagtgctct aaggctcttc agccctaggc tttgaaggga gtgatttctc 21840
agtattctta aacctctttc tgatgacact tgtacctgtg aggggtctag agagaaagag 21900
tagtagactc ctactttact acaattcagg atgcagggca tgagaggatt ccctctctcc 21960
tccaagggaa gaagcttttg gcgtgcacac atccctgaga agcaaagtgt ctttgtcttc 22020
agtcagatac ataggaccgt tttctgcccc atggcccgga agccaaaggc cttggctttc 22080
atgatcaacg gtctagggaa acatgcaaaa tttccatgtc tgtcccaaac tctgcccccg 22140
acagccaatt accacctgca gcccgcattg ccaaatgcgg tgccgtttgc atgaagattc 22200
agtagagttt cctagaaagg tgctacctcg tgagctcact ttccaatgag gaatctgatc 22260
tgttgtgttt ctctaaggtg tcaggtgaaa tatttccaag aacttactac agttctagaa 22320
tgggaggaat ctgttgcttt ggtgtttgtt tgttggtcgg ttttctcaca tccatctgcc 22380
tatggataag gaaaagagaa cggtcgtaat tctcatagac tcctttctgg ttgtgtcaca 22440
aatggcttca catgtttctc tatgctcaga gatactcagc ttgatttccc gtgttttcat 22500
ttcagcaccg actgagcaaa ggcctggggt gcaggagtgc taccatggta atggacagag 22560
ttatcgaggc acatactcca ccactgtcac aggaagaacc tgccaagctt ggtcatctat 22620
gacaccacac tcgcatagtc ggaccccaga atactaccca aatgcgtatg tctttgttct 22680
ttaccataag agaagaaagg gccaagtgaa gtttctgtta caagagatgt gtctcaagct 22740
gagttctccg aactcaactt gtgacagatg cagatggcgt agcaaaatgt ctcaggatga 22800
ttgccttgga gctaagggtc tgagagaagg gaaatgttaa gctccctctc cttcctccta 22860
gttctattga gcagaaggga aatctggagg tgaggagatc acattatgaa gaaagtcaga 22920
atgacaaagg accagacact tagattaccc ttccacaaca ccaactaaac gtcaatggag 22980
actttccagt tggaattccg ttattctggc ttccacttcc tgaagggaag gttgcgtttg 23040
ccttttctct ctgggttcaa gaggaaagaa taggtgctta tttatggaca ggtgaattga 23100
tctgtttcta tatctacgta tattccgatt gtcagaaaaa cactcgttcc taagtaccag 23160
tggcctgaag ggatacaggt tcccagcaag agaagatcca aggaaggaag gcagatgaga 23220
gtcagcacag agagggatgc tgaaaagtaa aagggatggg tggatggaga gaagcccggg 23280
tctgaccacc caatggccaa tattttggcc acaagcgact accagagaca tggaaaaatg 23340
gtttctacat gtgggacaac agatggtaga ggacctagag aattgagaga ggggcaatga 23400
tgggctccac tccgcagatg ccttggcttt cttcctggat acccttcctg cactgaatag 23460
caaggagatg gagcccaagc agactgtagc catcttgctg aatggaggag agggattgga 23520
gtttgggatg actgtggtag ctgaaatttt tctaggtctg ctagaaataa gaactggttt 23580
gtgtggagga aaagagctct acaaatacgc atagaagtct cctccagtcg ttggcctgac 23640
atgacgctgc ctgtgcacag gaaatggttc cacgagaaag tgtggcaaag aacatttact 23700
gagaaacagc aagtacaaga gcacaggaag ctcaataaag aagagagaga tcacatagca 23760
ctctgggata ctggagttct tcccagctag accagagagt cctcacggag cacattgcca 23820
attcagtgga gaccccagaa cagccgtaat ttaaaggtac acttagtata ttactagaat 23880
aaagtcagct gcagacaacc ccttgcacag ctggaaagca agtgtccaag catcaaatcg 23940
gtttccaatc aatgaagtgc ctgtgagagg aaatctcaac tctctttaga agtaaacaac 24000
aaagtcgatt gcctcagcta tgcggtatcc gcagagtgag tcctaaattt aaaatctgac 24060

-continued tacatgtaga aaagcgtttc gtgtgaccca tgaccaggaa ataaatcggg taatacaaac 24120
aggctcagga atgagagaaa tgattagaat tgcgtgaaaa tttgacatat cagtatgata 24180
actgatttca aatatttaaa aaaacaacat gcaagaaagc agatatcata tcaagagaaa 24240
ttaacagtac agaatagcca aattaaatta aagaggtagt ataaaaaaag tatgtcttaa 24300
ttgaaaaaaa ttactgtatg gccggctgat caatttagac gtttcagagg aaaacattac 24360
ccaacacaca attctagaga acctacagaa tgagctacac acacacacac acacacacac 24420
acacacactg aaaacacacc catactcaca cacacgcaga aactcacaag ttctaacaca 24480
cacagacacg cgcacccctg aagaaacagt gaaatataaa attaagcgag cctcacagac 24540
atgtaggaaa atatgaaaag atttcctgca tgtgggaagc aagtcacagt aaagagcaag 24600
ggagtttata atagaaacaa ataccagaat caaggatggc tgataacttt tcaattacga 24660
agaacattaa aaaaaatcac agaatcgtga aactcaaggg atcatatagg gaatttcgga 24720
aaaaaaaccc aacctgtatg atgtactttt gtacatcaca gttcgaaggt aacaaggcaa 24780
agatgtaata agaagaaacc tgtcacgaga aactggagga aaaagagctg tgtcttccta 24840
caagtacact gatacaaatt gccaatgtgt tcacctcaga aacactggaa gccagatacc 24900
agggaatatt gttaaaatga taatcaggaa caaaaagaga tcaaccggga atgctgaatc 24960
cagcaataaa atgccttgaa ggtcatccat gtcggataaa tgcatattgt gcactgcccc 25020
aaagaaagaa accggaaact gtaagaattg gaaatcagca ggcttatgta acaagagagg 25080
tgacccgaag gaattaggta gaagaagaat tgaacaagaa aggaactttc tgcagcccac 25140
gtaatgaaga atccagcaat tggcaaatgt agatagatgt aaatgcaaaa tattttcttg 25200
atcaaatttc tatatctttg taaatgagag ttgactactt gaaacaaaat gatagcaaga 25260
tatttaactt cagcatatgt agaggtaaga atttgaaatg gtagcataaa tcacgaaggg 25320
attaattcga agtgtaccgt tgtaagtttc tttacctcat gcacgatggt gtgtcatatt 25380
aataaaaggg tactgtgcgg gttcgaaggg atattgcaaa tcctagagca atcacaaagg 25440
tttgaactct gaggtttttg gtataataag aatagtccat gcattcaaaa gagggaagcc 25500
aaggaagaac tagaagtctt tcaagagctc aggctcttat acatccagtt gctcattgaa 25560
ccagcttcct ggaatggagg gtctggggtt gagactaggc cacaagtcta gagtctctag 25620
agagacagtg ttggaacccc atggcccata atacatttcc cattttctca ggcagccaga 25680
ggtcatgaat gtgaggatac tgggaggttg gagcaacgtt cttgggaggc ataaggaaga 25740
gcgaatgctt caagatcccc gcagcccaaa ctactcgcct gctttgcccc ctaatgcatt 25800
tttctctgct gctccgtagc tgtccgacct cttcagatct cttagtccac cctgccgtct 25860
tcctttatgc catgggtccc actgttcttt caactcatcc ccctttccct cagtcccgga 25920
gtagctgcgg ccagcagagg gtagactgag agcaggagag aaggacctgc ctaggaaccc 25980
cttctagaga tactgcatcc tgcctgggag caagttttcc agggcagctt tgagaagtct 26040
tggagaaaca aacctactaa acctgacaga cagtaatact atttgcacaa tgcttttctg 26100
tgggaaaggt agagcctttt cactacgtat tgagtacata gagtgtgagg gttgacctgg 26160
aacggctatc ctcctggatg acgtgtgttt tctgaagaac tacatgttcg ttgcaactcc 26220
cacattagaa tatgaagtcc taccgagaga gatacggaga ctagacagat acagatgcat 26280
ttgcatgtga atacacaatc ccacaataca gacgtcaaaa cccataccag ttattccaga 26340
gagatggatt gggcagaagg cagaaggaga atactctgat cgtttttcgg ccacgtgtgt 26400
gtgttatctc agtgtttcta agaagcgttt gctactttag atttttttatt taaaaaaata 26460

-continued

```
gtaataatct attaagtatg agagatgtgc agagaggatt agtgatcgag agccattttt  26520
gctggtggca atcatatggt acttttaatg ggaatattag aaaggcaccg gtaatgacct  26580
tgttgcagca caaaggagag agtgtggggt gcccctgcat gttgtcccac ctcttgtgac  26640
gtgtatcgtt ttggaatttc cagtggcttg atcatgaact actgcaggaa tccagatgct  26700
gtggcagctc cttattgtta tacgagggat cccggtgtca ggtgggagta ctgcaacctg  26760
acgcaatgct cagacgcaga agggactgcc gtcgcgcctc cgactgttac cccggttcca  26820
agcctagagg ctccttccga acaaggtaag gagtctgtgg ccagacatct acacgcttcg  26880
atgctgggat gaaaagccat ggaaattccc actgatgcag ccgccttcaa tggtaaacgg  26940
atgctcgagt gttgcctgag ttctaccatg taggaggaag cctccgtgca ctctctgggg  27000
gagccagcgg agtgatttct ggtgcaacgt ggttgggctt tgtctttagg atgggcacaa  27060
accctccagg gggatcgact tcaaaattca ccttgttgta aaacgggcta cctcagtgtc  27120
ccagccaaaa tttttattgt aacatgctgt caggtgtgtc actctttcca agccagtaag  27180
cttttccggg gatttcttca agtagccagc attcagagca atcttcagca ttgcagattc  27240
tgagaaatgt ggctctggag cctgtcaccc tcgagaaacc taagagggct gcattgattc  27300
catgtggccc tgggtctatg gagcagtaca tgagctccca gtgctctaag gctcttcagc  27360
cctaggcttt gaagggagtg atttctcagt attcttaaac ctctttctga tgacacttgt  27420
acctgtgagg ggtctagaga gaaagagtag tagactccta ctttactaca attcaggatg  27480
cagggcatga gaggattccc tctctcctcc aagggaagaa gcttttggcg tgcacacatc  27540
cctgagaagc aaagtgtctt tgtcttcagt cagatacata ggaccgtttt ctgccccatg  27600
gcccggaagc caaaggcctt ggctttcatg atcaacggtc tagggaaaca tgcaaaattt  27660
ccatgtctgt cccaaactct gcccccgaca gccaattacc acctgcagcc cgcattgcca  27720
aatgcggtgc cgtttgcatg aagattcagt agagtttcct agaaaggtgc tacctcgtga  27780
gctcactttc caatgaggaa tctgatctgt tgtgtttctc taaggtgtca ggtgaaatat  27840
ttccaagaac ttactacagt tctagaatgg gaggaatctg ttgctttggt gtttgtttgt  27900
tggtcggttt tctcacatcc atctgcctat ggataaggaa aagagaacgg tcgtaattct  27960
catagactcc tttctggttg tgtcacaaat ggcttcacat gtttctctat gctcagagat  28020
actcagcttg atttcccgtg ttttcatttc agcaccgact gagcaaaggc ctggggtgca  28080
ggagtgctac catggtaatg gacagagtta tcgaggcaca tactccacca ctgtcacagg  28140
aagaacctgc caagcttggt catctatgac accacactcg catagtcgga ccccagaata  28200
ctacccaaat gcgtatgtct ttgttcttta ccataagaga agaaagggcc aagtgaagtt  28260
tctgttacaa gagatgtgtc tcaagctgag ttctccgaac tcaacttgtg acagatgcag  28320
atggcgtagc aaaatgtctc aggatgattg ccttggagct aagggtctga gagaagggaa  28380
atgttaagct ccctctcctt cctcctagtt ctattgagca gaagggaaat ctggaggtga  28440
ggagatcaca ttatgaagaa agtcagaatg acaaaggacc agacacttag attacccttc  28500
cacaacacca actaaacgtc aatggagact ttccagttgg aattccgtta ttctggcttc  28560
cacttcctga agggaaggtt gcgtttgcct tttctctctg ggttcaagag gaaagaatag  28620
gtgcttattt atggacaggt gaattgatct gtttctatat ctacgtatat tccgattgtc  28680
agaaaaacac tcgttcctaa gtaccagtgg cctgaaggga tacaggttcc cagcaagaga  28740
agatccaagg aaggaaggca gatgagagtc agcacagaga gggatgctga aaagtaaaag  28800
```

-continued ggatgggtgg atggagagaa gcccgggtct gaccacccaa tggccaatat tttggccaca 28860
agcgactacc agagacatgg aaaaatggtt tctacatgtg ggacaacaga tggtagagga 28920
cctagagaat tgagagaggg gcaatgatgg gctccactcc gcagatgcct tggctttctt 28980
cctggatacc cttcctgcac tgaatagcaa ggagatggag cccaagcaga ctgtagccat 29040
cttgctgaat ggaggagagg gattggagtt tgggatgact gtggtagctg aaatttttct 29100
aggtctgcta gaaataagaa ctggtttgtg gaggaaaaga gctctacaaa tacgcataga 29160
agtctcctcc agtcgttggc ctgacatgac gctgcctgtg cacaggaaat ggttccacga 29220
gaaagtgtgg caaagaacat ttactgagaa acagcaagta caagagcaca ggaagctcaa 29280
taaagaagag agagatcaca tagcactctg ggatactgga gttcttccca gctagaccag 29340
agagtcctca cggagcacat tgccaattca gtggagaccc cagaacagcc gtaatttaaa 29400
ggtacactta gtatattact agaataaagt cagctgcaga caaccccttg cacagctgga 29460
aagcaagtgt ccaagcatca aatcggtttc caatcaatga agtgcctgtg agaggaaatc 29520
tcaactctct ttagaagtaa acaacaaagt cgattgcctc agctatgcgg tatccgcaga 29580
gtgagtccta aatttaaaat ctgactacat gtagaaaagc gtttcgtgtg acccatgacc 29640
aggaaataaa tcgggtaata caaacaggct caggaatgag agaaatgatt agaattgcgt 29700
gaaaatttga catatcagta tgataactga tttcaaatat ttaaaaaaac aacatgcaag 29760
aaagcagata tcatatcaag agaaattaac agtacagaat agccaaatta aattaaagag 29820
ctagtataaa aaaagtatgt cttaattgaa aaaaattact gtatggccgg ctgatcaatt 29880
tagacgtttc agaggaaaac attacccaac acacaattct agagaaccta cagaatgagc 29940
tacacacaca cacacacaca cacacacaaa ctgaaaacac acccatactc acacacacgc 30000
agaaactcac aagttctaac acacacagac acgcgcaccc ctgaagaaac agtgaaatat 30060
aaaattaagc gagcctcaca gacatgtagg aaaatatgaa aagatttcct gcatgtggga 30120
agcaagtcac agtaaagagc aagggagttt ggaatagaaa caaataccgg aatcaaggat 30180
ggctgataac ttttcaatta cgaagaacat taaaaaaaat cacagaatcg tgaaactcaa 30240
gggatcacat agggaatttc ggaaaaaaaa cccaacctgt atgatgtact tttgtacatc 30300
acagttcgaa ggtaacaagg caaagatata ataagaagaa acctgtcacg agaaactgga 30360
ggaaaaagag ctgtgtcttc ctacaagtac actgatacaa attgccaatg tgttcacctc 30420
agaaacactg gaagccagat accagggaat attgttaaaa tgataatcag gaacaaaaag 30480
agatcaaccg ggaatgctga atccagcaat aaaatgcctt gaagatcatc catgtcggat 30540
aaatgcatat tgtgcactgc cccaaagaaa gaaaccggaa actgtaagaa ttggaaatca 30600
gcaggcttat gtaacaagag aggtgacccg aaggaattag gtagaagaag aattgaacaa 30660
gaaaggaact ttctgcagcc cacgtaatga agaatccagc aattggcaaa tgtagataga 30720
tgtaaatgca aaatattttc ttgatcaaat ttctatatct ttgtaaatga gagttgacta 30780
cttgaaacaa aatgatagca agatatttaa cttcagcata tgtagaggta agaatttgaa 30840
atggtagcat aaatcacgaa gggattaatt cgaagtgtac cgttgtaagt ttctttacct 30900
catgcacgat ggtgtgtcat attaataaaa gggtactgtg cgggttcgaa gggatattgc 30960
aaatcctaga gcaatcacaa aggtttgaac tctgaggttt ttggtataat aagaatagtc 31020
catgcattca aaagagggaa gccaaggaag aactagaagt ctttcaagag ctcaggctct 31080
tatacatcca gttgctcatt gaaccagctt cctggaatgg agggtctggg gttgagacta 31140
ggccacaagt ctagagtctc tagagagaca gtgttggaac cccatggccc ataatacatt 31200

-continued

```
tcccattttc tcaggcagcc agaggtcatg aatgtgagga tactgggagg ttggagcaac  31260
gttcttggga ggcataagga agagcgaatg cttcaagatc cccgcagccc aaactactcg  31320
cctgctttgc cccctaatgc atttttctct gctgctccgt agctgtccga cctcttcaga  31380
tctcttagtc caccctgccg tcttccttta tgccatgggt cccactgttc tttcaactca  31440
tcccccttc cctcagtccc ggagtagctg cggccagcag agggtagact gagagcagga  31500
gagaaggacc tgcctaggaa ccccttctag agatactgca tcctgcctgg gagcaagttt  31560
tccagggcag ctttgagaag tcttggagaa acaaacctac taaacctgac agacagtaat  31620
actatttgca caatgctttt ctgtgggaaa ggtagagcct tttcactacg tattgagtac  31680
atagagtgtg agggttgacc tggaacggct atcctcctgg atgacgtgtg ttttctgaag  31740
aactacatgt tcgttgcaac tcccacatta gaatatgaag tcctaccgag agagatacgg  31800
agactagaca gatacagatg catttgcatg tgaatacaca atcccacaat acagacgtca  31860
aaacccatac cagttattcc agagagatgg attgggtagg aggcagaagg agaatactct  31920
gatcgttttt cggccacgtg tgtgtgttat ctcagtgttt ctaagaagcg tttgctactt  31980
tagatttttt atttaaaaaa aatagtaata atctattaag tatgagagat gtgcagagag  32040
gattagtgat cgagagccat ttttgctggt ggcaatcata tggtactttt aatgggaata  32100
ttagaaaggc accggtaatg accttgttgc agcacaaagg agagagtgtg gggtgcccct  32160
gcatgttgtc ccacctcttg tgacgtgtat cgttttggaa tttccagtgg cttgatcatg  32220
aactactgca ggaatccaga tgctgtggca gctccttatt gttatacgag ggatcccggt  32280
gtcaggtggg agtactgcaa cctgacgcaa tgctcagacg cagaagggac tgccgtcgcg  32340
cctccgactg ttaccccggt tccaagccta gaggctcctt ccgaacaagg taaggagtct  32400
gtggccagac atctacacgc ttcgatgctg ggatgaaaag ccatggaaat tcccactgat  32460
gcagccgcct tcaatggtaa acggatgctc gagtgttgcc ggagttctgc catgttgggg  32520
gaagcctccg tgtactctct gggggagcca gcggagtgat ttctggtgca acttgggtgg  32580
gctttgtctt tagaatgggc acaaaccttc cagggtgatg ggcttcacaa ctcacctcct  32640
tctaaaatgg gctatctcag tgtcttagcc aaaattttta ttgtaacgtg ctgtcaggtg  32700
tgtgattctt tctgtcgcag taagcttttc tggggatttc ttcaagtagc cagcagtcag  32760
tgcaatcttc agcattgcag atttcaaaaa atgtggctct ggagcctgtc atcctcgaga  32820
aacctaacag ggctgcatta attccatatg gtcctgggtc tatggagcag tatatgagct  32880
cccaatgctc taaggctctt cagtcctagg ctttgaaggg agtgatttct cagtgttctt  32940
aaacctcttt ctgatggcac ttgtacctgt gaggggtcta gagagaaagg ttagtagact  33000
tctcctttac tgcaattcag gatgcagggc atgagaagat tccctccctc ctccaaggga  33060
agaaggtttt ggcgtgcaca catccttgag aagcaaagtg tctttgcctt cagtcagata  33120
tataggatcg ttttctgccc catggcctgg aagccagagg ccttggcttt catgatcaac  33180
gatctaggga aacatgcaaa atttccatgt ctttcccctc ctctgccctc gacagccaat  33240
taccacctgc atcctgcatt gccaaatgca gtgccctttg tatgaacatt cagtagagtt  33300
tcatagaaag gtgctacttc gtgagcgcac tttgcagtga gaaggagtct gttctgttct  33360
gtttttctaa ggatttcagg tgaaatattt cctagaactt actacagttc tagattggta  33420
ggaatctgta ggtttgctgt atgttttttg gttggttttc tcccatccat ctgcctacag  33480
gtaagggaaa gataacgttc gtaattctca tagactcctt tctggttgtg tcataaatgg  33540
```

```
cttcacatat ttcgttattc tcagagatac tcagtttatt tcttgtgttt tcatttcagc  33600
accgactgag cagaggcctg gggtgcagga gtgctaccac ggtaatggac agagttatcg  33660
aggcacatac tccaccactg tcactggaag aacctgccaa gcttggtcat ctatgacacc  33720
acactcgcat agtcggaccc cagaatacta cccaaatgcg tatgtctttg ttctttacca  33780
taagagaaga aagggccaag tgaagtttct gttacaagag atgtgtctca agctgagttc  33840
tccgaactca acttgtgaca gatgcagatg gcgtagcaaa atgtctcagg atgattgcct  33900
tggagctaag ggtctgagag aagggaaatg ttaagctccc tctccttcct cctagttcta  33960
ttgagcagaa gggaaatctg gaggtgagga gatcacatta tgaagaaagt cagaatgaca  34020
aaggaccaga cacttagatt acccttccac aacaccaact aaacgtcaat ggagactttc  34080
cagttggaat tccgttattc tggcttccac ttcctgaagg gaaggttgcg tttgcctttt  34140
ctctctgggt tcaagaggaa agaataggtg cttatttatg gacaggtgaa ttgatctgtt  34200
tctatatcta cgtatattcc gattgtcaga aaaacactcg ttcctaagta ccagtggcct  34260
gaagggatac aggttcccag caagagaaga tccaaggaag gaaggcagat gagagccagc  34320
acagagaggg atgctgaaaa gtaaaaggga tgggtggatg gagagaagcc cgggtctgac  34380
cacccaatgg ccaatatttt ggccacaagc gactaccaga gacatggaaa aatggtttct  34440
acatgtggga caacagatgg tagaggacct agagaattga gagaggggca atgatgggct  34500
ccactccgca gatgccttgg ctttcttcct ggataccctt cctgcactga atagcaagga  34560
gatggagccc aagcagactg tagccatctt gctgaatgga ggagagggat tggagtttgg  34620
gatgactgtg gtagctgaaa tttttctagg tctgctagaa ataagaactg gtttgtggag  34680
gaaaagagct ctacaaatac gcatagaagt ctcctccagt cgttggcctg acatgacgct  34740
gcctgtgcac aggaaatggt tccacgagaa agtgtggcaa agaacattta ctgagaaaca  34800
gcaagtacaa gagcacagga agctcaataa agaagagaga gatcacatag cactctggga  34860
tactggagtt cttcccagct agaccagaga gtcctcacgg agcacattgc caattcagtg  34920
gagaccccag aacagccgta atttaaaggt acacttagta tattactaga ataaagtcag  34980
ctgcagacaa ccccttgcac agctggaaag caagtgtcca agcatcaaat cggtttccaa  35040
tcaatgaagt gcctgtggga ggaaatctca actctcttta gaagtaaaca acaaagtcga  35100
ttgcctcagc tatgcggtat ccgcagagtg agtcctaaat ttaaaatctg actacatgta  35160
gaaaagcgtt tcgtgtgacc catgaccagg aaataaatcg ggtaatacaa acaggctcag  35220
gaatgagaga aatgattaga attgcgtgaa aatttgacat atcagtatga taactgattt  35280
caaatattta aaaaaacaac atgcaagaaa gcagatatca tatcaagaga aattaacagt  35340
acagaatagc caaattaaat taaagagcta gtataaaaaa agtatgtctt aattgaaaaa  35400
aattactgta tggccggctg atcaaattag acgtttcaga ggaaaacatt acccaacaca  35460
caattctaga gaacctacag aatgagctac acacacacac acacacacac acacacacac  35520
tgaaaacaca cccatactca cacacacgca gaaactcaca agttctaaca cacacagaca  35580
cgcgcacccc tgaagaaaca gtgaaatata aaattaagcg agcctcacag acatgtagga  35640
aaatatgaaa agatttcctg catgtgggaa gcaagtcaca gtaaagagca agggagtttg  35700
gaatagaaac aaataccgga atcaaggatg gctgataact tttcaattac gaagaacatt  35760
aaaaaaaatc acagaatcgt gaaactcaag ggatcatata gggaatttcg gaaaaaaaac  35820
ccaacctgta tgatgtactt ttgtacatca cagttcgaag gtaacaaggc aaagatataa  35880
taagaagaaa cctgtcacga gaaactggag gaaaaagagc tgtgtcttcc tacaagtaca  35940
```

ctgatacaaa ttgccaatgt gttcacctca gaaacactgg aagccagata ccagggaata 36000
ttgttaaaat gataatcagg aacaaaaaga gatcaaccgg gaatgctgaa tccagcaata 36060
aaatgccttg aagatcatcc atgtcggata aatgcatatt gtgcactgcc ccaaagaaag 36120
aaaccggaaa ctgtcagaat tggaaatcag caggcttatg taacaagaga ggtgacccga 36180
aggaattagg tagaagaaga attgaacaag aaaggaactt tctgcagccc acgtaatgaa 36240
gaatccagca attggcaaat gtagatagat gtaaatgcaa aatattttct tgatcaaatt 36300
tctatatctt tgtaaatgag agttgactac ttgaaacaaa atgatagcaa gatatttaac 36360
ttcagcatat gtagaggtaa gaatttgaaa tggtagcata aatcacgaag ggattaattc 36420
gaagtgtacc gttgtaagtt tctttacctc atgcacgatg gtgtgtcata ttaataaaag 36480
ggtactgtgc gggttcgaag ggatattgca aatcctagag caatcacaaa ggtttgaact 36540
ctgaggtttt tggtataata agaatagtcc atgcattcaa aagagggaag ccaaggaaga 36600
actagaagtc tttcaagagc tcaggctctt atacatccag ttgctcattg aaccagcttc 36660
ctggaatgga gggtctgggg ttgagactag gccacaagtc tagagtctct agagagacag 36720
tgttggaacc ccatggccca taatacattt cccattttct caggcagcca gaggtcatga 36780
atgtgaggat actgggaggt tggagcaacg ttcttgggag gcataaggaa gagcgaatgc 36840
ttcaagatcc ccgcagccca aactactcgc ctgctttgcc ccctaatgca tttttctctg 36900
ctgctccgta gctgtccgac ctcttcagat ctcttagtcc accctgccgt cttcctttat 36960
gccatgggtc ccattgttct ttcaactcat ccccctttcc ctcagtcccg gagtagctgc 37020
ggccagcaga gggtagactg agagcaggag agaaggacct gcctaggaac cccttctaga 37080
gatactgcat cctgcctggg agcaagtttt ccagggcagc tttgagaagt cttggagaaa 37140
caaacctact aaacctgaca gacagtaata ctatttgcac aatgcttttc tgtgggaaag 37200
gtagagcctt ttcactacgt attgagtaca tagagtgtga gggttgacct ggaacggcta 37260
tcctcctgga tgacgtgcgt tttctgaaga actacatgtt cgttgcaact cccacattag 37320
aatatgaagt cctaccgaga gagatacgga gactagacag atacagatgc atttgcatgt 37380
gaatacacaa tcccacaata cagacgtcaa aacccatacc agttattcca gagagatgga 37440
ttgggcagaa ggcagaagga gaatactctg atcgtttttc ggccacgtgt gtgtgttatc 37500
tcagtgtttc taagaagcgt ttgctacttt agatttttta tttaaaaaaa atagtaataa 37560
tctattaagt atgagagatg tgcagagagg attagtgatc gagagccatt tttgctggtg 37620
gcaatcatat ggtactttta atgggaatat tagaaaggca ccggtaatga ccttgttgca 37680
gcacaaagga gagagtgtgg ggtgcccctg catgttgtcc cacctcttgt gacgtgtatc 37740
gttttggaat ttccagtggc ttgatcatga actactgcag gaatccagat gctgtggcag 37800
ctccttattg ttatacgagg gatcccggtg tcaggtggga gtactgcaac ctgacgcaat 37860
gctcagacgc agaagggact gccgtcgcgc ctccgactgt taccccggtt ccaagcctag 37920
aggctccttc cgaacaaggt aaggagtctg tggccagaca tctacacgct tcgatgctgg 37980
gatgaaaagc catggaaatt cccactgatg cagccgcctt caatggtaaa cggatgctcg 38040
agtgttgcct gagttctacc atgtaggagg aagcctccgt gcactctctg ggggagccag 38100
cggagtgatt tctggtgcaa cgtggttggg ctttgtcttt aggatgggca caaaccctcc 38160
agggggatcg acttcaaaat tcaccttgtt gtaaaacggg ctacctcagt gtcccagcca 38220
aaatttttat tgtaacatgc tgtcaggtgt gtcactcttt ccaagccagt aagcttttcc 38280
ggggatttct tcaagtagcc agcattcaga gcaatcttca gcattgcaga ttctgagaaa 38340
tgtggctctg gagcctgtca ccctcgagaa acctaagagg gctgcattga ttccatgtgg 38400
ccctgggtct atggagcagt acatgagctc ccagtgctct aaggctcttc agccctaggc 38460
tttgaaggga gtgatttctc agtattctta aacctctttc tgatgacact tgtacctgtg 38520
aggggtctag agagaaagag tagtagactc ctactttact acaattcagg atgcagggca 38580
tgagaggatt ccctctctcc tccaagggaa gaagcttttg gcgtgcacac atccctgaga 38640
agcaaagtgt ctttgtcttc agtcagatac ataggaccgt tttctgcccc atggcccgga 38700
agccaaaggc cttggctttc atgatcaacg gtctagggaa acatgcaaaa tttccatgtc 38760
tgtcccaaac tctgccccg acagccaatt accacctgca gcccgcattg ccaaatgcgg 38820
tgccgtttgc atgaagattc agtagagttt cctagaaagg tgctacctcg tgagctcact 38880
ttccaatgag gaatctgatc tgttgtgttt ctctaaggtg tcaggtgaaa tatttccaag 38940
aacttactac agttctagaa tgggaggaat ctgttgcttt ggtgtttgtt tgttggtcgg 39000
ttttctcaca tccatctgcc tatggataag gaaaagagaa cggtcgtaat tctcatagac 39060
tcctttctgg ttgtgtcaca aatggcttca catgtttctc tatgctcaga gatactcagc 39120
ttgatttccc gtgttttcat ttcagcaccg actgagcaaa ggcctggggt gcaggagtgc 39180
taccatggta atggacagag ttatcgaggc acatactcca ccactgtcac aggaagaacc 39240
tgccaagctt ggtcatctat gacaccacac tcgcatagtc ggaccccaga atactaccca 39300
aatgcgtatg tctttgttct ttaccataag agaagaaagg gccaagtgaa gtttctgtta 39360
caagagatgt gtctcaagct gagttctccg aactcaactt gtgacagatg cagatggcgt 39420
agcaaaatgt ctcaggatga ttgccttgga gctaagggtc tgagagaagg gaaatgttaa 39480
gctccctctc cttcctccta gttctattga gcagaaggga aatctggagg tgaggagatc 39540
acattatgaa gaaagtcaga atgacaaagg accagacact tagattaccc ttccacaaca 39600
ccaactaaac gtcaatggag actttccagt tggaattccg ttattctggc ttccacttcc 39660
tgaagggaag gttgcgtttg ccttttctct ctgggttcaa gaggaaagaa taggtgctta 39720
tttatggaca ggtgaattga tctgtttcta tatctacgta tattccgatt gtcagaaaaa 39780
cactcgttcc taagtaccag tggcctgaag ggatacaggt tcccagcaag agaagatcca 39840
aggaaggaag gcagatgaga gtcagcacag agagggatgc tgaaaagtaa aagggatggg 39900
tggatggaga gaagcccggg tctgaccacc caatggccaa tattttggcc acaagcgact 39960
accagagaca tggaaaaatg gtttctacat gtgggacaac agatggtaga ggacctagag 40020
aattgagaga ggggcaatga tgggctccac tccgcagatg ccttggcttt cttcctggat 40080
acccttcctg cactgaatag caaggagatg gagcccaagc agactgtagc catcttgctg 40140
aatggaggag agggattgga gtttgggatg actgtggtag ctgaaatttt tctaggtctg 40200
ctagaaataa gaactggttt gtggaggaaa agagctctac aaatacgcat agaagtctcc 40260
tccagtcgtt ggcctgacat gacgctgcct gtgcacagga aatggttcca cgagaaagtg 40320
tggcaaagaa catttactga gaaacagcaa gtacaagagc acaggaagct caataaagaa 40380
gagagagatc acatagcact ctgggatact ggagttcttc ccagctagac cagagagtcc 40440
tcacggagca cattgccaat tcagtggaga ccccagaaca gccgtaattt aaaggtacac 40500
ttagtatatt actagaataa agtcagctgc agacaacccc ttgcacagct ggaaagcaag 40560
tgtccaagca tcaaatcggt ttccaatcaa tgaagtgcct gtgagaggaa atctcaactc 40620
tctttagaag taaacaacaa agtcgattgc ctcagctatg cggtatccgc agagtgagtc 40680

-continued

```
ctaaatttaa aatctgacta catgtagaaa agcgtttcgt gtgacccatg accaggaaat  40740
aaatcgggta atacaaacag gctcaggaat gagagaaatg attagaattg cgtgaaaatt  40800
tgaaatatca gtatgataac tgatttcaaa tatttaaaaa aacaacatgc aagaaagcag  40860
atatcatatc aagagaaatt aacagtacag aatagccaaa ttaaattaaa gagctagtat  40920
aaaaaaagta tgtcttaatt gaaaaaaatt actgtatggc cggctgatca atttagacgt  40980
ttcagaggaa aacattaccc aacacacaat tctagagaac ctacagaatg agctacacac  41040
acacacacac acacacacac aaactgaaaa cacacccata ctcacacaca cgcagaaact  41100
cacaagttct aacacacaca gacacgcgca cccctgaaga aacagtgaaa tataaaatta  41160
agcgagcctc acagacatgt aggaaaatat gaaaagattt cctgcatgtg ggaagcaagt  41220
cacagtaaag agcaagggag tttggaatag aaacaaatac cagaatcaag gatggctgat  41280
aacttttcaa ttacgaagaa cattaaaaaa aatcacagaa tcgtgaaact caagggatca  41340
catagggaat ttcggaaaaa aaacccaacc tgtatgatgt acttttgtac atcacagttc  41400
gaaggtaaca aggcaaagat ataataagaa gaaacctgtc acgagaaact ggaggaaaaa  41460
gagctgtgtc ttcctacaag tacactgata caaattgcca atgtgttcac ctcagaaaca  41520
ctggaagcca gataccaggg aatattgtta aaatgataat caggaacaaa aagagatcaa  41580
ccgggaatgc tgaatccagc aataaaatgc cttgaagatc atccatgtcg gataaatgca  41640
tattgtgcac tgccccaaag aaagaaaccg gaaactgtaa gaattggaaa tcagcaggct  41700
tatgtaacaa gagaggtgac ccgaaggaat taggtagaag aagaattgaa caagaaagga  41760
actttctgca gcccacgtaa tgaagaatcc agcaattggc aaatgtagat agatgtaaat  41820
gcaaaatatt ttcttgatca aatttctata tctttgtaaa tgagagttga ctacttgaaa  41880
caaaatgata gcaagatatt taacttcagc atatgtagag gtaagaattt gaaatggtag  41940
cataaatcac gaagggatta attcgaagtg taccgttgta agtttcttta cctcatgcac  42000
gatggtgtgt catattaata aaagggtact gtgcgggttc gaagggatat tgcaaatcct  42060
agagcaatca caaaggtttg aactctgagg tttttggtat aataagaata gtccatgcat  42120
tcaaaagagg gaagccaagg aagaactaga agtctttcaa gagctcaggc tcttatacat  42180
ccagttgctc attgaaccag cttcctggaa tggagggtct ggggttgaga ctaggccaca  42240
agtctagagt ctctagagag acagtgttgg aaccccatgg cccataatac atttcccatt  42300
ttctcaggca gccagaggtc atgaatgtga ggatactggg aggttggagc aacgttcttg  42360
ggaggcataa ggaagagcga atgcttcaag atccccgcag cccaaactac tcgcctgctt  42420
tgccccctaa tgcatttttc tctgctgctc cgtagctgtc cgacctcttc agatctctta  42480
gtccaccctg ccgtcttcct ttatgccatg ggtcccactg ttctttcaac tcatccccct  42540
ttccctcagt cccggagtag ctgcggccag cagagggtag actgagagca ggagagaagg  42600
acctgcctag gaaccccttc tagagatact gcatcctgcc tgggagcaag ttttccaggg  42660
cagctttgag aagtcttgga gaaacaaacc tactaaacct gacagacagt aatactattt  42720
gcacaatgct tttctgtggg aaaggtagag ccttttcact acgtattgag tacatagagt  42780
gtgagggttg acctggaacg gctatcctcc tggatgacgt gtgttttctg aagaactaca  42840
tgttcgttgc aactcccaca ttagaaatatg aagtcctacc gagagagata cggagactag  42900
acagatacag atgcatttgc atgtgaatac acaatcccac aatacagacg tcaaaaccca  42960
taccagttat tccagagaga tggattgggc agaaggcaga aggagaatac tctgatcgtt  43020
```

```
tttcggccac gtgtgtgtgt tatctcagtg tttctaagaa gcgtttgcta ctttagattt  43080
tttatttaaa aaaaatagta ataatctatt aagtatgaga gatgtgcaga gaggattagt  43140
gatcgagagc catttttgct ggtggcaatc atatggtact tttaatggga atattagaaa  43200
ggcaccggta atgaccttgt tgcagcacaa aggagagagt gtggggtgcc cctgcatgtt  43260
gtcccacctc ttgtgacgtg tatcgttttg gaatttccag tggcttgatc atgaactact  43320
gcaggaatcc agatgctgtg gcagctcctt attgttatac gagggatccc ggtgtcaggt  43380
gggagtactg caacctgacg caatgctcag acgcagaagg gactgccgtc gcgcctccga  43440
ctgttacccc ggttccaagc ctagaggctc cttccgaaca aggtaaggag tctgtggcca  43500
gacatctaca cgcttcgatg ctgggatgaa aagccatgga aattcccact gatgcagccg  43560
ccttcaatgg taaacggatg ctcgagtgtt gcctgagttc taccatgtag gaggaagcct  43620
ccgtgcactc tctgggggag ccagcggagt gatttctggt gcaacgtggt tgggctttgt  43680
ctttaggatg ggcacaaacc ctccaggggg atcgacttca aaattcacct tgttgtaaaa  43740
cgggctacct cagtgtccca gccaaaattt ttattgtaac atgctgtcag gtgtgtcact  43800
ctttccaagc cagtaagctt ttccggggat ttcttcaagt agccagcatt cagagcaatc  43860
ttcagcattg cagattctga gaaatgtggc tctggagcct gtcaccctcg agaaacctaa  43920
gagggctgca ttgattccat gtggccctgg gtctatggag cagtacatga gctcccagtg  43980
ctctaaggct cttcagccct aggctttgaa gggagtgatt tctcagtatt cttaaacctc  44040
tttctgatga cacttgtacc tgtgaggggt ctagagagaa agagtagtag actcctactt  44100
tactacaatt caggatgcag ggcatgagag gattccctct ctcctccaag ggaagaagct  44160
tttggcgtgc acacatccct gagaagcaaa gtgtctttgt cttcagtcag atacatagga  44220
ccgttttctg ccccatggcc cggaagccaa aggccttggc tttcatgatc aacggtctag  44280
ggaaacatgc aaaatttcca tgtctgtccc aaactcttcc cccgacagcc aattaccacc  44340
tgcagcccgc attgccaaat gcggtgccgt ttgcatgaag attcagtaga gtttcctaga  44400
aaggtgctac ctcgtgagct cactttccaa tgaggaatct gatctgttgt gtttctctaa  44460
ggtgtcaggt gaaatatttc caagaactta ctacagttct agaatgggag gaatctgttg  44520
ctttggtgtt tgtttgttgg tcggttttct cacatccatc tgcctatgga taaggaaaag  44580
agaacggtcg taattctcat agactccttt ctggttgtgt cacaaatggc ttcacatgtt  44640
tctctatgct cagagatact cagcttgatt tcccgtgttt tcatttcagc accgactgag  44700
caaaggcctg ggtgcagga gtgctaccat ggtaatggac agagttatcg aggcacatac  44760
tccaccactg tcacaggaag aacctgccaa gcttggtcat ctatgacacc acactcgcat  44820
agtcggaccc cagaatacta cccaaatgcg tatgtctttg ttctttacca taagagaaga  44880
aagggccaag tgaagtttct gttacaagag atgtgtctca agctgagttc tccgaactca  44940
acttgtgaca gatgcagatg gcgtagcaaa atgtctcagg atgattgcct tggagctaag  45000
ggtctgagag aagggaaatg ttaagctccc tctccttcct cctagttcta ttgagcagaa  45060
gggaaatctg gaggtgagaa gatcacatta tgaagaaagt cagaatgaca aaggaccaga  45120
cacttagatt acccttccac aacaccaact aaacgtcaat ggagactttc cagttggaat  45180
tccgttattc tggcttccac ttcctgaagg gaaggttgcg tttgcctttt ctctctgggt  45240
tcaagaggaa agaataggtg cttatttatg gacaggtgaa ttgatctgtt tctatatcta  45300
cgtatattcc gattgtcaga aaaacactcg ttcctaagta ccagtggcct gaagggatac  45360
aggttcccag caagagaaga tccaaggaag gaaggcagat gagagtcagc acagagaggg  45420
```

atgctgaaaa gtaaaaggga tgggtggatg gagagaagcc cgggtctgac cacccaatgg 45480
ccaatatttt ggccacaagc gactaccaga gacatggaaa aatggtttct acatgtggga 45540
caacagatgg tagaggacct agagaattga gagaggggca atgatgggct ccactccgca 45600
gatgccttgg ctttcttcct ggataccctt cctgcactga atagcaagga gatggagccc 45660
aagcagactg tagccatctt gctgaatgga ggagagggat tggagtttgg gatgactgtg 45720
gtagctgaaa tttttctagg tctgctagaa ataagaactg gtttgtgtgg aggaaaagag 45780
ctctacaaat acgcatagaa gtctcctcca gtcgttggcc tgacatgacg ctgcctgtgc 45840
acaggaaatg gttccacgag aaagtgtggc aaagaacatt tactgagaaa cagcaagtac 45900
aagagcacag gaagctcaat aaagaagaga gagatcacat agcactctgg gatactggag 45960
ttcttcccag ctagaccaga gagtcctcac ggagcacatt gccaattcag tggagacccc 46020
agaacagccg taatttaaag gtacacttag tatattacta gaataaagtc agctgcagac 46080
aaccccttgc acagctggaa agcaagtgtc caagcatcaa atcggtttcc aatcaatgaa 46140
gtgcctgtga gaggaaatct caactctctt tagaagtaaa caacaaagtc gattgcctca 46200
gctatgcggt atccgcagag tgagtcctaa atttaaaatc tgactacatg tagaaaagcg 46260
tttcgtgtga cccatgacca ggaaataaat cgggtaatac aaacaggctc aggaatgaga 46320
gaaatgatta gaattgcgtg aaaatttgac atatcagtat gataactgat ttcaaatatt 46380
taaaaaaaca acatgcaaga aagcagatat catatcaaga gaaattaaca gtacagaata 46440
gccaaattaa attaaagagg tagtataaaa aaagtatgtc ttaattgaaa aaaattactg 46500
tatggccggc tgatcaattt agacgtttca gaggaaaaca ttacccaaca cacaattcta 46560
gagaacctac agaatgagct acacacacac acacacacac acacacaaac tgaaaacaca 46620
cccatactca cacacacgca gaaactcaca agttctaaca cacacagaca cgcgcacccc 46680
tgaagaaaca gtgaaatata aaattaagcg agcctcacag acatgtagga aaatatgaaa 46740
agatttcctg catgtgggaa gcaagtcaca gtaaagagca agggagtttg gaatagaaac 46800
aaataccgga atcaaggatg gctgataact tttcaattac gaagaacatt aaaaaaaatc 46860
acagaatcgt gaaactcaag ggatcacata gggaatttcg gaaaaaaaac ccaacctgta 46920
tgatgtactt ttgtacatca cagttcgaag gtaacaaggc aaagatataa taagaagaaa 46980
cctgtcacga gaaactggag gaaaaagagc tgtgtcttcc tacaagtaca ctgatacaaa 47040
ttgccaatgt gttcacctca gaaacactgg aagccagata ccagggaata ttgttaaaat 47100
gataatcagg aacaaaaaga gatcaaccgg gaatgctgaa tccagcaata aaatgccttg 47160
aaggtcatcc atgtcggata aatgcatatt gtgcactgcc ccaaagaaag aaaccggaaa 47220
ctgtaagaat tggaaatcag caggcttatg taacaagaga ggtgacccga aggaattagg 47280
tagaagaaga attgaacaag aaaggaactt tctgcagccc acgtaatgaa gaatccagca 47340
attggcaaat gtagatagat gtaaatgcaa aatattttct tgatcaaatt tctatatctt 47400
tgtaaatgag agttgactac ttgaaacaaa atgatagcaa gatatttaac ttcagcatat 47460
gtagaggtaa gaatttgaaa tggtagcata aatcacgaag ggattaattc gaagtgtacc 47520
gttgtaagtt tctttacctc atgcacgatg gtgtgtcata ttaataaaag ggtactgtgc 47580
gggttcgaag ggatattgca aatcctagag caatcacaaa ggtttgaact ctgaggtttt 47640
tggtataata agaatagtcc atgcattcaa aagagggaag ccaaggaaga actagaagtc 47700
tttcaagagc tcaggctctt atacatccag ttgctcattg aaccagcttc ctggaatgga 47760

-continued

```
gggtctgggg ttgagactag gccacaagtc tagagtctct agagagacag tgttggaacc  47820
ccatggccca taatacattt cccattttct caggcagcca gaggtcatga atgtgaggat  47880
actgggaggt tggagcaacg ttcttgggag gcataaggaa gagcgaatgc ttcaagatcc  47940
ccgcagccca aactactcgc ctgctttgcc ccctaatgca tttttctctg ctgctccgta  48000
gctgtccgac ctcttcagat ctcttagtcc accctgccgt cttcctttat gccatgggtc  48060
ccactgttct ttcaactcat cccccttttcc ctcagtcccg gagtagctgc ggccagcaga  48120
gggtagactg agagcaggag agaaggacct gcctaggaac cccttctaga gatactgcat  48180
cctgcctggg agcaagtttt ccagggcagc tttgagaagt cttggagaaa caaacctact  48240
aaacctgaca gacagtaata ctatttgcac aatgcttttc tgtgggaaag gtagagcctt  48300
ttcactacgt attgagtaca tagagtgtga gggttgacct ggaacggcta tcctcctgga  48360
tgacgtgcgt tttctgaaga actacatgtt cgttgcaact cccacattag aatatgaagt  48420
cctaccgaga gagatacgga gactagacag atacagatgc atttgcatgt gaatacacaa  48480
tcccacaata cagacgtcaa aacccatacc agttattcca gagagatgga ttgggcagaa  48540
ggcagaagga gaatactctg atcgtttttc ggccacgtgt gtgtgttatc tcagtgtttc  48600
taagaagcgt ttgctacttt agattttttta tttaaaaaaa atagtaataa tctattaagt  48660
atgagagatg tgcagagagg attagtgatc gagagccatt tttgctggtg gcaatcatat  48720
ggtactttta atgggaatat tagaaaggca ccggtaatga ccttgttgca gcacaaagga  48780
gagagtgtgg ggtgcccctg catgttgtcc cacctcttgt gacgtgtatc gttttggaat  48840
ttccagtggc ttgatcatga actactgcag gaatccagat gctgtggcag ctccttattg  48900
ttatacgagg gatcccggtg tcaggtggga gtactgcaac ctgacgcaat gctcagacgc  48960
agaagggact gccgtcgcgc ctccgactgt taccccggtt ccaagcctag aggctccttc  49020
cgaacaaggt aaggagtctg tggccagaca tctacacgct tcgatgctgg gatgaaaagc  49080
catggaaatt cccactgatg cagccgcctt caatggtaaa cggatgctcg agtgttgcct  49140
gagttctacc atgtaggagg aagcctccgt gcactctctg gggggagccag cggagtgatt  49200
tctggtgcaa cgtggttggg ctttgtcttt aggatgggca caaaccctcc agggggatcg  49260
acttcaaaat tcaccttgtt gtaaaacggg ctacctcagt gtcccagcca aaatttttat  49320
tgtaacatgc tgtcaggtgt gtcactcttt ccaagccagt aagcttttcc ggggatttct  49380
tcaagtagcc agcattcaga gcaatcttca gcattgcaga ttctgagaaa tgtggctctg  49440
gagcctgtca ccctcgagaa acctaagagg gctgcattga ttccatgtgg ccctgggtct  49500
atggagcagt acatgagctc ccagtgctct aaggctcttc agccctaggc tttgaaggga  49560
gtgatttctc agtattctta aacctctttc tgatgacact tgtacctgtg aggggtctag  49620
agagaaagag tagtagactc ctactttact acaattcagg atgcagggca tgagaggatt  49680
ccctctctcc tccaagggaa gaagcttttg gcgtgcacac atccctgaga agcaaagtgt  49740
ctttgtcttc agtcagatac ataggaccgt tttctgcccc atggcccgga agccaaaggc  49800
cttggctttc atgatcaacg gtctagggaa acatgcaaaa tttccatgtc tgtcccaaac  49860
tctgcccccg acagccaatt accacctgca gcccgcattg ccaaatgcgg tgccgtttgc  49920
atgaagattc agtagagttt cctagaaagg tgctacctcg tgagctcact ttccaatgag  49980
gaatctgatc tgttgtgttt ctctaaggtg tcaggtgaaa tatttccaag aacttactac  50040
agttctagaa tgggaggaat ctgttgcttt ggtgtttgtt tgttggtcgg ttttctcaca  50100
tccatctgcc tatggataag gaaaagagaa cggtcgtaat tctcatagac tcctttctgg  50160
```

ttgtgtcaca aatggcttca catgtttctc tatgctcaga gatactcagc ttgatttccc 50220
gtgttttcat ttcagcaccg actgagcaaa ggcctggggt gcaggagtgc taccatggta 50280
atggacagag ttatcgaggc acatactcca ccactgtcac aggaagaacc tgccaagctt 50340
ggtcatctat gacaccacac tcgcatagtc ggaccccaga atactaccca aatgcgtatg 50400
tctttgttct ttaccataag agaagaaagg gccaagtgaa gtttctgtta caagagatgt 50460
gtctcaagct gagttctccg aactcaactt gtgacagatg cagatggcgt agcaaaatgt 50520
ctcaggatga ttgccttgga gctaagggtc tgagagaagg gaaatgttaa gctccctctc 50580
cttcctccta gttctattga gcagaaggga aatctggagg tgaggagatc acattatgaa 50640
gaaagtcaga atgacaaagg accagacact tagattaccc ttccacaaca ccaactaaac 50700
gtcaatggag actttccagt tggaattccg ttattctggc ttccacttcc tgaagggaag 50760
gttgcgtttg ccttttctct ctgggttcaa gaggaaagaa taggtgctta tttatggaca 50820
ggtgaattga tctgtttcta tatctacgta tattccgatt gtcagaaaaa cactcgttcc 50880
taagtaccag tggcctgaag ggatacaggt tcccagcaag agaagatcca aggaaggaag 50940
gcagatgaga gtcagcacag agagggatgc tgaaaagtaa aagggatggg tggatggaga 51000
gaagcccggg tctgaccacc caatggccaa tattttggcc acaagcgact accagagaca 51060
tggaaaaatg gtttctacat gtgggacaac agatggtaga ggacctagag aattgagaga 51120
ggggcaatga tgggctccac tccgcagatg ccttggcttt cttcctggat acccttcctg 51180
cactgaatag caaggagatg gagcccaagc agactgtagc catcttgctg aatggaggag 51240
agggattgga gtttgggatg actgtggtag ctgaaatttt tctaggtctg ctagaaataa 51300
gaactggttt gtgtggagga aaagagctct acaaatacgc atagaagtct cctccagtcg 51360
ttggcctgac atgacgctgc ctgtgcacag gaaatggttc cacgagaaag tgtggcaaag 51420
aacatttact gagaaacagc aagtacaaga gcacaggaag ctcaataaag aagagagaga 51480
tcacatagca ctctgggata ctggagttct tcccagctag accagagagt cctcacggag 51540
cacattgcca attcagtgga gaccccagaa cagccgtaat ttaaaggtac acttagaata 51600
ttactagaat aaagtcagct gcagacaacc ccttgcacag ctggaaagca agtgtccaag 51660
catcaaatcg gtttccaatc aatgaagtgc ctgtgagagg aaatctcaac tctctttaga 51720
agtaaacaac aaagtcgatt gcctcagcta tgcggtatcc gcagagtgag tcctaaattt 51780
aaaatctgac tacatgtaga aaagcgtttc gtgtgaccca tgaccaggaa ataaatcggg 51840
taatacaaac aggctcagga atgagagaaa tgattagaat tgcgtgaaaa tttgacatat 51900
cagtatgata actgatttca aatatttaaa aaaacaacat gcaagaaagc agatatcata 51960
tcaagagaaa ttaacagtac agaatagcca aattaaatta aagagctagt ataaaaaaag 52020
tatgtcttaa ttgaaaaaaa ttactgtatg gccggctgat caaattagac gtttcagagg 52080
aaaacattac ccaacacaca attttagaga acctacagaa tgagctacac acacacacac 52140
acacacacac acacacacaa actgaaaaca cacccatact cacacacacg cagaaactca 52200
caagttctaa cacacacaga cacgcgcacc cctgaagaaa cagtgaaata taaaattaag 52260
cgagcctcac agacatgtag gaaaatatga aaagatttcc tgcatgtggg aagcaagtca 52320
cagtaaagag caagggagtt tataatagaa acaaatacca gaatcaagga tggctgataa 52380
cttttcaatt acgaagaaca ttaaaaaaaa tcacagaatc gtgaaactca agggatcata 52440
tagggaattt cggaaaaaaa acccaacctg tatgatgtac ttttgtacat cacagttcga 52500

-continued

```
aggtaacaag gcaaagatgt aataagaaga aacctgtcac gagaaactgg aggaaaaaga  52560
gctgtgtctt cctacaagta cactgataca aattgccaat gtgttcacct cagaaacact  52620
ggaagccaga taccagggaa tattgttaaa atgataatca ggaacaaaaa gagatcaacc  52680
gggaatgctg aatccagcaa taaaatgcct tgaaggtcat ccatgtcgga taaatgcata  52740
ttgtgcactg ccccaaagaa agaaaccgga aactgtaaga attggaaatc agcaggctta  52800
tgtaacaaga gaggtgaccc gaaggaatta ggtagaagaa gaattgaaca agaaaggaac  52860
tttctgcagc ccacgtaatg aagaatccag caattggcaa atgtagatag atgtaaatgc  52920
aaaatatttt cttgatcaaa tttctatatc tttgtaaatg agagttgact acttgaaaca  52980
aaatgatagc aagatattta acttcagcat atgtagaggt aagaatttga aatggtagca  53040
taaatcacga agggattaat tcgaagtgta ccgttgtaag tttctttacc tcatgcacga  53100
tggtgtgtca tattaataaa agggtactgt gcgggttcga agggatattg caaatcctag  53160
agcaatcaca aaggtttgaa ctctgaggtt tttggtataa taagaatagt ccatgcattc  53220
aaaagaggga agccaaggaa gaactagaag tctttcaaga gctcaggctc ttatacatcc  53280
agttgctcat tgaaccagct tcctggaatg gagggtctgg ggttgagact aggccacaag  53340
tctagagtct ctagagagac agtgttggaa ccccatggcc cataatacat ttcccatttt  53400
ctcaggcagc cagaggtcat gaatgtgagg atactgggag gttggagcaa cgttcttggg  53460
aggcataagg aagagcgaat gcttcaagat ccccgcagcc caaactactc gcctgctttg  53520
cccccctaatg catttttctc tgctgctccg tagctgtccg acctcttcag atctcttagt  53580
ccaccctgcc gtcttccttt atgccatggg tcccactgtt ctttcaactc atccccccttt  53640
ccctcagtcc cggagtagct gcggccagca gagggtagac tgagagcagg agagaaggac  53700
ctgcctagga acccccttcta gagatactgc atcctgcctg ggagcaagtt ttccagggca  53760
gctttgagaa gtcttggaga aacaaaccta ctaaacctga cagacagtaa tactatttgc  53820
acaatgcttt tctgtgggaa aggtagagcc ttttcactac gtattgagta catagagtgt  53880
gagggttgac ctggaacggc tatcctcctg gatgacgtgc gttttctgaa gaactacatg  53940
ttcgttgcaa ctcccacatt agaatatgaa gtcctaccga gagagatacg gagactagac  54000
agatacagat gcatttgcat gtgaatacac aatcccacaa tacagacgtc aaaacccata  54060
ccagttattc cagagagatg gattgggcag aaggcagaag gagaatactc tgatcgtttt  54120
tcggccacgt gtgtgtgtta tctcagtgtt tctaagaagc gtttgctact ttagattttt  54180
tatttaaaaa aaatagtaat aatctattaa gtatgagaga tgtgcagaga cgattagtga  54240
tcgagagcca tttttgctgg tggcaatcat atggtacttt taatgggaat attagaaagg  54300
caccggtaat gaccttgttg cagcacaaag gagagagtgt ggggtgcccc tgcatgttgt  54360
cccacctctt gtgacgtgta tcgttttgga atttccagtg gcttgatcat gaactactgc  54420
aggaatccag atgctgtggc agctccttat tgttatacga gggatcccgg tgtcaggtgg  54480
gagtactgca acctgacgca atgctcagac gcagaaggga ctgccgtcgc gcctccgact  54540
gttaccccgg ttccaagcct agaggctcct tccgaacaag gtaaggagtc tgtggccaga  54600
catctacacg cttcgatgct gggatgaaaa gccatggaaa ttcccactga tgcagccgcc  54660
ttcaatggta aacggatgct cgagtgttgc ctgagttcta ccatgtagga ggaagcctcc  54720
gtgcactctc tgggggagcc agcggagtga tttctggtgc aacgtggttg ggctttgtct  54780
ttaggatggg cacaaaccct ccagggggat cgacttcaaa attcaccttg ttgtaaaacg  54840
ggctacctca gtgtcccagc caaaattttt attgtaacat gctgtcaggt gtgtcactct  54900
```

-continued

```
ttccaagcca gtaagctttt ccggggattt cttcaagtag ccagcattca gagcaatctt  54960
cagcattgca gattctgaga aatgtggctc tggagcctgt catcctcgag aaacctaaca  55020
gggctgcatt aattccatat ggtcctgggt ctatggagca gtatatgagc tcccaatgct  55080
ctaaggctct tcagtcctag gctttgaagg gagtgatttc tcagtgttct taaacctctt  55140
tctgatggca cttgtacctg tgaggggtct agagagaaag gttagtagac ttctccttta  55200
ctgcaattca ggatgcaggg catgagaaga ttccctccct cctccaaggg aagaaggttt  55260
tggcgtgcac acatccttga gaagcaaagt gtctttgcct tcagtcagat atataggatc  55320
gttttctgcc ccatggcctg gaagccagag gccttggctt tcatgatcaa cgatctaggg  55380
aaacatgcaa aatttccatg tctttcccct cctctgccct cgacagccaa ttaccacctg  55440
catcctgcat tgccaaatgc agtgcccttt gtatgaacat tcagtagagt ttcatagaaa  55500
ggtgctactt cgtgagcgca ctttgcagtg agaaggagtc tgttctgttc tgtttttcta  55560
aggatttcag gtgaaatatt tcctagaact tactacagtt ctagattggt aggaatctgt  55620
aggtttgctg tatgtttttt ggttggtttt ctcccatcca tctgcctaca ggtaagggaa  55680
agataacgtt cataattctc atagactcct ttctggttgt gtcataaatg gcttcacata  55740
tttcgttatt ctcagagata ctcagtttat ttcttgtgtt ttcatttcag caccgactga  55800
gcagaggcct ggggtgcagg agtgctacca cggtaatgga cagagttatc gaggcacata  55860
ctccaccact gtcactggaa gaacctgcca agcttggtca tctatgacac cacactcgca  55920
tagtcggacc ccagaatact acccaaatgc gtatgtcttt gttctttacc ataagagaat  55980
aaagggccaa ctgaagtttc tgtgacaaga gacatgcttc aagctgagtt ctccgaactc  56040
aacttgtgtc agattcagat ggtgtagcaa aatgtctcag gatgatttcc ttggagctaa  56100
gggtctgaga gaagagaaat gttaagctgc ctcaccttcc tcctagtttt gtggagcaga  56160
agggaaatga ggaggcgagg agatcacctt atgaagaaag tcagaatgac gaaccaccaa  56220
acacttagat tacccttgcc caacacccac taagcgtcaa tgaagacttt ccagttggaa  56280
ttccgttatt ctgacttcca attcctgaag ggaagattgt gtttgccttt tctgtctggg  56340
ctcatgagga aagtttatgt gcttacttat ggacaggtga attgatctgt ttctatttct  56400
acctgtattc caatagggag aaaatctctt ggtcctaagt accagtggcc tgaaaggata  56460
gaggttccca gcaagagaag atccaaggaa ggaaggcaga tgagagtcag cacagagagg  56520
gatgctgaaa agtaaaaggg atgggtagat ggatagaagc cctggtctga ccacccccatg  56580
gccaatcatt tggccataat caacaaccaa agacatggaa aaatggtttc tacatgtggg  56640
acaacagatg gtagaggacc tagagaattg agagagggcc aatgatgagc tcaactccat  56700
agatgccttg gctttcttcc tggataccct tcctgcactg aatagcaagg agatggagct  56760
caagcagcct gtagccatct agctgagcag aggagaggga ttggagtttg ggatgactct  56820
ggtattttct aggtccgcta caaataagaa ctggtttgtg gaggaaagga gctctacaaa  56880
tacgcataga agtctcctcc agtagttggc ctcacatgac actgcatgtg cacagaaaat  56940
ggttctacag aaagtgtggc aaagaacatt tactgagaaa cagcaactac aagagaacag  57000
caagctcaat taagaagata gagatcacat agcactctgt gttattggag ttcttaccag  57060
ctagatgaga gagtgctcac ggaacacatt gccaattcag tggagacccc agaacagcca  57120
taatttcaaa gtacaattag tatattacta gaataaaggc agctgcagac aacccccttgc  57180
acagctgaaa agcaagtgtc caagcatcaa atgggtttcc aatcaatgaa gtgcctgtga  57240
```

gaggaaatct caactctctt cagaagtaaa caacaaagtc aattgcctca gctatgcggt 57300
atccccagag tgagtcctaa attaaaaatt tgactacgtg tagaaaagaa tttcgtgtga 57360
tccatgacca gaaaataaat caggcaatac aaacaggctc agaaatgaca tcgataatta 57420
gaattgcatg aaaatttgac atatcagtat gataactgat ttcagatatt taaaaaaagt 57480
gcaacaaagc aggtatcata tcaagacaaa ttaatagtat agaatagcca aatcaaatta 57540
aagaactatt atacaaaaag tatgtcttaa atgaagaaat tactgtatgt ccgcctgaaa 57600
aatttagatg tttcagaaga aaaaattaac caaaaacaat tctgcagaac ctacagaatg 57660
agccacacac acacacattc aaaacacacc catacacaca cacatgcaaa aactcacaag 57720
ttctaacaca cacacaaaca cacacacaca tgcacatccc taaagaaata gggaaatata 57780
aaattaaccg accctcagag acatgcagga aaatataaga agatttcctg catgtgggaa 57840
gcaagtcaca gtaaagagca agggagtttg gagtagatac aaataccgga atcacggatg 57900
gctgataact tttcaattat gaagaacgtt agaaaaatca cagattcatg aaactaaagg 57960
gatcaaatag gaaatttcga gaaaaaaaac tacatgatgc acttctctac atcacagttc 58020
aaaggtaaca aggcaaggat ataagaagaa gaaacatctc acgagaaact ggagaaaaaa 58080
gagctgtgtc ttcctagagt acagtgatac aaattgctaa tgcgttcacc tcagaaacac 58140
tggaagccag ataccaggga atattattaa aatgataatg aggaacaaga agagatcaac 58200
cgagaatgct gaatccagca ataaaatgcc ttgaagatca tccatgttgg ataaatgcat 58260
attgtgcact gcccaaaaca aagaaactgg aaagtgtaag actttggaat cagcaggctt 58320
atgtagcaac agaggtgacc cgaaagaatt aggtataaga agaatagaag aattgcatga 58380
aaatttgaca tatgactaag ataactattt caaatattta aaaaaagatg aatatgtaat 58440
aaaacagata aaatatcaaa agaaagtaac agtattgact agccaaatca aattaaagac 58500
ttagtgtaaa aagctatgtc ttaaaagaaa aaattactgg atggctgcct gatcaattta 58560
gacatttctg aataggaaac taaccaaaaa tcaattctac agaaccaact acacacatat 58620
atacacatac aacacaccca tacacaccca cgcaaaaact cacaagttca cacacacaca 58680
cacacacaca caaccctcaa gaaatagtga aatagaaaac caaccgaacc tcacagacat 58740
gttgcaaaat aggaaaagat ttcctgcata tgggaagcaa gtcacagaaa agagaacggg 58800
agattggaaa cagaaacaaa taccggaatc aaggatggcc gaaaactttt cattgatcaa 58860
gaatattaac aaaatcgcaa aaacacgaaa ttcaatgcat caaataggcg tttcgaaaaa 58920
aagaaaaaat ctggtatgat gcacttttgt acttcacatt ttcacggtaa gaagacaaag 58980
atataataac aagaaacttc ttatgagaaa ctggggaaaa acaagctgtt tcttgctaga 59040
agaacagtga tacaaattgc taatgcattc tcgtcaaaaa cactggaagc cagataccgg 59100
gaatgttatt aatgtggtaa acaggaacaa gaagagatca accaagaatg ctaaatccag 59160
caataaaatg ccttgaagat catccatgct gcataaatgt atgttgtgca ctgccccaaa 59220
caaagaaacc ggaaactgta agaatttgga atcagcaggc tgatgtaaca agagaggtga 59280
cccaaaggaa ttaggtagaa gaagaatagt acaagaaggg aactttctgc agcccatgta 59340
atgaagaacc cagcaattgg caaatgtaga tgtaaatgca aaatattttc ttgaccaaat 59400
ttctatatat ttttaaatga gcgttgacta ctggaaacaa aatgatagca atatatttaa 59460
ttttagcata tgtagaggta agaatttgaa caagtagcgt aaatcatgta gggaataatt 59520
agaagtgtac cattgtaagt ttcttacctc atgcacaatg gtatgtaata ttaataaaat 59580
gttactgtgt gggttcaagg agatattgca aatcctagag caatcacaaa gttttgaact 59640

-continued

```
ctgaggtata ttgtataata agaatattcc atgtattcaa aagagagaag ccaaggaaga  59700
aagaaatttg tcacgagttt gggctcttag tacatcctgt agctcattga accagcttcc  59760
tggaatggag ggtctgggat tgacactagg ccacatgtat agagtctcta gagagacagt  59820
gtttcatccc catggcccgt aatacatttc ccattttctc aggcagccac aggtcatgaa  59880
tgtgaggata gagagaggtt ggagcaacgt tcttgggagg cataaggaag agcaaatgct  59940
tcaagatccc cgcagcccaa actcctacct gctttgcccc ctaatgcagt gttcctccgt  60000
agctgtccga cctcttcaga tctcttagtc taccctgcca tcttccttta tgccatgggt  60060
cccactgttc tttcaactca tccccctttc cctcagtgca gagtagctgc ggccagcaga  60120
gggtagactg agagcaggag agaaggtcct gcccaggaac ccattctaga gatgctgcat  60180
tctgcctggg agcaagtttt ccagggcagc tttgagaagt cttgcagaaa caaacctatt  60240
tgacccacat gatatgggaa tgacagaaag taatacaatt tgcacagtgc ttttccatgg  60300
gaaaagtaga gccttttcgc gaggttttga gtacatagag agtgaaggtt gacctggaaa  60360
ggttatcctc ctggatccca tgttttttct gaagaactac ctgttagttg caacttgcac  60420
attagaatat gaagtcctac cgagagagat acggagaact agataaatac agatactttt  60480
gtatgtgaat aaacgattcc acaatacaca catcaaaatc cataccagtt attccagaga  60540
gatggattgg gcagaaggca gaaggagaat actctgatcg ttttttgccc acgtgtatgt  60600
attatctcag tgtttctaag aagcgtttgc tactttagat ttttttttat aataataatc  60660
ttttaagtat gagaaatgtg cagacaggat tagtgattga gagccatttg tgcttgtggc  60720
aatcatatgg tacttttatg ggaatattag aaaggcactg gtaatgacct tgttgcagca  60780
caaaggagag ggtgtggggt gcccctgcat attgtcccac ctcttgtgac gtgtatcgtt  60840
ttggaatttc cagtggcttg atcatgaact actgcaggaa tccagatcct gtggcagccc  60900
cttattgtta tacgagggat cccagtgtca ggtgggagta ctgcaacctg acacaatgct  60960
cagacgcaga agggactgcc gtcgcgcctc caactattac cccgattcca agcctagagg  61020
ctccttctga acaaggtaag gagcctgtgg ccagaaacct acacgtttcg atgctgggat  61080
gaaaagccat ggaaattccc actgatgcag cagcctccaa tggtaaacgg atgctcgagt  61140
gttgactgag ttctgtcatg taggaggaag cctccgtgca ctctctgggg gagccagcgg  61200
attgatttct ggtacaacgt tgggtgggct gtgtctttag aattggcaca aaccctccag  61260
ggtgatcgac ttcacaactc acctcgttga aaaatgggct atctcagtgt cttagccaaa  61320
atttttattg taacatgctg tcagatgtgt gactctttcc aagccagtaa gcttttcctg  61380
ggacttcttc aattagccag cattcagtgc aatcttcagc attgcagatt cagagaaatg  61440
tggctctgga gcctgtcacc cttgagaaac agggctaaca gggttgcatt aattccaaat  61500
caccctggtt ctatggagca gtacatgaac tcccaatgat ctatgtttca ggacttcctc  61560
agtcataggt gggctctgca gccctaggtt tttaagtgag tgactgcccc gtgttctggt  61620
ggcagttgta cctgtgagcg gtctggatag aaagagtcgg agacttctgt attattgcaa  61680
ctcaggatgt gggtcatgag aggatttcat ctctcctgca ggggagtaag ctgttcgcct  61740
ccacccatcc ctgataactg aagtgtcttt gtctgcagtc ctagacgaag gactgttgtc  61800
tctcccatgg cccagaagct gaagaccttg ccttttgtta tgaaacgttc attgttttca  61860
tgtctgtccg tttctctgcc cctaacaccc aatcaccatg tatggcctgt acccccaaat  61920
gcatcgtgct ttgctgtttg ctgccccata gtcctcatga acattcagta gaaattccca  61980
```

```
taaatgtgct tgcacgtgag cacagtttcc attgagaagc cctctcattt gtccttttt  62040
tctaagcttt tatgtgaaat atttctaaga acttactaca gttctaaagt gttaggaatt  62100
tgtttctttg gtgtttttgt ttgttggttg gttgttgctt ttctcaagtc catctgccta  62160
caaataaaga aacaagaatg ttacttgtca tattctcctg aggtcataat tctcagagac  62220
tttttctgg tttgtgccat aagtggcttc acatgtttgt ctcttcttgg aaacactcag  62280
tttgatttct tttcttttca tttcagcacc aactgagcaa aggcctgggg tgcaggagtg  62340
ctaccacgga aatggacaga gttatcaagg cacatacttc attactgtca caggaagaac  62400
ctgccaagct tggtcatcta tgacaccaca ctcgcatagt cggaccccag catactaccc  62460
aaatgcgtat gtctattttc tttaccataa gtgaaggaag ggtcagtgga aatttctgtt  62520
agtagagtca tgcttcaagc tgagtgttca ggactcaagt tgtctcagat gaacagtgca  62580
tagcaaaatg tctcaggaac attgtctttg agcaaagagt ctaagagaag acaaatgtta  62640
atctggctct ccttcctcct agtttaatgg agcagaaagg tatctggagg caaggatatc  62700
acattaagaa acaagtcaag atgacaaatg atgaaactct tagagtaccc ttccacaaca  62760
cccactaagg ttcaatgcag ccttttctcc ttggaattct attaaactaa actccaattc  62820
ctgaagtgaa ggttctgttg gggttttctg ttttggctta caaggaaagt atatatgtat  62880
atctatggag aggcaaatct atctctttct atatctacgt ctattccaat atgtagaaac  62940
acagtcggtt ctgaccacca gtggtctgaa gggatactgg ttgttagaga ataaaaatgg  63000
caggaaggca gatgagagtc agcaaagaga gagatcctgt aaagtaaaag ggtggataga  63060
tggacagaag cccaggtctg accagcccat ggccaggctt taggccataa gtgacaccaa  63120
agacatggaa aaatggtttc tacatgttgg acaacagaca gtagtggacc aaaagaatag  63180
tgacaggggg aacaatgaga tcaactccat agataccttg gctttcttcc tggaggccct  63240
tcttgcactg aagagcaagg tgatggagcc cagatggact gtagccatct tcctgaatgc  63300
aggagagaga ttggaatttg ggactactgt ggtagctagg attttatagg cctgctgaga  63360
atgagaatgg atttgtggat gaaaggagct ccaggggcac gcatagtagt ctcctcgaat  63420
ctttggctaa acatgacgtt gcatgtgccc agaaaaaggt tccacaagaa agtagagaaa  63480
agaatatatc ctgaggaata gcaactgcga ttgaacagtg agctcaataa agaggacaga  63540
gccctcatag cattctggga tactggagtt ctgaccagct ggaggagaga cctcactgaa  63600
cctcttggga atacagtaga gactccagaa aagtcatact ttaggagtag aattagtaaa  63660
tttctagaaa aaaaggcagc tctagacaaa ccctggcaaa actgaaaagc aagtctccaa  63720
gcattaaaat catttccaag tcaattaact gcctgggaga ggaaaaccct ctttagaggt  63780
aaacaacaaa gtcaagtggc tcagctatgt ggtgttcaca gtgtgagttc taaatttaaa  63840
acttgactac acatagagaa gcttttagta tgaaccatga ccaggtgaaa aatcagtcaa  63900
tacaaataga cctagaaatg acagaaatga ttagaatggc aaaaaatttg acatatcaat  63960
atgtcaactg agttttaggt tttaagaaaa catgaatacg gaatgaagca gataccatat  64020
caagagacag taacagtata gaagagccaa attaaattaa agaactagta taagaaggta  64080
tgtcttaaat gaaaaaatta ctggatgtat tcccaatgga gtgagatgtt tcagaagtaa  64140
aaactaactg aaaaacaatt ttataccacc tacagaacca gctacacata cacaaatgac  64200
acacacatat acacacatac tcacacatgc acaggcttag aaacatgcac gcacacacac  64260
acacacacac acacacacct ccacaaatac taaaaaatga aatccactga tcctcacaga  64320
caggcgggaa aatataaaaa gatttcctgc atgtgggtag gaagtcacag aaggagagga  64380
```

aggagagatt gctacaggaa caaatactgg aagcaaggat agctaaaaac ttttcaaata 64440
agaagaatat taaaaaccac agattcaaga agctgaatga atcagacagg gaatttccaa 64500
aaaaaaaaaa aaaaaaactg tatgattcac ttttgtacat caccgttcaa cagtcagaag 64560
gcaaagatat aataacaaga aacatctcat gagaaactgg aggaaaaaga gctgtgtctt 64620
gctagaagaa cagtgataca aattgctaat gcattctcat cagaaacact ggaacccagt 64680
taacagggga tatcattaaa atgataaact agaaaaaaaa gagatcaaat gagaatgcta 64740
catccagcaa taaaatgcct tgaagatcat ccatgttgga taaatgcata ttgtgcactg 64800
ccccaaataa ataaaccaaa aactaataat ttggaatcag caggcttgtg taacaagaga 64860
tgttgcccaa agaaaattag ctagaagaag aatagttcaa gaggagaact ttctgcagcc 64920
cacgtaatga agaacccagc aaatggcaaa tgtagatgta aatgcaaaat attttcttga 64980
tcaaatttct atatcttttt aaatgagagt tgactacttg aagcaaaatg atagcaatat 65040
atttaacttt agcatatgta gaggtaaaaa tttgaacata tagactaaat catgtgggga 65100
ataattggaa gtgtaccatt gtaagtttct taccttatcc acgatggtat gtaatattaa 65160
tgaaaggttg aatttgtggg tccaaaggga tattgtaaat cctaaagcaa tcataaaatt 65220
ttgaattctg agggatatta tataataaga attttccatg tatccaaaag agggaagcca 65280
aggaagaaaa agaagtcttt caagtactca agctctgagc acatccagtt gctcattgaa 65340
ccagcttcct ggaatggagg gtctgggctt gagactaggt cacatgtgta gagtctctag 65400
agagacagtg ttggatcccc atggcccata atacatttcc cgttttccca ggcagccaca 65460
ggtcacgaat gggaggattc tgagaggttg gagcaatgtt cttaggaggc ataaggagga 65520
gtgaatgctc tgagatttcc ccagcctgag gtcctccata gctgcccgac ctcttcagac 65580
ctcatagtct gcccagctgt ctccctttat gccatgagtg ccactgttct ttcaactcat 65640
cccccattcc ctcagtcccg gaattgctgt ggccagcaga ggatggactg agagcaggag 65700
aggaagtcct gaccaggaac ccatcctaga gatactgcat cctgcctgaa agctaggttt 65760
ccagggcagc tttgagaagt cttgcagaaa gaaacccact tgacccacct gatacggtat 65820
cgacagacag gaatactttt tgtgcaatgg ttttacatgc tgaacataga gccttttggc 65880
tacattttga gtacattgaa tgagactgct ggcctgggaa ggatatcatg ctggatgcca 65940
tttttttctc tggagaacta tgtgttagtt ccaactcgca cattactata tgaagtccta 66000
cacagagaga tacggagagc tagacagata gagatacttt tgtatgtgca taaccaattc 66060
cacaatacac acgtcaaaat ccataccagt tattccagag agatggattg ggcagaaggc 66120
agaaggagga tattctgatc ccttttttggc cacatgtatg tataatctca gtgtttctag 66180
gaagtgtgtg ctgcattaga ttttttttct ttaaaaaaag tgataaatata ttaagtatga 66240
gaaatgtgca gagaggatta gagattgaga gccatttgtc attgtggcaa ttgtatggta 66300
tctcttttgg gaatatttca aaggcaccag taatgacctt gttgtagcaa aatatacagt 66360
gttcctgcat atgtacccat tttttgtgat gtgtattctt ttggaatttc cagtggcttg 66420
atcaagaact actgccgaaa tccagatcct gtggcagccc cttggtgtta tacaacagat 66480
cccagtgtca ggtgggagta ctgcaacctg acacgatgct cagatgcaga atggactgcc 66540
ttcgtccctc cgaatgttat tctggctcca agcctagagg cttttttttga acaaggtaag 66600
aagttgtgcc agacatttac ctgcttggat gctgggatga aaagccatgg atacccccac 66660
tgacgcacaa cccttcagtg ctacactggt tctcgtgtgt tggttctggg tctgccatgt 66720
gggaggaagc cttagcgcac tctctggggg agccagaggt gtgatttttg gtgcaacctg 66780
tgcgagctgt gtctttagga tgggcggaaa ccattctggg tgctcgactt caccactccc 66840
ctcattgtaa aaggggctat ctcattgtcc tagacaaaat tcttattgta atatgctgtc 66900
agatgtgtgt gtctttccaa gccagtaaac ttttccaggg atttcttcaa gtagacagca 66960
ttcagtgcaa tcttcagcat tgcagattcc gagaaatgtg gctctagatc ctgttatcct 67020
tgagaaacct aactgggttg cattaattcc atatctccct gggtctgtgg agtagtacat 67080
gagctcccga agctctatct ctcaggtctt tttcagtccg aggcaggttg tgcagttctt 67140
agctttgaag ggagtgattt tttcgtgtgc ttttgcctct ttctgatgga acttgtacct 67200
gcggggggtc tggagaaaaa gagtagtaga cttttgcttt attgcaatgc attatgctgg 67260
gcacgagagg attccctatc ttattgtagg tgataagctt ttggcctcca ctcatccctg 67320
agaagtgaag tgttgttgcc tacagtttta gctgcaggac tgttgtctgc cccatcacca 67380
ggagtttaat gctttctttt ttgagcaatc atctagggac acatgcaagg tttttatatg 67440
tccttgcctc ctccccaaaa aaccatttta atgcttggag acttgctttt cagctttgcc 67500
aaatgcatca ccctttcttc tatgctgttc catgtcgtca tgaacactct gtagagattc 67560
ctagaaatga gcttccatgt tagtggagtt tccgatgaga agcaatctga tatttctttt 67620
ccactaagtt ttacatgaaa tatttctaag aacttactac agttctagaa tggtaggcat 67680
ctcttacttt cgtgtttgtt tgtgtgtttt ctcatgtcca tttgcctatt aataaagaat 67740
agagaatggt tgtaaatctc agtgactctt ttttggttta tgtcataaat ggcttcctgt 67800
atttttctgt tctaggaaat aataagcttg atgtcttctg ttttaatttc agcactgact 67860
gaggaaaccc ccggggtaca ggactgctac taccattatg gacagagtta ccgaggcaca 67920
tactccacca ctgtcacagg aagaacttgc caagcttggt catctatgac accacaccag 67980
catagtcgga ccccagaaaa ctacccaaat gcgtacgtct ttgttcttta ccataagcga 68040
aggaagggcc aatggaagtt tctgttagaa gagtcatgct tcaaggtgac tgctcaggac 68100
tcaacttggc tcagatgcag aggaacattt cctgtgagca aaagttctta gagaagactt 68160
tgtttttttg agacagagtc ttgctttgtt gcccaggctg gagtgcagtg gcatgatctc 68220
ggctcactgc aagctccgcc tcccgggttc acaccattct cctgcttcag cctctctagc 68280
agctgggact acaggcaccc accaccacac ccggctaatt ttttgtattt ttagtagaga 68340
cagggtttca ctgttctagc caggatggtc ttggtctcct gacctcgtga tccgcctgcc 68400
tcagcctccc aaagtgctgg gattacaggc gtgagccacc gtgcctggct gagaagacat 68460
tttttaagct ggctctcctt cctcctagtt ttatggaagc agaaggatat atggagttga 68520
gaagatctta ttaataaaac agccgggatg acaaatgacc aaagagttag agtatccttc 68580
tacaacatcg gctgagggtt aatacaacct tttcaccttg gaattctatc attctaagct 68640
ctagtccctg aagtgaatgt tgtgttggcc ttttgcatct tgggtcacag ggaattgata 68700
cttgcacatc tatggagagg caaatctttt tctatctact tctttttcaa tgggtacaaa 68760
cacacttggt cctgagcacc agtggtctga agagatacgg tctgcccaga ggagaagaac 68820
aaaggcagga aagcagatga gagtcagcaa aggggcgatg ctgaaaagta aaaggggcgg 68880
gtagatggac agaagccatg atctggccat tctatggcca gtctttcggc cataagtgac 68940
taccaaagac acggcaaaac ggtttccaca tgttgaacaa cagatgctag aggaccaaga 69000
gtattgcaag agggagaaaa tgagatcaac ccatcaatgc cttggctttc ttcaaggaga 69060
cccttcctgc actgaagagc aaggagatgg agcccaagct gactgtagcc atgttgctga 69120

-continued

```
acagaggaga gtgattggac tttgggatta ctcaggtagt taggattttc tagccatgct  69180
aagagtaaga atggacttgt ggaggatagg agctccaggc atagaagtct cctcaagtgt  69240
tagtctaaac ataaagcagc acttgcatag aagattttcc acaagaaaat atggcaaaaa  69300
aacaccatat attgaggaac aacaactaca agggaacagt gagcttaata aaggtgacag  69360
agctcacata gtgctctgga atattggagt tttgaccagc tagagagaag agacctcatt  69420
gaaaatcttg ggcattcagt agagacctca gaaaagtcag actttatgag tagactttgt  69480
atattcctag aataaaggca gctccagaaa aaacctagca aagctgaaaa gcaaatctcc  69540
aagcattaaa atggtgtcct agtcaattaa ctgccttcta gaagaaaact caacactctt  69600
tacaggtgaa caacaaagtt aagttgctga gctatgcaat atccacagtg tgagtcctaa  69660
atttataact ttactacaca taaaaaagca tttagtgtga accataacca ggaaaataat  69720
cagtcaataa aaatagaacc aggaatgata gaaatgattt aaatggcatg agaatttgac  69780
atattagtat cataactgca ttgctggatt taagaaaaca taaacatgga acgtaacaga  69840
tatcatatca agggaaagta aaaggataaa agagtcaaat caaattaaag gactattaaa  69900
aggtatatct taaatgaaaa attcactgga tggtctccca atcaggttag ttgtttccag  69960
ggaaaaaatt aactgaaaaa taattcaata gaatctacag aaatagctgc acatatatac  70020
acacaatggc acacgtgcac acacccacac ccacacaggt gtgaatccta gagccacacg  70080
agcattgaaa catagagaag taaaaattgt tcattgagga atatgtagca atgctcaatg  70140
tgttttaccc taataagagc ttttgtgatg tatgattgaa aaactgacac aactgaagag  70200
agaaatagat aagcccacac tctgagttag agatttcctt gattctctca ctatggttat  70260
aaatctttcc caaacacaac aggctagaac aaatatgcag aaaattagac atagtatctt  70320
tgttctcaat aaaaacgtcg acctatttaa cattataccg aactaccgag tacacattaa  70380
agtgtgcatg gagcattcac tgaggtgtac tctacacatg accttccagc aagtctccat  70440
agatttaaaa gaattaaagt catacagagt gtgtcacttt attctcccag aataaagtga  70500
gatatgaata atgagaagtt tgccagcttc tcaaatattt gggagtcata cggtgcattt  70560
caaaatactc tttgggacaa agaaaacatc actaaggaat ttagaaaagt tttgaactga  70620
gtaagaatat aacacaattt atccaaactt aggagatgca gtgaatgtct ttaggctttt  70680
acataatttt agatgctctt agggaaaaac agaagcatgt aataatcaag atttcaaact  70740
gcaattctca aagtgtagtc tagagaaacc tgaggacctt tgagtacctt cagagacagt  70800
ccatgaggtt aaaggacttt gctacgtgaa aagtaagatg ctattggccc tttttacttt  70860
cattttccaa caagagaaga ggggagtttt ccagcagtta cataatatgt aatggcatca  70920
tgtctctgat ggctaagaaa atgggcaatt gttgactttg tgtgttaaaa aaattctcag  70980
tgttggtttc ttatactata aatattcatc ttgtgttttg aaaaagaaaa gctctttgga  71040
atcccctatg aacaaagact ttgacagttg ttgatctaag accacagctt aaatatctac  71100
acaagaaaaa aaaaaaaagc aaataagagc caaggaaagc agatggaagg aagtagtcca  71160
aaccagtgac attcagtgaa caagaaaaga gaccaacaag ggagtaaact cttgaaacag  71220
aaagttgatt ctttgaaaag atccatatga ttgaacacag tctggctaaa caaatgacag  71280
accaatgagg gtgcacaacc atcaccatct ggagtaacag aggagaggtg ccattactat  71340
agcatcttcc agttctgaaa gctgaaaaga agattttgag aacaattgta tgtgaataaa  71400
ttcaggaatg ttaatcatgt gggccaattc ctgaggaaga caacaaatca gcaaaccaga  71460
```

-continued

```
tgctgaatag ttagtgtagt cctgtagaga gacatacaga gaggctgaca gagaaatatt  71520
tgtatgtgca taaaacaatc tacaagacac acttcaaaat caatctcagt taatctggag  71580
gaacatattt cacagaaggt ggaaggaggg tattctgatc ctcttgtaca ttgtacaaca  71640
ttgtacaatg tacagagtat aattgtacaa gtacaattga agttgtacaa gtacaagtgc  71700
aacttgcaca atgtacagag taaacattga tgtttactct caattttctt atggagcaca  71760
gatgactttg gatgtgttac aatatgaatg ataatttgtc tttgagatgt tcgcagttgt  71820
ttagaagttg aggaccattt gtgcatatta tgggaccttt agtgaaaata tttcaaagtc  71880
tctttttaca ctttgttaca gcaaaatgta gagggcgcta agtgcccttg aatcttctcc  71940
catctctggt gacctgtgtt gttttgaaat ttgcagtggc ctgaccagga actactgcag  72000
gaatccagat gctgagattc gcccttggtg ttacaccatg gatcccagtg tcaggtggga  72060
gtactgcaac ctgacacaat gcctggtgac agaatcaagt gtccttgcaa ctctcacggt  72120
ggtcccagat ccaagcacag aggcttcttc tgaagaaggt aggaagtcta tggccagaca  72180
accacaccct aggacgttgg gatgaaaaga gttgcaaaat cttagtgata tagaagcctt  72240
ccatgctcac acaattccaa gtagaatgtg gactcagggt cagccactgg gaaggaacac  72300
tcagcgcctt ctctgggaga accagagctg tgatgtttgg taccctgtga aagggtggta  72360
tctataggaa gggtgcagac cctctagggc actggactta ccactcccct ggttattcaa  72420
aggatcattt tagtgtctta gccagaagaa tattctaaca ttttgccaaa tttgtgaaga  72480
tttaccaagc tcatgataag cctttcatgg tatttcttca agtagtcagt gttcattgca  72540
tctttggctt tgcggtttcg gaggaatgcg gtttttgagt ctgtcatcct tgagaaacct  72600
aatatgactt ttcttagttc catatacttc tgggtccagg tagcagtaca tagccaacaa  72660
atgctccatc gttctggcct atctccatct taagccagtc ctgcacaact aggctttgat  72720
gggagggatc tctcagtgtt cttgcccctc cttctcatgg aacatatatc tgtgttggtc  72780
tctgagaaga agagtagtgg atatctactt tgttgcaatg cagaatcctg ggccaaagat  72840
accagccatc cctccaaggg aataaaattt tggccagtag ccctctctga gagacaattt  72900
gtctttgcct acgagtccta gatgcaggac cgcttcctgc cccatcttca agaagctgaa  72960
ggctttggct ttggaggatc agcagtctag ggaaatgtgt gacggtttca tgtctgtccc  73020
cactgacagt caatcaccac ctacaacctg cacagcctga tgcatagcag tctagtttcc  73080
tgccttattc tcaggaacac ccagaagatg tctatattaa agagcatgca catgagtgca  73140
attttgactg ataggcactc tgatctttcc tttggtgcct gtgttttaaa ggaaatcttt  73200
ctaagaactc gttaaagttc tagaatgcta tgaatctttg ggttttatta ttggtatgtc  73260
catctgcctg ctagtacaga acagagcatg gtagtctttc tcagagacaa tgatcctgtt  73320
tcagtcacag atttcttctg atgcttctgt gttctagaaa ttactcagct tgatttctcc  73380
tctttgaatt tcagcaccaa cggagcaaag ccccggggtc caggattgct accatggtga  73440
tggacagagt tatcgaggct cattctctac cactgtcaca ggaaggacat gtcagtcttg  73500
gtcctctatg acaccacact ggcatcagag gacaacagaa tattatccaa atgggtacaa  73560
ccttgagttt tcttcaaaga cagacagcag ccccccttaca tttctcttgg aagggccatg  73620
cttccaacta acttcttatg acaaatttat ctcagatctg gaatgttggg tagaatgtct  73680
caggcttctt tcttcaggca cagtgtctga aaggagagaa atgtcaggcc agctctcttt  73740
tctcatagtt gacagaagca ggaggatatt tgaaggtggt gagttctcat gaatagaaag  73800
ctcaggacac atggccacgt gcttagaaat agcaccattc cacaatgccc actaaagacc  73860
```

-continued

```
aatgcaatag ttcaaccagg gatttctgtc attctaatct ccaagtcctg aagtgaaggt  73920
tgtattagcc atgttcatct tgggcaacaa ataaaggata tctatgttga catccagatc  73980
ttccaatcac tttctcctct aacctgtacc tgggttctga gaacaaggta tctgaagagc  74040
tatgtgttgc cagcacatga ggggcaaaag taggaaggca gctgagagtc aggaagtata  74100
aagattctga agagttacac atgcaggaag atggacagaa acccagttca gaccacgtca  74160
gcgtttctgc catgaaggac tatcaaatac ataggaaaag tgttttcata ggttggacaa  74220
cagacatgac aggcctgaga aaattcagaa agggaatcaa aggagatcaa ccttatcatg  74280
tccctggcat ccttccttga gacccttgaa gggcaagcag atggagccca gctgaccaca  74340
gcagtcttgc ttaactgagg agagagactg gagtttgtga tgcctcaggc atctgacgta  74400
ttctaggctg gctaagaatg agaggggatt tgtggaggaa aggagctcca agaatacaca  74460
ccgaagtctt ctcaaggctt tggctaaata caaagctgcg tatgcacaag gagagttttc  74520
acaaagaaag aacaataaag aaaagctact ggggaaagaa caactgcaag ggaacagtga  74580
gctcaatgga gatgctagag ctcacatagc actgggggat atttgagttc tgaccactca  74640
gaggagagac acctcactga acatcttggg cattcagtag aggtcaaaga aagccataat  74700
ttgggagtag gatcttcgga ttcctagaaa taaggtgact ccagaaacac tccagcaacc  74760
cttcttccaa gccagtctaa aaggatccaa atgatttcca agtaaattaa ctgccttcca  74820
gaaaaaagta aactcaaccc tccttagagg taaggaacga atacaagttt ctcagttata  74880
tgacatcccc agagtgcaac ttgcatttaa aaatttacta gacacaaaag aagttttcac  74940
tgtgatccat aactgggaga aaaatcactc aacacaaata ggcccagaaa taatagaaat  75000
tatggcattg gcaagaacat ttaaaatgca cctctgagaa ctgtgtttca ggaaaatgtc  75060
agcaaaagct gaccatgaga gaaatgaatg cataatatca gaaaagaaaa gaattgaaga  75120
gccaaatgga aatttaaaaa ctgagaaaag ttatatctgt aatgaggaat tcactggatg  75180
gccttataac cagtttagat attatggtag gaaaaggtga acgagaaaat gattcaatta  75240
aagctagaca aaccacaaga cagacagaca gacacaaata cacatacaca caatgactga  75300
accaattaat caacagagcc tcaaggacat ctaggaaaac atccacacat ttaatatatg  75360
tgttaggcaa gtcacagaaa gagaggaaaa agataatgtg acagaagtta tacttgaagc  75420
catgacggct gacaaatttc caaacataca gaaaatgaga aattcatagt catgaagctc  75480
aatgactcag gtatagattt ttaaagagca aaactctgat ttactggggt acatcatagt  75540
taaattgtct gatttcaaag ctaagaagaa aaaaaggggg ttcctatgaa caaacatttt  75600
gacagttgat ctaagaccac agcttaaata tctaggcaag gaaaagcaaa taagacacaa  75660
ggaaagggga tggatggaaa tagtccaaac caatgacatt cagtgaacaa gaaaatagac  75720
caacaaagga gtaaatccat gaaacagaaa gttggttctt tgaaaagatt catgtgattg  75780
accacagtct ggctgaacag atgacagacc aaggagggag tacaaccatc accatttgaa  75840
gtaacagggg agaggagcca ttgctatacc atactccagg tctgaaagct gacaagaaga  75900
tatcaagaaa aactgtatgt gaataaattc atgaatgtag atcatgtgga tcaattcctt  75960
aggtaaacaa caaatcagca aaccagatac tgaatagatt gggtactcct atagaaagac  76020
atacagatag ccagacagag aaacatttgt acgtgcataa aacaatctac aagactcact  76080
tcaaaatctc tcagttaatc caaagtaaca tatttggcag aaggtggaag gagggtattc  76140
tgatcctttc ttgtacacat tgatgttttc tctcggtttt cttatggagt atagacgagt  76200
```

-continued

```
ttggatgtgt tacaataaga atgataatct gtctttgaaa tgttcacagt tgtttagaag  76260
ttgaggacga tttgtgattg ttacaggacc tttagtgaga atatttcaaa gtcacttttt  76320
accactttgt tacaacaaaa tgtagaggat gtctggtgcc cttgtatctt ctcccatctc  76380
tggtgaactg tattgttttg taatttgcag tggcctgacc aggaactact gcaggaatcc  76440
agatgctgag attagtcctt ggtgttatac catggatccc aatgtcagat gggagtactg  76500
caacctgaca caatgtccag tgacagaatc aagtgtcctt gcgacgtcca cggctgtttc  76560
tgaacaaggt aagaagtctc tggccagaca accacaccct tggacgttgg gataaaaaga  76620
gttgcaaaat cttagtgata cagaagcctt ccatgctgca cgggaatctg aatgtggact  76680
cagggtcagc caatgggaag gaagcctcag cgccttctct gggggaacca gggctgagat  76740
ttttggcacc ccgtgacagg gtggtgtctt taggaagcgt gcagaccttc tagggcactg  76800
gatttaccac tcccctggtt attcaataga ttatttcagt gtcctagtga aaatggatat  76860
tctaacatcc tgccaaattt gtgatgattt accaagctca tcatgagcct ttcctggtat  76920
ttcttcaagt agacagtact cattgcaaac ttcagcttta cagtttcaga ggaatgtggt  76980
ttttgagtct gtcatccttg agaaacctga tatgacttta cttagttcca tatcctcctg  77040
ggtctaggta acagtacata gccagcaaat gctctatctc cctgtctacc ttaatcttag  77100
gcaggtgctg cacacctagg ctttgatgga agggatttct tagtgttctt gcccctcctt  77160
ctcatggaac acgtatctgt gttgctgttt gtgaagaaga gtagtggatg tctactttgt  77220
tgcaatgcag gatcctgggc ccaagatttc ccgccgtccc tccaagggaa taaaattttg  77280
gccagtaccc ctctctgaga gacaatgtgt ctttgcctgg aagtcctaga tggaggacca  77340
cttcctgccc catcttccag aaacttaagg ctttggcttt ggaggatcag tgctctggag  77400
aaatgtgtga cggtttcatg tctgccccca ctgacaacca ccacctacag cctgcaccgc  77460
ctgatgcatg gcactctggt ctcctgcctt gttctcagga acacccaaaa gagatctttg  77520
ccaaagaaca ggcacatgag tgcaattttg actgataggc actctgatct gtcctttggt  77580
gcccaggttt taaagaaaat ctttctaaaa actcattgaa gttccagaat gctatgaatc  77640
tttgagcttt gttattggca tgtccatctg cctactaatg tagaacagag catggtcgtc  77700
attttcagag atgatgtcct gtttctatca tggatttttt ttctcatgct tctgtgttct  77760
ggaaattact cagtttgttt tctcctcttt gaatttcagc accaacggag caaagcccca  77820
cagtccagga ctgctaccat ggtgatggac agagttatcg aggctcattc tccaccactg  77880
ttacaggaag gacatgtcag tcttggtcct ctatgacacc acactggcat cagagaacca  77940
cagaatacta cccaaatggg tatgtctttg agttttctcc caagagaaac agccacccac  78000
ttaaatttct cctggaagag ccatgcttcc agctaacttc ttatgaccca atttctctca  78060
gacccagaat gttggacaga atgtctcagg cttcttgctt tgggcacagg gtctgagagg  78120
agagaaatgt caggccagct ctcttttctc atagttgata gaagtaggag gatacttgga  78180
ggtggtgagg tctcatgaat agaaagctca gaagaacata tgaccatgtg cttagaaata  78240
gcaccattcc acaatgccca ctaaagacca gtgaaatagt tcaaccaggg aattctgtca  78300
ttctaatctc caagccctgg agtgaaggtt gtgtttgcca tgtttgtctt gggtaacaag  78360
tgaaggatat ctatattgac ttcgagatct tccgatcact ttctcctcta acctgtataa  78420
acacattggg ttctgagaac aaggtgtctg aaaagctatg tgttgccagc ccatgagggg  78480
caaaaggagg aaggcagctg agagtcagga agtatagaga tgctgaagag ttacacattc  78540
aggaagatgg acagaaaccc atgtctggct atgccagcct ttctgccatg aaggactatc  78600
```

aaatacatga gaaaacagtt ttcacaggtt ggacaacaga tatggtaggc ttgagagaac 78660
tgagaaaggg aatcaaagga gatcaacttc atcattaacc tgtcttcctt cctggacaca 78720
gtgttggatt gaaggacaag cagatggagc ccagctgacc acagcagtct tgcttaactg 78780
aggagagaga ctggagtctg cgatgcctca ggcagctgat gtgttctagg ctggctaaga 78840
atgagaaggg atttgtggaa gaaaggagct ccaggaatac acacagaagt ctcctcaagg 78900
ctttggctaa atacaaagct gcgtatgcac agggagagtt ttcataaaga aagaacaaca 78960
aagaaaagct acttgggaaa gaacaactgc aggggaacag taagctcaat ggagatgcca 79020
gagctcacat agcactgggg gatatttgaa ttctgaccac tcagaggaga aacacctcac 79080
tacattttgg gcattcagta gagaccaaag aaagctgtat tttgggattg ggatcatctt 79140
attcctagaa tcaaggtgac tccagaaaaa ctccaacaac ccttcttcca agccagtcta 79200
aaaggatcca aatgatctcc aagtaaatta actgcattcc acaagaaaaa aaaaactcaa 79260
ccccccttag aggcaaggga caaatacaag ttgctcagtt atatggcatt cctattgcgt 79320
tacttctatt taaaaattta atagagacac aagaagcttt cactgtgata cataactggg 79380
agaaaaaatc actcaacaca aacaggccca gaaattatag aattgatgac attggtgaga 79440
acatttaaaa tgcacctctg agaactgtgt ttcaggaaaa tgtcagcaaa agctgaccat 79500
gagagaaaca aaagcagaat agcaagagaa aagaaaagaa ccggagagcc aaatgaaaat 79560
taaagaactg agaaaaggta catctctaat gaagaactca ctggatggcc ttatcatcac 79620
tttagacatt acggtaggaa aggtgaccta gaaaataatt caataggagc tacacaaatc 79680
acaggacaga cagacagacc aacagacaga aacacacaca cacacacaca cacacacaca 79740
cacacacaca cacacacaca aagactgaac ctattaatca acagagcctc aagggcatct 79800
aggaaaaatc cacacattta atatatgtgt taggcaagtc acagaaggag aagaaaaaga 79860
tatcatgaca gacattatac ttgaagcgat gatggctcgc aacacgccaa atatacagaa 79920
aacaagaaac tcatagtcaa gaagctaaat gactcaggta tagaatttta aagagcaaaa 79980
ctctatgatt tactgggata tatcatagtt aagttgcctc aattcaaagc taaaaagaaa 80040
aaaagggggt tcctatgaac aacagctttg acagctgttg atctaagacc acagcttaaa 80100
tatctaggca aggaaaagca aataaggcac aaggaaagag gatggaagga aatagtccaa 80160
accaatgaca ttcagtggaa aagaaaatag accaacaaag gagtaaatcc atgaaacaga 80220
aagttaggtt ctttgaaaag tctatatgat tggccaaagt ctggctaaac agatgacaga 80280
ccaaggaggg agcatatcca tcaccatcat gagtaacagg agagagatgc cattgctata 80340
gcatcctcca ggtgtgaaag ctgagaagta gatattgaga tcaactgtat gtaaataaat 80400
tcatgaatgt agatcatgtg gatggattgc ttaggtaaat aacaaatcag caaatcaaac 80460
actgaataga tcatgcagtt ttatagagac ttacagacag cctgacagat aaacatttgt 80520
atgtacgtga aacaatctcc aagacacact tcaaaatccc tctcggttaa tccaaaggaa 80580
tgtatttggc agaaggtaga aggagggtat tctgatcctt tctggtacac attgatgttt 80640
tctctcagtt ttcttataaa gcatagatta ctttgaatgt gttacaataa gaatcataag 80700
ctgtctttga aatgttgaca gttgtttaga agttgaggac catttgtgag tgttatggga 80760
ctttagtgag aatatttcaa atttgcttgt ttacactttg ttacaagaaa acatagaggg 80820
tgccaggtgg tgctgtatct tctccaatct ctggtgacct gtattgtttt ggaatttgca 80880
gtggcctgac caggaactac tgcaggaatc cagatgctga gattcgccct tggtgttata 80940
ccatggatcc cagtgtcaga tgggagtact gcaacctgac gcaatgtcca gtgatggaat 81000
caactctcct cacaactccc acggtggtcc cagttccaag cacagagctt ccttctgaag 81060
aaggtaagaa gcctgcagtc agacaaccat accctcggac attgggataa aaagatttgc 81120
aaaatctttg tgatgcagaa aacttccatg ctgcacagga agtcgaaggt gaagtcatgg 81180
acagccaatg ggaaggaagc ttcagtgcct tctctggggg gaccagagct gggatgttga 81240
gtgccttgtg agggatggtg tctttaaaag gggcacagac cctctaggac actggattta 81300
tcacttccct gttatcaaac gaatcatatt agtgtcctag ccaagatgga tattctaaca 81360
tcctgccaaa cttgtgaaga tataccaagc tcctaagcct gtccagccct ttcttcaagt 81420
aggcagtgtt tattgcagtc ttcagcttta ccattttgaa ggaatgccat ttttgaggct 81480
gttgttcttg agaaacctaa catgtcttca ttagatccgt attgtcctga gactttgaag 81540
cagtacatag ccaccaaatt gtttatctcc ccagcctacc ttcatcttgg gcatgccttc 81600
cacacctagg atttgaggga agggatttct cagtgttctc atccctgctt ctcatggaac 81660
atttatctcc gttgtttttt gagaagaaga gtagtggatg tcagctttct tgtaatgagg 81720
gatcctgggc ccaagattcc ctgtctcccc tcctaggcta taaaattttg gcctgtactc 81780
cttctccctg agaggcaatg tgtctttacc tacaagtcct agatgcaaga tccttttctg 81840
ccccacaccc cagaatctga aggcttttgc tttggaggag cagtggtcta gtgtgcaagg 81900
gtttcatgta tacccccccac taacagccaa tcaccaccta tagcctgaac agcttgatgc 81960
atggcaccct ggtctcctgc cttgttctca tgaacaccca gaagaggtgt aagcaaaaga 82020
ccattcacat gagtgtaatt ttgaagtata ggcactctga tctgtttttt gtttgtttct 82080
ttgtttgttt gttttccagg gttgaattaa aatatttatg actacttatt aaatttctag 82140
aatcctataa gtctatttgt atttttattc tacatttcaa tttgcatgct aatatagaag 82200
agtgtaaatt gttaatcctc agattattcc actttgtgtg tcataatttt tttcacattt 82260
ccctttttcta ggcaatactg agcttgattt tctcttttaa tttcagcacc aactgaaaac 82320
agcactgggg tccaggactg ctaccgaggt gatggacaga gttatcgagg cacactctcc 82380
accactatca caggaagaac atgtcagtct tggtcgtcta tgacaccaca ttggcatcgg 82440
aggatcccat tatactatcc aaatgcgtat gtctatcatg ttagccataa aaggaacaat 82500
agtcaactaa aatttctctt agctggccca tgctacaagc tcacttccta ggtccaaatt 82560
tctcatagac tcagagtttg tagcaaaatg tctcaggaaa cttacttttg agcaaaaggt 82620
ctgaatgaag agaagtttta ggattgctat ctttcataac aatttgatgg aagcagcagg 82680
atatatggag gtggtgaagt ctcattaatg taaagctaag gagatcaaat gaccaaatgc 82740
tgagacaaag tatcattcca caatgcccac taaaggtcca tgcagtcttt caaccatgca 82800
attctatcat tctatcctcc attccctgaa gtgaaatttg tgtttgccat ttttgacacg 82860
aatcagaagt aacaaattca ggctgggtgc agtggctcag gcctgtgatc ccaacacttt 82920
gggaggacaa gacgggcaga tcaccagagg tcaggagttc aagaccagcc tggctaacat 82980
ggcaaaaccc catctctacg aaaaattaaa aaattagccg gtcatggtgg tgggtacctg 83040
taattccaac tacttgggag gctgaggcag gagaaacact tgagcctggg attcagagtt 83100
tgctgtgagc cgagaacatg ccactgcact ccagcctggg tgacagagca agactcaatc 83160
tcaaaaaaaa aaaaaaagaa gaagaagaag aaaagaagaa gaggaagaag aagaagagga 83220
agaagaagaa gaagaagaag aggaagagga agaggaggag gaggaggagg aggaagaaga 83280
agaagaagaa gaagaagaag aagaagaaga agaagaagaa gaagaagaag aagaagaaga 83340
aaatagaaat gagtgcatat atttatatat gagtactagc ctgtatgaac acactgggtt 83400
ctaagcacca gttttctgaa gggatatggg ttgtcaggca gagtaaaagc aggaatgcag 83460
atgagagtca ggaagtaaac agatgtggtg attaaaatgg gcaggtacat ggacaaaaaa 83520
atgcatgtct gacaaaaact ggcctcttgc cataagtgag tatgaataat atggaaaaac 83580
tgtttgcaca tgttgaacag cagacagtac aacctgagat agtttagaaa gggaaacaaa 83640
taagatcaac cccataatta cccttcctag acttaagggc aaagagtttt aaccaaagca 83700
ttccacagca gtcttgctaa actggggaga gagactggag ttttgtttac taataaaacc 83760
gagattttct aggttaggta ataatgagaa agtatttgtg gagaaaagga gctccaggaa 83820
tacacacaga agtctcttca agtctctggc tgaacagaaa gctgtgtatg cacagaaaga 83880
gtttccagag agaaaggaga acaaagaaca gctactgggg aaagaacaac tgctggggaa 83940
cagtgagctc aatgaagatg ccagagctca catagcactg ggaggtattt gagctctgac 84000
cagcctgagg agagacactt cattgaacat cttgggcatt cagcaaagac cccaaaaaac 84060
catacttcag gagtagaatt aatgcattcc tagaataaag tctactccag aaacacccta 84120
gaaaagctta gaaaccaagt ctaaaaagat ccaaatgatc tccaagtaaa ttaattgcct 84180
gtcagaagaa aacaacctct tcagaggtaa acaacaaaat taaattgctc aattatatag 84240
tatgcacaat gtgtggcata catttaaaaa tttgctaaac atacaaaaag catttagtgt 84300
gacccataac caggagaaaa atcagtcaat acaaatagac ccaaaaatga taaaaataac 84360
agaattggca aggagattta aaatgtatgt atcataattg tgttcaagga tttaaagaaa 84420
gcgtggacaa gaaataaata aatggataat atcaacagaa agaaaaattg taaaaggacc 84480
aaatggagag tcaagaactg aaaaaaaaga catctcttta atgagaaaat cactacatgg 84540
ccttataatc atattagata gtacagatga taaagctaac tagaaaatat tagggtggtg 84600
caaaccatag cacgcttata caaagcctga gaagataaac agagcctcaa ggacatctat 84660
gaaaatatca aaatatttaa tatttgttta aagcaagtca cagaggaagg gaaagagata 84720
ttggaacaga aaaaatactt gaagcagtga tggctgatga ctttctaaat atggaaaaaa 84780
tgataaactc acatagtcaa gaagctcaat ggatcagata taggatttta aaaagtaaag 84840
ctgtatgatt tatttggaca catcataatt aaattgtcca taatcaaaga tagaaagtaa 84900
aatcttattt gaagcccaag ggaaaaaaca tacctttaca tagagtaaca gtgacacaaa 84960
tgactgatgc cttctcatca gaaacaacac aaatcagaaa caatagaata acacctttag 85020
agtggtaaga agaaaaaaag atcaaatcag aaacaacaaa ataacacgtt tagagtggta 85080
aggaggaaaa caagatcaaa tcagaaacaa tggaataaca cctttagagt gtaagaaaga 85140
aaaaaagatc aaatcaggaa caacagaata acgccttcag agtggtaaga aggaaaacaa 85200
gataaaatca gaaacaatga aataacacct ttagagtagt aagaagaaga aaagatcagg 85260
tcagaaaaaa tggaataata tgctaagaag aaaaaaaaag atcaagtcag aaacaatgga 85320
ataacacctt tagagtgaaa agaaggaaaa aaacccagca agcttaaacg ctatgcacag 85380
caaacaattc cactgaaaat gaatgttacg taagtacata ttctgtcctc ctaaaaacaa 85440
agaacaaata aaagaatgtt tcatcagcag gattatgtaa taaaagatgt gaaagaatgc 85500
tatgtaagta gaagaaaaat aataccatat gggaattggc atcaaaacca caaaatacta 85560
tcaaaacaaa aaaactttat tgataaattt aacacaatat gcaaaagaac tataccatgt 85620
atactacata acattggtga gaagaaaatt agaagatcta aataaagaca catcatgctt 85680
atagattaaa aaatccaatg tcacttttca caaaactgat ctttagtttc aacccacacc 85740
caagcagaat tcctgcagtc ttttcttgaa aacctaacag aatgtatatg ctagaatcac 85800
caagacaatc tttaaaaaga ataaaaaact tggaataaaa tcacaagttt gtgggataga 85860
tgcatatggt aatatggaaa ttctcataaa gacacagtaa tcaagacatg tggtattggc 85920
tgggacgctt ggctgtaatc ctaacacttt gggaggccaa gatgagagga ttgcctgaga 85980
tgaggagttg cagacaagcc tggcaacat agcaagaccc tcatctctac aaatatttaa 86040
aaaaattagc caggtttggt gccatgtgcc tgtagtccca gctattcagg aagctgaggt 86100
gggaggatca ctggagccca tgaggtggag gctgaaatga gccatgattg tgctactgaa 86160
ctttagcctg ggagacagat taaaaccttc cctctctctc tcaaacaaac aaacaaaaaa 86220
tacatagtat tgggcaaaac atatgcaaac aaaaacagaa aagggtcagc ataaatttac 86280
atatatggtc aatttatttt caatacaggt agcaaagcaa tttaatgagg aaattttttt 86340
ccaaaattgg tctgaaacaa ctggatagcc atagaaaaaa actataacaa atgtgacgct 86400
tgaatcctac tgtatgactc aaattaaatt aatttgagat agctcttaga cctcaatgta 86460
acagctaatt ctgaggctga aatataagac tgctatgaaa aagtatagta tcttataacc 86520
ttggagaagg aaaaattttt tgagggaaga accagaaaac actaactgta aaagaaaaca 86580
aatgataatg tggacattca ttgaataaaa acttatgctc accaaatatg actgttaaga 86640
aaataaataa gtaagtaaca cactggaaga aaaacactct catccatata tctgacaaat 86700
ggcctgtatc cagagtatag aaacatttct cccactcact aatcagagga caaacaacct 86760
aatcaaaatg ggcaacaggc ttgaatagtc atttcttagg agaagatgca cacagagcca 86820
acaatcacct gaaaaagtgc acaacatctt agccatcaaa aatcaagagt tataaccctc 86880
ataagatgac actgaacatc cagtgtacat ggatatcatt aagaagacac aataataagt 86940
ggtgtcaccg atttggagct agaatgtgcc actctctcat atgctggtgg aagttcaaaa 87000
tcatacaaca aattaaaaaa tcagtctgat gctttcttat aaagttcgat aaatatgcat 87060
ctatcctaca aacctgtaat tctattcttg aatatttacc ccccaaaatg aaaacataag 87120
tccacaaaaa tctatataaa tattcatagc agctttatgt tttataaact caaaataaaa 87180
actatttcaa tgttttcatc aaaagaaaat gaaaactatt taaatggttt catcaaaaga 87240
aaatgaaaaa agaatttcca gtatatttat acaaaggaat actattcatc aacaaggaac 87300
aagttactga tagtctcaga agcatgaaca aacctcaaaa atatattaag gaaagaagcc 87360
agacgtcaaa gtgtatagtc tgtatgagtc cattcatgtg agtttataga aaacacaatt 87420
tatggtgaaa gaaaccaata gcatttgaca ctggccgtgg gaagagggta gcagagattg 87480
attgagcagc cacacaaggg agtttctggg gtggtgaaaa tgttctgcat tgtgagggca 87540
gtgtgggcta cacaagtata tgtatttatc aaatctcatc cagctacatt taagatctgt 87600
gcatctcact ctatgtgaaa atatactcaa ctgaaaaaca gagcaggtat ctgtttcagg 87660
tgctacatca cttgatacgt ccagttgtgt taaaaaccac tgcctaacat cctcaaatgg 87720
gggatctggg cttgagacta ggtcacatgt gtagagtctc tacagagacc gtgttggatt 87780
cccatgctcc ataatacgtt ccaagttttc tcagacagcc acaggtcatg aatgtgagga 87840
ttctgagagg ttggagcaac gttcttggga ggcataatgg ggaaggcatt ctccaagatt 87900
cctccagcct ggggtcttca cctgctgtgc ctcttactgc attgttttct gactcatcca 87960
tagccacttg accccttcag atcccatagt ctacctagcc gtctcccttt atgccttggg 88020
tcccgctgtt ctttcaactc atcacccatt ccttcagtcc cagagtggct gcagccagca 88080
gaggatggac tgagagcagg agaggaggtc gtgcccatga acccatccta gagaagcagc 88140
atcctgcctg ggagctagtt ttccagggaa gcttttataa gtcctgtaga cccaaaccca 88200
cttgctctac cagatacagt atttatagta atactatttt catgattatt ttatattgca 88260
aatgtagagc atttatgcta cactatgagt aaatagagta agggggctgg catgggaatt 88320
atataatctt ggatgccact tcttccttgg ggaaatgtat ttgagttcca acttacatat 88380
tactatatag tcttatagag agagagacaa agagctagac agacagagat atctttgtat 88440
gtgcattaaa aaatctaaga tacatatttc aaaatctgtg tcatttattc tggaggaaag 88500
tatttggcag aaggtgaaag gaagatattc tgatcctttc ttgtacagac atgtattatc 88560
tcagttttca tagagagcat atactacttt tgatgtttta aaacaaaaat tataatctgt 88620
gatgtgtcca cagttgttta aaagttgaag ctgaagacca tttgtgcttg tggcaatatt 88680
attgtggtat aatgggaata tttcaaaggc acttgttaac actttgttac agcaaaatgt 88740
agagggcgct aagtgccctt gaatattctc ccatctctgg tgacctgtgt tgttttgaaa 88800
tttgcagtgg cctgaccagg aactactgca ggaatccaga tgctgagatt cgccccttggt 88860
gttacaccat ggatcccagt gtcaggtggg agtactgcaa cctgacacga tgtccagtga 88920
cagaatcgag tgtcctcaca actcccacag tggccccggt tccaagcaca gaggctcctt 88980
ctgaacaagg taagaaattt gtggttagac atctatatac tgggatgaaa aaccatggaa 89040
aatcttactg atgcagaagc cttcagtggt acactggagg gttggttgag ggtctgcaat 89100
gtggaggaaa gcctcagcgc cctctctggg ggatccagaa ctgtgatttt tggcacgctg 89160
tgaggaggca gtgtctttag gaagggcacg gtgtctttag gaagggcaca gacccgccag 89220
ggcactggac ttaccactcc cctggttatt aaatgggtca tttcagtgtc ctagccaaaa 89280
tggatattct aacagcctgc caaatatgtg aagatttcca agccaataag cctttccagt 89340
gatttaaagt agactttttt cattgcaatc tacagtttgc agtttcttaa gaacatggcc 89400
tttgagtatg atatcctaga gaaacctaag gagactgcat tatttttcta ttgtcctggg 89460
gctgcatagc aggaggtaac caacgaatgc tgtctctccc tggcctatct cagtctttca 89520
caggctctgt tcacctcagc tttgaagtta gaaatttcta ggtgttcttg cctcttcttc 89580
tcatgaaacc tgcattggca gtgagtctac agaagaagag gaagagaatt ctgctttgtt 89640
acaattcagg actctgggca ctagaagatt ccctatctct cctccaaggg aataagttgt 89700
ttgtctctaa ccctccttga gaaacaatga gtctttgcct gcactcctaa atgtaggatg 89760
atttcctgcc caaattttca aaagattaag ccttttgcct tggtatgagc aatggtctag 89820
ggaaatgcgc aagggtcttg tgtcggcccc tgactgacca ccagtcacct cctacagcct 89880
gcaccaagga atgcattgca ttctggtctt ctgccctgtg gttctcatga aaaccagcag 89940
agattcatat gatggagctg cacatgaatg taatttccaa tgtccagcat tctcctctgt 90000
tctttatctt tagatttaaa aataatgttt ctatgaactt attaaaattc tagaatacta 90060
tgaatctact gggtcttttc acatcctttt gctactagta gaaaaaagaa tagtaataat 90120
tttcagaggc tactgtccag tatgtgacat aaattgtctc ccatgtttct ctgctcatgc 90180
aattactgag tatgatttat tttattttaa tttcagcacc acctgagaaa agccctgtgg 90240
tccaggattg ctaccatggt gatggacgga gttatcgagg catatcctcc accactgtca 90300
caggaaggac ctgtcaatct tggtcatcta tgataccaca ctggcatcag aggaccccag 90360
aaaactaccc aaatgcgtat gtatttgatt aaaaccataa gaggagcaac agccaactca 90420

-continued

```
aatattggtt agaagaccca tgctttaagc tcacttccta gggacaaatt tctcttagac  90480
tcacattttg gcaaaatgtc tcaggacctt tgcttttgag caaagagtct aagagaagag  90540
aaatttttagg cctgctattt ttcctaatag ttttatggaa ggagtagaat atacggaagt  90600
ggcgaagtca tattaatgta aagctcagaa gataaatgac caaagcttaa acacagcacc  90660
attccacaat gcccactaaa aatcaatgtc atctttcact cgtgcaattc tgtcattcta  90720
aatttcaatt cccgaaggtt tgtttgccat ttttgtcatg ggtaataagt aaaaaaaaaa  90780
aaattaagat gtgtatatat atatatatat atatatatat acacacacac acacacacac  90840
aaacatctga atatttatat atatgtctga atatttatat acttgtgtat aaaacttata  90900
tttaaatttt tgcataaatt tatatatttt taatatttca ttaaaaatta tattgtttca  90960
ctatgtatgt ctgagtattt ttatatattt taatataaca ttttaaatat ttatatataa  91020
atattcaggt atgtaactga atattcattt acacacacaa atatatgtgt gcatgtgtgt  91080
atatatatat atacccatat atatatatat atatatatat acatatatat atatatatat  91140
atatgtatat atatatatat atatatatat acacacacac acacacacac atacatacag  91200
gtataaacac actgggcctg aagcaccagt ggtctgaaag gacatgtgtt gccaggactt  91260
gaagagcaaa agcaggaagg cggatgagag tcaggaggta cacaaacgct gaaaagtaaa  91320
atggacaagt acatggacaa aaagcaggta taagcataac agccttttgg aagtaaatga  91380
ctataaaata tatgaaaata ctgttttcac aagttgcaca acagatagta gtgtattgag  91440
ataatttaga acagaaaaca aatgtgatca accccataag tgtgctgtat ttcatcatgg  91500
attgaaggaa aaagagatgg agcccaagaa gaccacagca gtcttgatga actgagagac  91560
accagagttt gggattacaa aggcagctgg gattttctac acttggtaat aatgagaaag  91620
aatttgtgga gataaagagc tacagtcatg tacctagaag tcacctcagt gtaatataaa  91680
tctgcatatg cacagggagt gattccacaa tgaaagtagg acaaagaaca gctactgggg  91740
aaagaataac tacaagggaa caatgagttc aatggagatg gcagagctca caaagcactg  91800
ggggatattt gagttcttac cagctagaaa agagacctca ttgcaaatct tgggcattca  91860
gtagagaccc cagaaaagcc actctttgga aacagagttg atgtatttta agagcaaaat  91920
ctactccaca aaaatcctag caaaattgaa aagcaagtca gaaagaccaa aatcctctca  91980
acataaatta gttgcccatc agaagaaagc ttaacctctt cataggtaaa caataaaatc  92040
aaattgctca gttatctggc atccacaata tgtgacataa atttaaaaat ttactagaca  92100
tacaagaagc atttagtgtg atccataacc aggagaaaaa tcattcaata caaatagacc  92160
cagaaatgac agaaatgata gaattagcaa aaacatttaa aatatacata tgatcatttg  92220
atcttgtgat cagatatcac aagagaagaa agagatactt gaacagaaaa aatgcctgaa  92280
gcaatgatgg ctgaaaactt tccaaatatg aagaaaaaaa agctcacaga ttcaagaaaa  92340
ctaatcaatc agaaatatga ttttgaaaag taaaaatgta tgatttactt tggcaaatct  92400
tcttggttaa attgtctaaa atcaaagaaa gctaggaaaa ttttataagc cagaggaaaa  92460
aagattgttt atataaagga acagttacac aaatgactga tgccttctca tcagaaacaa  92520
tgaaagtcag aaacaataaa gtaacatctt taaagtaata gaagaaaaac ccaagaggtg  92580
agggatcgtg gcagacagga ggcaggacta gattgcagct ctggacagag cagcatgcag  92640
aggctcatat tgtgaatttt agccccatat tgactgcaag aacagaccag caatcctgag  92700
aggacccaca gaccgtgtga aggaagcaga ctgctcctgc aggataaggg agacacccca  92760
aatactgtga gttccccaac tgcagaagtg gaaaagggag gccttactcc ctcaaacaca  92820
```

-continued ccccacaact ggagaagctg aaagtctgtt tgcaggagaa gttcccaact ttacctgggc 92880
ctcagtaaat ttagagagct gagccaagca aaatataggg gtagaggaag cagcagagaa 92940
gacctcagag cttgctggat ccccaagcag ctcattcctg cctggcacca cagagatcca 93000
tcagaagtgt ggccaaagga acagagggta aaactccaca tggaggactg ctctacctga 93060
actttctaac aatttgaaca gggggagaag cctcctggcc agaacttggg ggagggcatg 93120
aatctggttt gcagacttca caggtggggg aaggactaaa gcccttttct ttcacagctg 93180
ggaggtggaa agcctcaggc aagttttcaa gcctgacttt ccccccacct ggaaacagac 93240
ttggagctgt tgcggggttg gggcatggt gggagtaaga ccagcccttc agtttgcatg 93300
ggtgctgggt gaggcctgtg actgacagct tccctccact tccccgacaa ctcagatgac 93360
tcagcagagg cagccataat cctcctaggt acacaactcc agtgacctgg gaacttcacc 93420
cccacaccat acagaagctt cagtaagacg tgcccaagga aagtctgagc tcagacacgc 93480
ctagtcccac ccccaactga tggtccttcc ctacccaccc tggtagcaga agacaaagag 93540
catataatct ttggagttct agggcccacc cacctctagt ccctctccac actagtatag 93600
ctgatgcagg aggccaacca gcacaaaaat agagcattaa accaccaaag ctaggaaccc 93660
ctatggagtc cattgcaccc tcctccacct ccaccagaac aggcactggt atccacagct 93720
gagagaccca tagatggttc acatcacagg actctgtaca gacagtcccc agtaccagcc 93780
cagagctggg tagacttgct aggtggcaag acccagaaga caggcaataa tcactgcagt 93840
tcagctcaca ggaagccaca tccataggaa aagagggaga gtactacatc aagggaacac 93900
cccatgggat aaaaacatct gaacaacagc cttcagccct accttccctc tgacacagtc 93960
tacccaaatg agaaggaacc agaaaaccaa ccctggtaat atgacaaaac aaggctcatc 94020
acactcccag ttcaccagca atggatccaa accaagaaga aatccctgat ttacctgaaa 94080
gagaattcag gaggttagtt attaagctaa tcagggaggg accagagaaa ggcaaagccc 94140
aatgcaagga aatccaaaaa aaaaaaggta taagaagtaa aaggtgaaat attcaacaaa 94200
atagatagct taataaaaaa acaataaaaa attcagtaga ctttggacac acctttggaa 94260
atgtgacatg ctctggaaag tctcagcaat agaactgaac aagtagaaaa aataaattca 94320
gagctcaaag acaaggactt caaattaacc caatccaaca aagacaaaga ataaaggata 94380
agaaaatatg aacaaagcct tcaagatgtc tgggattatg ttaaatgacc aaatataaga 94440
ataatcgtgg ctcctgagga aaaagacaat actaaaagct tggaaaacat atttgggga 94500 ataactgggg aaaacttacc tggccttgct ggacacctag acatgcaaat acaagaaaca 94560
caaagaacat gtaaatacaa gcagcacaaa gaacacctgg gaaattcatc acaaaaagat 94620
cttagcctag gcacattctc atcaggttat gcaaagttaa gacgaaggca agaatcttaa 94680
gagctgtgag acagaagcac caggtaatgt ataaaggaaa ccctatcaga ttaacagcca 94740
gtttttcagc aggaactgta caagctataa aggattggag ccctatcata gcctcctcaa 94800
acaaaacaat tatcagtcaa gaattttgta tccagcgaaa gtaagcatca tatatgaagg 94860
aaagatacag tcgtttttgg acaaacaaat gctaagagaa ttcaccatta ccaagtcacc 94920
actagaagaa ctgctaaaag gagctctaaa tcttgaaaca aatcctagaa acacatgaaa 94980
acagaatctc tttaaagcat aaatcacaca ggacctataa aacaaaagta caagttaaaa 95040
aacaaaaaca aaaaacaaaa ccaaagtacg gaggcaataa agaatatgat gaatgcagtg 95100
gcacctcaca tttcaatgct aaaattgaat ctaaatggcc taaatgctcc acttaaagga 95160

```
tacaaaaaga gttggtggct ggcaagatgg ctgaatagga acagctccag tctgccgctc  95220
cccgtgagat caacacatag ggtgggtcat ttctgcattt ccaaccaagg tacccggctc  95280
atctcattgg gactggttag acagtgggtg cagcccacag agggtgacct gaagcagggt  95340
ggggtgtcac ctcacctggg aagtggaagg ggtcagggaa ctccctcccc tagccaaagg  95400
aagccgtgag ggactgtgcc gtgaagacca gtgcattctg gcacaaatac tatgcttttc  95460
ccacggtctt tgcaacctga agaccaggag attcccttgg gtgcctacac caccagggcc  95520
ctggatttca agcccaaaac tgggctggca tttgggcaga cactaagcta gctgcaggag  95580
tttttttca taccccagtg gtccctggaa tgccagcaag acagaaccat tcaccccgt  95640
gaagaaaggg ctgaagccag ggagctaagt ggtctttctc agtggatccc acccccatgg  95700
agcccagcaa gctaagctcc actggcttga aattcttgct gccagcacag cagtctgaag  95760
ttgacctggg acgctcaagc ttggtgggag gaggggtatc cacaaatact ggggcttgag  95820
taggaggttt tcccctcaca gtgtaagcaa aaccgctagg aagtttgaac tgggcagggt  95880
gcactgcagc ttggcaaagc cattgtagca agagtgcctc tctagattcc tcctctctgg  95940
gcagggcatc tctgaaagaa aggcagcagc cccagtcaga agcttataga taaaactccc  96000
atctccctgg gacagagcaa ctggaggaag gggtggctgt gagtgcagct ccagcagact  96060
tagtttcctg cctgccagct ctgaaaagag caccagatcc cccaacacag cactagagct  96120
ctgataaggg acagactgcc tcctcaagtg ggtcctggtt tcagaagata ataagaaact  96180
cctctgagct aaaggagcat gttctaacac aatgcaagga agctaagaac cttgaaaaag  96240
gtcagaggaa ttgctaacta cagtaagcag tttagagaag aacataaatg accttaggga  96300
gctgaaaaac acagcacgag aacttcatga cacatacaca agtatcaata gcaaaatcga  96360
tcaagtggaa gaaaggatat cagagattga aaatcaactt aatgaagtaa agcgtgaaaa  96420
caagattaag gaataaagaa tgaaaaggaa tgaacaaatc ctccaagtat gggactatgt  96480
gaaaagattg aacctacgtt tgattggtgt acctgaaagt gatgggagaa tggaaccaag  96540
ttggaaaaca ctcttcagga tattatccag gagaacttcc ccaacctagc aagacaggcc  96600
aacattcaaa ttaaggaaat acagagaata ccacattcaa attcaggaaa tacagagaac  96660
accacaaaga tactcctcaa gaagagcaac ctgaagacac ataatcgtca gattcaccaa  96720
ggttgaaatg aaggaaaaaa atgttgaggg cagccagaga gaaagtttgg gttacccaca  96780
aagggaaccc catcagacta acagtggatc ttcctgcaga aactctacaa gccagaagag  96840
agtgggaggc caatattcaa cattcttttt tactattatt atactttaag ttctagggta  96900
catgtgcaca aggtgcaggt ttgttacata tgtatacatg tgccatgttg gtgtgctgca  96960
cccattaact cttcatttac attaggtata tctcctaata ctatccctcc ccactccccc  97020
catcccatga caggccccgg tgtgtgatgt tccccactct gtgtccatgt actctcattg  97080
ttcaattccc acctatgagt gagaacattc ggtgtttgga tttctgtcct tgtgatagtt  97140
tgctgagaat gatggtttcc agcttcatcc acatccctac aaaggacatg aagtcatcct  97200
tctttatggc tgcatagtat tccatggtgt atatgtgcca cattttctta atccagtcta  97260
ccattgatgg acgtttgtgt tggttccaag tctttgctat tgtgaatagt gccgcaataa  97320
acatatgtgt gcatgtgtct ttatagcagc atgatttata atcctttaga tatatatcca  97380
gtaattgtat ggctgtgtca aatggtattt ctagttctaa atccttgagg aatcaccgca  97440
ctgtcttcca caatggttga actagtttac agtcccacca ccagtgtaaa aatgttccta  97500
tttctccaca tcctctctag catctgttgt ttcctgactt tttaatgatc accattctaa  97560
```

```
ctggtatgag atggtatctc attgtggttt tgatttgcat ttctctgatg gccagtgatg  97620
gtgagcactt tttcatgtgt ctcttgactg cataaaagtt ttcttttgag aattgtctgt  97680
taatatcctt tgccaacttt ttgatggggt tgtttgattt tttttcttgt aaatttgttt  97740
atgttctttg tagattctgg atattagccc tttgtcagat gggtagattg taaaaatttt  97800
ctcccattct gtagcttgcc tgttcattct gagggtagtt tcttttgctg tgcagaagct  97860
ctttagttta attagatccc attggtcaat tttggctttt gttgctattg cttttggtga  97920
tttagtcatg aagtccttgc ccatgcctat gtcctgaatg gtattgctta ggttttcttc  97980
tagggtttat atggttttag gtctaacatt taagtcttta atccatcttg aattaatttt  98040
tatataaggt gtaaggaagg gatccagttt cagctttcta catatggcta ggcagttttc  98100
ccagcaccat gtattaaata gggaaacctt tccctatttc ttgtttttgt caggtttgtc  98160
atagatcaga tggttgtaga tgtgtggtat tatttctgag ggctctgttc tgttccattg  98220
gtctatatct ctgttttggt accagtacca tgctgttttg gttactgtag ccttgtaatg  98280
tagtttgaag tcaggcagag tgatgcctcc agctttgctt ttttggctta ggattgtctt  98340
ggcaatgcat gctctttttt gttccatatg aactttaaag tagtttttc caattctgtg  98400
aagaaagtca ttggtagctt gatggggatg gcattgaatc tataaattac cttaggcagt  98460
atggccattt tcacaatatt gattcttcct atccatgagc atggaatgtt cttccatttg  98520
tttgtgtcct cttttatttc attaagcagt ggtttgtagt tctccttgaa gaggtccttc  98580
ccatcccttg taagttggat tcctaggtat tttattctct ttgaagcaat tgtgaatggg  98640
agttcatcca tgtccctaca aaggacatga agtcatgtat gggaatgctt gtgatttttg  98700
cacattgatt ttgtatcttg agactttgct gaagttgctt atcagcttaa ggagattttg  98760
gtctgagaag atggggtttt ctaaatatac aatcatgtca tctgcaaaca gggacaattt  98820
aacttcctct ttcctaact gaatacctt tatttccttc tcctgcctaa ttgccctggc  98880
cagaacttcc aacactatgt tgaataggag tggtgagaga gggcatccct gtcttgtgcc  98940
agttttcaaa gggaatgctt ccagtttttg cccattcagt atgatattgg ctatgggttt  99000
gtcataaata gctcttatta ttttgagata tgtcccatca atacatagtt tattgagagt  99060
tcagcatgga gagctgttga attttgtcaa aggccttttc tgcatctatt gagataatca  99120
tgtggttttt gtctttggtt ctgtttatat gatggattac atttattgat ttgcatatgt  99180
tgaaccagcc ttgcatccca gggataaagc caacttgatc atggtggata agctttttga  99240
tgtgctgctg gattcggttt gccagtattt tattgaggat ttttgcatca atgttcatca  99300
tggatgttgg tctaaaattc tcatttttgt tgtgtctctg ccaggatttg gtatcaggat  99360
gatgctggcc tcataaaatg agttagggag gattccctct ttttctatga ttggaatagt  99420
ttcagaagaa ttggtaccag ctcctctttg tatctgtggt agaattcggc tatgaatctc  99480
tcctggactt tttttggttg gtaggctctt aattattgcc tcaatttcag agcctgttat  99540
tggtctattc aaggattcaa tttctttctg gtttagtctt ggtagggtgt atgtgtccag  99600
gaatttttcc atttcttcta gattttctag tttatttgca cagaggtgtt tataatattc  99660
tctgatggta gtttgtattt ctgtgggatt ggtagtgata tccccttttat catttttttat  99720
tgcatctatt tgattcttct ctcttttctt ctttattagt cttgctagtg gtctatcaat  99780
tttgttgatc ttttcaaaaa accagctcct ggattcattg atgttttgaa ggtttttttg  99840
tgtctctatc tccttcagtt ctgctctggt cttagttatt tcttgccttc tgctagcttt  99900
```

-continued

```
ttaatgtgtt tgctcttgct tctctagttc ttttaatggt gatgttaggg tgtcaatttt  99960
agatctttcc tgctttctct tgtgggcatt tagtgctgta aatctccccc tacacactgc 100020
tttaaatgtg tcccagagat tctggtatgt tgtgtctttg ttgtcattgg tttcaaagaa 100080
tatctttatt tctgccttca tttcgttaca tacccagtag tcactcaggt gcaggttgtt 100140
cagtttccat atagttgagc agtttttaat gagtttctta atcctgagtc ctagtttgat 100200
tgcactgtgg tctgagagac agtttgttat aatttctgtt cttttacatt tgctgaggaa 100260
tgcctcactt ccaactatct ggtcaatttc agaataagtg cgatgtggtg ctgagaagaa 100320
tgtatattct gttgatttgg ggtggagagt tctgtagatg tctattaggt ctgcttggtg 100380
cagagctgag ttcaattcct ggatatccat gttaactttc tgtctcattg atctgtctaa 100440
tgttgacagt ggggtgttaa agtctcccat tattattgtg tgggagtcta agtctctttg 100500
taggtctcta aggacttgct ttatgaatct aggtgctcct gtattgggtg catatatatt 100560
taggatagtt agctcttctt gttaaattgg tccctttacc attatgtaat ggccttcttt 100620
gtctcttttg atctttgtta gtttaaagtc tgttttatca gagactagga ttgcaacccc 100680
tgcttttttt gttgttttcc atttgcttgg tagatcttcc tccatccctt tattttgagc 100740
ctatgtgtgt ctctgcacgt gagatgtgtc ttcagaatac agcacactga tggatcttga 100800
ctctttatcc aattttccag tctgtgtctt ttaattggag catttagccc atttacattt 100860
aaggttaata tttttatgtg tgaatttgat cctgtcatca tgatgttcgc tggttatttt 100920
gctcattagt tgatgcagtt tcttcctagc atcgatggtt tttacaattt ggcatgtttg 100980
tgcagtggct gataccgatt gtttctttcc atgtttagtg cttccttcag gagctcttgt 101040
aaggcaggcc tggtggtgac aaaatctctc agcatttgct tgtctgtaaa ggattttatt 101100
tctccttcac ttatgaagct tagtttggct ggatatgata ttctcagttg aaaattcttt 101160
tctttaagaa tgttgaatat tggctgccac tctcttctgg cttgtagagt ttctgctgag 101220
agatctgctg ttagtctgat gggcttccct ttgtgggtaa cccgaccttt ctggtgaatc 101280
tgacaattat gtgtcttgga gttactcttc tcgaggagta tttttgtggc attctctgta 101340
tttcctgaat ttgaatgttg gcctgccttt gtaggttggg gaagttctcc tggataaatat 101400
cctgaagagt gttttccaac ttggttccat tctcctcgtc actttcaggt acaccaagca 101460
gatgtagatt tggtcttttc acatagtccc atatttattg gaggctttgt tcatttcttt 101520
ttactccttt ttttctctaa acttctcttc tcgcttcatt tcattcattt gatctttaat 101580
cactgatacc ctttcttcca cttgattgaa tcaactactg aaacttgttc atgtgtcacg 101640
tagttctcgt gccatggttt tcagctccat tagatcattt aaggtcttct ctatgctgtt 101700
tattttagtc tgccattcat ctaaactttt tcaaggtttt tagcttcttt gcaatgggtt 101760
cgaacatcct tctttagctc ggagaaattt gttattacag atcgtctgaa gccttcttct 101820
ctcaactcat caaagtcatt ctctgtccag ctttgttctg ttgctcgtga ggagctgcgt 101880
tccttcggag gagaagaggc accctgattt ttagaatttt cagctgttct gctctggttt 101940
ctccccatct ttgtggttta tctacctttg gttcttgatg atggtgatgt acagatgggg 102000
ttttggtgtg gatgtctttt ctgtttgtta gttttccttc taacagtcag gaccctcagc 102060
tgcaggtctg ttggagtttg ctggaggtcc actccagtcc ctgtttgcct gggtattacc 102120
agtggaggct gcagaacagc aaatattaca gaacagcaaa tgttgctgcc tgattcttcc 102180
tctggaagct tcatctcaga ggggcaccca gctgtatgag gtgtcagttg gcccctactg 102240
ggaggtgtcc cccagttagg ctactcgggg gtcacggacc cacttgagga ggcagtctgt 102300
```

ccattctcag atctcaaact ctctgctggg agaaccacta ctctcttcaa agctgtcaga 102360
cagggatgtt taagtctgca gaagtttctg ctgccttttg ttcagctatg ccctgccccc 102420
agaggtggag tctacagagg caggcaggtc tccttgagct gtggtgggct ccacccagtt 102480
tgagcttcct ggtcgctttg tttacctact caagtctcag caatggcaga cgcccctccc 102540
ccagctttgc tgccgccttg cagttcggtc tcagactact gtgctagcag ttcaatctca 102600
gactgctgta ctagcagtga gcaaggctct gtgggcatgg gaccctctga gccatgtgca 102660
ggatataatc tcctggtgtg ccgtttgcta agaccattgg aaaagtgcaa tattagggtg 102720
ggagtgtccc gattttccgg gtacatctgt catggcttcc cttggctagg aaagggaatt 102780
ccctgacccc ttacacttcc cgggtgaggc aatatcccgc cttgcttcgg ctcactctcc 102840
gtgggctgca cccactgtct gacaagcccc ggtgagatga acccagtacc tcagctggaa 102900
atgcagaaac cacccatctt ctgctttgct catgctggga actgtggact ggagctgttc 102960
ctattcggcc atcttgaaac ctcccctctc tcacgatcac aaggtcccac aataggccgt 103020
ctgcaggctg aggagcaaga aaagccagtc tgaattccaa aactgaagaa attggagtct 103080
gatgttcaag ggcaggaaac atccagtgcc aaagaaagat gtagaatatt caacattctt 103140
aaagaaaata attttcaacc tagaatttca tatccagcca aactaagctt tataacaaag 103200
gagaagtaaa atcctttaca aacaagcaaa tgctgaggaa ttttgtcaac accaggcctg 103260
ccttacaaga ggtcctgaag aaaacactaa atatggaaag gaaaaaccag taacagctac 103320
tgcaaaaaca taccaaattg taaacaccat caacactata aagaaactgc atcaactaat 103380
gggcaaaata gccagctagc atcataatga caggatcaaa ttcacacata acaatattaa 103440
ccttaaatgt aaatgggcta aatgccccaa ttaaaagaca cagactggga aattgaataa 103500
agagtcaaga cccattggtt tgctgtgttc agaagaccca tctcagggtg aaaagacata 103560
catgggctca aaataaagaa atgaaggaat atttaccaag caaatggaaa gaaaaaaaaa 103620
gcagcggttg caatcttagt ctttgatgaa acagacttta aaccatcaaa gatcaaaaga 103680
gacaaaggag ggcattacct aatggtaaaa gtatcaatgc aacaagaaga tctgactgtc 103740
ctacttatat atgcacccaa tacaggagca cccagattaa taaagcaagt tcttagagac 103800
ctacaaagag acttagactt ccacacaaaa atagtgggag actttaacac cccacagcca 103860
atattagatc gacgtgacag aaaattaaca aggatattca ggacgtgaat tcagctctgg 103920
accaagctga cctaatagac atctacagaa ctcgacacca caaatcaaca gaatatacat 103980
tcttctcagc accacattgc acttattcta aaattgacca cataattgga agtaaaacac 104040
ttctcagcaa atgccgtaga atggaaatca taacaaacag tctctcagac caaagtgcaa 104100
tcaaactaga actcaggatt aataaactca ctcaaaacca cacaactata tggaaactga 104160
acaacctgct cctgaattac tactgggtaa ataacaaaat taaggcagaa gtagataagt 104220
tcttagaaac caaagagaac aaagacacaa tgtgccagaa tctctggtac acagctaaag 104280
ccatgtttag agggaaattt atagcactaa atgcccacag gagaaagcgg gaaagatcta 104340
aaatcaacac cctaacatca caattcaaag aaccagagaa gcaagagcaa acaaatacaa 104400
aagctagcag aagacaagaa ataactaaga tcagagcaga actgaagggg ataaagacac 104460
gaaaaccctt taaaaaatta ataaatccaa gagctggttt tttgaaaaga ttaacaaaat 104520
acatagaagc ctagccagac taataaagaa gaaaatagag aagaatcaaa tagacacaat 104580
aaagaataat aaaggggata tcaccaatga tgccacagaa atacaaacta ccatcagaga 104640
atactttaaa cacctctatg caaataaaat agaaaatcta aaagaaatgg ataaattcct 104700
ggacacatac accctcccaa gactaaacca ggaagaagtc aaatccctga atagaccaat 104760
aacaagttct gaaatcgagg cagtaattaa tagcttacca accaaaaaaa gcccagacca 104820
gagggattaa cagtcaaatc ctaacagagg tacaaagaag agctagtact attccttctg 104880
aaactattcc acacaataga aaaagaggga ctcctgccta actcatttta tgaggccagc 104940
atcattctga taccaaaacc tggcagagac acaacaagaa aagaaaattt caggccaaca 105000
tccctgatga acatcaatgt gaaaatcctc aataaaatac tggcaaactg aatccagcag 105060
cacatcaaaa agcttatcca ccatgatcaa gttggcttca tccctgggat gcaaggctgg 105120
ttcaacatat tcaaatcaat aaacataatc catcacataa acagaaccaa tgacaaaaac 105180
cgtatgatta tcgcaataga cgcagaaaag gcctttgata aaattcaata cccaatcatg 105240
ctaaaaactc ttaataaact aggtattgat ggagcatgtc tcaaaataat aagagctact 105300
tatgacaaat gcatagccaa tatcatactg aatgagcaga agctggaagc attccctttg 105360
aaaaccagca caagacaagg atgccctctc tcaccactcc tattcaacat agtattggaa 105420
attctgtcca gggcaatcag gcaagagaaa gaaataaagg tattcaagtg ggaagagagg 105480
gagtcaaatt atttctcttt gcagatgaca tgattgtata tttagaaaac tctatcatct 105540
cagcccaaaa tctccttaag ctgataagca acttcagcaa agtctcagga tacaaaatca 105600
atgtgcaaaa atcacaagca ttcctataca ccaataagag acacagagcc aaatcctgag 105660
tgaattccca ttcacaattg ctacaaagag aataaaatat acctaggaat ccaacttaca 105720
agggatgtga aggacctctt caaggagaac tacaaaccac tgctcaagga aataagatag 105780
gacacaaaca aatggaaaaa cattccatgc taatggattg gaagaatcaa tattgtgaaa 105840
attgccatac tgcccaaagt gatttataga ttcaatgtta tccccatcaa gctaccattg 105900
atttcttcac ataattagaa aaaactactt tcaatttcat atggaataga aaaagggcct 105960
gtatatccaa gacaacctaa gcaaaaagaa caaagctgga ggcatcatgc tatctgactt 106020
caaaatatac tacaaggcta cagtaacaaa aacagcatgg tatggtactg gtaccaaaac 106080
agatatatag accaatagaa cagaacagag gcctcagaaa taacaccaca catctacaac 106140
tattggatct ttgacaaact ggacaaaaat aagcaatggg gaaaggattc cctatttaat 106200
aaatggtgtt gggaaaactg gctagccata tgcagaaaac tgaaactgga tcccttcctt 106260
acaccttata cacaaattaa ctcaagatag attaaagaat taaatgtaag acctaaaacc 106320
ataaaaaccc tagaagacac tttgggaggc cgaggtggat ggatcacgag gtcaggagat 106380
cgagaccatc ttggctaaca cagtgaaagc ccatctctac taaaaataca aaaaattagc 106440
tgggtgtggt cgtgggcacc tgtagtccca gctacttggg aggctgaggc aggagaatgg 106500
catgagctga ggaggttgag cttgcagcaa gccaagattg tgccactgca ctccagcctg 106560
ggcaacagag tgagactcca tcaaaaaaac aaaaacaaaa acaaaaaatc aaaccctaga 106620
agaaaacata ggcaatacca ttcaggacat aggcatggga gaagacttca tgactaaaac 106680
agcaaaacca atggcaacaa aagccaaaat ttacaaatca gatctaatta aaataaagag 106740
cttctgcaca gcaaaaaact ctcatcagag tgaaaaagca acctatggag aaaaattctg 106800
tggtctagcc atctgacaaa gggctaatgt ttagaatgta caagcaactt aaacaaatgt 106860
acaagaaaaa aaaaacaacc ccatcaaaaa gtgggcaaag gatatgaaca gacacttctg 106920
acaggaagac ctttatgtgg ctgacaaaca tgaaaaaagc tcatcatcac tgttaattag 106980
agaaatgcaa atcgaaacca caatgagata ccatctcatg cccgttagaa tggcgatcat 107040
taaaaagtca ggaaacaaca gatgctgaag aggatgtgtg gagaaagagg aacacattta 107100
cactgttggt gggagtgtaa attagttcaa ccattgtgga agacagtgcg gtgattcctc 107160
aaggatctag aaccagaagt accatttgac ccagcaatcc cattactggg tatataccca 107220
aaggattata aatcattcta caataaagac acatgcacac gtatgtttat tgtagcacta 107280
ttcacaatag caaagacttg gaaccaactg aaatgcccat caatgataga ctggataaag 107340
aaaatgtggc acatatacac tgtggaatac tatgcagcca taaaacagga tgagttcatg 107400
tcttttgcag ggacatggat gaagctggaa accatcattc tcagcaaact aacacaagaa 107460
cagaaaacca aacaccatat gttctcactc ataagtgtga gttgaacaat gagaacacat 107520
ggacacagga aggggaacat cacacacagg ggcctgttgg ggagttgagg ctaggggagg 107580
gattggatta ggagaaatac ctaatgtaga tgatgggttg ctgggtgcag caaaccacca 107640
tgacacgtgt atacctatgt aacaaaccca cacattctac acatgtatct cagaacttaa 107700
agtataataa taataagata cagaactgca gaatgaataa gaactcacca accatctgct 107760
gccttcagga gactcattta agacataagg actcacataa acttaaagta aatgggtgga 107820
aataataata agtggtgtca ctgatgtgga ggtagattat aaaactctta tcatatgctg 107880
gtggaagatc aaaatgataa aacgaattaa aaaatcagtc agatggtttc ttaaaaagtt 107940
ccatcaatat gcctctatct tacaaacctg caattctatt cctgaatctt tatcccaagg 108000
aaatgaaaaa gtaagtccac aaagagttct atatgaatat ttataggagc tttatttatt 108060
ataattcaaa ctgtaaaaat aatttcaatg ttcatcaata acaaaatgaa aaaataattt 108120
gcaacctact ggtacacttg aatactattc agcactgagt atcttaaata gcatggatgg 108180
agctcaaaaa tatactcagg aaagaagcca tgtatattct gtatgagttc atttacatga 108240
gatcatttac atttcctcca aaagaggaaa aactaatttc tgttgaaaga aaccaatgta 108300
tttgcctctg gcagtggtaa gggggtagca cagattaatt gggtagggac tcaagagagt 108360
ttctggggtc acagaaatgt tccgtgtggt gatgggagtt tgggctccac aggtataggt 108420
gttgatccaa aatcatcaaa aaaacaacat tgcagatctg tgcatctcac tctgtgggaa 108480
agtatatctc aactgtaaaa agggcagaaa ttgcttttaa acgctcagcc ttttagcaca 108540
tccagttgct tggagaacca gcttactcaa atgggggtct aggctggaga ctaggtcaca 108600
ggcatagagt ctctaaactt tcccatggca cataatacgt ttcaggtttt ctcagagagc 108660
tgcaggttag taatctgagg attctgacaa gttgggtcaa cgttcctagg aggcatgaat 108720
gggagtgcat tctctaagat ccctccaccc cagggtcctt gctttctgtg cctcttactc 108780
cattgttttc tgactcctct gtagccactc gacctcttca gatcccattg tctacccagc 108840
catcgccctt tatgacttgg gtcccactgt tctttcatct catcctccat tccctcagtt 108900
tcggagtggc tgccgctagc agaggatgga ctgagagcag gagaggtggt cctgcccagg 108960
aacccatcct agagaaatgg catcctgtct gggagctagt tttttagggc aggttttata 109020
agtcttgtaa agccagacac acttgatcta cctggtatgt tatttacagt aatactattt 109080
tcataattgc ttttcactct aaaagtagag ccttttagct acactgtgag taaataaagg 109140
ggctggcctg ggaatggtat catgttggat gttgtttctt ccctgaagta atatatatca 109200
gttacaattt acatgttact gcagagtcct agagagagac acagagaatg agacagatac 109260
caatacattt ttatgtgcat taaaaaaatc taaggccagg cgcagtggct cacacctgta 109320
atcccagcac tttgggaggc cgaggtgggt ggatcacgag gtcaggagat tgagaccatc 109380

-continued ctggctaaca cggtgaaacc ctgtctctac taaaaataca aaaaattagc caggcgtggt 109440
ggcgggcgcc tgtagtccca gctactcagg agactgaggc aggagaatgg cttgaaccca 109500
ggaggcagac cttgcagtga gccgagattg cgccactgca ctccagtctg ggcgacagag 109560
cgagactccg tcacaaaaaa aaaaaaaaat ctaaaatgca ctcttcaaaa tctatgtcat 109620
ttattctgga ggaatgcagt tggcagaagg aggaagatat tccgaatttt tcttgtatac 109680
atttatgtat gatctcagtt tttttatgga tcatagacca attttgatat tttaaaataa 109740
aaattataat ctatcttgga aatttacatg gttctttaga acttgaggac cgtttttgct 109800
tttcggaata ttattgtacc taaaatggga atattacaac gtcacttttt aacactttgt 109860
tataacaaag tttagacagc gctgggtgcc cctgaatttt ttcccgcctc ttgtgacctg 109920
tgttgttttg gaatttgcag tggcctgacc gagaactact gcaggaatcc agattctggg 109980
aaacaaccct ggtgttacac aaccgatccg tgtgtgaggt gggagtactg caatctgaca 110040
caatgctcag aaacagaatc aggtgtccta gagactccca ctgttgttcc agttccaagc 110100
atggaggctc attctgaagc aggtaagaag tctgtggcca gatatctaca catttgaaca 110160
ttgggatgaa aagagatgga aaatctgact gatgcagaag ccttccatgc tacacagaaa 110220
cttgagggta tggcaggtgg aaagaagcct cagcactctc tctggtggag caatttttgg 110280
cgcaacgtgc gtgggcggtg acttcaggaa tggtgcaaac ccacctgggc acttgactta 110340
ccactcactt tgttatgaaa ggggttatct cggtgttcca gacaaaattc caattctaac 110400
atcaggccaa atttgtgcca aatttcacac tagtgagtgt ttccaggcat ttattaaaat 110460
ggacagtgtt cattgcaatc ttcagcattg cagttgctga ggtatgtggc cgctgagttt 110520
gtcatcctgg ggaaacctaa tatgatgata tttattccat ctaatcctgg ggctatttgg 110580
cagtaaatac cacagaatac actatttctc tggcttattt cagtcttagg taggctctgc 110640
acacctatgc ttggaaggca ggaatttctt ggtgttcttg tgccttcttc tcatggaacg 110700
tgcatctttg gtgtgtgttg agaggaaggg tagtagactt ctgctttgtt gcaatgcagg 110760
atgctggaac aagaggattc cctgtctcta ctgtaaggga ataagatttt agcctccatc 110820
cttctctaag aagcaatgtg tctttgcctc caagtactag atgcaggacc atgaactgcc 110880
ccgtccacca gaagcttaag gctttggctt ttcaggagca atcatctagg gaactgtgca 110940
gggttttcat gtctgtcccc tactgacagc caatcaccat acagcctgca taacctaatc 111000
catcatcgtc tggtttcctg cctcattgtt ttcatgaaca accagtagag agccatacga 111060
aagagcttgc acatgagtct ttgttccaat tgtaagagca ctgataggtc cttttcccac 111120
caggttttga atataaaatt tctaagaact tattaaaata ttagaatgtt attaatctat 111180
tgtttttgct tcagcatgtc cttctgcttg tgagtatact aaagagaaca gtcataattc 111240
tgaaactact gtcctgtttg tgtcataaat tgcttcacat gtttctgcat actagtagtt 111300
actcagcttg attttgtcta ttttcagcac caactgagca aacccctgtg gtccggcagt 111360
gctaccatgg taatggccag agttatcgag gcacattctc caccactgtc acaggaagga 111420
catgtcaatc ttggtcatcc atgacaccac accggcatca gaggacccca gaaaactacc 111480
caaatgagta tgtctttgat gttacttgta agaggagcaa cagccaactt aagttcctcc 111540
tagaagagcc ttgcttcaag ctaacttgtt aggacaaatt tcccttagac ccagaaggtg 111600
tgtcaaaatg tccagacaac tttgcttttg atcaaagagt ctgagagaat aggtatttta 111660
ggcttgctat cttttctaat agtctgatgg aagcagaagg ctacatggag ctgatgaggt 111720
ctttttaata taaagctcaa gagatcaaat gatcaaatac ttagagtgcc attctacaag 111780
gctcataaaa gatcaatgca ctctttcacc catgcaattc tatcattcta acctcccttc 111840
tctgaaatga aggctttttg ccatttttgt catgggtcac aagtaaataa ttcacatgta 111900
tatgagtata tatataacca ggtgtgttta ttcagactag tatgtatata tatacatata 111960
tatgttcata taagttagta ttcatatata tgttcatata tatatgttca tacagactag 112020
tattcatata tatatacata tatatataca cacacatata tatatatata tatatgttct 112080
agggaaacat gcaaggtttt tatgtctgtc cctgactgat gaccaaatac cctatagcct 112140
gcacagctgc aagctgtata gccatacaat ttgcaggaca cacacacata cacacacaca 112200
cacacacaca cacacactaa catataatat aatataatat aatataatat aatataatat 112260
aatataatat aattaatata tataaacctg tgtgaacaca ctgggttcta agctccagtt 112320
ttctgaaggg atatgggttg ccaggagagg aagagcaaaa gcaagaatgt agatgagaat 112380
taggaagtaa acagatatgg agattaaaat gggcaggtac atggacaaaa aaccaggtct 112440
gacaaaaact ggctttctgc cataaatgac tataaaagat attaaaaaac actttccaca 112500
tgttggacaa gagacagtac aggactgaga taatttagaa aaggaaatga atgagcgcaa 112560
ctccgtaact attatgactt tcttcctgga gaaccttcct ggactgaagg gcaaggaatt 112620
ggagccaaag ccaaccacag cagtcttgct gaactgagga aagagactgg agtttgggat 112680
agctaagaaa atgtgtattt tctatgctag gtaataatga gaaagaattt gtggtgaaaa 112740
ggagctgaag gaatatgcat ggaagtctaa tataaactgc atatgcacag ggagaaattc 112800
tacaaagtgg gacagagaac cactactggg gaaaggacaa attcagggaa acagtgagct 112860
caatggtgac gccagagctc acgtagcact gggggatacc ggggttctga tcagcccgag 112920
gagagacacc tcattgaaca tctcgggcat tcagtagaga ccccagaaaa gtcatacttt 112980
aggagtagga tttatgcctt cttagaataa agactacccc agaaacaccc tagtaaagct 113040
taaaaaccaa gtctaaaagg acccaaatga tctccaagta aattaactgc ctgacagaag 113100
aaaactcaac catcactgga ggtaaataac atgattacag tgctctgtaa tgttgcattc 113160
acaaggagtg acatcattta aaaatttatg aggcaggaaa aagcaattag tgtgatccat 113220
aactaggaga aaaaccagtc aatacaaata gaccaagaaa tagtagaaac gatggaattg 113280
acaaagaaat taaaactgta tatatgataa ttgtgttcaa agatttaaag aaaacatgaa 113340
catgagggaa acaaatgcag aatataaaaa aaagcaaatg cgtaaaacaa ccaaatggaa 113400
attaaagaac tacaaaaaag tataacctta ataaaatact cactggatgg ccttaatatt 113460
agtttataca ttacagaaga aaaagtgaac cagaagataa ctcaatgaaa gccatacaat 113520
ctgtaagaca cacacacacg cacacgcgcg cgcgcgcaca cacacacaca cacagagaga 113580
gagagagaga gaaagagaga gagagaaagg ctgaaaaaaa taaatagaac cttaaggata 113640
tcagtgaaaa tagcaaaaga tttaatatat gggtaaagca agtcacagaa ggacgggaag 113700
gagatattgg gacagaaaaa aatactcaaa gcaatgatgg ctgaagactt tacacgtatg 113760
aagaaaatga taaactcaca gtcaagaagc tcaatgaatc agaaatagta tttttaaaag 113820
caaaactcta tgatttactt gggtacatta tagataaatc gtccaacatc aaagataaca 113880
aggataatct tataagccag aggaaaacaa tatcatttac atagagggac agtaatgaaa 113940
gtgaccgatg ccttctcctt ggaaacaatg gcataacatc tttaaagtga taaagagaaa 114000
taaaaacaga tcaacctagg acgacatgtc cagccaaaac aaacaaataa acaaaaaaac 114060
cctttaaaat aaacgtgatg taaatacgta ttctgccacc tccagaggaa acaagcaaaa 114120

-continued

```
aaacaaaaga atgtttccaa ggcaggcttc tgtattaaaa gattttaagg aaagttattc 114180
aggtagaaga aaaataatac cagatgggaa ctttaatcca tactaagtaa tgaagagccc 114240
tggaaatggc aaatggcaat gtcaatataa aatactctta tttatctaat ttttaaatgt 114300
atttaaagga caatttgtga tattaattaa aataatagga atatattgtt gtttcaacgt 114360
atgtagtagt aaaattcata aaaacagtag cacaaataat gcagatgata actggaagta 114420
tactgttaat gagttttttg cattatccat gaagttatat aatattaata gatggttgaa 114480
tgtgatagtt taaggtggga tattataaat cctaggacaa ccaaaaaaat ttaaactgag 114540
aggaatggat agtaagagga atagtccttt tatgcaaaag aaggaagaaa aagaggaata 114600
aagaatataa aagatatggt gtaaacagaa aatacatagc attattgtag acacaaactg 114660
aactacctta tgagtatatt aaatataaaa ggattaagca ttacaaataa aaggcagaga 114720
ttgtaaattg aataaaaacc acagctaagt gtgttctttt tagaataaat actctttaag 114780
tgtaaagatc tactttaaac accaaaatat gaaaaaggat atataccatg aaaacctgaa 114840
tcataaataa gctggagtgg tgattaatgg atgcaggcac tcctaaagac taataagtga 114900
atgtggtcaa attgaagaaa caaaagtata tacgtgctca atgtgcaaaa actttttctg 114960
tatacatgct atgatccttt ggaaaattaa agttttaaag caatatcact gacaatagta 115020
tcaaaaccaa aaaatattta gtgataaatt tcacacacta tgctcaagga ctatacacct 115080
tgcactagaa aacaatgttg aggaaagaat taaaagatct aaatatacac catgcttata 115140
gattaaaaga ctccatatca gttctcgtga aattgatctt tggatgaaac ccacacccaa 115200
gcactattgc aacagtcctt ttttggaaaa aaaaattgga ggacttatat accttaatat 115260
aaagacttat aaaagtacag gaatcaagac atgtggtatt ggcctggccc cttggctcat 115320
gcctgttacc ccaacatttt gggaggctga gtctggagga tggcttgagc ccagatgttc 115380
aagaccagcc ttagcaacag agtgagaccc tctctctaca aaaaataaac aattagatcg 115440
atgtgatgac ttgcacatgt agtttcagct actcggaatg ctgaggtgag aggattgctt 115500
gactcaggag gtctagccat gagtgagcat tgatcatgcc tctgcattcc agcctggatg 115560
atggaatgag acactgtctc aaaaaaaaaa aaaaaaaagg atatgtgtta ttggccaaaa 115620
aagtatgcaa acctaaaaag ggatggccca ccaccagacc cacatacata tatggtaaat 115680
ggattttccg tatagatggc aaagcaattc aatggagaca aaaatgtttt acaaaatcat 115740
tctgaaccat ttggatatcc atgatacaaa acaaaagcag aacttgactt ttgcttttca 115800
tctcaaatta ttttgatatc tcttccacct aagtgtcaga gctaaaactg aacctgaaat 115860
atgaaagttc catgaaaaaa tataaaatct tcacaacctt ggagaaggca aacttttttg 115920
aggcaggagt ctgtaaacac tcactataaa ataaaacaaa ttataatgtg ggctttcatg 115980
aaaactcatg cttaccaaaa gtcattgtta agaaaataaa taggcaagta acacatgaga 116040
agaaaaatgc tctctgtcca tatatctgac aaatggcttg tgtccagaat ataggaacat 116100
ttctcccact cactaaacag aggacaaaca actaatgggc aacagattga ataggcattt 116160
cttggggata gatagatgta cacatagcca ataagcacct gaaaaaatgt ccagtatctc 116220
agccatgaaa aataaagagt tataatcatc atgagatgtc accaaacacc caatggacat 116280
ggatattatt aagaagacac cacagtaact gatgtcactg atgtagagca aggatgtgaa 116340
actctctcat atgctggtga aagtgcaaaa tgatacaacc acttttgaaa tcagtctgat 116400
agtttctcca aaagttcaat aaatgcactt ttaccctaca aacctgcaat cctgtttgtg 116460
aatatttacc ccacagaaat ggaaacataa gtccacgaag acatctccaa gaatattcat 116520
```

agcagcttta ttttttataa ccccaaactg tagacaattt caatgtcaat caataagaaa 116580
atgaataaat aatttgtgaa ctagtcatac aatggcatac tgttcagcaa taaaagggag 116640
catgtttttg atactctcaa atagtatgga agatgctcaa aaatattaca ttaaagaaag 116700
atgccagata acaaaaatga acattatgta tgagtctatt gatgtaaggt tccagaaagg 116760
taaaactaat ttctggtgaa agaaaccaat atcatttgcc tctggccatg ggaagagagt 116820
agcagagatt gattgagcag taaaacgaag ttttttctg gggtgatgta aatgtcctgt 116880
attgtgattg aagtgtgagt tacacaagtg tacatgttca tcagaagtca tcaaactaca 116940
tctaagatct gtgcatttga ctatacatga aaatatacct cagttgaaaa tagatcaata 117000
acctccctca tatactatac ttgctaacac agccagctgc ttggagaacc agcttgctgg 117060
aatggagaat ctgggcttga gactgggtca catgtataga gtctctacag agacaatgtt 117120
gcattcccac ggtacataat acatttcaag gtttctcaga cagccacatg tcatgaatgt 117180
gaggattctg agaggttgga gcaacattcc tgggaggaac gaaggggagc acattctcca 117240
agatccccca ccaccggggt cctcaccggc tgtgcttttt tttttttttt tcttgacaga 117300
gtctcgctct gtcgccaggc aggagtgtaa tggcccaatc tcggctgatt gcagcctcca 117360
actccagggt tcaagagatt ctcctgcctc agcttcatga gtagctggga ctacagatgt 117420
gcgccactgc gcccagctaa tttttgtatt tttagtagag acggggtttt gccatgttgg 117480
ccaagatggt ctcgctctgt tgacctcgtg atccacccgc cttggcttcc caaagtgctg 117540
ggattacagg cgtgagccaa agcacccagc ctgtgcctct cacttactca attgtttttc 117600
tgaaccctcc atagctggtg gaccttttca gatcccatag tctagccagc cctctcactt 117660
tatgccttgg gtcccactgt tccttcatct catccccctt ctgtcagtcc cgcagtggct 117720
gtggccagta gaggatggac tgagagtagg agaggaggtt ctgcccagga acccatccta 117780
gagaaacagc atcctgcctg ggacctagtc ttccaggtca gcttttataa gtcttttaga 117840
ctcaaactca cttgacccac ctgaagtggt attgacaata atgctatttt catggttgtt 117900
tttcactgta aatgcagagc cttttagcta cacgactagt acagagagta agggaggctg 117960
gcctgggaat gatatcatct tggatggcat ttcctccttg gagaaatata tgttagttcc 118020
aactcacatg ttactataca gtcctgtaga aagagataca gagagttaga caggtataga 118080
cgcatttgta tatgcataac aatctataag acacacatca aaatccgtat accggttcct 118140
ctaggggtat gtgcttggca gaaggtagaa ggagggtatt ctggttcctt tcttttgcac 118200
atttatgtat gatctcagtt tttatatgga gcattgatag ggtttggcta tgtccccacc 118260
caaaatctca tcttgacttg taatctctat aatcctgata atccccatgt gtcaagggca 118320
ggaccaggtg gaggtaactg gatcatgggg gcagtttctc ccaggctgtt ctcatgacag 118380
tgagagagtc tcctgagatc tgatggtttt gtaagtgtct ggcatttccc ctacttgcac 118440
ttactctgtc ctgccgcctg tgaagaaggt gcctgtttct cccttgcctt ctgccatgac 118500
tgtaaatttc cagaggcctc cccagcaatg tggaactgtg agtcaattaa aactcttttc 118560
tttgtaactt acccagtctg tctcgggtat ttcctcatag caatgtgaga acgggctaat 118620
acaagcatat actacttttg atattttaaa ataaaaatta tcatctatct ttgaaaggca 118680
tgcacaaatg ggaagttgag gaacatttgt gttgtggcaa ttgtatgata cctttaatgg 118740
gaatatttca aagacacttg ttaagacttt gttagaacaa aatgtagagg gtgctggatg 118800
tccctgaata ttcttccgcc tcctgtaact tgtattgctt tggaatttcc agtggcctga 118860

-continued caatgaacta ctgcaggaat ccagatgccg atacaggccc ttggtgtttt accatggacc 118920
ccagcatcag gtgggagtac tgcaacctga cgcgatgctc agacacagaa gggactgtgg 118980
tcgctcctcc gactgtcatc caggttccaa gcctagggcc tccttctgaa caaggtaaga 119040
agtctgtgtc ttaccttgtc tagcacatac ctctctatgt gcttggacaa cgggatgaaa 119100
agacatgaaa aaccacactg atgcagaagc ctttagtgct acacgggagc tcgagtgttg 119160
gttgaggttc tgccatgacc aaggaagtct cagtgccgtc cctgggaaag ccagagctgt 119220
gatttttggc acaacttgtg ggagtagtga ctttaggact ggcgcaaaac ctccagggtg 119280
ctcaacttaa ccactcacct tattctaaaa tgggttattt cagtgtccca gtcaaattcc 119340
tattctaaca tgctgtcaac tgtgtgatta tttccaagcc aataagcatt tccagtaatt 119400
tcttaaaata gtgttcattg cagtcttcag cgttgtggct cctgagggat gtggcccctg 119460
attctgtcgt cctagagaag cctgacatga ctgcattgat tctgtatcgt cctgggtcta 119520
tgtggctgcc tggctgtctg taatcatctg ttttattttt atttttttct acagactgta 119580
tgtttgggaa tgggaaagga taccggggca agaaggcaac cactgttact gggacgccat 119640
gccaggaatg ggctgcccag gagccccata gacacagcac gttcattcca gggacaaata 119700
aatgggcagg tctggaaaaa aatgtaagcc actttgattt ggactctttt tccctttgct 119760
gacaaatctt ttcaaacaga agaggggcag aggaaaatac tggaaagact tcaggaggct 119820
aagcgtaatt agccttagca tggaaagtgc aagcagcaca ggccagcaaa gccccacgcg 119880
tgtgggggtt ctcaggcctc ttctcttttg acatttcttt actgtttcca ttgttgggtg 119940
ctgtttctcg tttctagtgc ttgtcctcta agccaggggt ccccactcca gtactggtac 120000
tggtactggt actggaactg gtaattatct gtggcctgtt aggaactggg ctgcacagca 120060
ggaggtgagc ttcgggggag caaacaaagc ttcatctgta ttttctgctg cttcccatca 120120
ctctcatagc tgcctgagct ctgccagctg tcagatcaga ggcagcatta gattatcata 120180
gcacaaaccc tattgtgaac tgcacatgtg aggaatctag attgcatgct ccttatgaga 120240
atctaatgcc tgatgatctg tcatgcttcc atcaccccca gatgggacca cctacttgca 120300
ggaaaattag ctcagggctc ccactgattt taccttatgg tgagatgcac atttatttca 120360
ttatatatta caatgtaata ataattgaaa taaagtgcac gataaatgga aggtacttga 120420
gtcatccttt aaccatcgcc ccctcacccc aggtgcacag aaaaattgcc ttttatgaaa 120480
ctggtctctg gtgccaaaaa agttggggaa ccacactgct ctgggttcta gtagtcagag 120540
atgccctcta tgaggcttaa gtcagatttt tctagaaaag atttggatgg gccatcaggt 120600
caccatgaga cttcccttag cctcatgcat tctctgtgat ggtttacttt ggggcctatg 120660
aatagggaag actgagatat aggaaaaacc aaagtgtctg tgttccccca ctctcacacc 120720
catgtaacat aacacttctc acaccagata tggggggatt tctcctcaca ccccaagcga 120780
gtctccagca gataccagct gggtgtccta caatgtaact cggtcctgac actctatctg 120840
gagacagtgt cagatcccac aagttaaggc tcagtcctac aagactgccc cactgcagat 120900
gccaatccca agttgcaggc tgtgacctgt acttctgccc agctggataa agatctgttt 120960
ttctatatga ccctccatgg gtttgattac tttgctagag tggctcacag aactcaggga 121020
aacacgttac ttttatttac ccatttatta taaaagatat taaaaaggat cctggtgaac 121080
agccaggtgg aagagatgca cagggcaagg cacgtgggaa ggggctcaga gcctctatgc 121140
cctctccagt gcaccagtcc ccagtaccct aagtgttcag caacccagaa gctctccaag 121200
tgcagtcttg ttgggttttt atggaggctt cattacagag gcacagttga ttacatcatt 121260

-continued ggccatcggt gatcggctca ccttcggccc ctcttccctc cctggaggtt ggagggtggg 121320
gctgaacagt tccaaccctc aagtcacatg gttggttccc ttggcaacca gcccctgggg 121380
ctatccagga acccaccaag agttgcttca ttgcagctcc cttcacccag gaaactccaa 121440
gggatttagg agctctgtgt taagaactgg ggggcagaga cccaatatac atttcttatt 121500
ctatcacaat atcacaggaa gctaaggatg atactgcctt tgtgtgtctt ggctgtggat 121560
ggtgcataat gcatggaagt aagcatttct gaatcaacag caaacaggct ttatcaggta 121620
gaagacccct cagcgcccca gggacaaagc tcatcaatga tgtcccactg tcctctgagg 121680
ctctagctct aagacctcca gtgggtcaag ctcctggaga agtggcacat tctccaaaga 121740
cccttcaggg tcaccacacc ctggttaagg gtgtggcctc ataactcctt ttgactatga 121800
ctgatggctt acagcataga aagaaataac tttgtcaaaa aatataataa tgatagaaag 121860
gaagaaggaa cgctcccttt tgtcttctaa gaatagatgt gaaatgtgtg tgccttagaa 121920
tatcttctcc ctctcctgct ccacgtgagc tggagcttac atgcctgctt gttttcagta 121980
ctgccgtaac cctgatggtg acatcaatgg tccctggtgc tacacaatga atccaagaaa 122040
actttttgac tactgtgata tccctctctg tggtaagttg ccttctgttt tggtaaggaa 122100
actgcttcct taatatggat ttggaaaaaa aaaagcaaaa aaaacagaaa atggcttttg 122160
agctgagtgc ttctggggag gagatggctg ccctctccac cagagcctgc ttttcatcat 122220
ggccaccttg aacctgccct actattggcc ccatttgtta ggaaaacacc cgcccctccc 122280
accacacaca cataaataaa ataaatgtca aattcccaaa gggcaaactt agaggtgatc 122340
taatcagccc gggatagtcc caccgaaccc ttctttgtct agcgtgggat gcatgaaaaa 122400
caaatttaga gtcattatga tgaaaaactg tcctcttctg cagctgagaa gaaaaaaaaa 122460
atacgagcag caggaaacag ctaagcatgt aatgcacatt gtaaacctca gatggccatc 122520
ctaggaaatc aatgaagggt agtgcagctc tttagcccca gatggccttt ctcgtaagat 122580
tactactcat gagtcccatt agcgacattg cttagagact gcttgttagg ttccttcctc 122640
attgctctga gactcttatt gggagtatga ggcttggatc aggggaaggg gaattgacat 122700
tagatcttaa atgattgggg taacaaatcc atgggggaaa aaaagccact tgtacttgtt 122760
ccctattttc ttcctgctga ccaatcaact tgtctgtccg agttacagaa caccaccctg 122820
gacttttctt ttgtgtaatt tggttgcttg tggttgggtc tgccatgtga agggaccttg 122880 agctgggggga agaaggttgg cctccaagtc cactgaagac cagcatcctg agattgcctg 122940
gggaggtggt acagggcagt gatgaagatc atgggagcca cactgcccat cgtcacattt 123000
gggccactcc tggggagagc aagagggaag aaggagaggt tagggtgata ggaaagattc 123060
tacttggcca atattattat aatgtggcat tgtggtctct ggatttagtg tgagttgata 123120
gctgactttt ttctcgagtg ggtgcttttg ttctattttg tcggtgctat tgcagaagca 123180
tcttggtggt tcctctacct caaagtctct tgatggggtc agttccagtt ctccgcttct 123240
ggccccatct agtacacgcc actgcctctc actgcctggg ctctctatcc ttgacaggct 123300
gccttgaatt taagcccagt ctgacttacc tgcctcaaac acccacagta gtgcctggga 123360
ctcatgcacc tttgactccc atggaaggga agtgcagtag cttcccaggt gcaattctgc 123420
tgtcctcacc cacattgagg atgtatgaga atcaggttct tagagattgg agaaagaagg 123480
aagaatggga acaagatttc ttccaatgga ctgtgaggtt ccccacctta ctttgatgta 123540
agacaagtga ggttaacccc aagcctggtg aggagggttc ccatcagaca cttggaaatc 123600

-continued ctgaggactg tttcctgcag aaggatgtgg ttggtgggat attcaggttt gactcatgat 123660
tgagaaagtt agagcctctg gttggagaaa gagtttaata actatttcat ttccaccaac 123720
acattcagta cgaataataa ataagtaaaa ataaatagaa acattcagtt ttattttgaa 123780
tagtaggagt agggtataat ttctgtagtt actcttttag tacaatgatg catgtttact 123840
gtatgtaagg catactagca gaaattgagc tcagcactag aaaagatgat tgcattccat 123900
gccatgcttc tttttacaa aagacttcta tagatagatt ctcaaaacaa cccacagcaa 123960
atgaaaagtt atttggaaaa ctcaggttcc agattcactg gagtgtagaa tctctggttg 124020
gttggggagg aatttcctct tgcagttgtt attaataatt atatgaataa ttattaacta 124080
tattaatatt tatagttttg aagaccttga agggctggag acaacagaga agcatttttg 124140
aacaccctct gtagcccctg cactgttgta ggcattgatg ggtggtacca aagatgggac 124200
actttcccta cctccagaga ccttgtgggc ttgctgcaga gagaaggcag ggaggaggaa 124260
aagaagaata gaggcacatg tgtgtaaatt acccccacag cagtcagtta gtcatgggag 124320
gctccccaga agaactgtcc tgaagctggc tgagagaagg caacatttca acataggaca 124380
gttatccttg ctacataaaa tcacatacac acatgcacat atgtccacac acagagactc 124440
acatgcaaaa gaatcctttg tgcctttcag taaactttac atggtttaga aagaacttat 124500
atttccttga aaggagagtg tcctttgttg tttactacca ctttttaaac ttagaaagaa 124560
aaatctaaag agtgtttatg attttaccat ttaatttcac ctttgagatg tgaaaaacta 124620
gtgcttggaa ttcgtcctga attaaacgac acaattgcta acttggactc aaatgcgact 124680
tcttttccca ccttgtgcca cagcatcctc ttcatttgat tgtgggaagc ctcaagtgga 124740
gccgaagaaa tgtcctggaa gcattgtagg ggggtgtgtg gcccacccac attcctggcc 124800
ctggcaagtc agtctcagaa caaggtaaga acaggcccag aaaccatcta tactgtcctt 124860
ccatgtaagc cccacaaaac ccttctacat ttacacagaa cccacacagc tgatgcatca 124920
atacctgcct ctctgttttc tgaaggagga aaaaatatag aaaaattaaa aaaagttata 124980
ttattatagg ttctctactt ggaaaatagc caaaatacaa atctttttct tgatctgggc 125040
agttccatca aaatctgtag gcacagtgat ttgcaccaag ttccaatact tttggaaaat 125100
attgaagatg ctctgagggt ttctatggat atccattgtc tcactgtcag atgaaaagaa 125160
agggaagttt ttagaaatgt gacactttgc agtgagggag gacaagagca aacttaccta 125220
cagtctatca caggcacaga ttttttttta cacttttgtg aatcattgaa ttcaatgccg 125280
aggctattca tctattcaca aacacatgaa caaattatgg gttgtgatcc ccataaatga 125340
agagtaatca gtccgaaccc acagaacctg gacattttgg gtatcgtttc agtggaacat 125400
gcaattcgta agttcagttt gcttgggtgt ctcttaggaa gaacacatag gacacagacc 125460
catctgcctg catgttttgc ttcctcatct cctttctaca ccagggcacc tgtgctcaat 125520
tgctgttctc ctctaaagag acttccttct gtaagtttgt gaaatgccat cgacaaacct 125580
gatcgcatcg catttcactc tgctgttgag ttgatttttc tttactttat cgtttgtaac 125640
ttcttgctct acagagcttt caccttccac atatttcaga ttcattcttt cctaaactgt 125700
gtggtggtct atgtcctcac tgactatcaa catactgcca tcatgcactt cctatctcta 125760
ttcctcttcg ttgcaatctg gctccaagtg gctcacacca ttattctgat ctatcaactg 125820
cctacacagt cctagaaagt aagtgagtca agaaacatcc cccaaaagta aacttttcag 125880
gtaagatcag aagaccctca tgagtcactg ctgctcagga tcgtatctgg ctccttgaag 125940
agtgaccttg catagatctt gtcataaaaa atgaaagaga ccttgggaag gtcttgggct 126000
ggtcactttt gtcagagtcc agggctgtgg ggtgaaagcc acagctatag agcttcattc 126060
tggagtcact tagctttgct ctcctgggga caggctgtgc ctattcttgc ctcaggcatc 126120
aaaaaaagtg gcacagatgg gcccttctga aaaatctcac tactggagca cagctcgaag 126180
tttctactat cctgacgttg ggcggtagtc ctttgctttg ggaatatgaa catgatcaaa 126240
actgagtgaa cttgtcttcc tggctttctg tacaatgaag tagaacaaac catccaattt 126300
gaccaaagcc ttggcatgtt ttctttctag gtttggaaag cacttctgtg gaggcacctt 126360
aatatcccca gagtgggtgc tgactgctgc tcactgcttg aagaagtacg tttaagggaa 126420
aactgacatg ggtcttatc ttcaagactt ttttcctccc tctcttcctc catcccttct 126480
ttcttcccac cctcccttc cttcctcccc acctctcttc cttttctgga aggaacacta 126540
ggaaccaggg aatgcatgca gaatcctgag gcagaatttc cagggcaatt ggatgagaga 126600
ggagggaagt gtttctagag ggaatctgca gagggaagac ccagtgcaag tgattttttg 126660
gacctgtata aaccgcagga cagagctgtt cactaccaga ggcatcaatc tgtattgcat 126720
tgctctagag caatatctga ggctgaataa tttataaaga aaagagttta attggcacat 126780
gtttctgcag gctttacagg aagcaggatg ctgtcatctc ctctgcttct gtgtgggcct 126840
aaggaagatt acaatcatgg tggagggcaa agtgggagca ggcatgtcac atggccagag 126900
caggagcaag agacagagag agatggggtg ggggtgctgc acaataccaa atgaccagac 126960
tttgcaagaa ctaagagtga gagctcactg atcaccatga agatgtggcc caagccattc 127020
aagagggatg cacctctatg atccaaaccc ctttcacagg ccatagctcc atcactgggg 127080
actacagttg aacacgagat ttaggtgggg acaaatatac aaactatatc acagtctctg 127140
atgaaacaga ttgagaacag accttaactg tcagtttcca gcaaattgtg aattttgttt 127200
cttgccactc ataagtcact gattctgggt ggccgagggt gtcagaggga cagcgccaag 127260
ttcatggcac agaggatacc tgaaggggct ggaccatatt tttctcttga catcctcatc 127320
ttttctaggt cctcaaggcc ttcatcctac aaggtcatcc tgggtgcaca ccaagaagtg 127380
aacctcgaat ctcatgttca ggaaatagaa gtgtctaggc tgttcttgga gcccacacaa 127440
gcagatattg ccttgctaaa gctaagcagg tactcgctca cctgtggtct tcaccccacg 127500
ctggtgaaga tatttgcttt atgtctgggt tttatgggcc atggccactg catggcagtg 127560
gggaggaact gtctatcaca tgaaaggctc aagggctttg gggacagcat caatcttcaa 127620
ccccagccct gccacatgtt agttgtgctc tttaaaaagg cagaaggatt cgtttcctca 127680
cgtggaaaaa gagataccct gttacccgta aaacttactt aatgttcacc agttcatcca 127740
cattcatgat cagggaaagg ttgttattcc aggctaacta ttctcctttc ataataatat 127800
gctggagaga atcaaatgag attgcatttc aaagcgcttg aaaaaccacc atatcgagcc 127860
atgcttagtg tgggcgcctc taatcactgc tattcaggag gctgacgagg aagaattgct 127920
tgagcccagg acttcaaggc tgtaggcagc tatgattgtg ccactgcact ccaggctggg 127980
tgacagatca agaccctgtc tcaacaaaag aaaagaaaac aaaacaaatg aacagaaata 128040
ttccacaatg tcaaaaaaaa aaaaaaccca cacaacatac aatttacaaa tgcaaataat 128100
aatattattg ttgtcttctt tgattttctc tttcctggtg aaattttgtt ttattaagcc 128160
tgacaaagtg ataccctttgc ttacatcact taaagttagt ctatttggac ctaggtgaca 128220
gtacaatcag ctaagaaaca gtatttgtag gagaggcagg tttgggacag gtgacaaggc 128280
atgtggggtg ctcgctgtgc tggtggctct ggaaggcagg gtgtcaatgc agacagggat 128340

-continued gagcatggcc tggttgggaa ggcatggggc aggcaggagc ctgagctgct ctcctgggcc 128400
tggtcacaag cccatggcag cttctctggg tctgtgaact gaggggtgat gtcctggaat 128460
cctctgacac tctaggaagg agagaagggc ctttctggct cagcctttat aaacagtagc 128520
tgatctccct cttgctcccc agggtcctcc ccaccatccc agcaaatgtg caaatacaag 128580
atctctgctc ctcatggtcc tcagagagct ggggtgttct gatggcttga acaagtcact 128640
taggaaatgt ggggttttgg aggcattctc tgataggctg atacgttttg agtttagagt 128700
tcccaccgca catccccaca cccctagagt ctagggcatt tagtgctcca tgagggaacc 128760
tgtagagtga ggacatctgc atcacaggct gggccttcta gtgtccagaa gcagaaagtg 128820
tgtctgcttc aaagttggtg ctaatgatga tttttggtca gaatacggca tttctcattt 128880
ccattccttt atccccttga acttactaaa gtagaatcag gtctaaaaac cagagttcta 128940
atctttaaga gtccctggga ttctaaggta tatgaatgtc cttggaaaac aataccattt 129000
agttcatgca aggtgcttat ttcccatcct ctttcatttg atgtctagca ttttactgca 129060
ttcttaccac cacggtttag taacattcac gaggaggaag tggaggatcc agatggagca 129120
acttgctctg ggcacacaag gcatttgcaa ttttataccc tcttgatgat gtctcagcca 129180
gacattctgc ccagtcatca atgccctctt caattaatat gaaaggacac acttggcatg 129240
agattccaat cgtgcacaga atatacatga gaagtgtgcc tttgtcatcc ctactttcaa 129300
aggctaaggc caccctcagt ttcttgcatg caactgatgc ctttcaaatg aaaccttaca 129360
tctgtgtagt ccataggcaa ccacaggcaa atgtgagggt gaaacgctgt gttctacatt 129420
gttctgtgtc agtgaagcaa ggcagtgcca gctcagaggg ctctggggct tcaaggcagg 129480
gatgcctggt tgtaggtact gccacttcca gctgggcagt gaaacataac tgctaatact 129540
ttccttacag gcctgccgtc atcactgaca aagtaatgcc agcttgtctg ccatccccag 129600
actacatggt caccgccagg actgaatgtt acatcactgg ctggggagaa acccaaggtg 129660
agatcaattc cattgcccac gtaacaaatt gtttttgacc ttcagtgcat gttacaaaat 129720
gagcattttg gagatagttg tacaaattcc tacccatgaa tgtggtctac ccactcctga 129780
ctttgcctgg acacctgtct atgtctccat aatcagtctt caagggactt gggcaagggg 129840
agcggtgcca tttccttgag tctctctctt ttttgttttc agaatctttt aatttttttt 129900
gtaatgattg tatgtttccc ttacaacaaa aacaaacacc agtagaggtc tttgagtctc 129960
ttaatcataa tttcagcatt catattgctt ccccaggtaa gtggggtttt gacccagccc 130020
tcaagttaag ggtgttagat tatttttcat gtgaaattag acagactgcg tttctaaaca 130080
tggtgcaaaa cagtaacgac aaaagttgta attaaactat tcttcttccc aaatacccac 130140
atgtctaatg tgtgtgtgag ggtgttaggc aggggacctg aagctggggg agaggcagac 130200
agttcccatg gccccaagtc taggatggca tttggtattg gttgatgggt gagagcaaga 130260
gagggaatat ttttgtgcat gatgtggtat cagcacctgt actacatttt atggattcct 130320
tcttctcttt gcggtatgcc ctgacaataa ttatatccgt cagccttacc cccttggcag 130380
taggaaaact gaaactgtct taaagtctca gctctacttt ctcagaggtg caggcaaggg 130440
cactgggagt ctggggccct ggaaaactgt tctgactctg ccacttgcca gatagacctg 130500
aactagacac gttacctctt tgtaccactt ggctctaatc ccttatctgt aaaaccagca 130560
ttttcaaatg gtgctttgca catcagcctt ttgcataagc tttgatttga taaaatgttt 130620
tttgtgtttt taaaaagatt aaaaaccaca ggtttagata atttcaaagt aggcttccct 130680
ttttctgtca ttttcctatt atttttaaaa cctcacctcc ttgactcctt gttccctttt 130740

-continued tctgcactgc tgagtctggg agcactgagg ccaggtaaaa ggaaacttgg caaatgaggg 130800
gcacctatgg gtgtgggagg ctgctcctgg tgtttgcata ttttaaaatt taaatgctac 130860
aaaccactgt gagttaggta ttattgttcc tattttacca ttgaggaagc tggggctcag 130920
agaaggtgga gggtggtaca gacaaacctg aattggaacc ctggctcctg cctatgggct 130980
gtcaggactt agaaaagtcg tgagctctcg ctgattgttt cctcagctga tgtgggctgc 131040
agggctgtta tgggggaaat aataagaaag tgcatcaagt gctgagcaca tcctaagcac 131100
tccatcatgg cagctcctac tactaataaa gaatagaatt atatctaaca tgattctttc 131160
ttgcaagtga cagaaaatcc aactcaaatt ggattaagca aaacaaggga aattcttagt 131220
gagctgcaaa gttttcaggc tcacatgatg gccccaaatc ccaggtcctc ccaatcatgg 131280
agtaggcact atttgggggc acaaaggtga cattcccatg gctgcagatg ctgtggtgct 131340
gtggctgtac cgggaaagaa taagaaaggc cactctccca attatgtgaa caatagtctg 131400
cccactctga gaagtcaaac ttgggtcaca gtcctgcccc tgaacccatc actgactggc 131460
tctgacctgc accaattgtt ccatgttgga ggtgaaggca agaccccact aatacccata 131520
aggggcaaaa gttagataga tccttcaaga ggattatggg aggtagggca aaaagctgct 131580
gggcagccag aaagcaaaca gagcctctat gatacctcaa ctgatgaaag catgaagcta 131640
aaatcataag gatctgggtg tgagttctgg ctctcccatc ttccatgtga cattgggcag 131700
ttatttaatc tcttttagcc tccgctttct catcttacat atgagataat tgtgaggatt 131760
aagattacac ataatcatca tcatcaccgt ccaccactac caccatcatc cccatcaaca 131820
tcatcgccac cactatcatc attcttactg gcactaccat caccatcacc accattccac 131880
caccatcacc aatatcatca ctgtcaacat cattaccacc atcaccatca ccaccaccat 131940
catcattact accactacca ctactaccac catcaccatc accaccattc caccaccatc 132000
accaatatca tcactctcaa catcatcacc atcaccatca ccaccaccat catcatcatt 132060
actaccacta ccactactac caccatcacc atcaccactg tcccactact atcagcatga 132120
catcaccatc accaccacca tcatcattac caccgctact accaacatca ccatcaccac 132180
aattctactg ccatcaccat taacattacc accaccatca tcactatcac catcaccacc 132240
atcatcacca ctgccattat cactgccacc atcatcacta tcctctatat ttcctcatct 132300
gtattatcat tactaccacc atcactatca ccaccatcgt caccatcata atcaccatca 132360
acaccatctc caataccacc atcactgtaa ccatcatcac caccaccatg atcactatca 132420
ccatcatcac aatgatcact gtaaccatca ttactaccca ccaccatcac cactactcca 132480
ccaccatcac cattatcatt accatcacca ttatcaccac catcatcatc accagcacca 132540
ccatcatcac cagcaccacc atcaccatca ccatcattaa caccatcact atcaccattg 132600
gtttaatcat caccaccatc atcataaata aacatcacat aaccagggtg tagctgggtg 132660
ttgaccccag agcccactca ctgtttcctc tctcccaccc ccatccacac atttctaacc 132720
accatcctgc actgggctcc cagtctcctc tggtctcacc cacatgtcca ctgagaaaag 132780
gattttcaga acaccaacta gaccaggagg agccacatac ataactcagg cctgcttatc 132840
aactttctac atgttaataa tgacatcaga tcaatgggtg ttctcagctt ctcagaagga 132900
ggtcaaaatt ctccccctct ccccttcatg tgtccagacc ttcccggatt tggatgtacc 132960
aagtgcagag tggtgttgag gccaaggggc tcatccatgt aagtctcatc tgcaatcact 133020
gggctgatcc cgtggccctg tctccagggc gccatcagag agggcttcaa tcctcaggtt 133080

-continued acctgtggcc caccctgccc tcagaggtgc catctctaca ttggccacga gatggcagca 133140
catactcata gactgcatta atttcccagc aactcctggt gggttttccc tcttatcagg 133200
atgtttgcct tgctcagaga gcaaatctga gagcagtgac acctaactta actttcagca 133260
aaatattttg agaagggtgc ccctttacac atctgtgcag tccaggtgat gcatcccatg 133320
cccaatgctc ggtagtcagg aggagcttcc tccatgcagc tctgcggaag agactcttcc 133380
acgctgctca tgtaaactcc agattcggtg tcagttttct gacaccgaag acaatgatct 133440
aagtgcagtc aagggctttg gggaaagcag gagagagtgc ctcagttcta gcctgtgcca 133500
tgcttgcaaa gttttgcaaa attctaatga gagctgggct tgcaacattg gaaacttgga 133560
ttatttgtga gagcactgag aaatccctgg gcatgtccat ctggaaaaac agcatttcct 133620
ctggcacttt agcagaggtt ctgtttcaat ttggcgaagg aaattaagca gtttttcaca 133680
aaagaagaac tacaacgagg agaattgtcc ctagtatttc ttctccctaa ttgtcaagga 133740
agtgtaaatt agaaaatgaa tcaggacaat ttccacctac tatgttagct aatattttaa 133800
aaattgaata tcacaagggt gaggcaaagt aattgttttc cagtgacatt ttccactgtc 133860
acaccctttt agagaataat ttggcaatgt tactgtgaga tagaaatatg tctatataat 133920
tatgggaact gagacttcag aaagtaataa ggaataagaa tgaaatttat gaacaaacat 133980
gtggaaggtt ggaagcaaga gtggggccaa cacgcatggg gaggaagcat ttgggcagcg 134040
actccgcaga cccagactca agctgagcta tacaacctcc ttacgcctca gtttcctcaa 134100
ctgaagaaca ggaatgacaa gtgcctgttt cataggaccg ttgtgaggat taagtgagat 134160
ataccacatt atgagcttgt gcctggaaag gttgattctt agtaaatgat gactattctt 134220
ttttattgca ataaaattta tacaacatag agttactatt ttaaccattt ttgcaggtac 134280
cactgagtgg cattcagtac attcacaatg gtgtgcaacc gtcaccatat ttccaggaca 134340
tttttctcat ccccaaagga aacctcatgc ccattaagca gtcactcctc attaaaatat 134400
tagttatgaa gactgtagca tttttttaaa aactcatgat ataacattga ttgaaaaaat 134460
cagtatagga aattgtgcat tatgatgtaa tagtaaaaga agcatataaa aatctgaaaa 134520
aagtatataa aaagaatagc aattgtattt ctcagactct ctttacattg taaaaatcat 134580
tttgatagct tcaaaagaaa agcaaaaagt acacaaacaa caaccaaccc caaagcagca 134640
tgacaaagcc cagattgttg aatccaggtc ttgggaacat aaaatcttat atgacatttg 134700
cactttaatg ggtcagagag tccagtggca ttgggagctg ccttgtgttc tgcagcctca 134760
cggacagaca ggaggtccag ctccactgct ctgttcttct ggaatttcct cgtgaacaag 134820
ctttggcctc agtaaccatt tctttcatct ttttaaacac aggtaccttt gggactggcc 134880
ttctcaagga agcccagctc cttgttattg agaatgaagt gtgcaatcac tataagtata 134940
tttgtgctga gcatttggcc agaggcactg acagttgcca ggtaagaaaa gatcaataga 135000
tcaaagtctt gtgctctccc gtctcagtct cagtccctta gacgtcagtc ccaaagtggc 135060
aaattcagga aggttttgtc agtggaagac cccagtctaa gtgttgctca gaaactcccc 135120
agatctgtcc ctgaatgcat attcagatca tctaaggaga cgtcttgggg cttgagttcc 135180
agatccatag caagggagcc gtaagtgcca taactacctc aggccactca ccttcctggt 135240
gtgtgctggt caccagtgac tgaagtggtg gcttttccag tagagaggaa ggtagagggt 135300
acaggaccga gacaaattac acacacttaa caatgatgtc caggctagcc cagtctaaag 135360
gaaacaccaa gttaggaagc aatgcatgca ggattcacaa gggattattt tttttcccag 135420
gaaaaaacta agtgatgtgg ttttgttgaa tagactttgc taagtactta agcactgcag 135480

-continued atgcttgagt aatatgctca taagttcctt tctgatttga attactggga aaatgtacat 135540
atggataaga gaaggatggc atcccatatt aaaaggttgg cagcttaaag ctcacatgaa 135600
ttttccccta cctctgttta gggtgacagt ggagggcctc tggtttgctt cgagaaggac 135660
aaatacattt tacaaggagt cacttcttgg ggtcttggct gtgcacgccc caataagcct 135720
ggtgtctatg ctcgtgtttc aaggtttgtt acttggattg agggaatgat gagaaataat 135780
taattggacg ggagacagag tgaagcatca acctacttag aagctgaaac gtgggtaagg 135840
atttagcatg ctggaaataa tagacagcaa tcaaacgaag acactgttcc cagctaccag 135900
ctatgccaaa ccttggcatt tttggtattt ttgtgtataa gcttttaagg tctgactgac 135960
aaattctgta ttaaggtgtc atagctatga catttgttaa aaataaactc tgcacttatt 136020
ttgatttgaa ttaattttgg ttttggtctt caaaattttc atgctctttt catcccatct 136080
atttttattt ttatttttta gactttacgt cctggggtac atgtgcagaa tgtgcaggtt 136140
tgttacatag atgtacacgt gccatggtag tttgctgcac ccatcaacct gtcatctaat 136200
tcggtatttc ttttagttct atccctcccc tagccctcca ccccttgaca ggcccaggtg 136260
tgtgatgttg ccctccctgt gtccatgtgt tctcattgtt caactcacac ttatgagtga 136320
gaacatgccg tgtttgtttt tctgttcttg tgttagtttg ctgagaatga tagtttccag 136380
cttcatccat gtccctgcaa aggacatgaa ctcatccttt tttatggctg catagaattc 136440
catggtgtat atgtgccaca ttttatccaa tctaacattg atgggcaatt gggttggttc 136500
caactctttg ctattgtgaa tagtgccaca ataaacatac gtgtgcatgt gttttcatag 136560
cagaatgatt tataatcctc tgggtatata cccagtaatg ggattgcagg gtcaaatggt 136620
gtttctggtg ctagatcttt gaggaatcac cacactgtct tccacaatgg ttgaactaat 136680
ttatgctccc accaacaata tcaaggcatt cctatttctc cacatcctct ccagcatctg 136740
ttgtttcctg actttttaat gatcgccatt ctaactggca tgagatggta tctcattgtg 136800
gttttgattt gcatttctct aatgatcagt gatgatgagc ttttctcata tgtttgttgg 136860
ctgcataaat gcctttttttg gagaagcatc tgttcatatc ctttgcccac tttttgatgg 136920
tgttgttttt ttctggtaaa tttgtttaag ttctttgtag attctggata ttagcctttt 136980
gtcagatgga tagatggcaa aaattttatc ctattatgta ggttgcctgt tcactccgat 137040
gatagtttct tttgctgtgc agaagctctt tggtttaatt agatctcatt tgtctatttt 137100
ggcttttgtt accattgctt ttagtgtttt agtcatgaag tcttctccca tgctatgtcc 137160
tgaatggtat tgcctaagtt ttcttccagg gtttttatgg ttttaggttt tgcatttaag 137220
tctttaatcc atcttgagtt aatttttgta taagtaatgc ccttctttgt ctcttttgat 137280
ctttgttggc ttaaagtata ttttatcaga gactagaatt gcaatccctg cttttttttt 137340
tctttttgct ttccttttgc ttggtaaata ttcttccatc cctttatttt gagcctatgt 137400
atgtctgcac atgagatagg tttcctgaat acagcacacc aatgggtctt gactctttat 137460
tcaatttgcc agtctgtgtc ttttaattgg gggcatttag tccatttaca tttaaggtta 137520
atattgttat gtgtgaattt gatcctgtca ttatgatgct agcgggttat tttgcccatt 137580
agttgatgca gtttcttcat agtgtggatg gcctttacaa tttggtagtt tttgcagtgg 137640
ctggtaccaa ttgttccttt ccatgtttag tgcttcgttc aggagctctt gtgaggcagg 137700
ccttgtggtg acaaaatctt tcagcatttg cttgtctgta aaggatttta tttctccttt 137760
gcttatgaag cttagtttcg ctgggtatga aattctgggt tgaaaattat tttcttttag 137820
aatgttgaat attggccccc actctcttcg ggcttgttgg gtttctgcag agagatccac 137880
tgttagtctg attggcttcc ctttccgggt aacccaacct ttctctctgg ctgcccttag 137940
aaatttttcc ttcatttcaa ccttggtgaa tctgacgatt atgtcttgag gtggctcttc 138000
t 138001

<210> SEQ ID NO 4
<211> LENGTH: 13938
<212> TYPE: DNA
<213> ORGANISM: Homo sapiens

<400> SEQUENCE: 4
ctgggattgg gacacacttt ctggacactg ctggccagtc ccaaaatgga acataaggaa 60
gtggttcttc tacttctttt atttctgaaa tcagcagcac ctgagcaaag ccatgtggtc 120
caggattgct accatggtga tggacagagt tatcgaggca cgtactccac cactgtcaca 180
ggaaggacct gccaagcttg gtcatctatg acaccacatc aacataatag gaccacagaa 240
aactacccaa atgctggctt gatcatgaac tactgcagga atccagatgc tgtggcagct 300
ccttattgtt atacgaggga tcccggtgtc aggtgggagt actgcaacct gacgcaatgc 360
tcagacgcag aagggactgc cgtcgcgcct ccgactgtta ccccggttcc aagcctagag 420
gctccttccg aacaagcacc gactgagcaa aggcctgggg tgcaggagtg ctaccatggt 480
aatggacaga gttatcgagg cacatactcc accactgtca caggaagaac ctgccaagct 540
tggtcatcta tgacaccaca ctcgcatagt cggaccccag aatactaccc aaatgctggc 600
ttgatcatga actactgcag gaatccagat gctgtggcag ctccttattg ttatacgagg 660
gatcccggtg tcaggtggga gtactgcaac ctgacgcaat gctcagacgc agaagggact 720
gccgtcgcgc ctccgactgt taccccggtt ccaagcctag aggctccttc cgaacaagca 780
ccgactgagc aaaggcctgg ggtgcaggag tgctaccatg gtaatggaca gagttatcga 840
ggcacatact ccaccactgt cacaggaaga acctgccaag cttggtcatc tatgacacca 900
cactcgcata gtcggacccc agaatactac ccaaatgctg gcttgatcat gaactactgc 960
aggaatccag atgctgtggc agctccttat tgttatacga gggatcccgg tgtcaggtgg 1020
gagtactgca acctgacgca atgctcagac gcagaaggga ctgccgtcgc gcctccgact 1080
gttaccccgg ttccaagcct agaggctcct tccgaacaag caccgactga gcaaaggcct 1140
ggggtgcagg agtgctacca tggtaatgga cagagttatc gaggcacata ctccaccact 1200
gtcacaggaa gaacctgcca agcttggtca tctatgacac cacactcgca tagtcggacc 1260
ccagaatact acccaaatgc tggcttgatc atgaactact gcaggaatcc agatgctgtg 1320
gcagctcctt attgttatac gagggatccc ggtgtcaggt gggagtactg caacctgacg 1380
caatgctcag acgcagaagg gactgccgtc gcgcctccga ctgttacccc ggttccaagc 1440
ctagaggctc cttccgaaca agcaccgact gagcaaaggc ctggggtgca ggagtgctac 1500
catggtaatg gacagagtta tcgaggcaca tactccacca ctgtcacagg aagaacctgc 1560
caagcttggt catctatgac accacactcg catagtcgga ccccagaata ctacccaaat 1620
gctggcttga tcatgaacta ctgcaggaat ccagatgctg tggcagctcc ttattgttat 1680
acgagggatc ccggtgtcag gtgggagtac tgcaacctga cgcaatgctc agacgcagaa 1740
gggactgccg tcgcgcctcc gactgttacc ccggttccaa gcctagaggc tccttccgaa 1800
caagcaccga ctgagcaaag gcctggggtg caggagtgct accatggtaa tggacagagt 1860
tatcgaggca catactccac cactgtcaca ggaagaacct gccaagcttg gtcatctatg 1920

-continued

```
acaccacact cgcatagtcg gaccccagaa tactacccaa atgctggctt gatcatgaac   1980
tactgcagga atccagatgc tgtggcagct ccttattgtt atacgaggga tcccggtgtc   2040
aggtgggagt actgcaacct gacgcaatgc tcagacgcag aagggactgc cgtcgcgcct   2100
ccgactgtta ccccggttcc aagcctagag gctccttccg aacaagcacc gactgagcaa   2160
aggcctgggg tgcaggagtg ctaccatggt aatggacaga gttatcgagg cacatactcc   2220
accactgtca caggaagaac ctgccaagct tggtcatcta tgacaccaca ctcgcatagt   2280
cggaccccag aatactaccc aaatgctggc ttgatcatga actactgcag gaatccagat   2340
gctgtggcag ctccttattg ttatacgagg gatcccggtg tcaggtggga gtactgcaac   2400
ctgacgcaat gctcagacgc agaagggact gccgtcgcgc ctccgactgt taccccggtt   2460
ccaagcctag aggctccttc cgaacaagca ccgactgagc aaaggcctgg ggtgcaggag   2520
tgctaccatg gtaatggaca gagttatcga ggcacatact ccaccactgt cacaggaaga   2580
acctgccaag cttggtcatc tatgacacca cactcgcata gtcggacccc agaatactac   2640
ccaaatgctg gcttgatcat gaactactgc aggaatccag atgctgtggc agctccttat   2700
tgttatacga gggatcccgg tgtcaggtgg gagtactgca acctgacgca atgctcagac   2760
gcagaaggga ctgccgtcgc gcctccgact gttaccccgg ttccaagcct agaggctcct   2820
tccgaacaag caccgactga gcaaaggcct ggggtgcagg agtgctacca tggtaatgga   2880
cagagttatc gaggcacata ctccaccact gtcacaggaa gaacctgcca agcttggtca   2940
tctatgacac cacactcgca tagtcggacc ccagaatact acccaaatgc tggcttgatc   3000
atgaactact gcaggaatcc agatgctgtg gcagctcctt attgttatac gagggatccc   3060
ggtgtcaggt gggagtactg caacctgacg caatgctcag acgcagaagg gactgccgtc   3120
gcgcctccga ctgttacccc ggttccaagc ctagaggctc cttccgaaca agcaccgact   3180
gagcaaaggc ctggggtgca ggagtgctac catggtaatg gacagagtta tcgaggcaca   3240
tactccacca ctgtcacagg aagaacctgc caagcttggt catctatgac accacactcg   3300
catagtcgga ccccagaata ctacccaaat gctggcttga tcatgaacta ctgcaggaat   3360
ccagatgctg tggcagctcc ttattgttat acgagggatc ccggtgtcag gtgggagtac   3420
tgcaacctga cgcaatgctc agacgcagaa gggactgccg tcgcgcctcc gactgttacc   3480
ccggttccaa gcctagaggc tccttccgaa caagcaccga ctgagcaaag gcctggggtg   3540
caggagtgct accatggtaa tggacagagt tatcgaggca catactccac cactgtcaca   3600
ggaagaacct gccaagcttg gtcatctatg acaccacact cgcatagtcg gaccccagaa   3660
tactacccaa atgctggctt gatcatgaac tactgcagga atccagatgc tgtggcagct   3720
ccttattgtt atacgaggga tcccggtgtc aggtgggagt actgcaacct gacgcaatgc   3780
tcagacgcag aagggactgc cgtcgcgcct ccgactgtta ccccggttcc aagcctagag   3840
gctccttccg aacaagcacc gactgagcaa aggcctgggg tgcaggagtg ctaccatggt   3900
aatggacaga gttatcgagg cacatactcc accactgtca caggaagaac ctgccaagct   3960
tggtcatcta tgacaccaca ctcgcatagt cggaccccag aatactaccc aaatgctggc   4020
ttgatcatga actactgcag gaatccagat gctgtggcag ctccttattg ttatacgagg   4080
gatcccggtg tcaggtggga gtactgcaac ctgacgcaat gctcagacgc agaagggact   4140
gccgtcgcgc ctccgactgt taccccggtt ccaagcctag aggctccttc cgaacaagca   4200
ccgactgagc aaaggcctgg ggtgcaggag tgctaccatg gtaatggaca gagttatcga   4260
```

-continued

```
ggcacatact ccaccactgt cacaggaaga acctgccaag cttggtcatc tatgacacca   4320
cactcgcata gtcggacccc agaatactac ccaaatgctg gcttgatcat gaactactgc   4380
aggaatccag atgctgtggc agctccttat tgttatacga gggatcccgg tgtcaggtgg   4440
gagtactgca acctgacgca atgctcagac gcagaaggga ctgccgtcgc gcctccgact   4500
gttaccccgg ttccaagcct agaggctcct tccgaacaag caccgactga gcaaaggcct   4560
ggggtgcagg agtgctacca tggtaatgga cagagttatc gaggcacata ctccaccact   4620
gtcacaggaa gaacctgcca agcttggtca tctatgacac cacactcgca tagtcggacc   4680
ccagaatact acccaaatgc tggcttgatc atgaactact gcaggaatcc agatgctgtg   4740
gcagctcctt attgttatac gagggatccc ggtgtcaggt gggagtactg caacctgacg   4800
caatgctcag acgcagaagg gactgccgtc gcgcctccga ctgttacccc ggttccaagc   4860
ctagaggctc cttccgaaca agcaccgact gagcaaaggc ctggggtgca ggagtgctac   4920
catggtaatg gacagagtta tcgaggcaca tactccacca ctgtcacagg aagaacctgc   4980
caagcttggt catctatgac accacactcg catagtcgga ccccagaata ctacccaaat   5040
gctggcttga tcatgaacta ctgcaggaat ccagatgctg tggcagctcc ttattgttat   5100
acgagggatc ccggtgtcag gtgggagtac tgcaacctga cgcaatgctc agacgcagaa   5160
gggactgccg tcgcgcctcc gactgttacc ccggttccaa gcctagaggc tccttccgaa   5220
caagcaccga ctgagcaaag gcctggggtg caggagtgct accatggtaa tggacagagt   5280
tatcgaggca catactccac cactgtcaca ggaagaacct gccaagcttg gtcatctatg   5340
acaccacact cgcatagtcg gaccccagaa tactacccaa atgctggctt gatcatgaac   5400
tactgcagga atccagatgc tgtggcagct ccttattgtt atacgaggga tcccggtgtc   5460
aggtgggagt actgcaacct gacgcaatgc tcagacgcag aagggactgc cgtcgcgcct   5520
ccgactgtta ccccggttcc aagcctagag gctccttccg aacaagcacc gactgagcaa   5580
aggcctgggg tgcaggagtg ctaccatggt aatggacaga gttatcgagg cacatactcc   5640
accactgtca caggaagaac ctgccaagct tggtcatcta tgacaccaca ctcgcatagt   5700
cggaccccag aatactaccc aaatgctggc ttgatcatga actactgcag gaatccagat   5760
gctgtggcag ctccttattg ttatacgagg gatcccggtg tcaggtggga gtactgcaac   5820
ctgacgcaat gctcagacgc agaagggact gccgtcgcgc ctccgactgt taccccggtt   5880
ccaagcctag aggctccttc cgaacaagca ccgactgagc aaaggcctgg ggtgcaggag   5940
tgctaccatg gtaatggaca gagttatcga ggcacatact ccaccactgt cacaggaaga   6000
acctgccaag cttggtcatc tatgacacca cactcgcata gtcggacccc agaatactac   6060
ccaaatgctg gcttgatcat gaactactgc aggaatccag atgctgtggc agctccttat   6120
tgttatacga gggatcccgg tgtcaggtgg gagtactgca acctgacgca atgctcagac   6180
gcagaaggga ctgccgtcgc gcctccgact gttaccccgg ttccaagcct agaggctcct   6240
tccgaacaag caccgactga gcaaaggcct ggggtgcagg agtgctacca tggtaatgga   6300
cagagttatc gaggcacata ctccaccact gtcacaggaa gaacctgcca agcttggtca   6360
tctatgacac cacactcgca tagtcggacc ccagaatact acccaaatgc tggcttgatc   6420
atgaactact gcaggaatcc agatgctgtg gcagctcctt attgttatac gagggatccc   6480
ggtgtcaggt gggagtactg caacctgacg caatgctcag acgcagaagg gactgccgtc   6540
gcgcctccga ctgttacccc ggttccaagc ctagaggctc cttccgaaca agcaccgact   6600
gagcaaaggc ctggggtgca ggagtgctac catggtaatg gacagagtta tcgaggcaca   6660
```

-continued

```
tactccacca ctgtcacagg aagaacctgc caagcttggt catctatgac accacactcg   6720
catagtcgga ccccagaata ctacccaaat gctggcttga tcatgaacta ctgcaggaat   6780
ccagatgctg tggcagctcc ttattgttat acgagggatc ccggtgtcag gtgggagtac   6840
tgcaacctga cgcaatgctc agacgcagaa gggactgccg tcgcgcctcc gactgttacc   6900
ccggttccaa gcctagaggc tccttccgaa caagcaccga ctgagcaaag gcctggggtg   6960
caggagtgct accatggtaa tggacagagt tatcgaggca catactccac cactgtcaca   7020
ggaagaacct gccaagcttg gtcatctatg acaccacact cgcatagtcg gaccccagaa   7080
tactacccaa atgctggctt gatcatgaac tactgcagga atccagatgc tgtggcagct   7140
ccttattgtt atacgaggga tcccggtgtc aggtgggagt actgcaacct gacgcaatgc   7200
tcagacgcag aagggactgc cgtcgcgcct ccgactgtta ccccggttcc aagcctagag   7260
gctccttccg aacaagcacc gactgagcaa aggcctgggg tgcaggagtg ctaccatggt   7320
aatggacaga gttatcgagg cacatactcc accactgtca caggaagaac ctgccaagct   7380
tggtcatcta tgacaccaca ctcgcatagt cggaccccag aatactaccc aaatgctggc   7440
ttgatcatga actactgcag gaatccagat gctgtggcag ctccttattg ttatacgagg   7500
gatcccggtg tcaggtggga gtactgcaac ctgacgcaat gctcagacgc agaagggact   7560
gccgtcgcgc ctccgactgt taccccggtt ccaagcctag aggctccttc cgaacaagca   7620
ccgactgagc aaaggcctgg ggtgcaggag tgctaccatg gtaatggaca gagttatcga   7680
ggcacatact ccaccactgt cacaggaaga acctgccaag cttggtcatc tatgacacca   7740
cactcgcata gtcggacccc agaatactac ccaaatgctg gcttgatcat gaactactgc   7800
aggaatccag atgctgtggc agctccttat tgttatacga gggatcccgg tgtcaggtgg   7860
gagtactgca acctgacgca atgctcagac gcagaaggga ctgccgtcgc gcctccgact   7920
gttaccccgg ttccaagcct agaggctcct tccgaacaag caccgactga gcagaggcct   7980
ggggtgcagg agtgctacca cggtaatgga cagagttatc gaggcacata ctccaccact   8040
gtcactggaa gaacctgcca agcttggtca tctatgacac cacactcgca tagtcggacc   8100
ccagaatact acccaaatgc tggcttgatc atgaactact gcaggaatcc agatgctgtg   8160
gcagctcctt attgttatac gagggatccc ggtgtcaggt gggagtactg caacctgacg   8220
caatgctcag acgcagaagg gactgccgtc gcgcctccga ctgttacccc ggttccaagc   8280
ctagaggctc cttccgaaca agcaccgact gagcaaaggc ctggggtgca ggagtgctac   8340
catggtaatg gacagagtta tcgaggcaca tactccacca ctgtcacagg aagaacctgc   8400
caagcttggt catctatgac accacactcg catagtcgga ccccagaata ctacccaaat   8460
gctggcttga tcatgaacta ctgcaggaat ccagatgctg tggcagctcc ttattgttat   8520
acgagggatc ccggtgtcag gtgggagtac tgcaacctga cgcaatgctc agacgcagaa   8580
gggactgccg tcgcgcctcc gactgttacc ccggttccaa gcctagaggc tccttccgaa   8640
caagcaccga ctgagcaaag gcctggggtg caggagtgct accatggtaa tggacagagt   8700
tatcgaggca catactccac cactgtcaca ggaagaacct gccaagcttg gtcatctatg   8760
acaccacact cgcatagtcg gaccccagaa tactacccaa atgctggctt gatcatgaac   8820
tactgcagga atccagatgc tgtggcagct ccttattgtt atacgaggga tcccggtgtc   8880
aggtgggagt actgcaacct gacgcaatgc tcagacgcag aagggactgc cgtcgcgcct   8940
ccgactgtta ccccggttcc aagcctagag gctccttccg aacaagcacc gactgagcag   9000
```

-continued

```
aggcctgggg tgcaggagtg ctaccacggt aatggacaga gttatcgagg cacatactcc   9060
accactgtca ctggaagaac ctgccaagct tggtcatcta tgacaccaca ctcgcatagt   9120
cggaccccag aatactaccc aaatgctggc ttgatcatga actactgcag gaatccagat   9180
gctgtggcag ctccttattg ttatacgagg gatcccggtg tcaggtggga gtactgcaac   9240
ctgacgcaat gctcagacgc agaagggact gccgtcgcgc ctccgactgt taccccggtt   9300
ccaagcctag aggctccttc cgaacaagca ccgactgagc agaggcctgg ggtgcaggag   9360
tgctaccacg gtaatggaca gagttatcga ggcacatact ccaccactgt cactggaaga   9420
acctgccaag cttggtcatc tatgacacca cactcgcata gtcggacccc agaatactac   9480
ccaaatgctg gcttgatcat gaactactgc aggaatccag atgctgtggc agctccttat   9540
tgttatacga gggatcccgg tgtcaggtgg gagtactgca acctgacgca atgctcagac   9600
gcagaaggga ctgccgtcgc gcctccgact gttaccccgg ttccaagcct agaggctcct   9660
tccgaacaag caccgactga gcagaggcct ggggtgcagg agtgctacca cggtaatgga   9720
cagagttatc gaggcacata ctccaccact gtcactggaa gaacctgcca agcttggtca   9780
tctatgacac cacactcgca tagtcggacc ccagaatact acccaaatgc tggcttgatc   9840
atgaactact gcaggaatcc agatgctgtg gcagctcctt attgttatac gagggatccc   9900
ggtgtcaggt gggagtactg caacctgacg caatgctcag acgcagaagg gactgccgtc   9960
gcgcctccga ctgttacccc ggttccaagc ctagaggctc cttccgaaca agcaccgact  10020
gagcagaggc ctggggtgca ggagtgctac cacggtaatg gacagagtta tcgaggcaca  10080
tactccacca ctgtcactgg aagaacctgc caagcttggt catctatgac accacactcg  10140
catagtcgga ccccagaata ctacccaaat gctggcttga tcatgaacta ctgcaggaat  10200
ccagatcctg tggcagcccc ttattgttat acgagggatc ccagtgtcag gtgggagtac  10260
tgcaacctga cacaatgctc agacgcagaa gggactgccg tcgcgcctcc aactattacc  10320
ccgattccaa gcctagaggc tccttctgaa caagcaccaa ctgagcaaag gcctggggtg  10380
caggagtgct accacggaaa tggacagagt tatcaaggca catacttcat tactgtcaca  10440
ggaagaacct gccaagcttg gtcatctatg acaccacact cgcatagtcg gaccccagca  10500
tactacccaa atgctggctt gatcaagaac tactgccgaa atccagatcc tgtggcagcc  10560
ccttggtgtt atacaacaga tcccagtgtc aggtgggagt actgcaacct gacacgatgc  10620
tcagatgcag aatggactgc cttcgtccct ccgaatgtta ttctggctcc aagcctagag  10680
gctttttttg aacaagcact gactgaggaa acccccgggg tacaggactg ctactaccat  10740
tatggacaga gttaccgagg cacatactcc accactgtca caggaagaac ttgccaagct  10800
tggtcatcta tgacaccaca ccagcatagt cggaccccag aaaactaccc aaatgctggc  10860
ctgaccagga actactgcag gaatccagat gctgagattc gcccttggtg ttacaccatg  10920
gatcccagtg tcaggtggga gtactgcaac ctgacacaat gcctggtgac agaatcaagt  10980
gtccttgcaa ctctcacggt ggtcccagat ccaagcacag aggcttcttc tgaagaagca  11040
ccaacggagc aaagccccgg ggtccaggat tgctaccatg gtgatggaca gagttatcga  11100
ggctcattct ctaccactgt cacaggaagg acatgtcagt cttggtcctc tatgacacca  11160
cactggcatc agaggacaac agaatattat ccaaatggtg gcctgaccag gaactactgc  11220
aggaatccag atgctgagat tagtccttgg tgttatacca tggatcccaa tgtcagatgg  11280
gagtactgca acctgacaca atgtccagtg acagaatcaa gtgtccttgc gacgtccacg  11340
gctgtttctg aacaagcacc aacggagcaa agccccacag tccaggactg ctaccatggt  11400
```

-continued gatggacaga gttatcgagg ctcattctcc accactgtta caggaaggac atgtcagtct 11460
tggtcctcta tgacaccaca ctggcatcag agaaccacag aatactaccc aaatggtggc 11520
ctgaccagga actactgcag gaatccagat gctgagattc gcccttggtg ttataccatg 11580
gatcccagtg tcagatggga gtactgcaac ctgacgcaat gtccagtgat ggaatcaact 11640
ctcctcacaa ctcccacggt ggtcccagtt ccaagcacag agcttccttc tgaagaagca 11700
ccaactgaaa acagcactgg ggtccaggac tgctaccgag gtgatggaca gagttatcga 11760
ggcacactct ccaccactat cacaggaaga acatgtcagt cttggtcgtc tatgacacca 11820
cattggcatc ggaggatccc attatactat ccaaatgctg gcctgaccag gaactactgc 11880
aggaatccag atgctgagat tcgcccttgg tgttacacca tggatcccag tgtcaggtgg 11940
gagtactgca acctgacacg atgtccagtg acagaatcga gtgtcctcac aactcccaca 12000
gtggccccgg ttccaagcac agaggctcct tctgaacaag caccacctga gaaaagccct 12060
gtggtccagg attgctacca tggtgatgga cggagttatc gaggcatatc ctccaccact 12120
gtcacaggaa ggacctgtca atcttggtca tctatgatac cacactggca tcagaggacc 12180
ccagaaaact acccaaatgc tggcctgacc gagaactact gcaggaatcc agattctggg 12240
aaacaaccct ggtgttacac aaccgatccg tgtgtgaggt gggagtactg caatctgaca 12300
caatgctcag aaacagaatc aggtgtccta gagactccca ctgttgttcc agttccaagc 12360
atggaggctc attctgaagc agcaccaact gagcaaaccc ctgtggtccg gcagtgctac 12420
catggtaatg gccagagtta tcgaggcaca ttctccacca ctgtcacagg aaggacatgt 12480
caatcttggt catccatgac accacaccgg catcagagga ccccagaaaa ctacccaaat 12540
gatggcctga caatgaacta ctgcaggaat ccagatgccg atacaggccc ttggtgtttt 12600
accatggacc ccagcatcag gtgggagtac tgcaacctga cgcgatgctc agacacagaa 12660
gggactgtgg tcgctcctcc gactgtcatc caggttccaa gcctagggcc tccttctgaa 12720
caagactgta tgtttgggaa tgggaaagga taccggggca agaaggcaac cactgttact 12780
gggacgccat gccaggaatg ggctgcccag gagccccata gacacagcac gttcattcca 12840
gggacaaata aatgggcagg tctggaaaaa aattactgcc gtaaccctga tggtgacatc 12900
aatggtccct ggtgctacac aatgaatcca agaaaacttt ttgactactg tgatatccct 12960
ctctgtgcat cctcttcatt tgattgtggg aagcctcaag tggagccgaa gaaatgtcct 13020
ggaagcattg taggggggtg tgtggcccac ccacattcct ggccctggca agtcagtctc 13080
agaacaaggt ttggaaagca cttctgtgga ggcaccttaa tatccccaga gtgggtgctg 13140
actgctgctc actgcttgaa gaagtcctca aggccttcat cctacaaggt catcctgggt 13200
gcacaccaag aagtgaacct cgaatctcat gttcaggaaa tagaagtgtc taggctgttc 13260
ttggagccca cacaagcaga tattgccttg ctaaagctaa gcaggcctgc cgtcatcact 13320
gacaaagtaa tgccagcttg tctgccatcc ccagactaca tggtcaccgc caggactgaa 13380
tgttacatca ctggctgggg agaaacccaa ggtacctttg ggactggcct tctcaaggaa 13440
gcccagctcc ttgttattga gaatgaagtg tgcaatcact ataagtatat ttgtgctgag 13500
catttggcca gaggcactga cagttgccag ggtgacagtg gagggcctct ggtttgcttc 13560
gagaaggaca aatacatttt acaaggagtc acttcttggg gtcttggctg tgcacgcccc 13620
aataagcctg gtgtctatgc tcgtgtttca aggtttgtta cttggattga gggaatgatg 13680
agaaataatt aattggacgg gagacagagt gaagcatcaa cctacttaga agctgaaacg 13740

```
tgggtaagga tttagcatgc tggaaataat agacagcaat caaacgaaga cactgttccc  13800

agctaccagc tatgccaaac cttggcattt ttggtatttt tgtgtataag cttttaaggt  13860

ctgactgaca aattctgtat taaggtgtca tagctatgac atttgttaaa aataaactct  13920

gcacttattt tgatttga                                                 13938


<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5

acagcaatca aacgaagaca ctg                                              23


<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6

agcttataca caaaaatacc aaaaatgc                                         28


<210> SEQ ID NO 7
<211> LENGTH: 27
<212> TYPE: DNA
<213> ORGANISM: Artificial Sequence
<220> FEATURE:
<223> OTHER INFORMATION: Probe

<400> SEQUENCE: 7

tcccagctac cagctatgcc aaacctt                                          27


<210> SEQ ID NO 8
<211> LENGTH: 16
<212> TYPE: DNA
<213> ORGANISM: Artificial Sequence
<220> FEATURE:
<223> OTHER INFORMATION: Primer

<400> SEQUENCE: 8

ccacagtggc cccggt                                                      16


<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9

acagggcttt tctcaggtgg t                                                21


<210> SEQ ID NO 10
<211> LENGTH: 28
<212> TYPE: DNA
<213> ORGANISM: Artificial Sequence
<220> FEATURE:
<223> OTHER INFORMATION: Probe

<400> SEQUENCE: 10

ccaagcacag aggctccttc tgaacaag                                         28
```

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ggcaggtcct tcctgtgaca 20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cctgtgacag tggtggagta 20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
tcctgtgaca gtggtggagt 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cttcctgtga cagtggtgga 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ccttcctgtg acagtggtgg 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tccttcctgt gacagtggtg 20

<210> SEQ ID NO 17
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 17
gtccttcctg tgacagtggt 20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ggtccttcct gtgacagtgg 20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aggtccttcc tgtgacagtg 20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
caggtccttc ctgtgacagt 20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gcaggtcctt cctgtgacag 20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tggcaggtcc ttcctgtgac 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ttggcaggtc cttcctgtga 20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
cttggcaggt ccttcctgtg 20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gcttggcagg tccttcctgt 20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
tcttcctgtg acagtggtgg 20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ttcttcctgt gacagtggtg 20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gttcttcctg tgacagtggt 20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ggttcttcct gtgacagtgg 20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
aggttcttcc tgtgacagtg 20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
caggttcttc ctgtgacagt 20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tggcaggttc ttcctgtgac 20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ttggcaggtt cttcctgtga 20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cttggcaggt tcttcctgtg 20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
agcttggcag gttcttcctg 20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
actatgcgag tgtggtgtca 20

<210> SEQ ID NO 37
<211> LENGTH: 20

<212> TYPE: DNA
<213> ORGANISM: Artificial Sequence
<220> FEATURE:
<223> OTHER INFORMATION: Synthetic oligonucleotide

<400> SEQUENCE: 37
gactatgcga gtgtggtgtc 20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
cgactatgcg agtgtggtgt 20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ccgactatgc gagtgtggtg 20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tccgactatg cgagtgtggt 20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gtccgactat gcgagtgtgg 20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ggtccgacta tgcgagtgtg 20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gggtccgact atgcgagtgt 20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
ctgctcagtc ggtgcttgtt 20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cctctgctca gtcggtgctt 20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gcctctgctc agtcggtgct 20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
cttccagtga cagtggtgga 20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ttcttccagt gacagtggtg 20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gttcttccag tgacagtggt 20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggttcttcca gtgacagtgg 20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gaccttaaaa gcttatacac 20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gtcagacctt aaaagcttat 20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
tgtcagtcag accttaaaag 20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gaatttgtca gtcagacctt 20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
agaatttgtc agtcagacct 20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ccttaataca gaatttgtca 20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gctccgttgg tgcttgttca 20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tgctccgttg gtgcttgttc 20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ttgctccgtt ggtgcttgtt 20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
tttgctccgt tggtgcttgt 20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ctttgctccg ttggtgcttg 20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tcctgtaaca gtggtggaga 20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ttcctgtaac agtggtggag 20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
cttcctgtaa cagtggtgga 20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
ccttcctgta acagtggtgg 20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tccttcctgt aacagtggtg 20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gtccttcctg taacagtggt 20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tgtccttcct gtaacagtgg 20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tggagccaga ataacattcg 20

<210> SEQ ID NO 70

<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cctctaggct tggagccaga 20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
agttcttcct gtgacagtgg 20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
gtccgactat gctggtgtgg 20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
ggtccgacta tgctggtgtg 20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
gggtccgact atgctggtgt 20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
cctctaggct tggaatcggg 20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gttcagaagg agcctctagg 20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tgttcagaag gagcctctag 20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
gcttgttcag aaggagcctc 20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
tgcttgttca gaaggagcct 20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
gtgcttgttc agaaggagcc 20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
ggtgcttgtt cagaaggagc 20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tggtgcttgt tcagaaggag 20

<210> SEQ ID NO 83
<211> LENGTH: 20
<212> TYPE: DNA

<213> ORGANISM: Artificial Sequence
<220> FEATURE:
<223> OTHER INFORMATION: Synthetic oligonucleotide

<400> SEQUENCE: 83
gctcagttgg tgcttgttca 20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tgctcagttg gtgcttgttc 20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gcttggatct gggaccaccg 20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
gcctccatgc ttggaactgg 20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
gctcagttgg tgctgcttca 20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
cctcgataac tctggccatt 20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tcctgtgaca gtggtggaga 20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
gtaggttgat gcttcactct 20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
cgtttgattg ctgtctatta 20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
ctctgtgctt ggatctggga 20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
cctctgtgct tggatctggg 20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
gcctctgtgc ttggatctgg 20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
agaagcctct gtgcttggat 20

<210> SEQ ID NO 96
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 96
ttcagaagaa gcctctgtgc 20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
gctccgttgg tgcttcttca 20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
tttgctccgt tggtgcttct 20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
gctttgctcc gttggtgctt 20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ggctttgctc cgttggtgct 20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gggctttgct ccgttggtgc 20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
ccttcctgtg acagtggtag 20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
tccttcctgt gacagtggta 20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
tgtccttcct gtgacagtgg 20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
cctctaggct tggaaccggg 20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
tgcttgttcg gaaggagcct 20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
gtgcttgttc ggaaggagcc 20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gcttggaact gggaccaccg 20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
ctgtgcttgg aactgggacc 20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
ctctgtgctt ggaactggga 20

<210> SEQ ID NO 111
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 111
cctgtgacag tggtgga 17

<210> SEQ ID NO 112
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 112
tcctgtgaca gtggtgg 17

<210> SEQ ID NO 113
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 113
ttcctgtgac agtggtg 17

<210> SEQ ID NO 114
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 114
cttcctgtga cagtggt 17

<210> SEQ ID NO 115
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 115
ccttcctgtg acagtgg 17

<210> SEQ ID NO 116
<211> LENGTH: 17

<212> TYPE: DNA
<213> ORGANISM: Artificial Sequence
<220> FEATURE:
<223> OTHER INFORMATION: Synthetic oligonucleotide

<400> SEQUENCE: 116
tccttcctgt gacagtg 17

<210> SEQ ID NO 117
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 117
gtccttcctg tgacagt 17

<210> SEQ ID NO 118
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 118
ggtccttcct gtgacag 17

<210> SEQ ID NO 119
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 119
ccgactatgc gagtgtg 17

<210> SEQ ID NO 120
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 120
gtccgactat gcgagtg 17

<210> SEQ ID NO 121
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 121
ggtccgacta tgcgagt 17

<210> SEQ ID NO 122
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 122
gtcagacctt aaaagct 17

<210> SEQ ID NO 123
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 123
aagcctctgt gcttgga 17

<210> SEQ ID NO 124
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 124
agcctctgtg cttggat 17

<210> SEQ ID NO 125
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 125
gcctctgtgc ttggatc 17

<210> SEQ ID NO 126
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 126
gctccgttgg tgcttct 17

<210> SEQ ID NO 127
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 127
ctctgtgctt ggaactg 17

<210> SEQ ID NO 128
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 128
tgcctcgata actctgt 17

<210> SEQ ID NO 129
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 129
tgtgcctcga taactct 17

<210> SEQ ID NO 130
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 130
gctcagttgg tgctgct 17

<210> SEQ ID NO 131
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 131
gcgtttgctc ttcttcttgc gtttttt 27

<210> SEQ ID NO 132
<211> LENGTH: 3987
<212> TYPE: DNA
<213> ORGANISM: Macaca mulatta

<400> SEQUENCE: 132
atgtatcgtt ttggaatttc cagtggcttg atcaggaact actgcaggaa tccagatcct 60
gtggcagccc cttattgtta tacgatggat cccaatgtca ggtgggagta ctgcaacctg 120
acacaatgct cagatgcaga agggactgcc gtcgcacctc cgaatgtcac cctggttcca 180
agcctagagg ctccttccga acaatcaccg actgagcaaa ggcctggggt gcaggagtgc 240
taccacggta atggacagag ttatcgaggc acatacttca ccactgtgac aggaagaacc 300
tgccaagctt ggtcatctat gacaccgcac tctcatagtc ggaccccgga aaactaccca 360
aatggtggct tgatcaggaa ctactgcagg aatccagatc ctgtggcagc cccttattgt 420
tataccatgg atcccaatgt caggtgggag tactgcaacc taacacaatg ctcagacgca 480
gaagggattg ccgtcacacc tctgactgtt accccggttc caagcctaga ggctccttcc 540
aagcaagcac caactgagca aaggcctggt gtccaggagt gctaccatgg taatggacag 600
agttatcgag gcacatactt caccactgtg acaggaagaa cctgccaagc ttggtcatct 660
atgacaccac attctcatag tcgtacccca gaaaactacc caaatggcag tccgacctct 720
tcagatctct tagtctaccc tgccgtcttc cttgatgcca tgggtcccac tgttctttca 780
actcatccgc tttccctcag tcccggagtg gctgcgacca gcagaggata tattgagagc 840
aagagagaag caccgactga gcaaaggcct ggggtgcagg agtgctacca cggtaatgga 900
cagagttatc gaggcacata cttcaccact gtgacaggaa gaacctgcca agcttggtca 960
tctatgacac cgcactctca tagtcggacc ccggaaaact acccaaatgg tggcttgatc 1020
aggaactact gcaggaatcc agatcctgtg gcagcccctt attgttatac catggatccc 1080
agtgtcaggt gggagtactg caacctgaca caatgctcag acgcagaagg gactgccgtc 1140
gcacctccga atgtcacccc ggttccaagc ctagaggctc cttctgagca agcaccaact 1200

-continued

```
gagcaaaggc ttggggtgca ggagtgctac cacagtaatg gacagagtta tcgaggcaca   1260
tacttcacca ctgtgacagg aagaacctgc caagcttggt catctatgac accacactct   1320
catagtcgga ccccagaaaa ctacccaaat gctggcttgg tcaagaacta ctgccgaaat   1380
ccagatcctg tggcagcccc ttggtgttat acaacggatc ccagtgtcag gtgggagtac   1440
tgcaacctga cacgatgctc agatgcagaa gggactgctg tcgtgcctcc aaatattatt   1500
ccggttccaa gcctagaggc ttttcttgaa caagaaccga ctgaggaaac ccccggggta   1560
caggagtgct actaccatta tggacagagt tatagaggca catactccac cactgttaca   1620
ggaagaactt gccaagcttg gtcatctatg acaccacacc agcatagtcg gaccccaaaa   1680
aactatccaa atgctggcct gaccaggaac tactgcagga atccagatgc tgagattcgc   1740
ccttggtgtt ataccatgga tcccagtgtc aggtgggagt actgcaacct gacacaatgt   1800
ctggtgacag aatcaagtgt ccttgaaact ctcacagtgg tcccagatcc aagcacacag   1860
gcttcttctg aagaagcacc aacggagcaa agtcccgagg tccaggactg ctaccatggt   1920
gatggacaga gttatcgagg ctcattctcc accactgtca caggaaggac atgtcagtct   1980
tggtcctcta tgacaccaca ctggcatcag aggacaacag aatattatcc agatggtggc   2040
ctgaccagga actactgcag gaatccagat gctgagattc gcccttggtg ttataccatg   2100
gatcccagtg tcaggtggga gtactgcaac ctgacacaat gtccagtgac agaatcaagt   2160
gtcctcgcaa cgtccatggc tgtttctgaa caagcaccaa tggagcaaag ccccggggtc   2220
caggactgct accatggtga tggacagagt tatcgaggtt cattctccac cactgtcaca   2280
ggaaggacat gtcagtcttg gtcctctatg acaccacact ggcatcagag gaccatagaa   2340
tactacccaa atggtggcct gaccaagaac tactgcagga atccagatgc tgagattcgc   2400
ccttggtgtt ataccatgga tcccagagtc agatgggagt actgcaacct gacacaatgt   2460
gtggtgatgg aatcaagtgt ccttgcaact cccatggtgg tcccagttcc aagcagagag   2520
gttccttctg aagaagcacc aactgaaaac agccctgggg tccaggactg ctaccaaggt   2580
gatggacaga gttatcgagg cacattctcc accactatca caggaagaac atgtcagtct   2640
tggttgtcta tgacaccaca tcggcatcgg aggatcccat tacgctatcc aaatgctggc   2700
ctgaccagga actattgcag aaatccagat gctgagattc gcccttggtg ttacaccatg   2760
gatcccagtg tcaggtggga gtactgcaac ctgacacaat gtccagtgac agaatcaagt   2820
gtcctcacaa ctcccacggt ggtcccggtt ccaagcacag aggctccttc tgaacaagca   2880
ccacctgaga aaagccctgt ggtccaggat tgctaccatg gtgatggaca gagttatcga   2940
ggcacatcct ccaccactgt cacaggaagg aactgtcagt cttggtcatc tatgatacca   3000
cactggcatc agaggacccc agaaaactac ccaaatgctg gcctgaccag gaactactgc   3060
aggaatccag attctgggaa acaaccctgg tgttacacga ctgatccatg tgtgaggtgg   3120
gagtactgca acctgacaca atgctcagaa acagaatcag gtgtcctaga gactcccact   3180
gttgttccgg ttccaagcat ggaagctcat tctgaagcag caccaactga gcaaacccct   3240
gtggtccagc agtgctacca tggtaatgga cagagttatc gaggcacatt ctccaccact   3300
gtcacaggaa ggacatgtca atcttggtca tccatgacac cacaccagca taagaggacc   3360
ccggaaaacc acccaaatga tggcttgaca atgaactact gcaggaatcc agatgctgac   3420
acaggccctt ggtgttttac catggacccc agcgtcaggc gggagtactg caacctgacg   3480
cgatgctcag acacagaagg gactgtggtc acacctccga ctgttatccc ggttccaagc   3540
ctagaggctc cttctgaaca agtgcttgga attcatcctg aattaaacga cacaattgct   3600
```

-continued

```
aacttggact caaaggtgaa ttctttccca ccttgtgcca cagcatcctc ttcatttgat   3660

tgtgggaagc ctcaagtgga gccaaagaaa tgtcctggaa gcattgtagg tgggtgtgtg   3720

gcccacccac attcctggcc ctggcaagtc agtcttagaa caaggtttgg aaagcacttc   3780

tgtggaggca ccttaatatc cccagagtgg gtgctgactg ctgcttgctg cttggagacg   3840

ttctcaaggc cttccttcta caaggtcatc ctgggtgcac accaagaagt gaatctcgaa   3900

tctcatgttc aagaaataga agtgtctagg ttgttcttgg agcccatagg agcagatatt   3960

gccttgctaa agctaagcag gtactaa                                      3987


<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133

ggttcttcca gtgacagtgg                                                20


<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134

atgcctcgat aactccgtcc                                                20
```